United States Patent
Liebowitz

(10) Patent No.: US 11,987,636 B2
(45) Date of Patent: May 21, 2024

(54) DOSING OF A BISPECIFIC ANTIBODY THAT BINDS CD20 AND CD3

(71) Applicant: XENCOR, INC., Pasadena, CA (US)

(72) Inventor: David Liebowitz, San Diego, CA (US)

(73) Assignee: XENCOR, INC., Pasadena, CA (US)

( * ) Notice: Subject to any disclaimer, the term of this patent is extended or adjusted under 35 U.S.C. 154(b) by 0 days.

(21) Appl. No.: 17/832,093

(22) Filed: Jun. 3, 2022

(65) Prior Publication Data

US 2023/0048390 A1 Feb. 16, 2023

Related U.S. Application Data

(60) Provisional application No. 63/197,218, filed on Jun. 4, 2021.

(51) Int. Cl.
| | | |
|---|---|---|
| *C07K 16/28* | (2006.01) | |
| *A61P 35/00* | (2006.01) | |
| *A61K 39/00* | (2006.01) | |

(52) U.S. Cl.
CPC .......... *C07K 16/2887* (2013.01); *A61P 35/00* (2018.01); *C07K 16/2809* (2013.01); *A61K 2039/545* (2013.01); *C07K 2317/31* (2013.01); *C07K 2317/565* (2013.01)

(58) Field of Classification Search
CPC ............ C07K 16/2887; C07K 16/2809; C07K 2317/31; A61K 2039/545; A61K 2039/505; A61K 39/0011
See application file for complete search history.

(56) References Cited

U.S. PATENT DOCUMENTS

| | | | |
|---|---|---|---|
| 2017/0349657 A1* | 12/2017 | Saville ............... | C07K 16/2887 |
| 2018/0134798 A1 | 5/2018 | Chu et al. | |
| 2018/0194841 A1 | 7/2018 | Smith et al. | |
| 2020/0325238 A1 | 10/2020 | Bacac et al. | |
| 2021/0032358 A1 | 2/2021 | Valbjoern et al. | |
| 2021/0095027 A1 | 4/2021 | Saville et al. | |

FOREIGN PATENT DOCUMENTS

| | | | |
|---|---|---|---|
| WO | WO-2016086189 A2 * | 6/2016 | ............. A61P 35/00 |
| WO | WO 2017210485 A1 | 12/2017 | |
| WO | WO 2018223004 A1 | 12/2018 | |

OTHER PUBLICATIONS

Patel et al. "Phase 1 Safety and Anti-tumor Activity of Plamotamab (XmAb13676), an Anti-CD20 x Anti-CD3 Bispecific Antibody, in Subjects with Relapsed/Refractory Non-Hodgkin's Lymphoma," ASH Poster, 13676-01, ASH Annual Meeting, Dec. 2021. (Year: 2021).*
Patel et al."A Phase 1 Study of Plamotamab, an Anti-CD20 x Anti-CD3 Bispecific Antibody, in Patients With Relapsed/ Refractory Non-Hodgkin's Lymphoma: Recommended Dose Safety/ Efficacy Update and Escalation Exposure-Response Analysis," ASH Poster, 13676-01, ASH Annual Meeting, Dec. 2022. (Year: 2022).*
International Searching Authority, International Search Report and Written Opinion for International Patent Application No. PCT/ US2022/032106 dated Aug. 24, 2022 (17 pages).
Patel et al., 2021, "Phase 1 Safety and Anti-tumor Activity of Plamotamab (XmAb13676), an Anti-CD20 x Anti-CD3 Bispecific Antibody, in Subjects with Relapsed/Refractory Non-Hodgkin's Lymphoma," ASH Poster, 13676-01, American Society for Hematology annual meeting held Dec. 2021 (ASH 2021) (11 pages).
Patel et al., 2022, "A Phase 1 Study of Plamotamab, an Anti-CD20 x Anti-CD3 Bispecific Antibody, in Patients With Relapsed/ Refractory Non-Hodgkin's Lymphoma: Recommended Dose Safety/ Efficacy Update and Escalation Exposure-Response Analysis," ASH Poster, 13676-01, American Society of Hematology Annual Meeting and Exposition, New Orleans, LA, USA, Dec. 10-13, 2022 (ASH 2022) (14 pages).

* cited by examiner

*Primary Examiner* — Nelson B Moseley, II
*Assistant Examiner* — Alyssa Rae Stonebraker
(74) *Attorney, Agent, or Firm* — JONES DAY

(57) ABSTRACT

Provided herein, in certain aspects, are methods for the treatment of a CD20-expressing cancer in a human subject, comprising administration of a bispecific anti-CD20×anti-CD3 antibody (e.g., XmAb® 13676) to the human subject in a flat escalation dosing regimen including at least four phases (e.g., five phases or more than five phases).

20 Claims, 18 Drawing Sheets

Specification includes a Sequence Listing.

Anti-CD20 x Anti-CD3 Fab-scFv-Fc

FIG. 2

XENP13676 Anti-CD20 x Anti-CD3 Fab-scFv-Fc Heavy Chain 1 (Anti-CD20 Fab-Fc (C2B8_H1))
QVQLVQSGAEVKKPGASVKVSCKASG<u>YTFTSYNMH</u>WVRQAPGQGLEWMGA<u>IYPGNG
D</u>TSYNQKFQGRVTITADKSISTAYMELSSLRSEDTAVYYCAR<u>STYYGGDWYFNV</u>WGAG
TLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSDTKVDKKV/EPKSCDKTHTCPPCP
APPVAGPSVFLFPPKPKDTLMISRTPEVTCVVVDVKHEDPEVKFNWYVDGVEVHNAKT
KPREEEYNSTYRVVSVLTVLHQDWLNGKEYKCKVSNKALPAPIEKTISKAKGQPREPQV
YTLPPSREEMTKNQVSLTCDVSGFYPSDIAVEWESDGQPENNYKTTPPVLDSDGSFFLYS
KLTVDKSRWEQGDVFSCSVMHEALHNHYTQKSLSLSPGK (SEQ ID NO:1)

XENP13676 Anti-CD20 x Anti-CD3 Fab-scFv-Fc Heavy Chain 2 (Anti-CD3 scFv-Fc (αCD3_H1.30_L1.47))
EVQLVESGGGLVQPGGSLRLSCAASGFTFS<u>TYAMN</u>WVRQAPGKGLEWVG<u>RIRSKYNN
YATYYADSVKG</u>RFTISRDDSKNTLYLQMNSLRAEDTAVYYCVR<u>HGNFGDSYVSWFAY</u>
WGQGTLVTVSS<u>GKPGSGKPGSGKPGSGKPGS</u>QAVVTQEPSLTVSPGGTVTLTC<u>GSSTGA
VTTSNYAN</u>WVQQKPGKSPRGLIG<u>GTNKRA</u>PGVPARFSGSLLGGKAALTISGAQPEDEAD
YYC<u>ALWYSNHWV</u>FGGGTKLTVL/EPKSSDKTHTCPPCPAPPVAGPSVFLFPPKPKDTLMI
SRTPEVTCVVVDVKHEDPEVKFNWYVDGVEVHNAKTKPREEQYNSTYRVVSVLTVLH
QDWLNGKEYKCKVSNKALPAPIEKTISKAKGQPREPQVYTLPPSREQMTKNQVKLTCL
VKGFYPSDIAVEWESNGQPENNYKTTPPVLDSDGSFFLYSKLTVDKSRWQQGNVFSCSV
MHEALHNHYTQKSLSLSPGK (SEQ ID NO:2)

XENP13676 Anti-CD20 x Anti-CD3 Fab-scFv-Fc Light Chain (Anti-CD20 LC (C2B8_L1))
QIVLTQSPSSLSASVGDRVTITCRASS<u>SVSYIH</u>WFQQKPGKSPKPLIY<u>ATSNLAS</u>GVPVRF
SGSGSGTDYTLTISSLQPEDFATYYCQQ<u>WTSNPPT</u>FGGGTKVEIK/RTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:3)

FIG. 3A

XENP13677 Anti-CD20 x Anti-CD3 Fab-scFv-Fc Heavy Chain 1 (Anti-CD20 Fab-Fc (C2B8_H1.202))
QVQLVQSGAEVKKPGASVKVSCKASG<u>YTFTSYNMH</u>WVRQAPGQRLEWMGA<u>IYPGNG
ATSYSQKFQG</u>RVTITADTSASTAYMELSSLRSEDTAVYYCAR<u>SYYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:4)

XENP13677 Anti-CD20 x Anti-CD3 Fab-scFv-Fc Heavy Chain 2 (Anti-CD3 scFv-Fc (αCD3_H1.30_L1.47))
EVQLVESGGGLVQPGGSLRLSCAASGFTFST<u>YAMN</u>WVRQAPGKGLEWVGR<u>IRSKYNN
YATYYADSVKG</u>RFTISRDDSKNTLYLQMNSLRAEDTAVYYCVR<u>HGNFGDSYVSWFAY</u>
WGQGTLVTVSS<u>GKPGSGKPGSGKPGSGKPGS</u>QAVVTQEPSLTVSPGGTVTLTC<u>GSSTGA
VTTSNYAN</u>WVQQKPGKSPRGLIG<u>GTNKRA</u>PGVPARFSGSLLGGKAALTISGAQPEDEAD
YYC<u>ALWYSNHWV</u>FGGGTKLTVLEPKSSDKTHTCPPCPAPPVAGPSVFLFPPKPKDTLMI
SRTPEVTCVVVDVKHEDPEVKFNWYVDGVEVHNAKTKPREEQYNSTYRVVSVLTVLH
QDWLNGKEYKCKVSNKALPAPIEKTISKAKGQPREPQVYTLPPSREQMTKNQVKLTCL
VKGFYPSDIAVEWESNGQPENNYKTTPPVLDSDGSFFLYSKLTVDKSRWQQGNVFSCSV
MHEALHNHYTQKSLSLSPGK (SEQ ID NO:5)

XENP13677 Anti-CD20 x Anti-CD3 Fab-scFv-Fc Light Chain (Anti-CD20 LC (C2B8_L1.113))
QIVLTQSPSSLSASVGDRVTITCRAS<u>WSVSYIH</u>WFQQKPGKSPKPLIY<u>ATSNLAS</u>GVPVRF
SGSGSGTDYTLTISSLQPEDFATYYC<u>QQWTHNPPT</u>FGGGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:6)

XENP14388 Anti-CD20 x Anti-CD3 Fab-scFv-Fc Heavy Chain 1 (Anti-CD20 Fab-Fc (C2B8_H1.202))
QVQLVQSGAEVKKPGASVKVSCKASG<u>YTFTSYNMH</u>WVRQAPGQRLEWMGA<u>IYPGNG
ATSYSQKFQG</u>RVTITADTSASTAYMELSSLRSEDTAVYYCAR<u>SYYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:7)

FIG. 3B

XENP14388 Anti-CD20 x Anti-CD3 Fab-scFv-Fc Heavy Chain 2 (Anti-CD3 scFv-Fc (αCD3_H1.31_L1.47))
EVQLVESGGGLVQPGGSLRLSCAASGFTFS<u>TYAMS</u>WVRQAPGKGLEWVG<u>RIRSKYNNY
ATYYADSVK</u>GRFTISRDDSKNTLYLQMNSLRAEDTAVYYCVR<u>HGNFGDSYVSWFAY</u>W
GQGTLVTVSSGKPGSGKPGSGKPGSGKPGSQAVVTQEPSLTVSPGGTVTLTC<u>GSSTGAV
TTSNYAN</u>WVQQKPGKSPRGLIG<u>GTNKRA</u>PGVPARFSGSLLGGKAALTISGAQPEDEADY
YC<u>ALWYSNHWV</u>FGGGTKLTVLEPKSSDKTHTCPPCPAPPVAGPSVFLFPPKPKDTLMIS
RTPEVTCVVVDVKHEDPEVKFNWYVDGVEVHNAKTKPREEQYNSTYRVVSVLTVLHQ
DWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSV
MHEALHNHYTQKSLSLSPGK (SEQ ID NO:8)

XENP14388 Anti-CD20 x Anti-CD3 Fab-scFv-Fc Light Chain (Anti-CD20 (C2B8_L1.113))
QIVLTQSPSSLSASVGDRVTITCRAS<u>WSVSY</u>IHWFQQKPGKSPKPLIY<u>ATSNLAS</u>GVPVRF
SGSGSGTDYTLTISSLQPEDFATYYCQQ<u>WTHNPPT</u>FGGGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:9)

XENP14389 Anti-CD20 x Anti-CD3 Fab-scFv-Fc Heavy Chain 1 (Anti-CD20 Fab-Fc (C2B8_H1.202))
QVQLVQSGAEVKKPGASVKVSCKASG<u>YTFTSYNMH</u>WVRQAPGQRLEWMGA<u>IYPGNG
ATSYSQKFQG</u>RVTITADTSASTAYMELSSLRSEDTAVYYCAR<u>SYYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:10)

XENP14389 Anti-CD20 x Anti-CD3 Fab-scFv-Fc Heavy Chain 2 (Anti-CD3 scFv-Fc (αCD3_H1.32_L1.47))
EVQLVESGGGLVQPGGSLRLSCAASGFTFS<u>TYAMN</u>WVRQAPGKGLEWVG<u>RIRSKANN
YATYYADSVK</u>GRFTISRDDSKNTLYLQMNSLRAEDTAVYYCVR<u>HGNFGDSYVSWFAY</u>
WGQGTLVTVSSGKPGSGKPGSGKPGSQAVVTQEPSLTVSPGGTVTLTC<u>GSSTGA
VTTSNYAN</u>WVQQKPGKSPRGLIG<u>GTNKRA</u>PGVPARFSGSLLGGKAALTISGAQPEDEAD
YYC<u>ALWYSNHWV</u>FGGGTKLTVLEPKSSDKTHTCPPCPAPPVAGPSVFLFPPKPKDTLMI
SRTPEVTCVVVDVKHEDPEVKFNWYVDGVEVHNAKTKPREEQYNSTYRVVSVLTVLH
QDWLNGKEYKCKVSNKALPAPIEKTISKAKGQPREPQVYTLPPSREQMTKNQVKLTCL
VKGFYPSDIAVEWESNGQPENNYKTTPPVLDSDGSFFLYSKLTVDKSRWQQGNVFSCSV
MHEALHNHYTQKSLSLSPGK (SEQ ID NO:11)

FIG. 3C

XENP14389 Anti-CD20 x Anti-CD3 Fab-scFv-Fc Light Chain (Anti-CD20 (C2B8_L1.113))
QIVLTQSPSSLSASVGDRVTITCRAS<u>WSVSYIH</u>WFQQKPGKSPKPLIY<u>ATSNLAS</u>GVPVRF
SGSGSGTDYTLTISSLQPEDFATYYCQQ<u>WTHNPPT</u>FGGGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:12)

XENP14390 Anti-CD20 x Anti-CD3 Fab-scFv-Fc Heavy Chain 1 (Anti-CD20 Fab-Fc
(C2B8_H1.202))
QVQLVQSGAEVKKPGASVKVSCKASG<u>YTFTSYNMH</u>WVRQAPGQRLEWMGA<u>IYPGNG
ATSYSQKFQG</u>RVTITADTSASTAYMELSSLRSEDTAVYYCAR<u>SYYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:13)

XENP14390 Anti-CD20 x Anti-CD3 Fab-scFv-Fc Heavy Chain 2 (Anti-CD3 scFv-Fc
(αCD3_H1.33_L1.47))
EVQLVESGGGLVQPGGSLRLSCAASGFTFS<u>TYAMN</u>WVRQAPGKGLEWVG<u>RIRSKYNN
YATYYADSVKG</u>RFTISRDDSKNTLYLQMNSLRAEDTAVYYCVR<u>HGNFGDSYVSWFDY</u>
WGQGTLVTVSSGKPGSGKPGSGKPGSQAVVTQEPSLTVSPGGTVTLTC<u>GSSTGA
VTTSNYAN</u>WVQQKPGKSPRGLIG<u>GTNKRA</u>PGVPARFSGSLLGGKAALTISGAQPEDEAD
YYC<u>ALWYSNHWV</u>FGGGTKLTVLEPKSSDKTHTCPPCPAPPVAGPSVFLFPPKPKDTLMI
SRTPEVTCVVVDVKHEDPEVKFNWYVDGVEVHNAKTKPREEQYNSTYRVVSVLTVLH
QDWLNGKEYKCKVSNKALPAPIEKTISKAKGQPREPQVYTLPPSREQMTKNQVKLTCL
VKGFYPSDIAVEWESNGQPENNYKTTPPVLDSDGSFFLYSKLTVDKSRWQQGNVFSCSV
MHEALHNHYTQKSLSLSPGK (SEQ ID NO:14)

XENP14390 Anti-CD20 x Anti-CD3 Fab-scFv-Fc Light Chain (Anti-CD20 (C2B8_L1.113))
QIVLTQSPSSLSASVGDRVTITCRAS<u>WSVSYIH</u>WFQQKPGKSPKPLIY<u>ATSNLAS</u>GVPVRF
SGSGSGTDYTLTISSLQPEDFATYYCQQ<u>WTHNPPT</u>FGGGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:15)

FIG. 3D

XENP14392 Anti-CD20 x Anti-CD3 Fab-scFv-Fc Heavy Chain 1 (Anti-CD20 Fab-Fc (C2B8_H1.202))
QVQLVQSGAEVKKPGASVKVSCKASG<u>YTFTSYN</u>MHWVRQAPGQRLEWMGAI<u>YPGNG
ATSYSQKFQG</u>RVTITADTSASTAYMELSSLRSEDTAVYYCARS<u>YYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:16)

XENP14392 Anti-CD20 x Anti-CD3 Fab-scFv-Fc Heavy Chain 2 (Anti-CD3 scFv-Fc (αCD3_H1.89_L1.47))
EVQLVESGGGLVQPGGSLRLSCAASGFTFS<u>TYAMN</u>WVRQAPGKGLEWV<u>GRIRSKYNN
YATYYADSVKG</u>RFTISRDDSKNTLYLQMNSLRAEDTAVYYCVR<u>HGNFGDEYVSWFAY</u>
WGQGTLVTVSSGKPGSGKPGSGKPGSQAVVTQEPSLTVSPGGTVTLTCGSSTGA
V<u>TTSNYAN</u>WVQQKPGKSPRGLIG<u>GTNKRAP</u>GVPARFSGSLLGGKAALTISGAQPEDEAD
YYC<u>ALWYSNHWV</u>FGGGTKLTVLEPKSSDKTHTCPPCPAPPVAGPSVFLFPPKPKDTLMI
SRTPEVTCVVVDVKHEDPEVKFNWYVDGVEVHNAKTKPREEQYNSTYRVVSVLTVLH
QDWLNGKEYKCKVSNKALPAPIEKTISKAKGQPREPQVYTLPPSREQMTKNQVKLTCL
VKGFYPSDIAVEWESNGQPENNYKTTPPVLDSDGSFFLYSKLTVDKSRWQQGNVFSCSV
MHEALHNHYTQKSLSLSPGK (SEQ ID NO:17)

XENP14392 Anti-CD20 x Anti-CD3 Fab-scFv-Fc Light Chain (Anti-CD20 (C2B8_L1.113))
QIVLTQSPSSLSASVGDRVTITCRAS<u>WSVSYIH</u>WFQQKPGKSPKPLIY<u>ATSNLAS</u>GVPVRF
SGSGSGTDYTLTISSLQPEDFATYYCQQ<u>WTHNPPT</u>FGGGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO:18)

XENP14393 Anti-CD20 x Anti-CD3 Fab-scFv-Fc Heavy Chain 1 (Anti-CD20 Fab-Fc (C2B8_H1.202))
QVQLVQSGAEVKKPGASVKVSCKASG<u>YTFTSYN</u>MHWVRQAPGQRLEWMGAI<u>YPGNG
ATSYSQKFQG</u>RVTITADTSASTAYMELSSLRSEDTAVYYCARS<u>YYMGGDWYFDV</u>WGA
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAK
TKPREEEYNSTYRVVSVLTVLHQDWLNGKEYKCKVSNKALPAPIEKTISKAKGQPREPQ
VYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK (SEQ ID NO:19)

FIG. 3E

XENP14393 Anti-CD20 x Anti-CD3 Fab-scFv-Fc Heavy Chain 2 (Anti-CD3 scFv-Fc (αCD3_H1.90_L1.47))
EVQLVESGGGLVQPGGSLRLSCAASGFTFS<u>TYAMN</u>WVRQAPGKGLEWVG<u>RIRSKYNN YATYYADSVKG</u>RFTISRDDSKNTLYLQMNSLRAEDTAVYYCVR<u>HGNFGDPYVSWFAY</u> WGQGTLVTVSSGKPGSGKPGSGKPGSGKPGSQAVVTQEPSLTVSPGGTVTLTC<u>GSSTGA VTTSNYAN</u>WVQQKPGKSPRGLIG<u>GTNKRA</u>PGVPARFSGSLLGGKAALTISGAQPEDEAD YYC<u>ALWYSNHWV</u>FGGGTKLTVLEPKSSDKTHTCPPCPAPPVAGPSVFLFPPKPKDTLMI SRTPEVTCVVVDVKHEDPEVKFNWYVDGVEVHNAKTKPREEQYNSTYRVVSVLTVLH QDWLNGKEYKCKVSNKALPAPIEKTISKAKGQPREPQVYTLPPSREQMTKNQVKLTCL VKGFYPSDIAVEWESNGQPENNYKTTPPVLDSDGSFFLYSKLTVDKSRWQQGNVFSCSV MHEALHNHYTQKSLSLSPGK (SEQ ID NO:20)

XENP14393 Anti-CD20 x Anti-CD3 Fab-scFv-Fc Light Chain (Anti-CD20 (C2B8_L1.113))
QIVLTQSPSSLSASVGDRVTITCRAS<u>WSVSYIH</u>WFQQKPGKSPKPLIY<u>ATSNLAS</u>GVPVRF SGSGSGTDYTLTISSLQPEDFATYYCQQ<u>WTHNPPT</u>FGGGTKVEIKRTVAAPSVFIFPPSDE QLKSGTASVVCLLNNFYPREAKVQWKVDNALQSGNSQESVTEQDSKDSTYSLSSTLTLS KADYEKHKVYACEVTHQGLSSPVTKSFNRGEC (SEQ ID NO:21)

FIG. 4C
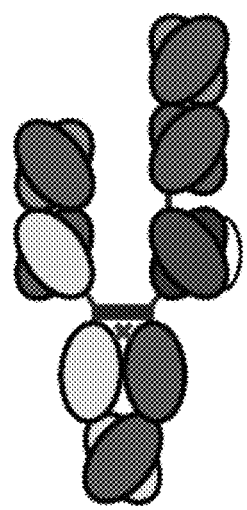 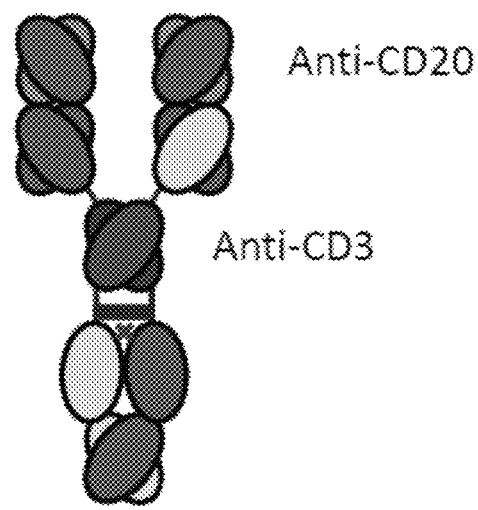

FIG. 4D
Constructs
One-arm central-scFv
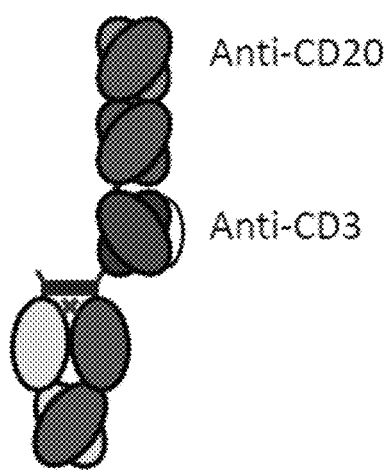
One-arm central-scFv
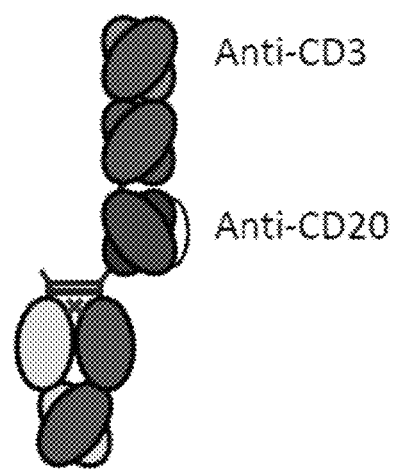
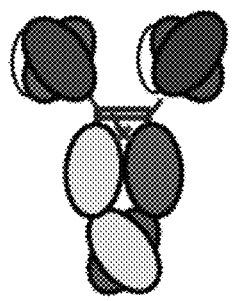
Dual scFv

DOSING OF A BISPECIFIC ANTIBODY THAT BINDS CD20 AND CD3

CROSS-REFERENCE TO RELATED APPLICATIONS

The present application claims the benefit of priority to U.S. Ser. No. 63/197,218 filed Jun. 4, 2021, the disclosure of which is incorporated herein by reference in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled "14718-023-999_SEQ_LISTING.txt," was created on May 28, 2022, and is 127,387 bytes in size.

FIELD

Provided herein, in certain aspects, are methods for the treatment of a CD20-expressing cancer in a human subject, comprising administration of a bispecific anti-CD20×anti-CD3 antibody.

BACKGROUND

Antibody-based therapeutics have been used successfully to treat a variety of diseases, including cancer and autoimmune/inflammatory disorders. Yet improvements to this class of drugs are still needed, particularly with respect to enhancing their clinical efficacy. One avenue being explored is the engineering of additional and novel antigen binding sites into antibody-based drugs such that a single immunoglobulin molecule co-engages two different antigens. Because the considerable diversity of the antibody variable region (Fv) makes it possible to produce an Fv that recognizes virtually any molecule, the typical approach to the generation of such bispecific antibodies is the introduction of new variable regions into the antibody.

A number of alternate antibody formats have been explored for bispecific targeting (Chames & Baty, 2009, mAbs 1[6]:1-9; Holliger & Hudson, 2005, Nature Biotechnology 23[9]:1126-1136; Kontermann, mAbs 4(2):182 (2012), all of which are expressly incorporated herein by reference). Initially, bispecific antibodies were made by fusing two cell lines that each produced a single monoclonal antibody (Milstein et al., 1983, Nature 305:537-540). Although the resulting hybrid hybridoma or quadroma did produce bispecific antibodies, they were only a minor population, and extensive purification was required to isolate the desired antibody. An engineering solution to this was the use of antibody fragments to make bispecifics. Because such fragments lack the complex quaternary structure of a full length antibody, variable light and heavy chains can be linked in single genetic constructs. Antibody fragments of many different forms have been generated, including diabodies, single chain diabodies, tandem scFvs, and Fab2 bispecifics (Chames & Baty, 2009, mAbs 1[6]:1-9; Holliger & Hudson, 2005, Nature Biotechnology 23[9]:1126-1136; expressly incorporated herein by reference). While these formats can be expressed at high levels in bacteria and may have favorable penetration benefits due to their small size, they clear rapidly in vivo and can present manufacturing obstacles related to their production and stability. A principal cause of these drawbacks is that antibody fragments typically lack the constant region of the antibody with its associated functional properties, including larger size, high stability, and binding to various Fc receptors and ligands that maintain long half-life in serum (i.e. the neonatal Fc receptor FcRn) or serve as binding sites for purification (i.e. protein A and protein G).

More recent work has attempted to address the shortcomings of fragment-based bispecifics by engineering dual binding into full length antibody-like formats (Wu et al., 2007, Nature Biotechnology 25[11]:1290-1297; U.S. Ser. No. 12/477,711; Michaelson et al., 2009, mAbs 1[2]:128-141; PCT/US2008/074693; Zuo et al., 2000, Protein Engineering 13[5]:361-367; U.S. Pat. No. 9,865,198; Shen et al., 2006, J Biol Chem 281[16]:10706-10714; Lu et al., 2005, J Biol Chem 280[20]:19665-19672; PCT/US2005/025472; expressly incorporated herein by reference). These formats overcome some of the obstacles of the antibody fragment bispecifics, principally because they contain an Fc region. One significant drawback of these formats is that, because they build new antigen binding sites on top of the homodimeric constant chains, binding to the new antigen is always bivalent.

For many antigens that are attractive as co-targets in a therapeutic bispecific format, the desired binding is monovalent rather than bivalent. For many immune receptors, cellular activation is accomplished by cross-linking of a monovalent binding interaction. The mechanism of cross-linking is typically mediated by antibody/antigen immune complexes, or via effector cell to target cell engagement. For example, the low affinity Fc gamma receptors (FcγRs) such as FcγRIIa, FcγRIIb, and FcγRIIIa bind monovalently to the antibody Fc region. Monovalent binding does not activate cells expressing these FcγRs; however, upon immune complexation or cell-to-cell contact, receptors are cross-linked and clustered on the cell surface, leading to activation. For receptors responsible for mediating cellular killing, for example FcγRIIIa on natural killer (NK) cells, receptor cross-linking and cellular activation occurs when the effector cell engages the target cell in a highly avid format (Bowles & Weiner, 2005, J Immunol Methods 304:88-99, expressly incorporated by reference). Similarly, on B cells the inhibitory receptor FcγRIIb downregulates B cell activation only when it engages into an immune complex with the cell surface B-cell receptor (BCR), a mechanism that is mediated by immune complexation of soluble IgG's with the same antigen that is recognized by the BCR (Heyman 2003, Immunol Lett 88[2]:157-161; Smith and Clatworthy, 2010, Nature Reviews Immunology 10:328-343; expressly incorporated by reference). As another example, CD3 activation of T-cells occurs only when its associated T-cell receptor (TCR) engages antigen-loaded MHC on antigen presenting cells in a highly avid cell-to-cell synapse (Kuhns et al., 2006, Immunity 24:133-139). Indeed nonspecific bivalent cross-linking of CD3 using an anti-CD3 antibody elicits a cytokine storm and toxicity (Perruche et al., 2009, J Immunol 183 [2]:953-61; Chatenoud & Bluestone, 2007, Nature Reviews Immunology 7:622-632; expressly incorporated by reference). Thus for practical clinical use, the preferred mode of CD3 co-engagement for redirected killing of targets cells is monovalent binding that results in activation only upon engagement with the co-engaged target.

Accordingly, there is a need for improved bispecific anti-CD-20×anti-CD3 antibodies and the use of such antibodies for use in therapy.

SUMMARY

The methods described here are directed to treating human subjects with bispecific anti-CD20×anti-CD3 antibodies.

In one aspect, provided herein is a method for treating a CD20-expressing cancer, comprising
administering to a human subject with the CD20-expressing cancer and in need of treatment thereof, a bispecific anti-CD20×anti-CD3 antibody in a first phase, a second phase, a third phase, and a fourth phase,
wherein in the first phase the bispecific anti-CD20×anti-CD3 antibody is administered once to the human subject in a first phase dose amount between about 0.5 mg and about 1.1 mg,
in the second phase the bispecific anti-CD20×anti-CD3 antibody is administered once to the human subject in a second phase dose amount between about 1.5 mg and about 2.5 mg,
in the third phase the bispecific anti-CD20×anti-CD3 antibody is administered once to the human subject in a third phase dose amount between about 18 mg and about 22 mg,
in the fourth phase the bispecific anti-CD20×anti-CD3 antibody is administered at least once to the human subject in a fourth phase dose amount between about 45 mg and about 55 mg,
wherein the time period between each administration is about 6 to about 8 days.

In one embodiment of the methods provided herein, the method consists essentially of: wherein the first phase dose amount is about 0.8 mg, wherein the second phase dose amount is about 2.0 mg, wherein the third phase dose amount is about 20 mg, and wherein the fourth phase dose amount is about 50 mg.

In one embodiment, the fourth phase is administered until a positive therapeutic response is achieved.

In one embodiment, the fourth phase is administered so long as there is a positive therapeutic response.

In one embodiment, the fourth phase is administered five times.

In one embodiment, the method further comprises a fifth phase, wherein the bispecific anti-CD20×anti-CD3 antibody is administered at least once to the human subject in a fifth phase dose amount between about 45 mg and about 55 mg, wherein if the fifth phase is administered more than once, then each fifth phase administration is between about 13 and about 15 days after the previous fifth phase administration.

In one embodiment, the fifth phase is administered so long as there is a positive therapeutic response.

In another aspect, provided is a method for treating a CD20-expressing cancer, comprising
administering to a human subject with the CD20-expressing cancer and in need of treatment thereof, a bispecific anti-CD20×anti-CD3 antibody in a first phase, a second phase, a third phase, a fourth phase, and a fifth phase,
wherein in the first phase the bispecific anti-CD20×anti-CD3 antibody is administered once to the human subject in a first phase dose amount between about 0.5 mg and about 1.1 mg,
in the second phase the bispecific anti-CD20×anti-CD3 antibody is administered once to the human subject in a second phase dose amount between about 1.5 mg and about 2.5 mg,
in the third phase the bispecific anti-CD20×anti-CD3 antibody is administered once to the human subject in a third phase dose amount between about 18 mg and about 22 mg,
in the fourth phase the bispecific anti-CD20×anti-CD3 antibody is administered once to the human subject in a fourth phase dose amount between about 30 mg and about 40 mg,
in the fifth phase the bispecific anti-CD20×anti-CD3 antibody is administered at least once to the human subject in a fifth phase dose amount between about 45 mg and about 55 mg,
wherein the time period between each administration is about 6 to about 8 days.

In one embodiment of the methods provided herein, the method consists essentially of: wherein the first phase dose amount is about 0.8 mg, wherein the second phase dose amount is about 2.0 mg, wherein the third phase dose amount is about 20 mg, wherein the fourth phase dose amount is about 35 mg, wherein the fifth phase dose amount is about 50 mg.

In one embodiment, the fifth phase is administered until a positive therapeutic response is achieved.

In one embodiment, the fifth phase is administered so long as there is a positive therapeutic response.

In one embodiment, the fifth phase is administered four times.

In some embodiments of the methods provided herein, the method further comprises a sixth phase, wherein the bispecific anti-CD20×anti-CD3 antibody is administered at least once to the human subject in a sixth phase dose amount between about 45 mg and about 55 mg,
wherein if the sixth phase is administered more than once, then each sixth phase administration is between about 13 and about 15 days after the previous sixth phase administration.

In one embodiment, the sixth phase is administered so long as there is a positive therapeutic response.

In one embodiment, the positive therapeutic response is a reduction in tumor size, a reduction in the rate of tumor growth, a reduction in the number of $CD20^+$ expressing cancer-associated cells, an increase in $CD20^+$ expressing cancer-associated cell death, an inhibition of $CD20^+$ expressing cancer-associated cell survival, an inhibition (i.e., slowing to some extent, preferably halting) of $CD20^+$ expressing cancer-associated proliferation, an increased human subject survival rate, an improvement in peripheral blood cytopenias associated with the CD20-expressing cancer, and any amount of relief (subjective and/or objective) from one or more symptoms of a CD20-expressing cancer.

In another aspect, provided herein is method for treating a CD20-expressing cancer, comprising
administering to a human subject with the CD20-expressing cancer and in need of treatment thereof, a bispecific anti-CD20×anti-CD3 antibody in a first phase, a second phase, a third phase, a fourth phase, and a fifth phase,
wherein in the first phase the bispecific anti-CD20×anti-CD3 antibody is administered once to the human subject in a first phase dose amount between about 20 µg/kg and about 30 µg/kg,
in the second phase the bispecific anti-CD20×anti-CD3 antibody is administered once to the human subject in a second phase dose amount between about 40 µg/kg and about 60 µg/kg,
in the third phase the bispecific anti-CD20×anti-CD3 antibody is administered once to the human subject in a third phase dose amount between about 100 µg/kg and about 140 µg/kg,
in the fourth phase the bispecific anti-CD20×anti-CD3 antibody is administered once to the human subject in a fourth phase dose amount between about 150 µg/kg and about 200 µg/kg, in the fifth phase the bispecific anti-CD20×anti-CD3 antibody is administered once to the human subject in a fifth phase dose amount between about 210 µg/kg and about 290 µg/kg,
wherein the time period between each administration is about 6 to about 8 days.

In one embodiment, the method consists essentially of: wherein the first phase dose amount is about 25 µg/kg, wherein the second phase dose amount is about 50 µg/kg, wherein the third phase dose amount is about 125 µg/kg, wherein the fourth phase dose amount is about 170 µg/kg, and wherein the fifth phase dose amount is about 250 µg/kg.

In one embodiment, the fifth phase is administered until a positive therapeutic response is achieved.

In one embodiment, the fifth phase is administered so long as there is a positive therapeutic response.

In one embodiment, the fifth phase is administered four times.

In one embodiment, the method further comprises a sixth phase, wherein the bispecific anti-CD20×anti-CD3 antibody is administered at least once to the human subject in a sixth phase dose amount between about 210 µg/kg and about 290 µg/kg,
wherein if the sixth phase is administered more than once, then each sixth phase administration is between about 13 and about 15 days after the previous sixth phase administration.

In one embodiment, the sixth phase is administered so long as there is a positive therapeutic response.

In one embodiment, the fifth phase is administered once, and then between about 6 and about 8 days after, further comprising a sixth phase, wherein the bispecific anti-CD20×anti-CD3 antibody is administered at least once to the human subject in a sixth phase dose amount between about 340 µg/kg and about 380 µg/kg,
wherein if the sixth phase is administered more than once, then each sixth phase administration is between about 6 and about 8 days after the previous sixth phase administration.

In one embodiment, the sixth phase dose amount is about 360 µg/kg.

In one embodiment, the sixth phase is administered until a positive therapeutic response is achieved.

In one embodiment, the sixth phase is administered so long as there is a positive therapeutic response.

In one embodiment, the sixth phase is administered three times.

In one embodiment, the method further comprises a seventh phase, wherein the bispecific anti-CD20×anti-CD3 antibody is administered at least once to the human subject in a seventh phase dose amount between about 340 µg/kg and about 380 µg/kg,
wherein if the seventh phase is administered more than once, then each seventh phase administration is between about 13 and about 15 days after the previous seventh phase administration.

In one embodiment, the seventh phase is administered so long as there is a positive therapeutic response.

In one embodiment, the sixth phase is administered once, and then between about 6 and about 8 days after, further comprising a seventh phase, wherein the bispecific anti-CD20×anti-CD3 antibody is administered at least once to the human subject in a seventh phase dose amount between about 475 µg/kg and about 525 µg/kg, wherein if the seventh phase is administered more than once, then each seventh phase administration is between about 6 and about 8 days after the previous seventh phase administration.

In one embodiment, the seventh phase dose amount is about 500 µg/kg.

In one embodiment, the seventh phase is administered until a positive therapeutic response is achieved.

In one embodiment, the seventh phase is administered so long as there is a positive therapeutic response.

In one embodiment, the seventh phase is administered two times.

In one embodiment, the method further comprises an eighth phase, wherein the bispecific anti-CD20×anti-CD3 antibody is administered at least once to the human subject in an eighth phase dose amount between about 475 µg/kg and about 525 µg/kg, wherein if the eighth phase is administered more than once, then each eighth phase administration is between about 13 and about 15 days after the previous eighth phase administration.

In one embodiment, the eighth phase is administered so long as there is a positive therapeutic response.

In another aspect, provided is a method for treating a CD20-expressing cancer, comprising
administering to a human subject with the CD20-expressing cancer and in need of treatment thereof, a bispecific anti-CD20×anti-CD3 antibody in a first phase, a second phase, a third phase, a fourth phase, a fifth phase, and a sixth phase,
wherein in the first phase the bispecific anti-CD20×anti-CD3 antibody is administered once to the human subject in a first phase dose amount between about 8 µg/kg and about 12 µg/kg,
in the second phase the bispecific anti-CD20×anti-CD3 antibody is administered once to the human subject in a second phase dose amount between about 20 µg/kg and about 30 µg/kg,
in the third phase the bispecific anti-CD20×anti-CD3 antibody is administered once to the human subject in a third phase dose amount between about 100 µg/kg and about 140 µg/kg,
in the fourth phase the bispecific anti-CD20×anti-CD3 antibody is administered once to the human subject in a fourth phase dose amount between about 150 µg/kg and about 200 µg/kg,
in the fifth phase the bispecific anti-CD20×anti-CD3 antibody is administered once to the human subject in a fifth phase dose amount between about 210 µg/kg and about 290 µg/kg,
in the sixth phase the bispecific anti-CD20×anti-CD3 antibody is administered at least once to the human subject in a sixth phase dose amount between about 340 µg/kg and about 380 µg/kg,
wherein the time period between each administration is about 6 to about 8 days.

In one embodiment of the methods provided herein, the method consists essentially of
wherein the first phase dose amount is about 10 µg/kg,
wherein the second phase dose amount is about 25 µg/kg,
wherein the third phase dose amount is about 125 µg/kg,
wherein the fourth phase dose amount is about 170 µg/kg,
wherein the fifth phase dose amount is about 250 µg/kg, and
wherein the sixth phase dose amount is about 360 µg/kg.

In one embodiment, the sixth phase is administered until a positive therapeutic response is achieved.

In one embodiment, the sixth phase is administered so long as there is a positive therapeutic response.

In one embodiment, the sixth phase is administered three times.

In one embodiment of the methods provided herein, the method further comprises a seventh phase, wherein the bispecific anti-CD20×anti-CD3 antibody is administered at least once to the human subject in a seventh phase dose amount between about 340 μg/kg and about 380 μg/kg, wherein if the seventh phase is administered more than once, then each seventh phase administration is between about 13 and about 15 days after the previous seventh phase administration.

In one embodiment of the methods provided herein, the method further comprises a seventh phase, wherein the bispecific anti-CD20×anti-CD3 antibody is administered at least once to the human subject in a seventh phase dose amount between about 450 μg/kg and about 550 μg/kg, wherein if the seventh phase is administered more than once, then each seventh phase administration is between about 13 and about 15 days after the previous seventh phase administration.

In one embodiment, the seventh phase is administered so long as there is a positive therapeutic response.

In another aspect, provided herein is a method for treating a CD20-expressing cancer, comprising
administering to a human subject with the CD20-expressing cancer and in need of treatment thereof, a bispecific anti-CD20×anti-CD3 antibody in a first phase, a second phase, a third phase, a fourth phase, a fifth phase, a sixth phase, and a seventh phase;
wherein in the first phase the bispecific anti-CD20×anti-CD3 antibody is administered once to the human subject in a first phase dose amount between about 8 μg/kg and about 12 μg/kg,
in the second phase the bispecific anti-CD20×anti-CD3 antibody is administered once to the human subject in a second phase dose amount between about 20 μg/kg and about 30 μg/kg,
in the third phase the bispecific anti-CD20×anti-CD3 antibody is administered once to the human subject in a third phase dose amount between about 100 μg/kg and about 140 μg/kg,
in the fourth phase the bispecific anti-CD20×anti-CD3 antibody is administered once to the human subject in a fourth phase dose amount between about 150 μg/kg and about 200 μg/kg,
in the fifth phase the bispecific anti-CD20×anti-CD3 antibody is administered once to the human subject in a fifth phase dose amount between about 210 μg/kg and about 290 μg/kg,
in the sixth phase the bispecific anti-CD20×anti-CD3 antibody is administered once to the human subject in a sixth phase dose amount between about 340 μg/kg and about 380 μg/kg,
in the seventh phase the bispecific anti-CD20×anti-CD3 antibody is administered at least once to the human subject in a seventh phase dose amount between about 450 μg/kg and about 550 μg/kg, wherein the time period between each administration is about 6 to about 8 days.

In one embodiment of the methods provided herein, the method consists essentially of: wherein the first phase dose amount is about 10 μg/kg, wherein the second phase dose amount is about 25 μg/kg, wherein the third phase dose amount is about 125 μg/kg, wherein the fourth phase dose amount is about 170 μg/kg, wherein the fifth phase dose amount is about 250 μg/kg, wherein the sixth phase dose amount is about 360 μg/kg, and wherein the seventh phase dose amount is about 500 μg/kg.

In one embodiment, the seventh phase is administered until a positive therapeutic response is achieved.

In one embodiment, the seventh phase is administered so long as there is a positive therapeutic response.

In one embodiment, the seventh phase is administered four times.

In one embodiment of the methods provided herein, wherein if the seventh phase is administered more than once, then each seventh phase administration is between about 6 and about 8 days after the previous seventh phase administration. In one embodiment of the methods provided herein, wherein if the seventh phase is administered more than once, then each seventh phase administration is between about 13 and about 15 days after the previous seventh phase administration.

In another aspect, provided herein is a method for treating a CD20-expressing cancer, comprising
administering to a human subject with the CD20-expressing cancer and in need of treatment thereof, a bispecific anti-CD20×anti-CD3 antibody in a first phase,
wherein in the first phase the bispecific anti-CD20×anti-CD3 antibody is administered at least once to the human subject in a first phase dose amount between about 200 μg/kg and about 650 μg/kg,
wherein if the first phase is administered more than once, then each first phase administration is between about 6 and about 8 days after the previous first phase administration.

In one embodiment, the first phase dose amount is between about 240 μg/kg and about 260 μg/kg, or between about 350 μg/kg and about 370 μg/kg, or between about 475 μg/kg and about 525 μg/kg.

In one embodiment, the first phase dose amount is about 250 μg/kg, or about 360 μg/kg, or about 500 μg/kg.

In one embodiment, the first phase is administered until a positive therapeutic response is achieved.

In one embodiment, the first phase is administered so long as there is a positive therapeutic response.

In one embodiment, the first phase is administered eight times.

In one embodiment, the method further comprises a second phase, wherein the bispecific anti-CD20×anti-CD3 antibody is administered at least once to the human subject in a second phase dose amount between about 240 μg/kg and about 260 μg/kg, or between about 350 μg/kg and about 370 μg/kg, or between about 475 μg/kg and about 525 μg/kg,
wherein if the second phase is administered more than once, then each second phase administration is between about 13 and about 15 days after the previous second phase administration.

In one embodiment, the second phase is administered so long as there is a positive therapeutic response.

In one embodiment of the methods provided herein, the positive therapeutic response is a reduction in tumor size, a reduction in the rate of tumor growth, a reduction in the number of $CD20^+$ expressing cancer-associated cells, an increase in $CD20^+$ expressing cancer-associated cell death, an inhibition of $CD20^+$ expressing cancer-associated cell survival, an inhibition (i.e., slowing to some extent, preferably halting) of $CD20^+$ expressing cancer-associated proliferation, an increased human subject survival rate, an improvement in peripheral blood cytopenias associated with the CD20-expressing cancer, and any amount of relief (subjective and/or objective) from one or more symptoms of a CD20-expressing cancer.

In one embodiment of the methods provided herein, the bispecific anti-CD20×anti-CD3 antibody is administered between about 115 minutes and about 125 minutes.

In one embodiment of the methods provided herein, the CD20-expressing cancer is a hematologic cancer.

In one embodiment of the methods provided herein, the CD20-expressing cancer is a lymphoma.

In one embodiment of the methods provided herein, the lymphoma is a Non-Hodgkin lymphoma.

In one embodiment of the methods provided herein, the Non-Hodgkin lymphoma is B-cell NHL.

In one embodiment of the methods provided herein, the Non-Hodgkin lymphoma is selected from the group consisting of Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. In one embodiment of the methods provided herein, the Non-Hodgkin lymphoma is chronic lymphocytic leukemia (CLL)/small lymphocytic lymphoma (SLL). In one embodiment, the lymphoma is Burkitt's lymphoma. In one embodiment, the lymphoma is Endemic Burkitt's Lymphoma. In one embodiment, the lymphoma is Sporadic Burkitt's Lymphoma. In one embodiment, the lymphoma is Cutaneous B-Cell Lymphoma. In one embodiment, the lymphoma is Cutaneous Marginal Zone Lymphoma (MZL). In one embodiment, the lymphoma is Diffuse Large Cell Lymphoma (DLBCL). In one embodiment, the lymphoma is Diffuse Mixed Small and Large Cell Lymphoma. In one embodiment, the lymphoma is Diffuse Small Cleaved Cell. In one embodiment, the lymphoma is Diffuse Small Lymphocytic Lymphoma. In one embodiment, the lymphoma is Extranodal Marginal Zone B-cell lymphoma. In one embodiment, the lymphoma is follicular lymphoma. In one embodiment, the lymphoma is Follicular Small Cleaved Cell (Grade 1). In one embodiment, the lymphoma is Follicular Mixed Small Cleaved and Large Cell (Grade 2). In one embodiment, the lymphoma is Follicular Large Cell (Grade 3). In one embodiment, the lymphoma is Intravascular Large B-Cell Lymphoma. In one embodiment, the lymphoma is Intravascular Lymphomatosis. In one embodiment, the lymphoma is Large Cell Immunoblastic Lymphoma. In one embodiment, the lymphoma is Large Cell Lymphoma (LCL). In one embodiment, the lymphoma is Lymphoblastic Lymphoma. In one embodiment, the lymphoma is MALT Lymphoma. In one embodiment, the lymphoma is Mantle Cell Lymphoma (MCL). In one embodiment, the lymphoma is immunoblastic large cell lymphoma. In one embodiment, the lymphoma is precursor B-lymphoblastic lymphoma. In one embodiment, the lymphoma is mantle cell lymphoma. In one embodiment, the lymphoma is chronic lymphocytic leukemia (CLL)/small lymphocytic lymphoma (SLL). In one embodiment, the lymphoma is extranodal marginal zone B-cell lymphoma-mucosa-associated lymphoid tissue (MALT) lymphoma. In one embodiment, the lymphoma is Mediastinal Large B-Cell Lymphoma. In one embodiment, the lymphoma is nodal marginal zone B-cell lymphoma. In one embodiment, the lymphoma is splenic marginal zone B-cell lymphoma. In one embodiment, the lymphoma is primary mediastinal B-cell lymphoma. In one embodiment, the lymphoma is lymphoplasmocytic lymphoma. In one embodiment, the lymphoma is hairy cell leukemia. In one embodiment, the lymphoma is Waldenstrom's Macroglobulinemia. In one embodiment, the lymphoma is primary central nervous system (CNS) lymphoma. In a specific embodiment of the methods provided herein, the bispecific anti-CD20×anti-CD3 antibody comprises SEQ ID NO:1, SEQ ID NO: 2 and SEQ ID NO: 3.

In one embodiment of the methods provided herein, the bispecific anti-CD20×anti-CD3 antibody consists of SEQ ID NO:1, SEQ ID NO: 2 and SEQ ID NO: 3. In one embodiment of the methods provided herein, the method further comprises assessing the weight of the human subject prior to the administering of the first phase of the bispecific anti-CD20×anti-CD3 antibody.

In one embodiment of the methods provided herein, the method further comprises administering to the human subject one or more therapeutic agents prior to the administering of the first phase of the bispecific anti-CD20×anti-CD3 antibody.

In one embodiment of the methods provided herein, the method further comprises administering to the human subject one or more therapeutic agents prior to each administering of the bispecific anti-CD20×anti-CD3 antibody.

In one embodiment, the one or more therapeutic agents ameliorates the side effects of the bispecific anti-CD20×anti-CD3 antibody administration.

In one embodiment, the one or more therapeutic agents is a steroid, an antihistamine, an anti-allergic agent, an antinausea agent (or anti-emetic), an analgesic agent, an antipyretic agent, a cytoprotective agent, a vasopressor agent, an anticonvulsant agent, an anti-inflammatory agent, or any combination thereof.

In one embodiment, the one or more therapeutic agents is a combination of a corticosteroid, diphenhydramine, and acetaminophen.

In any of the methods provided herein, the bispecific anti-CD20×anti-CD3 antibody is XmAb® 13676 (also referred to as "plamotamab").

BRIEF DESCRIPTION OF THE DRAWINGS

FIG. 2 depicts the sequences of the three polypeptide chains that make up XmAb® 13676, an anti-CD20×anti-CD3 antibody of particular use in the methods provided herein. The CDRs are underlined and the junction between domains is denoted by a slash ("/"). The charged scFv linker is double underlined; as will be appreciated by those in the art, the linker may be substituted with other linkers, and particularly other charged linkers that are depicted in FIG. 7 of US Publication Number 2014/0288275, which is herein incorporated by reference in its entirety, or other non-charged linkers (SEQ ID NO:441 of US Publication Number 2014/0288275, which is herein incorporated by reference in its entirety).

FIGS. 3A-3E depict additional anti-CD20×anti-CD3 sequences provided herein, with the CDRs underlined.

FIGS. 4A-4D depict additional bispecific formats of use in the present methods, as are generally described in FIG. 1 and the accompanying Legend and supporting text of U.S. Pat. No. 10,889,652, which is herein incorporated by reference in its entirety.

DETAILED DESCRIPTION

Figure 1:
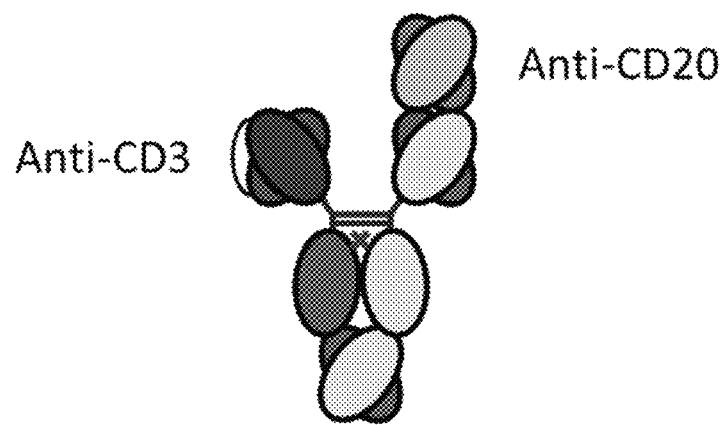
FIG. 1 depicts a particularly useful bispecific format provided herein, referred to as a "bottle opener", which is also the format of XmAb® 13676. It should be noted that the scFv and Fab domains can be switched (e.g., anti-CD3 as a Fab, and anti-CD20 as a scFv).

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification controls.

I. DEFINITIONS

In order that the application may be more completely understood, several definitions are set forth below. The definitions also include all grammatical equivalents.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

The term "about" in relation to a reference numerical value can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

Unless otherwise indicated, the term "at least" preceding a series of elements is to be understood to refer to every element in the series.

Those skilled in the art will recognize or be able to ascertain using no more than routine experimentation, many equivalents to the specific embodiments described herein. Such equivalents are intended to be encompassed by the invention.

As used herein, and unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The terms "CD3" or "cluster of differentiation 3" means a T-cell co-receptor that helps in activation of both cytotoxic T-cell (e.g., CD8+ naïve T cells) and T helper cells (e.g., CD4+ naïve T cells) and is composed of four distinct chains: one CD3γ chain (e.g., Genbank Accession Numbers NM_000073 and MP_000064 (human)), one CD3δ chain (e.g., Genbank Accession Numbers NM_000732, NM_001040651, NP 00732 and NP_001035741 (human)), and two CD3ε chains (e.g., Genbank Accession Numbers NM_000733 and NP_00724 (human)). The chains of CD3 are highly related cell-surface proteins of the immunoglobulin superfamily containing a single extracellular immunoglobulin domain. CD3 molecule associates with the T-cell receptor (TCR) and chain to form the T-cell receptor (TCR) complex, which functions in generating activation signals in T lymphocytes.

By "B-lymphocyte antigen CD20" or "CD20" or "CD20 antigen" or "CD20 Receptor" or "Membrane Spanning 4-Domains A1" or "Membrane-Spanning 4-Domains, Subfamily A, Member 1" or "Leukocyte Surface Antigen Leu-16" or "Bp35" or "B-Lymphocyte Cell-Surface Antigen 1" or "LEU-16" or "CVIDS" or "MS4A1" or "Bl" or "S7" herein is meant an activated-glycosylated phosphoprotein expressed on the surface of B-cells and is encoded by the MS4A1 gene in humans (e.g., Genbank Accession Numbers NM_152866, NM_021950, NP_068769 and NP_690605 (human)). CD20 plays a role in the development and differentiation of B-cells into plasma cells.

By "bispecific" or "bispecific antibody" herein is meant any non-native or alternate antibody formats, including those described herein, that engage two different antigens (e.g., bispecific anti-CD20×anti-CD3 antibodies, such as XmAb® 13676).

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233-, E233_ or E233# designates a deletion a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides". The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of certain antibodies provided herein are defined according to the amino acid modifications that compose them. Thus, for example, N434S or 434S is an Fc variant with the substitution serine at position 434 relative to the parent Fc polypeptide, where the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, N434S/M428L is the same Fc variant as M428L/N434S, and so on. For all positions discussed herein that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124: 9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g., not an amino acid that is coded for by DNA); as will be appreciated by those in the art. For example, homophenylalanine, citrulline, ornithine and noreleucine are considered synthetic amino acids herein, and both D- and L-(R or S) configured amino acids may be utilized. The variants herein may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635):964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

As used herein, the term "antibody" is used in a broad sense and includes immunoglobulin or antibody molecules. In general, antibodies are proteins or peptide chains that exhibit binding specificity to a specific antigen. In specific embodiments, the antibodies provided herein are based on IgG1, IgG2, or IgG4. In some embodiments, the antibodies provided herein are based on IgG1, IgG2, or IgG4 and contain amino acid variants. In many preferred embodiments, the antibodies provided herein are based on human IgG1, and contain amino acid variants as outlined herein. Antibody light chains of vertebrate species can be assigned to one of two clearly distinct types, namely kappa and lambda, based on the amino acid sequences of their constant domains. In one embodiment, an antibody provided herein comprises a kappa light chain. In other embodiments, an antibody provided herein comprises a lambda light chain. In certain embodiments, an antibody provided herein comprises a kappa light chain and a lambda light chain. Accordingly, the antibodies provided herein can, in certain embodiments, contain a kappa light chain constant domain. In other embodiments, antibodies provided herein can, in certain embodiments, contain lambda light chain constant domains. In some embodiments, the antibodies provided herein can contain kappa light chain and lambda light chain constant domains.

In addition to the heavy and light constant domains, antibodies contain an antigen-binding region that is made up of a light chain variable (VL) domain (or region) and a heavy chain variable (VH) domain (or region). The term "hypervariable region", such as a VH or VL, when used herein refers to the regions of an antibody variable region that are hypervariable in sequence and/or form structurally defined loops. Generally, antibodies comprise six hypervariable regions; three in the VH (HCDR1, HCDR2, HCDR3), and three in the VL (LCDR1, LCDR2, LCDR3). A "CDR" refers to one of three hypervariable regions (VH CDR1, VH CDR2 or VH CDR3) within the non-framework region of the immunoglobulin (Ig or antibody) VH β-sheet framework, or one of three hypervariable regions (VL CDR1, VL CDR2 or VL CDR3) within the non-framework region of the antibody VL β-sheet framework. Accordingly, CDRs are variable region sequences interspersed within the framework region sequences. The light chain variable region CDR1 domain is interchangeably referred to herein as LCDR1 or VL CDR1. The light chain variable region CDR2 domain is interchangeably referred to herein as LCDR2 or VL CDR2. The light chain variable region CDR3 domain is interchangeably referred to herein as LCDR3 or VL CDR3. The heavy chain variable region CDR1 domain is interchangeably referred to herein as HCDR1 or VH CDR1. The heavy chain variable region CDR2 domain is interchangeably referred to herein as HCDR2 or VH CDR2. The heavy chain variable region CDR1 domain is interchangeably referred to herein as HCDR3 or VH CDR3.

A number of hypervariable region delineations are in use and are encompassed herein, for example, in the tables and/or Examples provided below. The "Kabat" CDRs are based on sequence variability and are the most commonly used (see, e.g., Kabat et al., Sequences of Proteins of Immunological Interest, 5th Ed. Public Health Service, National Institutes of Health, Bethesda, MD (1991)). "Chothia" refers instead to the location of the structural loops (see, e.g., Chothia and Lesk, J. Mol. Biol. 196:901-917 (1987)). The end of the Chothia CDR-HCDR1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The "AbM" hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). "Contact" hypervariable regions are based on an analysis of the available complex crystal structures. An additional a universal numbering system can also be used, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MEW) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Pluckthun, J. Mol. Biol. 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lafranc et al., supra). An Exemplary system may also be used that combines Kabat and Chothia.

|  | Exemplary (Kabat + Chothia) | IMGT | Kabat | AbM | Chothia | Contact | Xencor |
|---|---|---|---|---|---|---|---|
| $V_H$ CDR1 | 26-35 | 27-38 | 31-35 | 26-35 | 26-32 | 30-35 | 27-35 |
| $V_H$ CDR2 | 50-65 | 56-65 | 50-65 | 50-58 | 53-55 | 47-58 | 54-61 |
| $V_H$ CDR3 | 95-102 | 105-117 | 95-102 | 95-102 | 96-101 | 93-101 | 103-116 |
| $V_L$ CDR1 | 24-34 | 27-38 | 24-34 | 24-34 | 26-32 | 30-36 | 27-38 |
| $V_L$ CDR2 | 50-56 | 56-65 | 50-56 | 50-56 | 50-52 | 46-55 | 56-62 |
| $V_L$ CDR3 | 89-97 | 105-117 | 89-97 | 89-97 | 91-96 | 89-96 | 97-105 |

Hypervariable regions may comprise "extended hypervariable regions" as follows: 24-36 or 24-34 (LCDR1), 46-56 or 50-56 (LCDR2) and 89-97 or 89-96 (LCDR3) in the VL and 26-35 or 26-35A (HCDR1), 50-65 or 49-65 (HCDR2) and 93-102, 94-102, or 95-102 (HCDR3) in the VH. CDR sequences, reflecting each of the above numbering schemes, are provided herein.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CHL hinge, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

By "antigen binding domain" or "ABD" herein is meant a set of six Complementary Determining Regions (CDRs) that, when present as part of a polypeptide sequence, specifically binds a target antigen as discussed herein. Thus, a "checkpoint antigen binding domain" binds a target checkpoint antigen as outlined herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. Thus, in some cases, the six CDRs of the antigen binding domain are contributed by a variable heavy and a variable light domain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker (a "scFv linker") as outlined herein, into a single polypeptide sequence, which can be either (starting from the N-terminus) vh-linker-vl or vl-linker-vh. In general, the C-terminus of the scFv domain is attached to the N-terminus of the hinge in the second monomer.

By "Fab" or "Fab region" as used herein is meant the polypeptide that comprises the VH, CH1, VL, and CL immunoglobulin domains, as, for example, on two different polypeptide chains (e.g. VH-CH1 on one chain and VL-CL on the other). Fab may refer to this region in isolation, or this region in the context of a bispecific antibody, or this region in the context of a full-length antibody, antibody fragment or Fab fusion protein. In the context of a Fab, the Fab can comprise an Fv region in addition to the CH1 and CL domains.

By "Fv" or "Fv fragment" or "Fv region" as used herein is meant a polypeptide that comprises the VL and VH domains of an ABD. Fv regions can be formatted as both Fabs (as discussed above, generally two different polypeptides that also include the constant regions as outlined above) and scFvs, where the vl and vh domains are combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (vh-linker-vl or vl-linker-vh). In the sequences depicted in the sequence listing and in the figures, the order of the vh and vl domain is indicated in the name, e.g., H.X_L.Y means N- to C-terminal is vh-linker-vl, and L.Y_H.X is vl-linker-vh. In general, the C-terminus of the scFv domain is attached to the N-terminus of a domain linker in the second monomer. In certain embodiments, the domain linker is a hinge. In some embodiments, the domain linker is a GS linker (single or multiple GS amino acids). In other embodiments, the domain linker is a truncated hinge.

The terms "Fc," "Fc region," or "Fc domain" as used herein refer to the polypeptide comprising the CH2-CH3 domains of an IgG molecule, and in some cases, inclusive of the hinge. In EU numbering for human IgG1, the CH2-CH3 domain comprises amino acids 231 to 447, and the hinge is 216 to 230. Thus the definition of "Fe domain" includes both amino acids 231-447 (CH2-CH3) or 216-447 (hinge-CH2-CH3), or fragments thereof. An "Fc fragment" in this context may contain fewer amino acids from either or both of the N- and C-termini but still retains the ability to form a dimer with another Fc domain or Fc fragment as can be detected using standard methods, generally based on size (e.g., non-denaturing chromatography, size exclusion chromatography, etc.) Human IgG Fc domains can be used in embodiments herein, and can be the Fc domain from human IgG1, IgG2 or IgG4.

As used herein, "heavy chain constant region" refers to the CH1-hinge-CH2-CH3 portion of an antibody (or fragments thereof), excluding the variable heavy domain; in EU numbering of human IgG1 this is amino acids 118-447. As is known in the art, there can be C-terminal protease clipping during protein expression and thus the IgG1 terminal lysine (1(447), and additional residues, may be missing from the protein.

By "amino acid" and "amino acid identity" as used herein is meant one of the 20 naturally occurring amino acids that are coded for by DNA and RNA.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fe gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRlllb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants can be used to increase binding to the FcRn receptor, and in some cases, to increase serum half-life.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin. polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "position" as used herein is meant a location in the sequence of a protein. Positions may be numbered sequentially, or according to an established format, for example the EU index for antibody numbering.

By "target antigen" as used herein is meant the molecule that is bound specifically by the antigen binding domain comprising the variable regions of a given antibody. The two target antigens of antibodies used in the methods provided herein are human CD3 and human CD20.

By "strandedness" in the context of the monomers of the heterodimeric antibodies provided herein is meant that, similar to the two strands of DNA that "match", heterodimerization variants are incorporated into each monomer so as to preserve the ability to "match" to form heterodimers. For example, if some pI variants are engineered into monomer A (e.g., making the pI higher) then steric variants that are "charge pairs" that can be utilized as well do not interfere with the pI variants, e.g., the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer that incorporates one set of the pair will go, such that pI separation is maximized using the pI of the skews as well.

By "target cell" as used herein is meant a cell that expresses a target antigen.

By "host cell" in the context of producing a bispecific antibody herein is meant a cell that contains the exogenous nucleic acids encoding the components of the bispecific antibody and is capable of expressing the bispecific antibody under suitable conditions. Suitable host cells are discussed herein.

The terms "patient," "subject," and "human subject" are used interchangeably herein.

By "variable region" or "variable domain" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively, and contains the CDRs that confer antigen specificity. Thus, a "variable heavy domain" pairs with a "variable light domain" to form an antigen binding domain ("ABD"). In addition, each variable domain comprises three hypervariable regions ("complementary determining regions," "CDRs") (vhCDR1, vhCDR2 and vhCDR3 for the variable heavy domain and vlCDR1, vlCDR2 and vlCDR3 for the variable light domain) and four framework (FR) regions, arranged from amino-terminus to carboxy-terminus in the following order: FR1-CDR1-FR2-CDR2-FR3-CDR3-FR4.

Sequence identity between two similar sequences (e.g., antibody variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, C D. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see https://blast.ncbi.nlm.nih.gov/Blast.cgi. When using any of the aforementioned algorithms, the default parameters (for Window length, gap penalty, etc.) are used. In one embodiment, sequence identity is done using the BLAST algorithm, using default parameters.

By "wild type or WT" herein is meant an amino acid sequence or a nucleotide sequence that is found in nature, including allelic variations. A WT protein has an amino acid sequence or a nucleotide sequence that has not been intentionally modified.

The antibodies used in the methods provided herein are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogenous host cells, and they can be isolated as well.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ at least about $10^{-11}$ M, at least about $10^{-12}$ M, M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore, SPR or BLI assay.

As used herein, the term "target activity" refers to a biological activity capable of being modulated by a selective modulator. Certain exemplary target activities include, but are not limited to, binding affinity, signal transduction, enzymatic activity, tumor growth, and effects on particular biomarkers related to solid cancerous tumor pathology.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

As used herein, the $IC_{50}$ refers to an amount, concentration or dosage of a particular test compound that achieves a 50% inhibition of a maximal response, such as inhibition of the biological activity of CD20, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "positive therapeutic response" in relation to cancer means a decrease in or disappearance of signs (e.g., tumor size, biomarkers) and/or symptoms of cancer. In some cases, the positive therapeutic response can be partial or complete. For example, a positive therapeutic response can involve the reduction or amelioration or elimination of the progression, severity and/or effect associated with a CD20-expressing cancer (e.g., a hematological cancer) and/or an improvement in one or more symptoms associated with a CD20-expressing cancer. In some cases, a positive therapeutic response can be associated with an increase in the immune system response of the human subject, or the amelioration of one or more symptoms of a CD20-expressing cancer, that result from the administration of an antibody described herein. In certain cases, a positive therapeutic response can result in the amelioration of at least one measurable physical parameter of a cancer, such as tumor size, rate of tumor growth, number of tumor cells, tumor invasiveness, presence of lymphoma involvement in lymph nodes, or extent of extranodal lymph node involvement (e.g., liver, spleen, bone, etc.). In other cases, a positive therapeutic response can involve the inhibition of the progression of a CD20-expressing cancer, either physically by, e.g., stabilization of a discernible symptom, physiologically by, e.g., stabilization of a physical parameter, or both. In some cases, a positive therapeutic response can be associated with one or more of the following: (1) a reduction in the number of $CD20^+$ expressing cancer-associated cells, including $CD20^+$ peripheral blood cells and/or marrow cells, such as for example a reduction to levels below the detection limits of a MRD (minimal residual disease) assay (i.e. flow cytometry assay, RT-qPCR assay, or next-gen sequencing based MRD assay); (2) an increase in $CD20^+$ expressing cancer-associated cell death; (3) inhibition of $CD20^+$ expressing cancer-associated cell survival; (5) inhibition (i.e., slowing to some extent, preferably halting) of $CD20^+$ expressing cancer-associated proliferation; (6) an increased human subject survival rate; (7) improvement in peripheral blood cytopenias associated with the CD20-expressing cancer; and (8) any amount of relief (subjective and/or objective) from one or more symptoms of a CD20-expressing cancer. In an exemplary embodiment, the positive therapeutic response is determined by one or more of the following: physical examination by a medical professional such as lymph node measurement and/or spleen measurement and/or liver size assessment by, for example, palpation, bone marrow biopsy, bone marrow aspirate, computerized tomography (CT) scan, positron emission tomography (PET) scan, combined PET/CT scan, complete blood count (CBC) with differential and blast count, IgM quantification, serum free light-chain assay, serum protein electrophoresis (SPEP), and serum immunofixation. If the human subject achieves a complete response, a positive therapeutic response can be ascertained by local assessment of minimal residual disease (MRD). In an exemplary embodiment, the time period sufficient to treat a CD20 expressing cancer described herein is the time period sufficient to achieve a positive therapeutic response.

Tumor evaluations can be performed using assessments that are appropriate for a human subject's diagnosis (Cheson et al. J Clin Oncol. 2014; 32(27):3059-68; Robak et al Ann Oncol. 2015; 26 Suppl 5:v100-7; Owen et al., Br J Haematol. 2013; 160(2):171-63; Hallek et al. Blood. 2018; 131 (25):2745-60). Evaluations (i.e., imaging, blood, bone marrow, physical examination) can be performed at baseline and at all other disease assessment time points. In an exemplary embodiment, evaluations can be performed before the start of a method described herein, during a method described herein, and/or after a method described herein. In an exemplary embodiment, evaluations can be performed before the first administration of an antibody described herein (such as within 21 days before the first antibody administration), between day 50 and day 60 after the first administration of an antibody described herein, between day 52 and day 56 after the first administration of an antibody described herein, between the third and fourth administration of the fifth phase, between the eleventh and twelfth administration of the fifth phase, between the nineteenth and twentieth administration of the fifth phase, every eight weeks after the nineteenth and twentieth administration of the fifth phase, during a method described herein, and/or after a method described herein.

A positive therapeutic response can be determined by standardized response criteria specific to that CD20-expressing cancer. An example of such response criteria for NHL include the Lugano Classification found in Cheson et al., J Clin Oncol, 2014; 32(27):3059-68. Response criteria for hairy cell leukemia can be found in Robak et al Ann Oncol. 2015; 26 Suppl 5:v100-7. Response criteria for Waldenstrom macroglobulinemia can be found in Owen et al., Br J Haematol. 2013; 160(2):171-63. For CLL, an example includes Halek et al., Blood, 2018; 131(25); 2745-60.

Improvement in one or more symptoms associated with a CD20-expressing cancer include feeling less tired, feeling less weak, feeling less dizzy or lightheaded, reduction in shortness of breath, reduction in fever, fewer infections, quicker recovery from infections, reduction in ease of bruising, reduction in bleeding episodes, weight gain, reduction in night sweats, gain of appetite, reduction in abdominal swelling, reduction in lymph node swelling, reduction in bone or joint pain, and reduction in thymus swelling.

An improvement in the CD20-expressing cancer can be characterized as a "complete remission" or "complete response". The terms "complete remission" or "complete response" in relation to cancer can mean all signs and/or symptoms of cancer have disappeared, although in some cases, a cancer human subject may still have cancer cells in the body. Complete remission can result in an absence of clinically detectable disease with normalization of any previously abnormal radiographic studies, bone marrow, and cerebrospinal fluid (CSF).

Alternatively, an improvement in the CD20-expressing cancer can be characterized as a "partial remission" or "partial response". The term "partial remission" or "partial response" in relation to cancer can mean that some, but not all, signs and/or symptoms of cancer have disappeared. For example, in some cases, partial response can convey that at least about a 5% decrease in at least one measurable tumor burden (i.e., the number of malignant cells present in the subject, or the measured bulk of tumor masses or the quantity of abnormal monoclonal protein) in the absence of new lesions, which can persist for 4 to 8 weeks, or 6 to 8 weeks. In some cases, partial response can lead to at least about a 10% decrease in at least one measurable tumor burden. In some cases, partial response means at least about a 15% decrease in at least one measurable tumor burden. In some cases, partial response means at least about a 20% decrease in at least one measurable tumor burden. In some cases, partial response means at least about a 25% decrease in at least one measurable tumor burden. In some cases, partial response means at least about a 30% decrease in at least one measurable tumor burden. In some cases, partial response means at least about a 35% decrease in at least one measurable tumor burden. In some cases, partial response means at least about a 40% decrease in at least one measurable tumor burden. In some cases, partial response means at least about a 45% decrease in at least one measurable tumor burden. In some cases, partial response means at least about a 50% decrease in at least one measurable tumor burden. In some cases, partial response means at least about a 60% decrease in at least one measurable tumor burden. In some cases, partial response means at least about a 70% decrease in at least one measurable tumor burden. In some cases, partial response means at least about an 80% decrease in at least one measurable tumor burden. In some cases, partial response means at least about a 90% decrease in at least one measurable tumor burden.

II. OVERVIEW

Disclosed herein are methods of treating a cancer that include cells expressing CD20 ("CD20-expressing cancer"), for example, a hematologic cancer, such as leukemia, through the administration of certain bispecific anti-CD20× anti-CD3 antibodies at particular dosages. The term "CD20-expressing cancer" can refer to a cancer that expresses CD20 or a cancer that overexpresses CD20. Also provided is methods of combination therapies, for example, methods of treating a cancer that include cells expressing CD20 ("CD20-expressing cancer"), e.g., a hematologic cancer, such as leukemia, through the administration of certain bispecific anti-CD20×anti-CD3 antibodies (e.g., XmAb® 13676) in combination with one or more therapies that can ameliorate side effects of an anti-CD20×anti-CD3 bispecific antibody.

It will be understood that XmAb® 13676 can be used as the bispecific anti-CD20×anti-CD3 antibody in all methods of the invention provided herein.

It will also be understood that that a biosimilar of XmAb® 13676 can be used as the bispecific anti-CD20×anti-CD3 antibody in all methods of the invention provided herein.

It will further be understood that a bioequivalent of XmAb® 13676 can be used as the bispecific anti-CD20× anti-CD3 antibody in all methods of the invention provided herein.

III. ANTIBODIES

The methods provided herein are directed to the administration of bispecific anti-CD20×anti-CD3 antibodies (e.g., XmAb® 13676) for the treatment of particular lymphomas as outlined herein, as outlined in U.S. Ser. Nos. 14/952,714, 15/141,350, and 62/085,027, all of which are expressly incorporated herein by reference, particularly for the bispecific formats of the figures, as well as all sequences, Figures and accompanying Legends therein.

Amino acid sequences of exemplary bispecific anti-CD20×anti-CD3 antibodies useful in the methods provided herein are shown in Table 1 below.

TABLE 1

Amino Acid Sequences of Exemplary Bispecific Anti-CD20 x Anti-CD3 Antibodies

| Description | Sequence | SEQ ID NO: |
|---|---|---|
| XmAb®13676 Anti-CD20 VH-CH1-hinge-CH2-CH3 XENP13676 Anti-CD20 x Anti-CD3 Fab-scFv-Fc Heavy Chain 1 (Anti-CD20 Fab-Fc (C2B8_H1)) | QVQLVQSGAEVKKPGASVKVSCKASGYTFTSYNMH WVRQAPGQGLEWMGAIYPGNGDTSYNQKFQGRVTI TADKSISTAYMELSSLRSEDTAVYYCARSTYYGGD WYFNVWGAGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SDTKVDKKVEPKSCDKTHTCPPCPAPPVAGPSVFL FPPKPKDTLMISRTPEVTCVVVDVKHEDPEVKFNW YVDGVEVHNAKTKPREEEYNSTYRVVSVLTVLHQD WLNGKEYKCKVSNKALPAPIEKTISKAKGQPREPQ VYTLPPSREEMTKNQVSLTCDVSGFYPSDIAVEWE SDGQPENNYKTTPPVLDSDGSFFLYSKLTVDKSRW EQGDVFSCSVMHEALHNHYTQKSLSLSPGK | 1 |

TABLE 1-continued

Amino Acid Sequences of Exemplary Bispecific Anti-CD20 × Anti-CD3 Antibodies

| Description | Sequence | SEQ ID NO: |
|---|---|---|
| XmAb®13676 Anti-CD3 scFv-linker-CH2-CH3 XENP13676 Anti-CD20 × Anti-CD3 Fab-scFv-Fc Heavy Chain 2 (Anti-CD3 scFv-Fc (αCD3_H1.30_L1.47)) | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DSYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 2 |
| XmAb®13676 Anti-CD20 VL-CL XENP13676 Anti-CD20 × Anti-CD3 Fab-scFv-Fc Light Chain (Anti-CD20 LC (C2B8_L1)) | QIVLTQSPSSLSASVGDRVTITCRASSSVSYIHWF QQKPGKSPKPLIYATSNLASGVPVRFSGSGSGTDY TLTISSLQPEDFATYYCQQWTSNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 3 |
| XENP13677 Anti-CD20 × Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHT FPAVLQSSGLYSLSSVVTVPSSSLGTQTYICNVNH KPSDTKVDKKVEPKSCDKTHTCPPCPAPPVAGPSV FLFPPKPKDTLMISRTPEVTCVVVDVKHEDPEVKF NWYVDGVEVHNAKTKPREEEYNSTYRVVSVLTVLH QDWLNGKEYKCKVSNKALPAPIEKTISKAKGQPRE PQVYTLPPSREEMTKNQVSLTCDVSGFYPSDIAVE WESDGQPENNYKTTPPVLDSDGSFFLYSKLTVDKS RWEQGDVFSCSVMHEALHNHYTQKSLSLSPGK | 4 |
| XENP13677 Anti-CD20 × Anti-CD3 Fab-scFv-Fc Heavy Chain 2 (Anti-CD3 scFv-Fc (αCD3_H1.30_L1.47)) | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DSYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 5 |
| XENP13677 Anti-CD20 × Anti-CD3 Fab-scFv-Fc Light Chain (Anti-CD20 LC (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 6 |
| XENP14388 Anti-CD20 × Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SDTKVDKKVEPKSCDKTHTCPPCPAPPVAGPSVFL FPPKPKDTLMISRTPEVTCVVVDVKHEDPEVKFNW YVDGVEVHNAKTKPREEEYNSTYRVVSVLTVLHQD WLNGKEYKCKVSNKALPAPIEKTISKAKGQPREPQ VYTLPPSREEMTKNQVSLTCDVSGFYPSDIAVEWE SDGQPENNYKTTPPVLDSDGSFFLYSKLTVDKSRW EQGDVFSCSVMHEALHNHYTQKSLSLSPGK | 7 |

TABLE 1-continued

Amino Acid Sequences of Exemplary Bispecific Anti-CD20 x Anti-CD3 Antibodies

| Description | Sequence | SEQ ID NO: |
|---|---|---|
| XENP14388 Anti-CD20 x Anti-CD3 Fab-scFv-Fc Heavy Chain 2 (Anti-CD3 scFv-Fc (αCD3_H1.31_L1.47)) | EVQLVESGGGLVQPGGSLRLSCAASGFTFSTYAMS WVRQAPGKGLEWVGRIRSKYNNYATYYADSVKGRF TISRDDSKNTLYLQMNSLRAEDTAVYYCVRHGNFG DSYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 8 |
| XENP14388 Anti-CD20 x Anti-CD3 Fab-scFv-Fc Light Chain (Anti-CD20 (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 9 |
| XENP14389 Anti-CD20 x Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SDTKVDKKVEPKSCDKTHTCPPCPAPPVAGPSVFL FPPKPKDTLMISRTPEVTCVVVDVKHEDPEVKFNW YVDGVEVHNAKTKPREEEYNSTYRVVSVLTVLHQD WLNGKEYKCKVSNKALPAPIEKTISKAKGQPREPQ VYTLPPSREEMTKNQVSLTCDVSGFYPSDIAVEWE SDGQPENNYKTTPPVLDSDGSFFLYSKLTVDKSRW EQGDVFSCSVMHEALHNHYTQKSLSLSPGK | 10 |
| XENP14389 Anti-CD20 x Anti-CD3 Fab-scFv-Fc Heavy Chain 2 (Anti-CD3 scFv-Fc (αCD3_H1.32_L1.47)) | EVQLVESGGGLVQPGGSLRLSCAASGFTFSTYAMN WVRQAPGKGLEWVGRIRSKANNYATYYADSVKGRF TISRDDSKNTLYLQMNSLRAEDTAVYYCVRHGNFG DSYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 11 |
| XENP14389 Anti-CD20 x Anti-CD3 Fab-scFv-Fc Light Chain (Anti-CD20 (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 12 |
| XENP14390 Anti-CD20 x Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SDTKVDKKVEPKSCDKTHTCPPCPAPPVAGPSVFL FPPKPKDTLMISRTPEVTCVVVDVKHEDPEVKFNW YVDGVEVHNAKTKPREEEYNSTYRVVSVLTVLHQD WLNGKEYKCKVSNKALPAPIEKTISKAKGQPREPQ VYTLPPSREEMTKNQVSLTCDVSGFYPSDIAVEWE SDGQPENNYKTTPPVLDSDGSFFLYSKLTVDKSRW EQGDVFSCSVMHEALHNHYTQKSLSLSPGK | 13 |

TABLE 1-continued

Amino Acid Sequences of Exemplary Bispecific Anti-CD20 × Anti-CD3 Antibodies

| Description | Sequence | SEQ ID NO: |
|---|---|---|
| XENP14390 Anti-CD20 × Anti-CD3 Fab-scFv-Fc Heavy Chain 2 (Anti-CD3 scFv-Fc (αCD3_H1.33_L1.47)) | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DSYVSWFDYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 14 |
| XENP14390 Anti-CD20 × Anti-CD3 Fab-scFv-Fc Light Chain (Anti-CD20 (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 15 |
| XENP14392 Anti-CD20 × Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SDTKVDKKVEPKSCDKTHTCPPCPAPPVAGPSVFL FPPKPKDTLMISRTPEVTCVVVDVKHEDPEVKFNW YVDGVEVHNAKTKPREEEYNSTYRVVSVLTVLHQD WLNGKEYKCKVSNKALPAPIEKTISKAKGQPREPQ VYTLPPSREEMTKNQVSLTCDVSGFYPSDIAVEWE SDGQPENNYKTTPPVLDSDGSFFLYSKLTVDKSRW EQGDVFSCSVMHEALHNHYTQKSLSLSPGK | 16 |
| XENP14392 Anti-CD20 × Anti-CD3 Fab-scFv-Fc Heavy Chain 2 (Anti-CD3 scFv-Fc (αCD3_H1.89_L1.47)) | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DEYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVKHEDPEVKFNW YVDGVEVHNAKTKPREEQYNSTYRVVSVLTVLHQD WLNGKEYKCKVSNKALPAPIEKTISKAKGQPREPQ VYTLPPSREQMTKNQVKLTCLVKGFYPSDIAVEWE SNGQPENNYKTTPPVLDSDGSFFLYSKLTVDKSRW QQGNVFSCSVMHEALHNHYTQKSLSLSPGK | 17 |
| XENP14392 Anti-CD20 × Anti-CD3 Fab-scFv-Fc Light Chain (Anti-CD20 (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 18 |
| XENP14393 Anti-CD20 × Anti-CD3 Fab-scFv-Fc Heavy Chain 1 (Anti-CD20 Fab-Fc (C2B8_H1.202)) | QVQLVQSGAEVKKPGASVKVSCKASGYTFTSYNMH WVRQAPGQRLEWMGAIYPGNGATSYSQKFQGRVTI TADTSASTAYMELSSLRSEDTAVYYCARSYYMGGD WYFDVWGAGTLVTVSSASTKGPSVFPLAPSSKSTS GGTAALGCLVKDYFPEPVTVSWNSGALTSGVHT FPAVLQSSGLYSLSSVVTVPSSSLGTQTYICNVNH KPSDTKVDKKVEPKSCDKTHTCPPCPAPPVAGPSV FLFPPKPKDTLMISRTPEVTCVVVDVKHEDPEVKF NWYVDGVEVHNAKTKPREEEYNSTYRVVSVLTVLH QDWLNGKEYKCKVSNKALPAPIEKTISKAKGQPRE PQVYTLPPSREEMTKNQVSLTCDVSGFYPSDIAVE WESDGQPENNYKTTPPVLDSDGSFFLYSKLTVDKS RWEQGDVFSCSVMHEALHNHYTQKSLSLSPGK | 19 |

TABLE 1-continued

Amino Acid Sequences of Exemplary Bispecific Anti-CD20 x Anti-CD3 Antibodies

| Description | Sequence | SEQ ID NO: |
|---|---|---|
| XENP14393 Anti-CD20 x Anti-CD3 Fab-scFv-Fc Heavy Chain 2 (Anti-CD3 scFv-Fc (αCD3_H1.90_L1.47)) | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DPYVSWFAYWGQGTLVTVSSGKPGSGKPGSGKPGS GKPGSQAVVTQEPSLTVSPGGTVTLTCGSSTGAVT TSNYANWVQQKPGKSPRGLIGGTNKRAPGVPARFS GSLLGGKAALTISGAQPEDEADYYCALWYSNHWVF GGGTKLTVLEPKSSDKTHTCPPCPAPPVAGPSVFL FPPKPKDTLMISRTPEVTCVVVDVSHEDPEVKFNW YVDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK | 20 |
| XENP14393 Anti-CD20 x Anti-CD3 Fab-scFv-Fc Light Chain (Anti-CD20 (C2B8_L1.113)) | QIVLTQSPSSLSASVGDRVTITCRASWSVSYIHWF QQKPGKSPKPLIYATSNLASGVPVRFSGSGSGTDY TLTISSLQPEDFATYYCQQWTHNPPTFGGGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 21 |
| XmAb®13676 Anti-CD3 VH CDR1 | TYAMN | 22 |
| XmAb®13676 Anti-CD3 VH CDR2 | RIRSKYNNYATYYADSVKG | 23 |
| XmAb®13676 Anti-CD3 VH CDR3 | HGNFGDSYVSWFAY | 24 |
| XmAb®13676 Anti-CD3 VL CDR1 | GSSTGAVTTSNYAN | 25 |
| XmAb®13676 Anti-CD3 VL CDR2 | GTNKRAP | 26 |
| XmAb®13676 Anti-CD3 VL CDR3 | ALWYSNHWV | 27 |
| XmAb®13676 Anti-CD20 VH CDR1 | SYNMH | 28 |
| XmAb®13676 Anti-CD20 VH CDR2 | AIYPGNGDTSYNQKFQG | 29 |
| XmAb®13676 Anti-CD20 VH CDR3 | STYYGGDWYFNV | 30 |
| XmAb®13676 Anti-CD20 VL CDR1 | RASSSVSYIH | 31 |
| XmAb®13676 Anti-CD20 VL CDR2 | ATSNLAS | 32 |
| XmAb®13676 Anti-CD20 VL CDR3 | QQWTSNPPT | 33 |
| XmAb®13676 Anti-CD3 VH | EVQLVESGGGLVQPGGSLRLSCAASGFTFSTYAMN WVRQAPGKGLEWVGRIRSKYNNYATYYADSVKGRF TISRDDSKNTLYLQMNSLRAEDTAVYYCVRHGNFG DSYVSWFAYWGQGTLVTVSS | 34 |
| XmAb®13676 Anti-CD3 VL | QAVVTQEPSLTVSPGGTVTLTCGSSTGAVTTSNYA NWVQQKPGKSPRGLIGGTNKRAPGVPARFSGSLLG GKAALTISGAQPEDEADYYCALWYSNHWVFGGGTK LTVL | 35 |
| XmAb®13676 Anti-CD20 VH | QVQLVQSGAEVKKPGASVKVSCKASGYTFTSYNMH WVRQAPGQGLEWMGAIYPGNGDTSYNQKFQGRVTI TADKSISTAYMELSSLRSEDTAVYYCARSTYYGGD WYFNVWGAGTLVTVSs | 36 |

TABLE 1-continued

Amino Acid Sequences of Exemplary Bispecific Anti-CD20 x Anti-CD3 Antibodies

| Description | Sequence | SEQ ID NO: |
|---|---|---|
| XmAb®13676 Anti-CD20 VL | QIVLTQSPSSLSASVGDRVTITCRASSSVSYIHWF QQKPGKSPKPLIYATSNLASGVPVRFSGSGSGTDY TLTISSLQPEDFATYYCQQWTSNPPTFGGGTKVEI K | 37 |
| mosunetuzumab anti-CD3e heavy chain | EVQLVQSGAEVKKPGASVKVSCKASGYTFTNYYIH WVRQAPGQGLEWIGWIYPGDGNTKYNEKEKGRATL TADTSTSTAYLELSSLRSEDTAVYYCARDSYSNYY FDYWGQGTLVTVSSASTKGPSVEPLAPSSKSTSGG TAALGCLVKDYFPEPVTVSWNSGALTSGVHTFPAV LQSSGLYSLSSVVTVPSSSLGTQTYICNVNHKPSN TKVDKKVEPKSCDKTHTCPPCPAPELLGGPSVELF PPKPKDTLMISRTPEVTCVVVDVSHEDPEVKENWY VDGVEVHNAKTKPREEQYGSTYRVVSVLTVLHQDW LNGKEYKCKVSNKALPAPIEKTISKAKGQPREPQV YTLPPSREEMTKNQVSLSCAVKGFYPSDIAVEWES NGQPENNYKTTPPVLDSDGSFFLVSKLTVDKSRWQ QGNVFSCSVMHEALHNHYTQKSLSLSPGK | 38 |
| mosunetuzumab anti-CD3e light chain | DIVMTQSPDSLAVSLGERATINCKSSQSLLNSRTR KNYLAWYQQKPGQPPKLLIYWASTRESGVPDRESG SGSGTDETLTISSLQAEDVAVYYCTQSFILRTFGQ GTKVEIKRTVAAPSVFIFPPSDEQLKSGTASVVCL LNNFYPREAKVQWKVDNALQSGNSQESVTEQDSKD STYSLSSTLTLSKADYEKHKVYACEVTHQGLSSPV TKSENRGEC | 39 |
| mosunetuzumab anti-CD20 heavy chain | EVQLVESGGGLVQPGGSLRLSCAASGYTFTSYNMH WVRQAPGKGLEWVGAIYPGNGDTSYNQKEKGRFTI SVDKSKNTLYLQMNSLRAEDTAVYYCARVVYYSNS YWYFDVWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVDVSHEDPEVKF NWYVDGVEVHNAKTKPREEQYGSTYRVVSVLTVLH QDWLNGKEYKCKVSNKALPAPIEKTISKAKGQPRE PQVYTLPPSREEMTKNQVSLWCLVKGFYPSDIAVE WESNGQPENNYKTTPPVLDSDGSFFLYSKLTVDKS RWQQGNVFSCSVMHEALHNHYTQKSLSLSPGK | 40 |
| mosunetuzumab anti-CD20 light chain | DIQMTQSPSSLSASVGDRVTITCRASSSVSYMHWY QQKPGKAPKPLIYAPSNLASGVPSRFSGSGSGTDF TLTISSLQPEDFATYYCQQWSENPPTFGQGTKVEI KRTVAAPSVFIFPPSDEQLKSGTASVVCLLNNFYP REAKVQWKVDNALQSGNSQESVTEQDSKDSTYSLS STLTLSKADYEKHKVYACEVTHQGLSSPVTKSFNR GEC | 41 |
| epcoritamab anti-CD3e heavy chain | EVKLVESGGGLVQPGGSLRLSCAASGFTFNTYAMN WVRQAPGKGLEWVARIRSKYNNYATYYADSVKDRF TISRDDSKSSLYLQMNNLKTEDTAMYYCVRHGNFG NSYVSWFAYWGQGTLVTVSSASTKGPSVFPLAPSS KSTSGGTAALGCLVKDYFPEPVTVSWNSGALTSGV HTFPAVLQSSGLYSLSSVVTVPSSSLGTQTYICNV NHKPSNTKVDKRVEPKSCDKTHTCPPCPAPEFEGG PSVFLFPPKPKDTLMISRTPEVTCVVVAVSHEDPE VKFNWYVDGVEVHNAKTKPREEQYNSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFLLYSKLTV DKSRWQQGNVFSCSVMHEALHNHYTQKSLSLSPG | 42 |
| epcoritamab anti-CD3e light chain | QAVVTQEPSFSVSPGGTVTLTCRSSTGAVTTSNYA NWVQQTPGQAFRGLIGGTNKRAPGVPARFSGSLIG DKAALTITGAQADDESIYFCALWYSNLWVFGGGTK LTVLGQPKAAPSVTLFPPSSEELQANKATLVCLIS DFYPGAVTVAWKADSSPVKAGVETTTPSKQSNNKY AASSYLSLTPEQWKSHRSYSCQVTHEGSTVEKTVA PTECS | 43 |

TABLE 1-continued

Amino Acid Sequences of Exemplary Bispecific Anti-CD20 x Anti-CD3 Antibodies

| Description | Sequence | SEQ ID NO: |
|---|---|---|
| epcoritamab anti-CD20 heavy chain | EVQLVESGGGLVQPDRSLRLSCAASGFTFHDYAMH WVRQAPGKGLEWVSTISWNSGTIGYADSVKGRFTI SRDNAKNSLYLQMNSLRAEDTALYYCAKDIQYGNY YYGMDVWGQGTTVTVSSASTKGPSVFPLAPSSKST SGGTAALGCLVKDYFPEPVTVSWNSGALTSGVHTF PAVLQSSGLYSLSSVVTVPSSSLGTQTYICNVNHK PSNTKVDKRVEPKSCDKTHTCPPCPAPEFEGGPSV FLFPPKPKDTLMISRTPEVTCVVVAVSHEDPEVKF NWYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSRLTVDKS RWQQGNVFSCSVMHEALHNHYTQKSLSLSPG | 44 |
| epcoritamab anti-CD20 light chain | EIVLTQSPATLSLSPGERATLSCRASQSVSSYLAW YQQKPGQAPRLLIYDASNRATGIPARFSGSGSGTD FTLTISSLEPEDFAVYYCQQRSNWPITFGQGTRLE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC | 45 |
| odronextamab anti-CD3 heavy chain | EVQLVESGGGLVQPGRSLRLSCAASGFTFDDYTMH WVRQAPGKGLEWVSGISWNSGSIGYADSVKGRFTI SRDNAKKSLYLQMNSLRAEDTALYYCAKDNSGYGH YYYGMDVWGQGTTVTVASASTKGPSVFPLAPCSRS TSESTAALGCLVKDYFPEPVTVSWNSGALTSGVHT FPAVLQSSGLYSLSSVVTVPSSSLGTKTYTCNVDH KPSNTKVDKRVESKYGPPCPPCPAPPVAGPSVFLF PPKPKDTLMISRTPEVTCVVVDVSQEDPEVQFNWY VDGVEVHNAKTKPREEQFNSTYRVVSVLTVLHQDW LNGKEYKCKVSNKGLPSSIEKTISKAKGQPREPQV YTLPPSQEEMTKNQVSLTCLVKGFYPSDIAVEWES NGQPENNYKTTPPVLDSDGSFFLYSRLTVDKSRWQ EGNVFSCSVMHEALHNRFTQKSLSLSLGK | 46 |
| odronextamab light chain | EIVMTQSPATLSVSPGERATLSCRASQSVSSNLAW YQQKPGQAPRLLIYGASTRATGIPARFSGSGSGTE FTLTISSLQSEDFAVYYCQHYINWPLTFGGGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC | 47 |
| odronextamab anti-CD20 heavy chain | EVQLVESGGGLVQPGRSLRLSCVASGFTFNDYAMH WVRQAPGKGLEWVSVISWNSDSIGYADSVKGRFTI SRDNAKNSLYLQMHSLRAEDTALYYCAKDNHYGSG SYYYYQYGMDVWGQGTTVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPPVAGPS VFLFPPKPKDTLMISRTPEVTCVVVDVSQEDPEVQ FNWYVDGVEVHNAKTKPREEQFNSTYRVVSVLTVL HQDWLNGKEYKCKVSNKGLPSSIEKTISKAKGQPR EPQVYTLPPSQEEMTKNQVSLTCLVKGFYPSDIAV EWESNGQPENNYKTTPPVLDSDGSFFLYSRLTVDK SRWQEGNVFSCSVMHEALHNYTQKSLSLSLGK | 48 |
| glofitamab anti-CD20/CD3 heavy chain | QVQLVQSGAEVKKPGSSVKVSCKASGYAFSYSWIN WVRQAPGQGLEWMGRIFPGDGDTDYNGKFKGRVTI TADKSTSTAYMELSSLRSEDTAVYYCARNVFDGYW LVYWGQGTLVTVSSASTKGPSVFPLAPSSKSTSGG TAALGCLVEDYFPEPVTVSWNSGALTSGVHTFPAV LQSSGLYSLSSVVTVPSSSLGTQTYICNVNHKPSN TKVDEKVEPKSCDGGGSGGGGSQAVVTQEPSLTV SPGGTVTLTCGSSTGAVTTSNYANWVQEKPGQAFR GLIGGTNKRAPGTPARFSGSLLGGKAALTLSGAQP EDEAEYYCALWYSNLWVFGGGTKLTVLSSASTKGP SVFPLAPSSKSTSGGTAALGCLVKDYFPEPVTVSW NSGALTSGVHTFPAVLQSSGLYSLSSVVTVPSSSL GTQTYICNVNHKPSNTKVDKKVEPKSCDKTHTCPP CPAPEAAGGPSVFLFPPKPKDTLMISRTPEVTCVV VDVSHEDPEVKFNWYVDGVEVHNAKTKPREEQYNS TYRVVSVLTVLHQDWLNGKEYKCKVSNKALGAP1E KTISKAKGQPREPQVYTLPPCRDELTKNQVSLWCL | 49 |

TABLE 1-continued

Amino Acid Sequences of Exemplary Bispecific Anti-CD20 × Anti-CD3 Antibodies

| Description | Sequence | SEQ ID NO: |
|---|---|---|
| | VKGFYPSDIAVEWESNGQPENNYKTTPPVLDSDGS<br>FFLYSKLTVDKSRWQQGNVFSCSVMHEALHNHYTQ<br>KSLSLSPGK | |
| glofitamab<br>anti-CD3e light chain | EVQLLESGGGLVQPGGSLRLSCAASGFTFSTYAMN<br>WVRQAPGKGLEWVSRIRSKYNNYATYYADSVKGRF<br>TISRDDSKNTLYLQMNSLRAEDTAVYYCVRHGNFG<br>NSYVSWFAYWGQGTLVTVSSASVAAPSVFIFPPSD<br>EQLKSGTASVVCLLNNFYPREAKVQWKVDNALQSG<br>NSQESVTEQDSKDSTYSLSSTLTLSKADYEKHKVY<br>ACEVTHQGLSSPVTKSFNRGEC | 50 |
| glofitamab<br>anti-CD20 heavy<br>chain | QVQLVQSGAEVKKPGSSVKVSCKASGYAFSYSWIN<br>WVRQAPGQGLEWMGRIFPGDGDTDYNGKFKGRVTI<br>TADKSTSTAYMELSSLRSEDTAVYYCARNVFDGYW<br>LVYWGQGTLVTVSSASTKGPSVFPLAPSSKSTSGG<br>TAALGCLVEDYFPEPVTVSWNSGALTSGVHTFPAV<br>LQSSGLYSLSSVVTVPSSSLGTQTYICNVNHKPSN<br>TKVDEKVEPKSCDKTHTCPPCPAPEAAGGPSVFLF<br>PPKPKDTLMISRTPEVTCVVVDVSHEDPEVKFNWY<br>VDGVEVHNAKTKPREEQYNSTYRVVSVLTVLHQDW<br>LNGKEYKCKVSNKALGAPIEKTISKAKGQPREPQV<br>CTLPPSRDELTKNQVSLSCAVKGFYPSDIAVEWES<br>NGQPENNYKTTPPVLDSDGSFFLVSKLTVDKSRWQ<br>QGNVFSCSVMHEALHNHYTQKSLLSPGK | 51 |
| glofitamab<br>anti-CD20 light chain | DIVMTQTPLSLPVTPGEPASISCRSSKSLLHSNGI<br>TYLYWYLQKPGQSPQLLIYQMSNLVSGVPDRFSGS<br>GSGTDFTLKISRVEAEDVGVYYCAQNLELPYTFGG<br>GTKVEIKRTVAAPSVFIFPPSDRKLKSGTASVVCL<br>LNNFYPREAKVQWKVDNALQSGNSQESVTEQDSKD<br>STYSLSSTLTLSKADYEKHKVYACEVTHQGLSSPV<br>TKSFNRGEC | 52 |

In some embodiments, the bispecific anti-CD20×anti-CD3 antibodies (e.g., XmAb® 13676) have a "bottle opener" format (also referred to as the "triple F" format or 1+1 Fab-scFv-Fc format) as is generally depicted in FIG. 1. In this embodiment, the anti-CD3 antigen binding domain is the scFv-Fc domain monomer and the anti-CD20 antigen binding domain is the Fab monomer (terms as used in US Publication Nos. 2014/0288275 and 2014-0294823 as well as in U.S. Ser. No. 15/141,350, all of which are expressly incorporated by reference in their entirety and specifically for all the definitions, sequences of anti-CD3 antigen binding domains and sequences of anti-CD20 antigen binding domains).

Figure 4A:
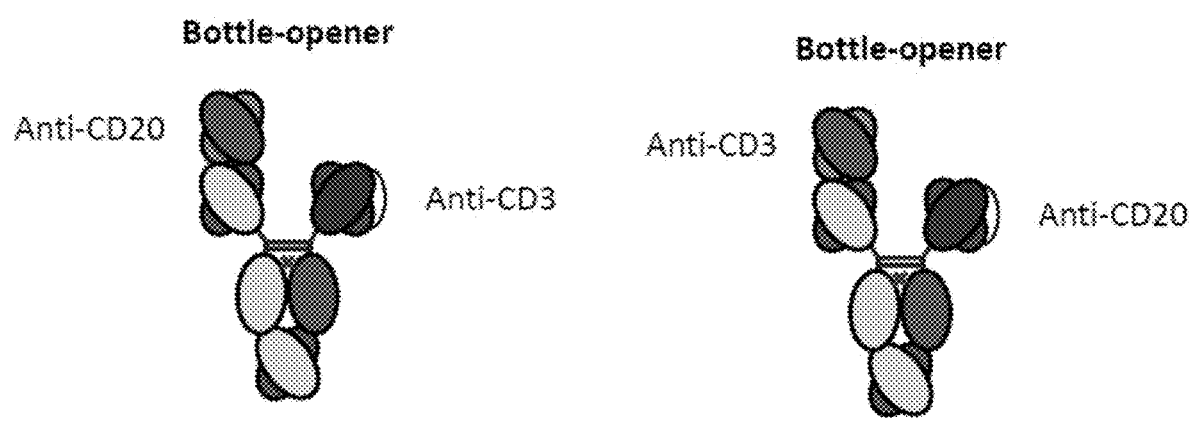
Figure 4B:
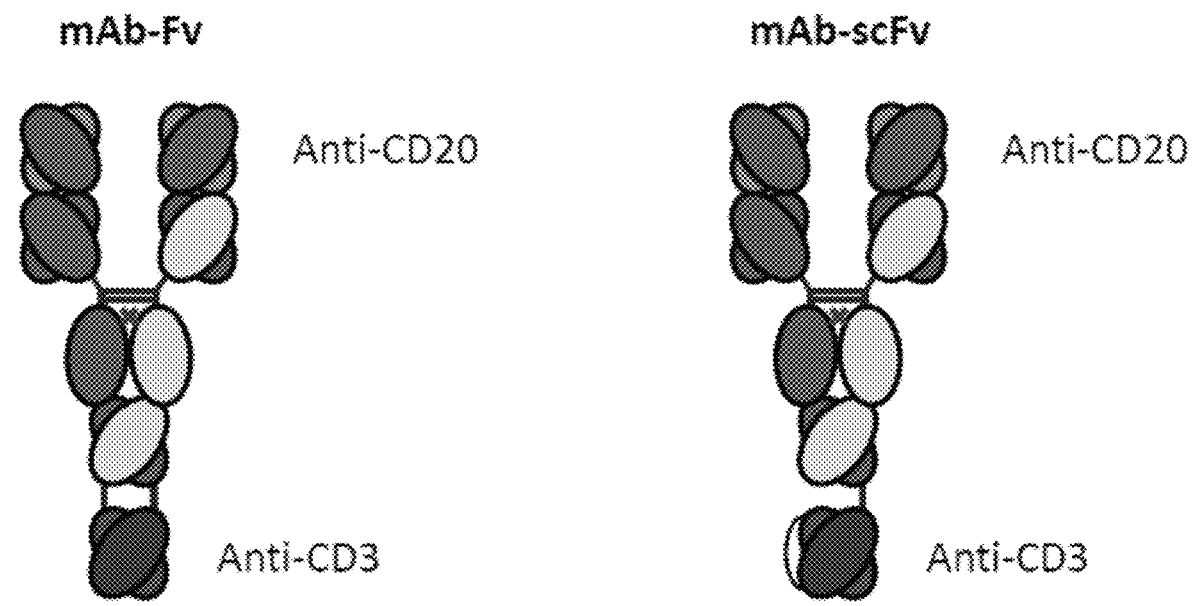

Alternate formats for the bispecific, heterodimeric anti-CD20×anti-CD3 antibodies that can be used in the methods provided herein are shown in FIG. 4, which also generally rely on the use of Fabs and scFv domains in different formats.

In addition, it is also possible to make non-heterodimeric anti-CD20×anti-CD3 bispecific antibodies as are known in the art, that can be dosed at the same dosage levels as described herein for the heterodimeric bispecific anti-CD20×anti-CD3 antibodies.

Figure 6:
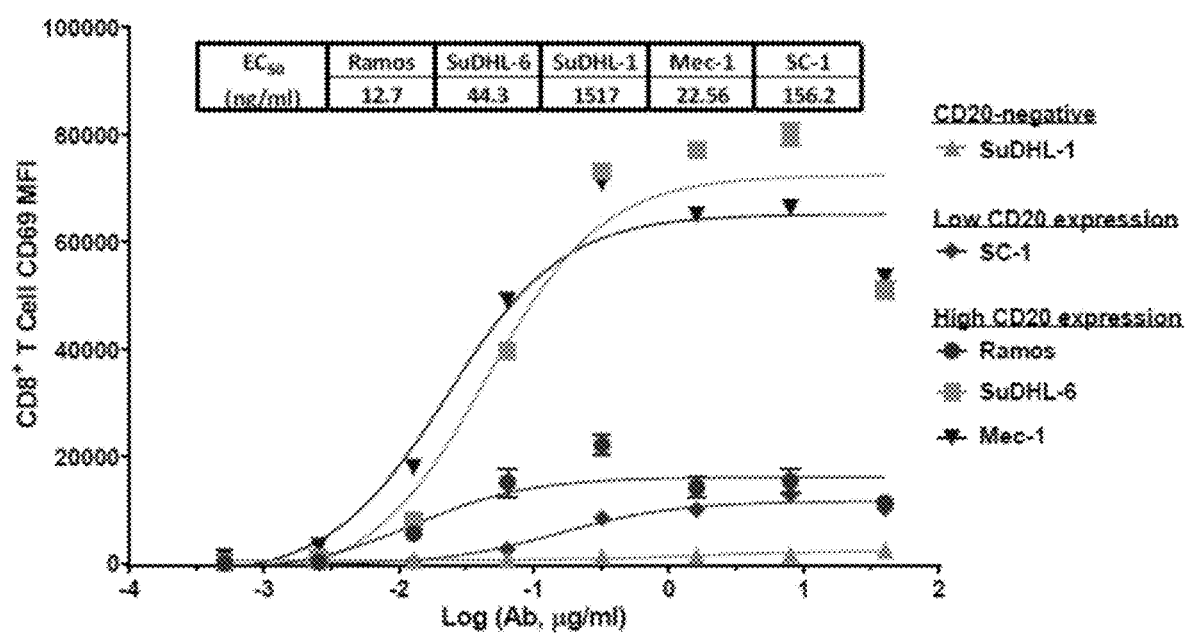
FIG. 6 is a line graph showing XmAb® 13676 stimulates activation of CD8+ T cells in the presence of CD20-expressing B cell lines.

The anti-CD3 scFv antigen binding domain can have the sequence depicted in FIG. 2, Table 1, or can be selected from:

1) the set of 6 CDRs (vhCDR1, vhCDR2, vhCDR3, vlCDR1, vlCDR2 and vlCDR3) from any anti-CD3 antigen binding domain sequence depicted in FIGS. 2 and 6 of US Publication No. 2014/0288275, which are herein incorporated by reference in their entirety;

2) the variable heavy and variable light chains from any anti-CD3 antigen binding domain sequence depicted in FIGS. 2 and 6 of US Publication No. 2014/0288275, which are herein incorporated by reference in their entirety;

3) the scFv domains from any anti-CD3 scFv sequence depicted in FIG. 2 of US Publication No. 2014/0288275, which are herein incorporated by reference in their entirety;

4) any of the anti-CD3 antigen binding domains of FIGS. 2, 3, 4, 5, 6, and 7 of U.S. Ser. No. 14/952,714, which are herein incorporated by reference in their entirety;

5) other anti-CD3 variable heavy and variable light chains as are known in the art, that can be combined to form scFvs (or Fabs, when the format is reversed or an alternative format is used), which are herein incorporated by reference in their entirety; and 6) any of the anti-CD3 antigen binding domains of FIGS. 2, 3, 4, 5, 6, and 7 of U.S. Ser. No. 14/952,714, which are herein incorporated by reference in their entirety.

Figure 12:
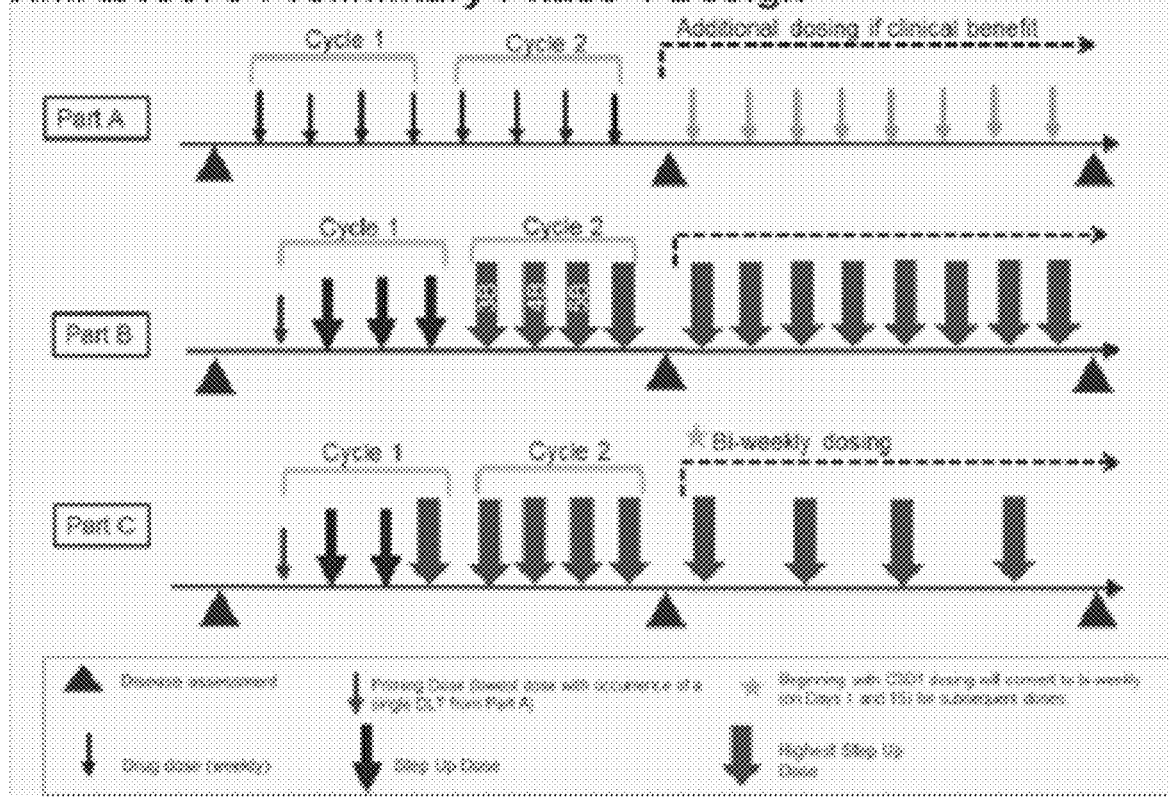
FIG. 12 depicts a flow chart for a preliminary Phase 1 exemplary design using XmAb® 13676 provided in Example 1.

The anti-CD20 Fab binding domain can have the sequence depicted in FIG. 2, FIG. 4, Table 1, or can be selected from:

1) The set of 6 CDRs (vhCDR1, vhCDR2, vhCDR3, vlCDR1, vlCDR2 and vlCDR3) from any anti-CD20 antigen binding domain sequence depicted in U.S. Ser. No. 62/084,908, which are herein incorporated by reference in their entirety;

2) The variable heavy and variable light chains from any anti-CD20 antigen binding domain sequence depicted in U.S. Ser. No. 62/084,908, including those depicted in FIGS. 2, 3 and 12, which are herein incorporated by reference in their entireties; and 3) Other anti-CD20 variable heavy and variable light chains as are known in the art, that can be combined to form Fabs (or scFvs, when the format is reversed or an alternative format is used).

One bispecific antibody of particular use in any of the methods of the present invention, XmAb® 13676, is shown in FIG. 2 and Table 1. The XmAb® 13676 antibody includes a first monomer comprising SEQ ID NO: 1, a second monomer comprising SEQ ID NO: 2, and a light chain comprising SEQ ID NO: 3.

In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system. Exemplary sets of 6 CDRs (VH CDR1-3 and VL CDR1-3) of certain antibody embodiments are provided herein. Other sets of CDRs are contemplated and within the scope of the antibody embodiments provided herein.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1.

In one embodiment, the bispecific anti-CD20×anti-CD3 antibody comprises a first antigen binding domain that binds to CD3, wherein the first antigen binding domain comprises a VL comprising a VL CDR1, VL CDR2 and VL CDR3 having an amino acid sequence of a VL CDR1, VL CDR2 and VL CDR3, respectively, of a VL having an amino acid sequence provided in Table 1.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1, and a VL comprising a VL comprising a VL CDR1, VL CDR2 and VL CDR3 having an amino acid sequence of a VL CDR1, VL CDR2 and VL CDR3, respectively, of a VL having an amino acid sequence provided in Table 1.

In one embodiment, the bispecific anti-CD20×anti-CD3 antibody comprises a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1.

In one embodiment, the bispecific anti-CD20×anti-CD3 antibody comprises a second antigen binding domain that binds to CD20, wherein the second antigen binding domain comprises a VL comprising a VL CDR1, VL CDR2 and VL CDR3 having an amino acid sequence of a VL CDR1, VL CDR2 and VL CDR3, respectively, of a VL having an amino acid sequence provided in Table 1.

In one embodiment, the bispecific anti-CD20×anti-CD3 antibody comprises a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1, and a VL comprising a VL CDR1, VL CDR2 and VL CDR3 having an amino acid sequence of a VL CDR1, VL CDR2 and VL CDR3, respectively, of a VL having an amino acid sequence provided in Table 1.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1, and a VL comprising a VL CDR1, VL CDR2 and VL CDR3 having an amino acid sequence of a VL CDR1, VL CDR2 and VL CDR3, respectively, of a VL having an amino acid sequence provided in Table 1, and a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence provided in Table 1, and a VL comprising a VL CDR1, VL CDR2 and VL CDR3 having an amino acid sequence of a VL CDR1, VL CDR2 and VL CDR3, respectively, of a VL having an amino acid sequence provided in Table 1.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 34.

In one embodiment, the bispecific anti-CD20×anti-CD3 antibody comprises a first antigen binding domain that binds to CD3, wherein the first antigen binding domain comprises a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 35.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 34, and a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 35.

In one embodiment, the bispecific anti-CD20×anti-CD3 antibody comprises a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 36.

In one embodiment, the bispecific anti-CD20×anti-CD3 antibody comprises a second antigen binding domain that binds to CD20, wherein the first antigen binding domain comprises a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 37.

In one embodiment, the bispecific anti-CD20×anti-CD3 antibody comprises a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 36, and a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 37.

In one embodiment, the bispecific anti-CD20×anti-CD3 antibody comprises a first antigen binding domain that binds to CD3, wherein the first antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 34, and a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 35, and a second antigen binding domain that binds to CD20, wherein the second antigen binding domain comprises a VH comprising a VH CDR1, VH CDR2 and VH CDR3 having an amino acid sequence of a VH CDR1, VH CDR2 and VH CDR3, respectively, of a VH having an amino acid sequence of SEQ ID NO: 36, and a VL comprising a VL CDR1, VL CDR2 and VL CDR3 having an amino acid sequence of a VL CDR1, VL CDR2 and VL CDR3, respectively, of a VL having an amino acid sequence of SEQ ID NO: 37.

In one embodiment, the bispecific anti-CD20×anti-CD3 antibody comprises a first antigen binding domain that binds to CD3, wherein the first antigen binding domain comprises a VH domain comprising a VH CDR1, a VH CDR2, and a VH CDR3 having an amino acid sequence of SEQ ID NO:22, SEQ ID NO:23, and SEQ ID NO:24, respectively.

In one embodiment, the bispecific anti-CD20×anti-CD3 antibody comprises a first antigen binding domain that binds to CD3, wherein the first antigen binding domain comprises a VL domain comprising a VL CDR1, a VL CDR2, and a VL CDR3 having an amino acid sequence of SEQ ID NO:25, SEQ ID NO:26, and SEQ ID NO:27, respectively.

In one embodiment, the bispecific anti-CD20×anti-CD3 antibody comprises a first antigen binding domain that binds to CD3, wherein the first antigen binding domain comprises a VH domain comprising a VH CDR1, a VH CDR2, and a VH CDR3 having the amino acid sequence of SEQ ID NO:22, SEQ ID NO:23, and SEQ ID NO:24, respectively, and a VL domain comprising a VL CDR1, a VL CDR2, and a VL CDR3 having an amino acid sequence of SEQ ID NO:25, SEQ ID NO:26, and SEQ ID NO:27, respectively.

In one embodiment, the bispecific anti-CD20×anti-CD3 antibody comprises a second antigen binding domain that binds to CD20, wherein the second antigen binding domain comprises a VH domain comprising a VH CDR1, a VH CDR2, and a VH CDR3 having an amino acid sequence of SEQ ID NO:28, SEQ ID NO:29, and SEQ ID NO:30, respectively.

In one embodiment, the bispecific anti-CD20×anti-CD3 antibody comprises a second antigen binding domain that binds to CD20, wherein the second antigen binding domain comprises a VL domain comprising a VL CDR1, a VL CDR2, and a VL CDR3 having an amino acid sequence of SEQ ID NO:31, SEQ ID NO:32, and SEQ ID NO:33, respectively.

In one embodiment, the bispecific anti-CD20×anti-CD3 antibody comprises a second antigen binding domain that binds to CD20, wherein the second antigen binding domain comprises a VH domain comprising a VH CDR1, a VH CDR2, and a VH CDR3 having an amino acid sequence of SEQ ID NO:28, SEQ ID NO:29, and SEQ ID NO:30, respectively, and a VL domain comprising a VL CDR1, a VL CDR2, and a VL CDR3 having an amino acid sequence of SEQ ID NO:31, SEQ ID NO:32, and SEQ ID NO:33, respectively.

In one embodiment, the bispecific anti-CD20×anti-CD3 antibody comprises a first antigen binding domain that binds to CD3 and a second antigen binding domain that binds to CD20, wherein the first antigen binding domain comprises a VH domain comprising a VH CDR1, a VH CDR2, and a VH CDR3 having an amino acid sequence of SEQ ID NO:22, SEQ ID NO23, and SEQ ID NO:24, respectively, and a VL domain comprising a VL CDR1, a VL CDR2, and a VL CDR3 having an amino acid sequence of SEQ ID NO:25, SEQ ID NO:26, and SEQ ID NO:27, respectively, and the second antigen binding domain comprises a VH domain comprising a VH CDR1, a VH CDR2, and a VH CDR3 having an amino acid sequence of SEQ ID NO:28, SEQ ID NO:29, and SEQ ID NO:30, respectively, and a VL domain comprising a VL CDR1, a VL CDR2, and a VL CDR3 having an amino acid sequence of SEQ ID NO:31, SEQ ID NO:32, and SEQ ID NO:33, respectively.

In one embodiment, the bispecific anti-CD20×anti-CD3 antibody comprises a first antigen binding domain that binds to CD3, wherein the first antigen binding domain comprises a VH domain having an amino acid sequence that is about 90%, 95%, 98%, 99%, or 100% identical to the amino acid sequence of SEQ ID NO:34. In one embodiment, the first antigen binding domain comprises a VH domain having an amino acid sequence that is about 90% identical to the amino acid sequence of SEQ ID NO:34. In another embodiment, the first antigen binding domain comprises a VH domain having an amino acid sequence that is about 95% identical to the amino acid sequence of SEQ ID NO:34. In another embodiment, the first antigen binding domain comprises a VH domain having an amino acid sequence that is about 98% identical to the amino acid sequence of SEQ ID NO:34. In another embodiment, the first antigen binding domain comprises a VH domain having an amino acid sequence that is about 99% identical to the amino acid sequence of SEQ ID NO:34. In one embodiment, the first antigen binding domain comprises a VH domain having an amino acid sequence that is about 100% identical to the amino acid sequence of SEQ ID NO:34.

In one embodiment, the bispecific anti-CD20×anti-CD3 antibody comprises a first antigen binding domain that binds to CD3, wherein the first antigen binding domain comprises a VL domain having an amino acid sequence that is about 90%, 95%, 98%, 99%, or 100% identical to the amino acid sequence of SEQ ID NO:35. In one embodiment, the first antigen binding domain comprises a VL domain having an amino acid sequence that is about 90% identical to the amino acid sequence of SEQ ID NO:35. In another embodiment, the first antigen binding domain comprises a VL domain having an amino acid sequence that is about 95% identical to the amino acid sequence of SEQ ID NO:35. In another embodiment, the first antigen binding domain comprises a VL domain having an amino acid sequence that is about 98% identical to the amino acid sequence of SEQ ID NO:35. In another embodiment, the first antigen binding domain comprises a VL domain having an amino acid sequence that is about 99% identical to the amino acid sequence of SEQ ID NO:35. In another embodiment, the first antigen binding domain comprises a VL domain having an amino acid sequence that is about 100% identical to the amino acid sequence of SEQ ID NO:

In one embodiment, the bispecific anti-CD20×anti-CD3 antibody comprises a first antigen binding domain that binds to CD3, wherein the first antigen binding domain comprises a VH domain having an amino acid sequence that is about 90%, 95%, 98%, 99%, or 100% identical to the amino acid sequence of SEQ ID NO:34 and a VL domain having an amino acid sequence that is about 90%, 95%, 98%, 99%, or 100% identical to the amino acid sequence of SEQ ID NO:35. In one embodiment, the first antigen binding domain comprises a VH domain having an amino acid sequence that is about 90%, identical to the amino acid sequence of SEQ ID NO:34 and a VL domain having an amino acid sequence that is about 90% identical to the amino acid sequence of SEQ ID NO:35. In another embodiment, the first antigen binding domain comprises a VH domain having an amino acid sequence that is about 95%, identical to the amino acid sequence of SEQ ID NO:34 and a VL domain having an amino acid sequence that is about 95% identical to the amino acid sequence of SEQ ID NO:35. In another embodiment, the first antigen binding domain comprises a VH domain having an amino acid sequence that is about 98%, identical to the amino acid sequence of SEQ ID NO:34 and a VL domain having an amino acid sequence that is about 98% identical to the amino acid sequence of SEQ ID NO:35. In another embodiment, the first antigen binding domain comprises a VH domain having an amino acid sequence that is about 99%, identical to the amino acid sequence of SEQ ID NO:34 and a VL domain having an amino acid sequence that is about 99% identical to the amino acid sequence of SEQ ID NO:35. In another embodiment, the first antigen binding domain comprises a VH domain having an amino acid sequence that is about 100%, identical to the amino acid sequence of SEQ ID NO:34 and a VL domain having an amino acid sequence that is about 100% identical to the amino acid sequence of SEQ ID NO:35.

In one embodiment, the bispecific anti-CD20×anti-CD3 antibody comprises a second antigen binding domain that binds to CD20, wherein the second antigen binding domain comprises a VH domain having an amino acid sequence that is about 90%, 95%, 98%, 99%, or 100% identical to the amino acid sequence of SEQ ID NO:36. In one embodiment, the second antigen binding domain comprises a VH domain having an amino acid sequence that is about 90% identical to the amino acid sequence of SEQ ID NO:36. In another embodiment, the second antigen binding domain comprises a VH domain having an amino acid sequence that is about 95% identical to the amino acid sequence of SEQ ID NO:36. In another embodiment, the second antigen binding domain comprises a VH domain having an amino acid sequence that is about 98% identical to the amino acid sequence of SEQ ID NO:36. In another embodiment, the second antigen binding domain comprises a VH domain having an amino acid sequence that is about 99% identical to the amino acid sequence of SEQ ID NO:36. In another embodiment, the second antigen binding domain comprises a VH domain having an amino acid sequence that is about 100% identical to the amino acid sequence of SEQ ID NO:36.

In one embodiment, the bispecific anti-CD20×anti-CD3 antibody comprises a second antigen binding domain that binds to CD20, wherein the second antigen binding domain comprises a VL domain having an amino acid sequence that is about 90%, 95%, 98%, 99%, or 100% identical to the amino acid sequence of SEQ ID NO:37. In one embodiment, the second antigen binding domain comprises a VL domain having an amino acid sequence that is about 90% identical to the amino acid sequence of SEQ ID NO:37. In another embodiment, the second antigen binding domain comprises a VL domain having an amino acid sequence that is about 95% identical to the amino acid sequence of SEQ ID NO:37. In another embodiment, the second antigen binding domain comprises a VL domain having an amino acid sequence that is about 98% identical to the amino acid sequence of SEQ ID NO:37. In another embodiment, the second antigen binding domain comprises a VL domain having an amino acid sequence that is about 99% identical to the amino acid sequence of SEQ ID NO:37. In another embodiment, the second antigen binding domain comprises a VL domain having an amino acid sequence that is about 100% identical to the amino acid sequence of SEQ ID NO:37.

In one embodiment, the bispecific anti-CD20×anti-CD3 antibody comprises a second antigen binding domain that binds to CD20, wherein the second antigen binding domain comprises a VH domain having an amino acid sequence that is about 90%, 95%, 98%, 99%, or 100% identical to the amino acid sequence of SEQ ID NO:36 and a VL domain having an amino acid sequence that is about 90%, 95%, 98%, 99%, or 100% identical to the amino acid sequence of SEQ ID NO:37. In one embodiment, the second antigen binding domain comprises a VH domain having an amino acid sequence that is about 90%, identical to the amino acid sequence of SEQ ID NO:36 and a VL domain having an amino acid sequence that is about 90% identical to the amino acid sequence of SEQ ID NO:37. In another embodiment, the second antigen binding domain comprises a VH domain having an amino acid sequence that is about 95%, identical to the amino acid sequence of SEQ ID NO:36 and a VL domain having an amino acid sequence that is about 95% identical to the amino acid sequence of SEQ ID NO:37. In another embodiment, the second antigen binding domain comprises a VH domain having an amino acid sequence that is about 98%, identical to the amino acid sequence of SEQ ID NO:36 and a VL domain having an amino acid sequence that is about 98% identical to the amino acid sequence of SEQ ID NO:37. In another embodiment, the second antigen binding domain comprises a VH domain having an amino acid sequence that is about 99%, identical to the amino acid sequence of SEQ ID NO:36 and a VL domain having an amino acid sequence that is about 99% identical to the amino acid sequence of SEQ ID NO:37. In another embodiment, the second antigen binding domain comprises a VH domain having an amino acid sequence that is about 100%, identical to the amino acid sequence of SEQ ID NO:36 and a VL domain having an amino acid sequence that is about 100% identical to the amino acid sequence of SEQ ID NO:37.

In one embodiment, the bispecific anti-CD20×anti-CD3 antibody comprises a first antigen binding domain that binds to CD3 and a second antigen binding domain that binds to CD20, wherein the first antigen binding domain comprises a VH domain having an amino acid sequence that is about 90%, 95%, 98%, 99%, or 100% identical to the amino acid sequence of SEQ ID NO:34 and a VL domain having an amino acid sequence that is about 90%, 95%, 98%, 99%, or 100% identical to the amino acid sequence of SEQ ID NO:35, and the second antigen binding domain comprises a VH domain having an amino acid sequence that is about 90%, 95%, 98%, 99%, or 100% identical to the amino acid sequence of SEQ ID NO:36 and a VL domain having an amino acid sequence that is about 90%, 95%, 98%, 99%, or 100% identical to the amino acid sequence of SEQ ID NO:37. In one embodiment, the first antigen binding domain comprises a VH domain having an amino acid sequence that is about 90%, identical to the amino acid sequence of SEQ ID NO:34 and a VL domain having an amino acid sequence that is about 90% identical to the amino acid sequence of SEQ ID NO:35, and the second antigen binding domain comprises a VH domain having an amino acid sequence that is about 90%, identical to the amino acid sequence of SEQ ID NO:36 and a VL domain having an amino acid sequence that is about 90% identical to the amino acid sequence of SEQ ID NO:37. In another embodiment, the first antigen binding domain comprises a VH domain having an amino acid sequence that is about 95%, identical to the amino acid sequence of SEQ ID NO:34 and a VL domain having an amino acid sequence that is about 95% identical to the amino acid sequence of SEQ ID NO:35, and the second antigen binding domain comprises a VH domain having an amino acid sequence that is about 95%, identical to the amino acid sequence of SEQ ID NO:36 and a VL domain having an amino acid sequence that is about 95% identical to the amino acid sequence of SEQ ID NO:37. In another embodiment, the first antigen binding domain comprises a VH domain having an amino acid sequence that is about 98%, identical to the amino acid sequence of SEQ ID NO:34 and a VL domain having an amino acid sequence that is about 98% identical to the amino acid sequence of SEQ ID NO:35, and the second antigen binding domain comprises a VH domain having an amino acid sequence that is about 98%, identical to the amino acid sequence of SEQ ID NO:36 and a VL domain having an amino acid sequence that is about 98% identical to the amino acid sequence of SEQ ID NO:37. In another embodiment, the first antigen binding domain comprises a VH domain having an amino acid sequence that is about 99%, identical to the amino acid sequence of SEQ ID NO:34 and a VL domain having an amino acid sequence that is about 99% identical to the amino acid sequence of SEQ ID NO:35, and the second antigen binding domain comprises a VH domain having an amino acid sequence that is about 99%, identical to the amino acid sequence of SEQ ID NO:36 and a VL domain having an amino acid sequence that is about 99% identical to the amino acid sequence of SEQ ID NO:37. In another embodiment, the first antigen binding domain comprises a VH domain having an amino acid sequence that is about 100%, identical to the amino acid sequence of SEQ ID NO:34 and a VL domain having an amino acid sequence that is about 100% identical to the amino acid sequence of SEQ ID NO:35, and the second antigen binding domain comprises a VH domain having an amino acid sequence that is about 100%, identical to the amino acid sequence of SEQ ID NO:36 and a VL domain having an amino acid sequence that is about 100% identical to the amino acid sequence of SEQ ID NO:37.

In a specific embodiment, the bispecific anti-CD20×anti-CD3 antibody is plamotamab (XmAb® 13676). In one embodiment, the bispecific anti-CD20×anti-CD3 antibody is a biosimilar of plamotamab. In one embodiment, the bispecific anti-CD20×anti-CD3 antibody is a bioequivalent of plamotamab. In one embodiment, the bispecific anti-CD20× anti-CD3 antibody comprises an amino acid sequence of a VH CDR1, VH CDR2, and VH CDR3 of the CD3 antigen binding domain of plamotamab. In one embodiment, the bispecific anti-CD20×anti-CD3 antibody comprises an amino acid sequence of a VL CDR1, VL CDR2, and VL CDR3 of the CD3 antigen binding domain of plamotamab. In one embodiment, the bispecific anti-CD20×anti-CD3 antibody comprises an amino acid sequence of a VH CDR1, VH CDR2, and VH CDR3 of the CD20 antigen binding domain of plamotamab. In one embodiment, the bispecific anti-CD20×anti-CD3 antibody comprises an amino acid sequence of a VL CDR1, VL CDR2, and VL CDR3 of the CD20 antigen binding domain of plamotamab. In one embodiment, the bispecific anti-CD20×anti-CD3 antibody comprises an amino acid sequence of a VH CDR1, VH CDR2, and VH CDR3 of the CD3 antigen binding domain of plamotamab, and a VL CDR1, VL CDR2, and VL CDR3 of the CD3 antigen binding domain of plamotamab. In one embodiment, the bispecific anti-CD20×anti-CD3 antibody comprises an amino acid sequence of a VH CDR1, VH CDR2, and VH CDR3 of the CD20 antigen binding domain of plamotamab, and a VL CDR1, VL CDR2, and VL CDR3 of the CD20 antigen binding domain of plamotamab. In one embodiment, the bispecific anti-CD20×anti-CD3 antibody comprises an amino acid sequence of a VH CDR1, VH CDR2, and VH CDR3 of the CD3 antigen binding domain of plamotamab, a VL CDR1, VL CDR2, and VL CDR3 of the CD3 antigen binding domain of plamotamab, a VH CDR1, VH CDR2, and VH CDR3 of the CD20 antigen binding domain of plamotamab, and a VL CDR1, VL CDR2, and VL CDR3 of the CD20 antigen binding domain of plamotamab. In one embodiment, the bispecific anti-CD20× anti-CD3 antibody comprises an amino acid sequence of a VH of the CD3 antigen binding domain of plamotamab. In one embodiment, the bispecific anti-CD20×anti-CD3 antibody comprises an amino acid sequence of a VL of the CD3 antigen binding domain of plamotamab. In one embodiment, the bispecific anti-CD20×anti-CD3 antibody comprises an amino acid sequence of a VH of the CD20 antigen binding domain of plamotamab. In one embodiment, the bispecific anti-CD20×anti-CD3 antibody comprises an amino acid sequence of a VL of the CD20 antigen binding domain of plamotamab. In one embodiment, the bispecific anti-CD20× anti-CD3 antibody comprises an amino acid sequence of a VH of the CD3 antigen binding domain of plamotamab, and a VL of the CD3 antigen binding domain of plamotamab. In one embodiment, the bispecific anti-CD20×anti-CD3 antibody comprises an amino acid sequence of a VH of the CD20 antigen binding domain of plamotamab, and a VL of the CD20 antigen binding domain of plamotamab. In one embodiment, the bispecific anti-CD20×anti-CD3 antibody comprises an amino acid sequence of a VH of the CD3 antigen binding domain of plamotamab, a VL of the CD3 antigen binding domain of plamotamab, a VH of the CD20 antigen binding domain of plamotamab, and a VL of the CD20 antigen binding domain of plamotamab. Exemplary CD3 and CD20 antigen binding domains of plamotamab are provided in Table 1. In one embodiment, the bispecific anti-CD20×anti-CD3 antibody comprises a first monomer having the amino acid sequence of SEQ ID NO:1. In another embodiment, the bispecific anti-CD20×anti-CD3 antibody comprises a second monomer having the amino acid sequence of SEQ ID NO:2. In another embodiment, the bispecific anti-CD20×anti-CD3 antibody comprises a third monomer having the amino acid sequence of SEQ ID NO:3. In another embodiment, the bispecific anti-CD20×anti-CD3 antibody comprises a first monomer having the amino acid sequence of SEQ ID NO:1, a second monomer having the amino acid sequence of SEQ ID NO:2, and a third having the amino acid sequence of SEQ ID NO:3.

In another embodiment, the bispecific anti-CD20×anti-CD3 antibody is mosunetuzumab. In one embodiment, the bispecific anti-CD20×anti-CD3 antibody is a biosimilar of mosunetuzumab. In one embodiment, the bispecific anti-CD20×anti-CD3 antibody is a bioequivalent of mosunetuzumab. In one embodiment, the bispecific anti-CD20×anti-CD3 antibody comprises an amino acid sequence of a VH CDR1, VH CDR2, and VH CDR3 of the CD3 antigen binding domain of mosunetuzumab. In one embodiment, the bispecific anti-CD20×anti-CD3 antibody comprises an amino acid sequence of a VL CDR1, VL CDR2, and VL CDR3 of the CD3 antigen binding domain of mosunetuzumab. In one embodiment, the bispecific anti-CD20×anti-CD3 antibody comprises an amino acid sequence of a VH CDR1, VH CDR2, and VH CDR3 of the CD20 antigen binding domain of mosunetuzumab. In one embodiment, the bispecific anti-CD20×anti-CD3 antibody comprises an amino acid sequence of a VL CDR1, VL CDR2, and VL CDR3 of the CD20 antigen binding domain of mosunetuzumab. In one embodiment, the bispecific anti-CD20×anti-CD3 antibody comprises an amino acid sequence of a VH CDR1, VH CDR2, and VH CDR3 of the CD3 antigen binding domain of mosunetuzumab, and a VL CDR1, VL CDR2, and VL CDR3 of the CD3 antigen binding domain of mosunetuzumab. In one embodiment, the bispecific anti-CD20×anti-CD3 antibody comprises an amino acid sequence of a VH CDR1, VH CDR2, and VH CDR3 of the CD20 antigen binding domain of mosunetuzumab, and a VL CDR1, VL CDR2, and VL CDR3 of the CD20 antigen binding domain of mosunetuzumab. In one embodiment, the bispecific anti-CD20×anti-CD3 antibody comprises an amino acid sequence of a VH CDR1, VH CDR2, and VH CDR3 of the CD3 antigen binding domain of mosunetuzumab, a VL CDR1, VL CDR2, and VL CDR3 of the CD3 antigen binding domain of mosunetuzumab, a VH CDR1, VH CDR2, and VH CDR3 of the CD20 antigen binding domain of mosunetuzumab, and a VL CDR1, VL CDR2, and VL CDR3 of the CD20 antigen binding domain of mosunetuzumab. In one embodiment, the bispecific anti-CD20×anti-CD3 antibody comprises an amino acid sequence of a VH of the CD3 antigen binding domain of mosunetuzumab. In one embodiment, the bispecific anti-CD20×anti-CD3 antibody comprises an amino acid sequence of a VL of the CD3 antigen binding domain of mosunetuzumab. In one embodiment, the bispecific anti-CD20×anti-CD3 antibody comprises an amino acid sequence of a VH of the CD20 antigen binding domain of mosunetuzumab. In one embodiment, the bispecific anti-CD20×anti-CD3 antibody comprises an amino acid sequence of a VL of the CD20 antigen binding domain of mosunetuzumab. In one embodiment, the bispecific anti-CD20×anti-CD3 antibody comprises an amino acid sequence of a VH of the CD3 antigen binding domain of mosunetuzumab, and a VL of the CD3 antigen binding domain of mosunetuzumab. In one embodiment, the bispecific anti-CD20×anti-CD3 antibody comprises an amino acid sequence of a VH of the CD20 antigen binding domain of mosunetuzumab, and a VL of the CD20 antigen binding domain of mosunetuzumab. In one embodiment, the bispecific anti-CD20×anti-CD3 antibody comprises an amino acid sequence of a VH of the CD3 antigen binding domain of mosunetuzumab, a VL of the CD3 antigen binding domain of mosunetuzumab, a VH of the CD20 antigen binding domain of mosunetuzumab, and a VL of the CD20 antigen binding domain of mosunetuzumab. Exemplary CD3 and CD20 antigen binding domains of mosunetuzumab are provided in Table 1. In one embodiment, the CD3 antigen binding domain of the bispecific anti-CD20×anti-CD3 antibody comprises the amino acid sequence of SEQ ID NO:38 and/or SEQ ID NO:39. In one embodiment, the CD20 antigen binding domain of the bispecific anti-CD20×anti-CD3 antibody comprises the amino acid sequence of SEQ ID NO:40 and/or SEQ ID NO:41. In one embodiment, the CD3 antigen binding domain of the bispecific anti-CD20×anti-CD3 antibody comprises the amino acid sequence of SEQ ID NO:38 and/or SEQ ID NO:39, and the CD20 antigen binding domain of the bispecific anti-CD20×anti-CD3 antibody comprises the amino acid sequence of SEQ ID NO:40 and/or SEQ ID NO:41.

In another embodiment, the bispecific anti-CD20×anti-CD3 antibody is epcoritamab. In one embodiment, the bispecific anti-CD20×anti-CD3 antibody is a biosimilar of epcoritamab. In one embodiment, the bispecific anti-CD20×anti-CD3 antibody is a bioequivalent of epcoritamab. In one embodiment, the bispecific anti-CD20×anti-CD3 antibody comprises an amino acid sequence of a VH CDR1, VH CDR2, and VH CDR3 of the CD3 antigen binding domain of epcoritamab. In one embodiment, the bispecific anti-CD20×anti-CD3 antibody comprises an amino acid sequence of a VL CDR1, VL CDR2, and VL CDR3 of the CD3 antigen binding domain of epcoritamab. In one embodiment, the bispecific anti-CD20×anti-CD3 antibody comprises an amino acid sequence of a VH CDR1, VH CDR2, and VH CDR3 of the CD20 antigen binding domain of epcoritamab. In one embodiment, the bispecific anti-CD20×anti-CD3 antibody comprises an amino acid sequence of a VL CDR1, VL CDR2, and VL CDR3 of the CD20 antigen binding domain of epcoritamab. In one embodiment, the bispecific anti-CD20×anti-CD3 antibody comprises an amino acid sequence of a VH CDR1, VH CDR2, and VH CDR3 of the CD3 antigen binding domain of epcoritamab, and a VL CDR1, VL CDR2, and VL CDR3 of the CD3 antigen binding domain of epcoritamab. In one embodiment, the bispecific anti-CD20×anti-CD3 antibody comprises an amino acid sequence of a VH CDR1, VH CDR2, and VH CDR3 of the CD20 antigen binding domain of epcoritamab, and a VL CDR1, VL CDR2, and VL CDR3 of the CD20 antigen binding domain of epcoritamab. In one embodiment, the bispecific anti-CD20×anti-CD3 antibody comprises an amino acid sequence of a VH CDR1, VH CDR2, and VH CDR3 of the CD3 antigen binding domain of epcoritamab, a VL CDR1, VL CDR2, and VL CDR3 of the CD3 antigen binding domain of epcoritamab, a VH CDR1, VH CDR2, and VH CDR3 of the CD20 antigen binding domain of epcoritamab, and a VL CDR1, VL CDR2, and VL CDR3 of the CD20 antigen binding domain of epcoritamab. In one embodiment, the bispecific anti-CD20×anti-CD3 antibody comprises an amino acid sequence of a VH of the CD3 antigen binding domain of epcoritamab. In one embodiment, the bispecific anti-CD20×anti-CD3 antibody comprises an amino acid sequence of a VL of the CD3 antigen binding domain of epcoritamab. In one embodiment, the bispecific anti-CD20×anti-CD3 antibody comprises an amino acid sequence of a VH of the CD20 antigen binding domain of epcoritamab. In one embodiment, the bispecific anti-CD20×anti-CD3 antibody comprises an amino acid sequence of a VL of the CD20 antigen binding domain of epcoritamab. In one embodiment, the bispecific anti-CD20×anti-CD3 antibody comprises an amino acid sequence of a VH of the CD3 antigen binding domain of epcoritamab, and a VL of the CD3 antigen binding domain of epcoritamab. In one embodiment, the bispecific anti-CD20×anti-CD3 antibody comprises an amino acid sequence of a VH of the CD20 antigen binding domain of epcoritamab, and a VL of the CD20 antigen binding domain of epcoritamab. In one embodiment, the bispecific anti-CD20×anti-CD3 antibody comprises an amino acid sequence of a VH of the CD3 antigen binding domain of epcoritamab, a VL of the CD3 antigen binding domain of epcoritamab, a VH of the CD20 antigen binding domain of epcoritamab, and a VL of the CD20 antigen binding domain of epcoritamab. Exemplary CD3 and CD20 antigen binding domains of epcoritamab are provided in Table 1. In one embodiment, the CD3 antigen binding domain of the bispecific anti-CD20×anti-CD3 antibody comprises the amino acid sequence of SEQ ID NO:42 and/or SEQ ID NO:43. In one embodiment, the CD20 antigen binding domain of the bispecific anti-CD20×anti-CD3 antibody comprises the amino acid sequence of SEQ ID NO:44 and/or SEQ ID NO:45. In one embodiment, the CD3 antigen binding domain of the bispecific anti-CD20×anti-CD3 antibody comprises the amino acid sequence of SEQ ID NO:42 and/or SEQ ID NO:43, and the CD20 antigen binding domain of the bispecific anti-CD20×anti-CD3 antibody comprises the amino acid sequence of SEQ ID NO:44 and/or SEQ ID NO:45.

In another embodiment, the bispecific anti-CD20×anti-CD3 antibody is odronextamab. In one embodiment, the bispecific anti-CD20×anti-CD3 antibody is a biosimilar of odronextamab. In one embodiment, the bispecific anti-CD20×anti-CD3 antibody is a bioequivalent of odronextamab. In one embodiment, the bispecific anti-CD20×anti-CD3 antibody comprises an amino acid sequence of a VH CDR1, VH CDR2, and VH CDR3 of the CD3 antigen binding domain of odronextamab. In one embodiment, the bispecific anti-CD20×anti-CD3 antibody comprises an amino acid sequence of a VL CDR1, VL CDR2, and VL CDR3 of the CD3 antigen binding domain of odronextamab. In one embodiment, the bispecific anti-CD20×anti-CD3 antibody comprises an amino acid sequence of a VH CDR1, VH CDR2, and VH CDR3 of the CD20 antigen binding domain of odronextamab. In one embodiment, the bispecific anti-CD20×anti-CD3 antibody comprises an amino acid sequence of a VL CDR1, VL CDR2, and VL CDR3 of the CD20 antigen binding domain of odronextamab. In one embodiment, the bispecific anti-CD20×anti-CD3 antibody comprises an amino acid sequence of a VH CDR1, VH CDR2, and VH CDR3 of the CD3 antigen binding domain of odronextamab, and a VL CDR1, VL CDR2, and VL CDR3 of the CD3 antigen binding domain of odronextamab. In one embodiment, the bispecific anti-CD20×anti-CD3 antibody comprises an amino acid sequence of a VH CDR1, VH CDR2, and VH CDR3 of the CD20 antigen binding domain of odronextamab, and a VL CDR1, VL CDR2, and VL CDR3 of the CD20 antigen binding domain of odronextamab. In one embodiment, the bispecific anti-CD20×anti-CD3 antibody comprises an amino acid sequence of a VH CDR1, VH CDR2, and VH CDR3 of the CD3 antigen binding domain of odronextamab, a VL CDR1, VL CDR2, and VL CDR3 of the CD3 antigen binding domain of odronextamab, a VH CDR1, VH CDR2, and VH CDR3 of the CD20 antigen binding domain of odronextamab, and a VL CDR1, VL CDR2, and VL CDR3 of the CD20 antigen binding domain of odronextamab. In one embodiment, the bispecific anti-CD20×anti-CD3 antibody comprises an amino acid sequence of a VH of the CD3 antigen binding domain of odronextamab. In one embodiment, the bispecific anti-CD20×anti-CD3 antibody comprises an amino acid sequence of a VL of the CD3 antigen binding domain of odronextamab. In one embodiment, the bispecific anti-CD20×anti-CD3 antibody comprises an amino acid sequence of a VH of the CD20 antigen binding domain of odronextamab. In one embodiment, the bispecific anti-CD20×anti-CD3 antibody comprises an amino acid sequence of a VL of the CD20 antigen binding domain of odronextamab. In one embodiment, the bispecific anti-CD20×anti-CD3 antibody comprises an amino acid sequence of a VH of the CD3 antigen binding domain of odronextamab, and a VL of the CD3 antigen binding domain of odronextamab. In one embodiment, the bispecific anti-CD20×anti-CD3 antibody comprises an amino acid sequence of a VH of the CD20 antigen binding domain of odronextamab, and a VL of the CD20 antigen binding domain of odronextamab. In one embodiment, the bispecific anti-CD20×anti-CD3 antibody comprises an amino acid sequence of a VH of the CD3 antigen binding domain of odronextamab, a VL of the CD3 antigen binding domain of odronextamab, a VH of the CD20 antigen binding domain of odronextamab, and a VL of the CD20 antigen binding domain of odronextamab. Exemplary CD3 and CD20 antigen binding domains of odronextamab are provided in Table 1. In one embodiment, the bispecific anti-CD20×anti-CD3 antibody comprises a first monomer having the amino acid sequence of SEQ ID NO:46. In another embodiment, the bispecific anti-CD20×anti-CD3 antibody comprises a second monomer having the amino acid sequence of SEQ ID NO:47. In another embodiment, the bispecific anti-CD20×anti-CD3 antibody comprises a third monomer having the amino acid sequence of SEQ ID NO:48. In another embodiment, the bispecific anti-CD20×anti-CD3 antibody comprises a first monomer having the amino acid sequence of SEQ ID NO:46, a second monomer having the amino acid sequence of SEQ ID NO:47, and a third having the amino acid sequence of SEQ ID NO:48.

In another embodiment, the bispecific anti-CD20×anti-CD3 antibody is glofitamab. In one embodiment, the bispecific anti-CD20×anti-CD3 antibody is a biosimilar of glofitamab. In one embodiment, the bispecific anti-CD20×anti-CD3 antibody is a bioequivalent of glofitamab. In one embodiment, the bispecific anti-CD20×anti-CD3 antibody comprises an amino acid sequence of a VH CDR1, VH CDR2, and VH CDR3 of the CD3 antigen binding domain of glofitamab. In one embodiment, the bispecific anti-CD20×anti-CD3 antibody comprises an amino acid sequence of a VL CDR1, VL CDR2, and VL CDR3 of the CD3 antigen binding domain of glofitamab. In one embodiment, the bispecific anti-CD20×anti-CD3 antibody comprises an amino acid sequence of a VH CDR1, VH CDR2, and VH CDR3 of the CD20 antigen binding domain of glofitamab. In one embodiment, the bispecific anti-CD20×anti-CD3 antibody comprises an amino acid sequence of a VL CDR1, VL CDR2, and VL CDR3 of the CD20 antigen binding domain of glofitamab. In one embodiment, the bispecific anti-CD20×anti-CD3 antibody comprises an amino acid sequence of a VH CDR1, VH CDR2, and VH CDR3 of the CD3 antigen binding domain of glofitamab, and a VL CDR1, VL CDR2, and VL CDR3 of the CD3 antigen binding domain of glofitamab. In one embodiment, the bispecific anti-CD20×anti-CD3 antibody comprises an amino acid sequence of a VH CDR1, VH CDR2, and VH CDR3 of the CD20 antigen binding domain of glofitamab, and a VL CDR1, VL CDR2, and VL CDR3 of the CD20 antigen binding domain of glofitamab. In one embodiment, the bispecific anti-CD20×anti-CD3 antibody comprises an amino acid sequence of a VH CDR1, VH CDR2, and VH CDR3 of the CD3 antigen binding domain of glofitamab, a VL CDR1, VL CDR2, and VL CDR3 of the CD3 antigen binding domain of glofitamab, a VH CDR1, VH CDR2, and VH CDR3 of the CD20 antigen binding domain of glofitamab, and a VL CDR1, VL CDR2, and VL CDR3 of the CD20 antigen binding domain of glofitamab. In one embodiment, the bispecific anti-CD20×anti-CD3 antibody comprises an amino acid sequence of a VH of the CD3 antigen binding domain of glofitamab. In one embodiment, the bispecific anti-CD20×anti-CD3 antibody comprises an amino acid sequence of a VL of the CD3 antigen binding domain of glofitamab. In one embodiment, the bispecific anti-CD20×anti-CD3 antibody comprises an amino acid sequence of a VH of the CD20 antigen binding domain of glofitamab. In one embodiment, the bispecific anti-CD20×anti-CD3 antibody comprises an amino acid sequence of a VL of the CD20 antigen binding domain of glofitamab. In one embodiment, the bispecific anti-CD20×anti-CD3 antibody comprises an amino acid sequence of a VH of the CD3 antigen binding domain of glofitamab, and a VL of the CD3 antigen binding domain of glofitamab. In one embodiment, the bispecific anti-CD20×anti-CD3 antibody comprises an amino acid sequence of a VH of the CD20 antigen binding domain of glofitamab, and a VL of the CD20 antigen binding domain of glofitamab. In one embodiment, the bispecific anti-CD20×anti-CD3 antibody comprises an amino acid sequence of a VH of the CD3 antigen binding domain of glofitamab, a VL of the CD3 antigen binding domain of glofitamab, a VH of the CD20 antigen binding domain of glofitamab, and a VL of the CD20 antigen binding domain of glofitamab. Exemplary CD3 and CD20 antigen binding domains of glofitamab are provided in Table 1. In one embodiment, the CD3 antigen binding domain of the bispecific anti-CD20×anti-CD3 antibody comprises the amino acid sequence of SEQ ID NO:49 and/or SEQ ID NO:50. In one embodiment, the CD20 antigen binding domain of the bispecific anti-CD20×anti-CD3 antibody comprises the amino acid sequence of SEQ ID NO:51 and/or SEQ ID NO:52. In one embodiment, the CD3 antigen binding domain of the bispecific anti-CD20×anti-CD3 antibody comprises the amino acid sequence of SEQ ID NO:49 and/or SEQ ID NO:50, and the CD20 antigen binding domain of the bispecific anti-CD20×anti-CD3 antibody comprises the amino acid sequence of SEQ ID NO:51 and/or SEQ ID NO:52.

In another embodiment, the bispecific anti-CD20×anti-CD3 antibody is XENP13677. In one embodiment, the bispecific anti-CD20×anti-CD3 antibody is a biosimilar of XENP13677. In one embodiment, the bispecific anti-CD20×anti-CD3 antibody is a bioequivalent of XENP13677. In one embodiment, the bispecific anti-CD20×anti-CD3 antibody comprises an amino acid sequence of a VH CDR1, VH CDR2, and VH CDR3 of the CD3 antigen binding domain of XENP13677. In one embodiment, the bispecific anti-CD20×anti-CD3 antibody comprises an amino acid sequence of a VL CDR1, VL CDR2, and VL CDR3 of the CD3 antigen binding domain of XENP13677. In one embodiment, the bispecific anti-CD20×anti-CD3 antibody comprises an amino acid sequence of a VH CDR1, VH CDR2, and VH CDR3 of the CD20 antigen binding domain of XENP13677. In one embodiment, the bispecific anti-CD20×anti-CD3 antibody comprises an amino acid sequence of a VL CDR1, VL CDR2, and VL CDR3 of the CD20 antigen binding domain of XENP13677. In one embodiment, the bispecific anti-CD20×anti-CD3 antibody comprises an amino acid sequence of a VH CDR1, VH CDR2, and VH CDR3 of the CD3 antigen binding domain of XENP13677, and a VL CDR1, VL CDR2, and VL CDR3 of the CD3 antigen binding domain of XENP13677. In one embodiment, the bispecific anti-CD20×anti-CD3 antibody comprises an amino acid sequence of a VH CDR1, VH CDR2, and VH CDR3 of the CD20 antigen binding domain of XENP13677, and a VL CDR1, VL CDR2, and VL CDR3 of the CD20 antigen binding domain of XENP13677. In one embodiment, the bispecific anti-CD20×anti-CD3 antibody comprises an amino acid sequence of a VH CDR1, VH CDR2, and VH CDR3 of the CD3 antigen binding domain of XENP13677, a VL CDR1, VL CDR2, and VL CDR3 of the CD3 antigen binding domain of XENP13677, a VH CDR1, VH CDR2, and VH CDR3 of the CD20 antigen binding domain of XENP13677, and a VL CDR1, VL CDR2, and VL CDR3 of the CD20 antigen binding domain of XENP13677. In one embodiment, the bispecific anti-CD20×anti-CD3 antibody comprises an amino acid sequence of a VH of the CD3 antigen binding domain of XENP13677. In one embodiment, the bispecific anti-CD20×anti-CD3 antibody comprises an amino acid sequence of a VL of the CD3 antigen binding domain of XENP13677. In one embodiment, the bispecific anti-CD20×anti-CD3 antibody comprises an amino acid sequence of a VH of the CD20 antigen binding domain of XENP13677. In one embodiment, the bispecific anti-CD20×anti-CD3 antibody comprises an amino acid sequence of a VL of the CD20 antigen binding domain of XENP13677. In one embodiment, the bispecific anti-CD20×anti-CD3 antibody comprises an amino acid sequence of a VH of the CD3 antigen binding domain of XENP13677, and a VL of the CD3 antigen binding domain of XENP13677. In one embodiment, the bispecific anti-CD20×anti-CD3 antibody comprises an amino acid sequence of a VH of the CD20 antigen binding domain of XENP13677, and a VL of the CD20 antigen binding domain of XENP13677. In one embodiment, the bispecific anti-CD20×anti-CD3 antibody comprises an amino acid sequence of a VH of the CD3 antigen binding domain of XENP13677, a VL of the CD3 antigen binding domain of XENP13677, a VH of the CD20 antigen binding domain of XENP13677, and a VL of the CD20 antigen binding domain of XENP13677. Exemplary CD3 and CD20 antigen binding domains of XENP13677 are provided in Table 1. In one embodiment, the bispecific anti-CD20×anti-CD3 antibody comprises a first monomer having the amino acid sequence of SEQ ID NO:4. In another embodiment, the bispecific anti-CD20×anti-CD3 antibody comprises a second monomer having the amino acid sequence of SEQ ID NO:5. In another embodiment, the bispecific anti-CD20×anti-CD3 antibody comprises a third monomer having the amino acid sequence of SEQ ID NO:6. In another embodiment, the bispecific anti-CD20×anti-CD3 antibody comprises a first monomer having the amino acid sequence of SEQ ID NO:4, a second monomer having the amino acid sequence of SEQ ID NO:5, and a third having the amino acid sequence of SEQ ID NO:6.

In another embodiment, the bispecific anti-CD20×anti-CD3 antibody is XENP14388. In one embodiment, the bispecific anti-CD20×anti-CD3 antibody is a biosimilar of XENP14388. In one embodiment, the bispecific anti-CD20×anti-CD3 antibody is a bioequivalent of XENP14388. In one embodiment, the bispecific anti-CD20×anti-CD3 antibody comprises an amino acid sequence of a VH CDR1, VH CDR2, and VH CDR3 of the CD3 antigen binding domain of XENP14388. In one embodiment, the bispecific anti-CD20×anti-CD3 antibody comprises an amino acid sequence of a VL CDR1, VL CDR2, and VL CDR3 of the CD3 antigen binding domain of XENP14388. In one embodiment, the bispecific anti-CD20×anti-CD3 antibody comprises an amino acid sequence of a VH CDR1, VH CDR2, and VH CDR3 of the CD20 antigen binding domain of XENP14388. In one embodiment, the bispecific anti-CD20×anti-CD3 antibody comprises an amino acid sequence of a VL CDR1, VL CDR2, and VL CDR3 of the CD20 antigen binding domain of XENP14388. In one embodiment, the bispecific anti-CD20×anti-CD3 antibody comprises an amino acid sequence of a VH CDR1, VH CDR2, and VH CDR3 of the CD3 antigen binding domain of XENP14388, and a VL CDR1, VL CDR2, and VL CDR3 of the CD3 antigen binding domain of XENP14388. In one embodiment, the bispecific anti-CD20×anti-CD3 antibody comprises an amino acid sequence of a VH CDR1, VH CDR2, and VH CDR3 of the CD20 antigen binding domain of XENP14388, and a VL CDR1, VL CDR2, and VL CDR3 of the CD20 antigen binding domain of XENP14388. In one embodiment, the bispecific anti-CD20×anti-CD3 antibody comprises an amino acid sequence of a VH CDR1, VH CDR2, and VH CDR3 of the CD3 antigen binding domain of XENP14388, a VL CDR1, VL CDR2, and VL CDR3 of the CD3 antigen binding domain of XENP14388, a VH CDR1, VH CDR2, and VH CDR3 of the CD20 antigen binding domain of XENP14388, and a VL CDR1, VL CDR2, and VL CDR3 of the CD20 antigen binding domain of XENP14388. In one embodiment, the bispecific anti-CD20×anti-CD3 antibody comprises an amino acid sequence of a VH of the CD3 antigen binding domain of XENP14388. In one embodiment, the bispecific anti-CD20×anti-CD3 antibody comprises an amino acid sequence of a VL of the CD3 antigen binding domain of XENP14388. In one embodiment, the bispecific anti-CD20×anti-CD3 antibody comprises an amino acid sequence of a VH of the CD20 antigen binding domain of XENP14388. In one embodiment, the bispecific anti-CD20×anti-CD3 antibody comprises an amino acid sequence of a VL of the CD20 antigen binding domain of XENP14388. In one embodiment, the bispecific anti-CD20×anti-CD3 antibody comprises an amino acid sequence of a VH of the CD3 antigen binding domain of XENP14388, and a VL of the CD3 antigen binding domain of XENP14388. In one embodiment, the bispecific anti-CD20×anti-CD3 antibody comprises an amino acid sequence of a VH of the CD20 antigen binding domain of XENP14388, and a VL of the CD20 antigen binding domain of XENP14388. In one embodiment, the bispecific anti-CD20×anti-CD3 antibody comprises an amino acid sequence of a VH of the CD3 antigen binding domain of XENP14388, a VL of the CD3 antigen binding domain of XENP14388, a VH of the CD20 antigen binding domain of XENP14388, and a VL of the CD20 antigen binding domain of XENP14388. Exemplary CD3 and CD20 antigen binding domains of XENP14388 are provided in Table 1. In one embodiment, the bispecific anti-CD20×anti-CD3 antibody comprises a first monomer having the amino acid sequence of SEQ ID NO:7. In another embodiment, the bispecific anti-CD20×anti-CD3 antibody comprises a second monomer having the amino acid sequence of SEQ ID NO:8. In another embodiment, the bispecific anti-CD20×anti-CD3 antibody comprises a third monomer having the amino acid sequence of SEQ ID NO:9. In another embodiment, the bispecific anti-CD20×anti-CD3 antibody comprises a first monomer having the amino acid sequence of SEQ ID NO:7, a second monomer having the amino acid sequence of SEQ ID NO:8, and a third having the amino acid sequence of SEQ ID NO:9.

In another embodiment, the bispecific anti-CD20×anti-CD3 antibody is XENP14389. In one embodiment, the bispecific anti-CD20×anti-CD3 antibody is a biosimilar of XENP14389. In one embodiment, the bispecific anti-CD20×anti-CD3 antibody is a bioequivalent of XENP14389. In one embodiment, the bispecific anti-CD20×anti-CD3 antibody comprises an amino acid sequence of a VH CDR1, VH CDR2, and VH CDR3 of the CD3 antigen binding domain of XENP14389. In one embodiment, the bispecific anti-CD20×anti-CD3 antibody comprises an amino acid sequence of a VL CDR1, VL CDR2, and VL CDR3 of the CD3 antigen binding domain of XENP14389. In one embodiment, the bispecific anti-CD20×anti-CD3 antibody comprises an amino acid sequence of a VH CDR1, VH CDR2, and VH CDR3 of the CD20 antigen binding domain of XENP14389. In one embodiment, the bispecific anti-CD20×anti-CD3 antibody comprises an amino acid sequence of a VL CDR1, VL CDR2, and VL CDR3 of the CD20 antigen binding domain of XENP14389. In one embodiment, the bispecific anti-CD20×anti-CD3 antibody comprises an amino acid sequence of a VH CDR1, VH CDR2, and VH CDR3 of the CD3 antigen binding domain of XENP14389, and a VL CDR1, VL CDR2, and VL CDR3 of the CD3 antigen binding domain of XENP14389. In one embodiment, the bispecific anti-CD20×anti-CD3 antibody comprises an amino acid sequence of a VH CDR1, VH CDR2, and VH CDR3 of the CD20 antigen binding domain of XENP14389, and a VL CDR1, VL CDR2, and VL CDR3 of the CD20 antigen binding domain of XENP14389. In one embodiment, the bispecific anti-CD20×anti-CD3 antibody comprises an amino acid sequence of a VH CDR1, VH CDR2, and VH CDR3 of the CD3 antigen binding domain of XENP14389, a VL CDR1, VL CDR2, and VL CDR3 of the CD3 antigen binding domain of XENP14389, a VH CDR1, VH CDR2, and VH CDR3 of the CD20 antigen binding domain of XENP14389, and a VL CDR1, VL CDR2, and VL CDR3 of the CD20 antigen binding domain of XENP14389. In one embodiment, the bispecific anti-CD20×anti-CD3 antibody comprises an amino acid sequence of a VH of the CD3 antigen binding domain of XENP14389. In one embodiment, the bispecific anti-CD20×anti-CD3 antibody comprises an amino acid sequence of a VL of the CD3 antigen binding domain of XENP14389. In one embodiment, the bispecific anti-CD20×anti-CD3 antibody comprises an amino acid sequence of a VH of the CD20 antigen binding domain of XENP14389. In one embodiment, the bispecific anti-CD20×anti-CD3 antibody comprises an amino acid sequence of a VL of the CD20 antigen binding domain of XENP14389. In one embodiment, the bispecific anti-CD20×anti-CD3 antibody comprises an amino acid sequence of a VH of the CD3 antigen binding domain of XENP14389, and a VL of the CD3 antigen binding domain of XENP14389. In one embodiment, the bispecific anti-CD20×anti-CD3 antibody comprises an amino acid sequence of a VH of the CD20 antigen binding domain of XENP14389, and a VL of the CD20 antigen binding domain of XENP14389. In one embodiment, the bispecific anti-CD20×anti-CD3 antibody comprises an amino acid sequence of a VH of the CD3 antigen binding domain of XENP14389, a VL of the CD3 antigen binding domain of XENP14389, a VH of the CD20 antigen binding domain of XENP14389, and a VL of the CD20 antigen binding domain of XENP14389. Exemplary CD3 and CD20 antigen binding domains of XENP14389 are provided in Table 1. In one embodiment, the bispecific anti-CD20×anti-CD3 antibody comprises a first monomer having the amino acid sequence of SEQ ID NO:10. In another embodiment, the bispecific anti-CD20×anti-CD3 antibody comprises a second monomer having the amino acid sequence of SEQ ID NO:11. In another embodiment, the bispecific anti-CD20×anti-CD3 antibody comprises a third monomer having the amino acid sequence of SEQ ID NO:12. In another embodiment, the bispecific anti-CD20×anti-CD3 antibody comprises a first monomer having the amino acid sequence of SEQ ID NO:10, a second monomer having the amino acid sequence of SEQ ID NO:11, and a third having the amino acid sequence of SEQ ID NO:12.

In another embodiment, the bispecific anti-CD20×anti-CD3 antibody is XENP14390. In one embodiment, the bispecific anti-CD20×anti-CD3 antibody is a biosimilar of XENP14390. In one embodiment, the bispecific anti-CD20×anti-CD3 antibody is a bioequivalent of XENP14390. In one embodiment, the bispecific anti-CD20×anti-CD3 antibody comprises an amino acid sequence of a VH CDR1, VH CDR2, and VH CDR3 of the CD3 antigen binding domain of XENP14390. In one embodiment, the bispecific anti-CD20×anti-CD3 antibody comprises an amino acid sequence of a VL CDR1, VL CDR2, and VL CDR3 of the CD3 antigen binding domain of XENP14390. In one embodiment, the bispecific anti-CD20×anti-CD3 antibody comprises an amino acid sequence of a VH CDR1, VH CDR2, and VH CDR3 of the CD20 antigen binding domain of XENP14390. In one embodiment, the bispecific anti-CD20×anti-CD3 antibody comprises an amino acid sequence of a VL CDR1, VL CDR2, and VL CDR3 of the CD20 antigen binding domain of XENP14390. In one embodiment, the bispecific anti-CD20×anti-CD3 antibody comprises an amino acid sequence of a VH CDR1, VH CDR2, and VH CDR3 of the CD3 antigen binding domain of XENP14390, and a VL CDR1, VL CDR2, and VL CDR3 of the CD3 antigen binding domain of XENP14390. In one embodiment, the bispecific anti-CD20×anti-CD3 antibody comprises an amino acid sequence of a VH CDR1, VH CDR2, and VH CDR3 of the CD20 antigen binding domain of XENP14390, and a VL CDR1, VL CDR2, and VL CDR3 of the CD20 antigen binding domain of XENP14390. In one embodiment, the bispecific anti-CD20×anti-CD3 antibody comprises an amino acid sequence of a VH CDR1, VH CDR2, and VH CDR3 of the CD3 antigen binding domain of XENP14390, a VL CDR1, VL CDR2, and VL CDR3 of the CD3 antigen binding domain of XENP14390, a VH CDR1, VH CDR2, and VH CDR3 of the CD20 antigen binding domain of XENP14390, and a VL CDR1, VL CDR2, and VL CDR3 of the CD20 antigen binding domain of XENP14390. In one embodiment, the bispecific anti-CD20×anti-CD3 antibody comprises an amino acid sequence of a VH of the CD3 antigen binding domain of XENP14390. In one embodiment, the bispecific anti-CD20×anti-CD3 antibody comprises an amino acid sequence of a VL of the CD3 antigen binding domain of XENP14390. In one embodiment, the bispecific anti-CD20×anti-CD3 antibody comprises an amino acid sequence of a VH of the CD20 antigen binding domain of XENP14390. In one embodiment, the bispecific anti-CD20×anti-CD3 antibody comprises an amino acid sequence of a VL of the CD20 antigen binding domain of XENP14390. In one embodiment, the bispecific anti-CD20×anti-CD3 antibody comprises an amino acid sequence of a VH of the CD3 antigen binding domain of XENP14390, and a VL of the CD3 antigen binding domain of XENP14390. In one embodiment, the bispecific anti-CD20×anti-CD3 antibody comprises an amino acid sequence of a VH of the CD20 antigen binding domain of XENP14390, and a VL of the CD20 antigen binding domain of XENP14390. In one embodiment, the bispecific anti-CD20×anti-CD3 antibody comprises an amino acid sequence of a VH of the CD3 antigen binding domain of XENP14390, a VL of the CD3 antigen binding domain of XENP14390, a VH of the CD20 antigen binding domain of XENP14390, and a VL of the CD20 antigen binding domain of XENP14390. Exemplary CD3 and CD20 antigen binding domains of XENP14390 are provided in Table 1. In one embodiment, the bispecific anti-CD20×anti-CD3 antibody comprises a first monomer having the amino acid sequence of SEQ ID NO:13. In another embodiment, the bispecific anti-CD20×anti-CD3 antibody comprises a second monomer having the amino acid sequence of SEQ ID NO:14. In another embodiment, the bispecific anti-CD20×anti-CD3 antibody comprises a third monomer having the amino acid sequence of SEQ ID NO:15. In another embodiment, the bispecific anti-CD20×anti-CD3 antibody comprises a first monomer having the amino acid sequence of SEQ ID NO:13, a second monomer having the amino acid sequence of SEQ ID NO:14, and a third having the amino acid sequence of SEQ ID NO:15.

In another embodiment, the bispecific anti-CD20×anti-CD3 antibody is XENP14392. In one embodiment, the bispecific anti-CD20×anti-CD3 antibody is a biosimilar of XENP14392. In one embodiment, the bispecific anti-CD20×anti-CD3 antibody is a bioequivalent of XENP14392. In one embodiment, the bispecific anti-CD20×anti-CD3 antibody comprises an amino acid sequence of a VH CDR1, VH CDR2, and VH CDR3 of the CD3 antigen binding domain of XENP14392. In one embodiment, the bispecific anti-CD20×anti-CD3 antibody comprises an amino acid sequence of a VL CDR1, VL CDR2, and VL CDR3 of the CD3 antigen binding domain of XENP14392. In one embodiment, the bispecific anti-CD20×anti-CD3 antibody comprises an amino acid sequence of a VH CDR1, VH CDR2, and VH CDR3 of the CD20 antigen binding domain of XENP14392. In one embodiment, the bispecific anti-CD20×anti-CD3 antibody comprises an amino acid sequence of a VL CDR1, VL CDR2, and VL CDR3 of the CD20 antigen binding domain of XENP14392. In one embodiment, the bispecific anti-CD20×anti-CD3 antibody comprises an amino acid sequence of a VH CDR1, VH CDR2, and VH CDR3 of the CD3 antigen binding domain of XENP14392, and a VL CDR1, VL CDR2, and VL CDR3 of the CD3 antigen binding domain of XENP14392. In one embodiment, the bispecific anti-CD20×anti-CD3 antibody comprises an amino acid sequence of a VH CDR1, VH CDR2, and VH CDR3 of the CD20 antigen binding domain of XENP14392, and a VL CDR1, VL CDR2, and VL CDR3 of the CD20 antigen binding domain of XENP14392. In one embodiment, the bispecific anti-CD20×anti-CD3 antibody comprises an amino acid sequence of a VH CDR1, VH CDR2, and VH CDR3 of the CD3 antigen binding domain of XENP14392, a VL CDR1, VL CDR2, and VL CDR3 of the CD3 antigen binding domain of XENP14392, a VH CDR1, VH CDR2, and VH CDR3 of the CD20 antigen binding domain of XENP14392, and a VL CDR1, VL CDR2, and VL CDR3 of the CD20 antigen binding domain of XENP14392. In one embodiment, the bispecific anti-CD20×anti-CD3 antibody comprises an amino acid sequence of a VH of the CD3 antigen binding domain of XENP14392. In one embodiment, the bispecific anti-CD20×anti-CD3 antibody comprises an amino acid sequence of a VL of the CD3 antigen binding domain of XENP14392. In one embodiment, the bispecific anti-CD20×anti-CD3 antibody comprises an amino acid sequence of a VH of the CD20 antigen binding domain of XENP14392. In one embodiment, the bispecific anti-CD20×anti-CD3 antibody comprises an amino acid sequence of a VL of the CD20 antigen binding domain of XENP14392. In one embodiment, the bispecific anti-CD20×anti-CD3 antibody comprises an amino acid sequence of a VH of the CD3 antigen binding domain of XENP14392, and a VL of the CD3 antigen binding domain of XENP14392. In one embodiment, the bispecific anti-CD20×anti-CD3 antibody comprises an amino acid sequence of a VH of the CD20 antigen binding domain of XENP14392, and a VL of the CD20 antigen binding domain of XENP14392. In one embodiment, the bispecific anti-CD20×anti-CD3 antibody comprises an amino acid sequence of a VH of the CD3 antigen binding domain of XENP14392, a VL of the CD3 antigen binding domain of XENP14392, a VH of the CD20 antigen binding domain of XENP14392, and a VL of the CD20 antigen binding domain of XENP14392. Exemplary CD3 and CD20 antigen binding domains of XENP14392 are provided in Table 1. In one embodiment, the bispecific anti-CD20×anti-CD3 antibody comprises a first monomer having the amino acid sequence of SEQ ID NO:16. In another embodiment, the bispecific anti-CD20×anti-CD3 antibody comprises a second monomer having the amino acid sequence of SEQ ID NO:17. In another embodiment, the bispecific anti-CD20×anti-CD3 antibody comprises a third monomer having the amino acid sequence of SEQ ID NO:18. In another embodiment, the bispecific anti-CD20×anti-CD3 antibody comprises a first monomer having the amino acid sequence of SEQ ID NO:16, a second monomer having the amino acid sequence of SEQ ID NO:17, and a third having the amino acid sequence of SEQ ID NO:18.

In another embodiment, the bispecific anti-CD20×anti-CD3 antibody is XENP14393. In one embodiment, the bispecific anti-CD20×anti-CD3 antibody is a biosimilar of XENP14393. In one embodiment, the bispecific anti-CD20×anti-CD3 antibody is a bioequivalent of XENP14393. In one embodiment, the bispecific anti-CD20×anti-CD3 antibody comprises an amino acid sequence of a VH CDR1, VH CDR2, and VH CDR3 of the CD3 antigen binding domain of XENP14393. In one embodiment, the bispecific anti-CD20×anti-CD3 antibody comprises an amino acid sequence of a VL CDR1, VL CDR2, and VL CDR3 of the CD3 antigen binding domain of XENP14393. In one embodiment, the bispecific anti-CD20×anti-CD3 antibody comprises an amino acid sequence of a VH CDR1, VH CDR2, and VH CDR3 of the CD20 antigen binding domain of XENP14393. In one embodiment, the bispecific anti-CD20×anti-CD3 antibody comprises an amino acid sequence of a VL CDR1, VL CDR2, and VL CDR3 of the CD20 antigen binding domain of XENP14393. In one embodiment, the bispecific anti-CD20×anti-CD3 antibody comprises an amino acid sequence of a VH CDR1, VH CDR2, and VH CDR3 of the CD3 antigen binding domain of XENP14393, and a VL CDR1, VL CDR2, and VL CDR3 of the CD3 antigen binding domain of XENP14393. In one embodiment, the bispecific anti-CD20×anti-CD3 antibody comprises an amino acid sequence of a VH CDR1, VH CDR2, and VH CDR3 of the CD20 antigen binding domain of XENP14393, and a VL CDR1, VL CDR2, and VL CDR3 of the CD20 antigen binding domain of XENP14393. In one embodiment, the bispecific anti-CD20×anti-CD3 antibody comprises an amino acid sequence of a VH CDR1, VH CDR2, and VH CDR3 of the CD3 antigen binding domain of XENP14393, a VL CDR1, VL CDR2, and VL CDR3 of the CD3 antigen binding domain of XENP14393, a VH CDR1, VH CDR2, and VH CDR3 of the CD20 antigen binding domain of XENP14393, and a VL CDR1, VL CDR2, and VL CDR3 of the CD20 antigen binding domain of XENP14393. In one embodiment, the bispecific anti-CD20×anti-CD3 antibody comprises an amino acid sequence of a VH of the CD3 antigen binding domain of XENP14393. In one embodiment, the bispecific anti-CD20×anti-CD3 antibody comprises an amino acid sequence of a VL of the CD3 antigen binding domain of XENP14393. In one embodiment, the bispecific anti-CD20×anti-CD3 antibody comprises an amino acid sequence of a VH of the CD20 antigen binding domain of XENP14393. In one embodiment, the bispecific anti-CD20×anti-CD3 antibody comprises an amino acid sequence of a VL of the CD20 antigen binding domain of XENP14393. In one embodiment, the bispecific anti-CD20×anti-CD3 antibody comprises an amino acid sequence of a VH of the CD3 antigen binding domain of XENP14393, and a VL of the CD3 antigen binding domain of XENP14393. In one embodiment, the bispecific anti-CD20×anti-CD3 antibody comprises an amino acid sequence of a VH of the CD20 antigen binding domain of XENP14393, and a VL of the CD20 antigen binding domain of XENP14393. In one embodiment, the bispecific anti-CD20×anti-CD3 antibody comprises an amino acid sequence of a VH of the CD3 antigen binding domain of XENP14393, a VL of the CD3 antigen binding domain of XENP14393, a VH of the CD20 antigen binding domain of XENP14393, and a VL of the CD20 antigen binding domain of XENP14393. Exemplary CD3 and CD20 antigen binding domains of XENP14393 are provided in Table 1. In one embodiment, the bispecific anti-CD20×anti-CD3 antibody comprises a first monomer having the amino acid sequence of SEQ ID NO:19. In another embodiment, the bispecific anti-CD20×anti-CD3 antibody comprises a second monomer having the amino acid sequence of SEQ ID NO:20. In another embodiment, the bispecific anti-CD20×anti-CD3 antibody comprises a third monomer having the amino acid sequence of SEQ ID NO:21. In another embodiment, the bispecific anti-CD20×anti-CD3 antibody comprises a first monomer having the amino acid sequence of SEQ ID NO:19, a second monomer having the amino acid sequence of SEQ ID NO:20, and a third having the amino acid sequence of SEQ ID NO:21.

The bispecific anti-CD20×anti-CD3 antibodies useful in the methods provided herein are made as is known in the art. Also provided are nucleic acid compositions encoding the bispecific anti-CD20×anti-CD3 antibodies (e.g., XmAb® 13676) provided herein. As will be appreciated by those in the art, the nucleic acid compositions will depend on the format and scaffold of the bispecific anti-CD20×anti-CD3 antibodies (e.g., XmAb® 13676). Thus, for example, when the format requires three amino acid sequences, such as for the triple F format (e.g., a first amino acid monomer comprising an Fc domain and a scFv, a second amino acid monomer comprising a heavy chain and a light chain), three nucleic acid sequences can be incorporated into one or more expression vectors for expression. Similarly, some formats (e.g., dual scFv formats such as disclosed in FIG. 4) only two nucleic acids are needed; again, they can be put into one or two expression vectors.

As is known in the art, the nucleic acids encoding the components provided herein can be incorporated into expression vectors as is known in the art, and depending on the host cells used to produce the bispecific anti-CD20×anti-CD3 antibodies provided herein (e.g., XmAb® 13676). Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors provided herein are then transformed into any number of different types of host cells as is well known in the art, including mammalian, bacterial, yeast, insect and/or fungal cells, with mammalian cells (e.g., CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use, each of these two or three nucleic acids are contained on a different expression vector.

The heterodimeric bispecific anti-CD20×anti-CD3 antibodies provided herein (e.g., XmAb® 13676) are made by culturing host cells comprising the expression vector(s) as is well known in the art. Once produced, traditional antibody purification steps are done, including an ion exchange chromatography step. As discussed in U.S. Ser. No. 14/205,248 and WO2014/145806, hereby incorporated by reference in their entirety and particularly for the discussions concerning purification, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "triple F" heterodimer (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

Once made, the bispecific anti-CD20×anti-CD3 antibodies (e.g., XmAb® 13676) are administered to human subjects in dose amounts as outlined herein.

IV. PHARMACEUTICAL COMPOSITIONS AND PHARMACEUTICAL ADMINISTRATION

Bispecific anti-CD20×anti-CD3 antibodies (e.g., XmAb® 13676) provided herein can be incorporated into pharmaceutical compositions suitable for administration to a human subject according to a dosage regimen described herein. As used herein, "dosage regimen" refers to a systematic plan of drug administration regarding formulation, route of administration, drug dose, dosing interval and treatment duration. Typically, the pharmaceutical composition comprises a bispecific anti-CD20×anti-CD3 antibody (e.g., XmAb® 13676) and a pharmaceutically acceptable carrier. As used herein, "pharmaceutically acceptable carrier" includes any and all solvents, dispersion media, coatings, isotonic and absorption delaying agents, and the like that are physiologically compatible and are suitable for administration to a subject for the methods described herein. Examples of pharmaceutically acceptable carriers include one or more of water, saline, phosphate buffered saline, dextrose, glycerol, ethanol and the like, as well as any combination thereof. In some cases, isotonic agents can be included, for example, sugars, polyalcohols such as mannitol, sorbitol, or sodium chloride in the composition. Pharmaceutically acceptable carriers may further comprise minor amounts of auxiliary substances such as surfactants (such as nonionic surfactants) wetting or emulsifying agents (such as a polysorbate), preservatives or buffers (such as an organic acid, which as a citrate or an acetate), which enhance the shelf life or effectiveness of the bispecific antibody. Examples of pharmaceutically acceptable carriers include polysorbates (polysorbate-80).

In one embodiment, the pharmaceutical composition comprises a bispecific anti-CD20×anti-CD3 antibody (e.g., XmAb® 13676) provided herein and a preservative or buffer. In one embodiment, the pharmaceutical composition comprises a bispecific anti-CD20×anti-CD3 antibody (e.g., XmAb® 13676) and an acetate. In one embodiment, the pharmaceutical composition comprises a bispecific anti-CD20×anti-CD3 antibody (e.g., XmAb® 13676) and sodium acetate. In one embodiment, the pharmaceutical composition comprises a bispecific anti-CD20×anti-CD3 antibody (e.g., XmAb® 13676) and a citrate. In one embodiment, the pharmaceutical composition comprises a bispecific anti-CD20×anti-CD3 antibody (e.g., XmAb® 13676) and sodium citrate. In one embodiment, the pharmaceutical composition comprises a bispecific anti-CD20×anti-CD3 antibody (e.g., XmAb® 13676) and a succinate. In one embodiment, the pharmaceutical composition comprises a bispecific anti-CD20×anti-CD3 antibody (e.g., XmAb® 13676) and sodium succinate.

In one embodiment, the pharmaceutical composition comprises a bispecific anti-CD20×anti-CD3 antibody (e.g., XmAb® 13676) and an isotonic agent. In one embodiment, the pharmaceutical composition comprises a bispecific anti-CD20×anti-CD3 antibody (e.g., XmAb® 13676) and a polyalcohol. In one embodiment, the pharmaceutical composition comprises a bispecific anti-CD20×anti-CD3 antibody (e.g., XmAb® 13676) and mannitol. In one embodiment, the pharmaceutical composition comprises a bispecific anti-CD20×anti-CD3 antibody (e.g., XmAb® 13676) and sorbitol. In one embodiment, the pharmaceutical composition comprises a bispecific anti-CD20×anti-CD3 antibody (e.g., XmAb® 13676) and sodium chloride. In one embodiment, the pharmaceutical composition comprises a bispecific anti-CD20×anti-CD3 antibody (e.g., XmAb® 13676) and potassium chloride.

In one embodiment, the pharmaceutical composition comprises a bispecific anti-CD20×anti-CD3 antibody (e.g., XmAb® 13676) and a wetting or emulsifying agent. In one embodiment, the pharmaceutical composition comprises a bispecific anti-CD20×anti-CD3 antibody (e.g., XmAb® 13676) and sucrose. In one embodiment, the pharmaceutical composition comprises a bispecific anti-CD20×anti-CD3 antibody (e.g., XmAb® 13676) and a polysorbate. In one embodiment, the pharmaceutical composition comprises a bispecific anti-CD20×anti-CD3 antibody (e.g., XmAb® 13676) and polysorbate-80.

In one embodiment, the pharmaceutical composition comprises a bispecific anti-CD20×anti-CD3 antibody (e.g., XmAb® 13676) and an intravenous solution stabilizer. In one embodiment, the intravenous solution stabilizer comprises a polysorbate and a citrate. In one embodiment, the pharmaceutical composition comprises a bispecific anti-CD20×anti-CD3 antibody (e.g., XmAb® 13676) and sodium citrate and polysorbate-80. In one embodiment, the intravenous solution stabilizer comprises a polysorbate and a succinate. In one embodiment, the pharmaceutical composition comprises a bispecific anti-CD20×anti-CD3 antibody (e.g., XmAb® 13676) and sodium succinate and polysorbate-80.

In one embodiment, the pharmaceutical composition comprises a bispecific anti-CD20×anti-CD3 antibody (e.g., XmAb® 13676) and a buffer and an isotonic agent. In one embodiment, the pharmaceutical composition comprises a bispecific anti-CD20×anti-CD3 antibody (e.g., XmAb® 13676) and a buffer and sodium chloride. In one embodiment, the pharmaceutical composition comprises a bispecific anti-CD20×anti-CD3 antibody (e.g., XmAb® 13676) and a succinate and an isotonic agent. In one embodiment, the pharmaceutical composition comprises a bispecific anti- CD20×anti-CD3 antibody (e.g., XmAb® 13676) and a succinate and sodium chloride. In one embodiment, the pharmaceutical composition comprises a bispecific anti-CD20× anti-CD3 antibody (e.g., XmAb® 13676) and sodium succinate and sodium chloride.

In one embodiment, the pharmaceutical composition comprises a bispecific anti-CD20×anti-CD3 antibody (e.g., XmAb® 13676) and a buffer and an isotonic agent and an intravenous solution stabilizer. In one embodiment, the pharmaceutical composition comprises a bispecific anti-CD20×anti-CD3 antibody (e.g., XmAb® 13676) and a buffer and sodium chloride and an intravenous solution stabilizer. In one embodiment, the pharmaceutical composition comprises a bispecific anti-CD20×anti-CD3 antibody (e.g., XmAb® 13676) and a succinate and an isotonic agent and an intravenous solution stabilizer. In one embodiment, the pharmaceutical composition comprises a bispecific anti-CD20×anti-CD3 antibody (e.g., XmAb® 13676) and a succinate and sodium chloride and an intravenous solution stabilizer. In one embodiment, the pharmaceutical composition comprises a bispecific anti-CD20×anti-CD3 antibody (e.g., XmAb® 13676) and sucrose and sodium chloride and an intravenous solution stabilizer.

In one embodiment, the pharmaceutical composition comprises a bispecific anti-CD20×anti-CD3 antibody (e.g., XmAb® 13676) and sodium succinate and sucrose. In one embodiment, the pharmaceutical composition comprises a bispecific anti-CD20×anti-CD3 antibody (e.g., XmAb® 13676) and sodium succinate and polysorbate-80. In one embodiment, the pharmaceutical composition comprises a bispecific anti-CD20×anti-CD3 antibody (e.g., XmAb® 13676) and sodium succinate and sodium chloride. In one embodiment, the pharmaceutical composition comprises a bispecific anti-CD20×anti-CD3 antibody (e.g., XmAb® 13676) and sucrose and polysorbate-80. In one embodiment, the pharmaceutical composition comprises a bispecific anti-CD20×anti-CD3 antibody (e.g., XmAb® 13676) and sucrose and sodium chloride. In one embodiment, the pharmaceutical composition comprises a bispecific anti-CD20× anti-CD3 antibody (e.g., XmAb® 13676) and sucrose and polysorbate-80. In one embodiment, the pharmaceutical composition comprises a bispecific anti-CD20×anti-CD3 antibody (e.g., XmAb® 13676) and polysorbate-80 and sodium chloride. In one embodiment, the pharmaceutical composition comprises a bispecific anti-CD20×anti-CD3 antibody (e.g., XmAb® 13676) and sodium succinate and sucrose and polysorbate-80. In one embodiment, the pharmaceutical composition comprises a bispecific anti-CD20× anti-CD3 antibody (e.g., XmAb® 13676) and sodium succinate and sucrose and sodium chloride. In one embodiment, the pharmaceutical composition comprises a bispecific anti-CD20×anti-CD3 antibody (e.g., XmAb® 13676) and sucrose and polysorbate-80 and sodium chloride. In one embodiment, the pharmaceutical composition comprises a bispecific anti-CD20×anti-CD3 antibody (e.g., XmAb® 13676) and sucrose and polysorbate-80 and sodium chloride and sodium succinate.

The pharmaceutical compositions can be in a variety of forms. These include, for example, liquid, semi-solid and solid dosage forms, such as liquid solutions (e.g., injectable and infusible solutions), dispersions or suspensions. The form depends on the intended mode of administration and therapeutic application. Exemplary compositions are in the form of injectable or infusible solutions, such as compositions similar to those used for passive immunization of humans with other antibodies. In one embodiment, the mode of administration is intravenous. In one embodiment, the antibody is administered by intravenous infusion or injection.

Pharmaceutical compositions typically must be sterile and stable under the conditions of manufacture and storage. Sterile injectable solutions can be prepared by incorporating the antibody in the required amount in an appropriate solvent with one or any combination of ingredients enumerated herein, as required, followed by filtered sterilization. Generally, dispersions are prepared by incorporating the antibody into a sterile vehicle that contains a basic dispersion medium and the required other ingredients from those enumerated herein.

A bispecific anti-CD20×anti-CD3 antibody (e.g., XmAb® 13676) provided herein can be administered by any known method. In one embodiment, the route/mode of administration is intravenous injection. The route and/or mode of administration can vary depending upon the desired results.

In some embodiments, the antibody comprises a bispecific anti-CD20×anti-CD3 antibody (e.g., XmAb® 13676) that is administered intravenously. In some embodiments, the bispecific anti-CD20×anti-CD3 antibody is administered via continuous infusion. In some embodiments, the bispecific anti-CD20×anti-CD3 antibody is administered intravenously, continuous infusion, or both. Should there be more than two treatments, any combination of intravenous administration or continuous infusion can be used. In some embodiments, the bispecific anti-CD20×anti-CD3 antibody (e.g., XmAb® 13676) is administered until non-efficacy is determined, an unacceptable level of toxicity is observed, or is terminated (whether voluntarily or involuntarily) by the human subject.

In some embodiments, the bispecific anti-CD20×anti-CD3 antibody (e.g., XmAb® 13676) is a front line therapy, second line therapy, third line therapy, fourth line therapy, fifth line therapy, or sixth line therapy.

A medical professional can readily determine and prescribe the effective amount of the antibody composition required. For example, a physician could start doses of the medicament employed in the antibody composition at levels lower than that required in order to achieve the desired therapeutic effect and gradually increase the dosage until the desired effect is achieved.

Combination Therapy

In specific embodiments the bispecific anti-CD20×anti-CD3 antibody (e.g., XmAb® 13676) is the only therapeutic antibody administered to the subject during the treatment methods provided herein In some embodiments, a method of the disclosure comprises administering the bispecific anti-CD20×anti-CD3 antibody (e.g., XmAb® 13676) to a subject as a monotherapy. As used herein, the term "monotherapy" refers to the use of a single agent (e.g., the bispecific anti-CD20× anti-CD3 antibody (e.g., XmAb® 13676)), without a second active agent, to treat the same indication, e.g., the same CD20-expressing cancer. In some embodiments, the term "monotherapy" does not exclude one or more additional agent(s) from being administered to a subject if the one or more additional agent(s) is/are not administered for treating the same CD20-expressing cancer in the subject. For example, in some embodiments, the term "monotherapy" does not exclude one or more additional agent(s) used to prevent or ameliorate injection site side effects, fever, and/or any other side effect associated with the bispecific anti-CD20×anti-CD3 antibody (e.g., XmAb® 13676) of the disclosure from being administered to a subject. In some embodiments, the term "monotherapy" does not exclude treatment with one or more additional agent(s) used for treating or ameliorating another disease or disorder in the subject (e.g., a disease or disorder that is not the CD20-expressing cancer that the bispecific anti-CD20×anti-CD3 antibody (e.g., XmAb® 13676) of the disclosure is being used to treat). In some embodiments, the another disease or disorder in the subject is another cancer that is not a CD20-expressing cancer. In some embodiments, the another disease or disorder in the subject is another cancer that is not the CD20-expressing cancer that the bispecific anti-CD20×anti-CD3 antibody (e.g., XmAb® 13676) of the disclosure is being used to treat. In some embodiments, the term "monotherapy" does not exclude previous treatment with another agent that was used for treating or attempting to treat the CD20-expressing cancer in a subject (e.g., a subject undergoing monotherapy treatment with the bispecific anti-CD20×anti-CD3 antibody (e.g., XmAb® 13676) of the disclosure can be a subject that was previously treated with another agent for the CD20-expressing cancer). In some embodiments, a subject receiving monotherapy treatment with the bispecific anti-CD20×anti-CD3 antibody (e.g., XmAb® 13676) of the disclosure is a subject with a CD20-expressing cancer that is resistant to agents that were previously used for treating the CD20-expressing cancer. In some embodiments, the term "monotherapy" does not exclude previous treatment with another agent prior to the first dose of the bispecific anti-CD20×anti-CD3 antibody (e.g., XmAb® 13676) of the disclosure. In some embodiments, the term "monotherapy" does not exclude premedication (e.g., premedication with antihistamine, acetaminophen, hypertension agents, steroids, and the like).

However, in certain instances, a bispecific anti-CD20×anti-CD3 antibody (e.g., XmAb® 13676) described herein can be used in combination with another therapeutic agent. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, combination with another therapeutic agent refers to another therapeutic agent that is known to treat or is used to treat the same disease or disorder that the bispecific anti-CD20×anti-CD3 antibody of the disclosure is being used to treat in the subject (e.g., a CD20-expressing cancer). In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces one or more symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The bispecific anti-CD20×anti-CD3 antibody (e.g., XmAb® 13676) and at least one additional therapeutic agent can be administered simultaneously, in the same or in separate compositions, or sequentially. For sequential administration, the bispecific anti-CD20×anti-CD3 antibody (e.g., XmAb®13676) described herein can be administered first, and the additional agent can be administered second, or vice versa.

The bispecific anti-CD20×anti-CD3 antibody (e.g., XmAb® 13676) and/or one or more additional therapeutic agents, procedures or modalities can be administered during periods of active disorder, or during a period of positive therapeutic response or less active disease. The bispecific anti-CD20×anti-CD3 antibody (e.g., XmAb® 13676) can be administered before the other treatment, concurrently with the treatment, post-treatment, or during a positive therapeutic response to the disorder.

When administered in combination, the bispecific anti-CD20×anti-CD3 antibody (e.g., XmAb® 13676) and the one or more additional agents (e.g., second or third agent) can be administered in an amount or dose that is higher, lower or the same than the amount or dosage of each agent used individually, e.g., as a monotherapy. In some embodiments, the administered amount or dosage of the bispecific anti-CD20×anti-CD3 antibody (e.g., XmAb® 13676) and the one or more additional agents (e.g., second or third agent), is lower (e.g., at least about 10%, at least about 20%, at least about 30%, at least about 40%, or at least about 50%) than the amount or dosage of each agent used individually, e.g., as a monotherapy. In other embodiments, the amount or dosage of the bispecific anti-CD20×anti-CD3 antibody (e.g., XmAb®13676) and the one or more additional agents (e.g., second or third agent, that results in a desired effect (e.g., treatment of cancer) is lower (e.g., at least about 10%, at least about 20%, at least about 30%, at least about 40%, or at least about 50%) than the amount or dosage of each agent used individually, e.g., as a monotherapy, required to achieve the same therapeutic effect.

Combination Therapy: Side-Effect Ameliorating Agent

In some embodiments, a bispecific antibody is administered to a human subject in combination with one or more side-effect ameliorating agent(s). In an exemplary embodiment, the one or more side-effect ameliorating agent(s) is administered prior to the first administration of the bispecific antibody. In an exemplary embodiment, the one or more side-effect ameliorating agent(s) is administered prior to each administration of the bispecific antibody.

Side effects associated with the administration of the CD123×CD3 bispecific antibody, include, but are not limited to cytokine release syndrome ("CRS"). Other possible side effects include lymphopenia (lymphocyte count decreased), increased amounts of gamma-glutamyl transpeptidase (GGT) in the blood, increased amounts of alanine transaminase (ALT) in the blood, increased amounts of aspartate transaminase (AST) in the blood, fever, vomiting, nausea, diarrhea, hypotension, hypoxia, rash, dysphagia, gastroparesis, capillary leak syndrome, hypophosphatemia, anemia, fatigue, and increased lipase in the blood.

Symptoms of CRS can include high fevers, nausea, transient hypotension, hypoxia, and the like. CRS can include clinical constitutional signs and symptoms such as fever, fatigue, anorexia, myalgias, arthalgias, nausea, vomiting, and headache. CRS can include clinical skin signs and symptoms such as rash. CRS can include clinical gastrointestinal signs and symptoms such as nausea, vomiting and diarrhea. CRS can include clinical respiratory signs and symptoms such as tachypnea and hypoxemia. CRS can include clinical cardiovascular signs and symptoms such as tachycardia, widened pulse pressure, hypotension, increased cardiac output (early) and potentially diminished cardiac output. CRS can include clinical coagulation signs and symptoms such as elevated d-dimer, hypofibrinogenemia with or without bleeding. CRS can include clinical renal signs and symptoms such as azotemia. CRS can include clinical hepatic signs and symptoms such as transaminitis and hyperbilirubinemia. CRS can include clinical neurologic signs and symptoms such as headache, mental status changes, confusion, delirium, word finding difficulty or frank aphasia, hallucinations, tremor, dymetria, altered gait, and seizures.

In an exemplary embodiment, the administration of XmAb® 13676 described herein to the human subject produces a low rate of one or more CRS symptoms described herein. In an exemplary embodiment, the administration of XmAb® 13676 described herein to the human subject produces a low level of one or more CRS symptoms described herein. In an exemplary embodiment, the administration of XmAb® 13676 described herein to the human subject produces a low Grade (such as Grade 1 or Grade 2) of one or more CRS symptoms described herein. In an exemplary embodiment, the administration of XmAb® 13676 described herein to the human subject produces a low Grade (such as Grade 1 or Grade 2) of CRS.

In one embodiment, the one or more side-effect ameliorating agent(s) include steroids, antihistamines, anti-allergic agents, antinausea agents (or anti-emetics), analgesic agents, antipyretic agents, cytoprotective agents, vasopressor agents, anticonvulsant agents, antiinflammatories, or any combination thereof.

Combination Therapy: Side-Effect Ameliorating Agent, Steroid

In one embodiment, the side-effect ameliorating agent is a steroid. In one embodiment, the steroid is a corticosteroid. In one embodiment, the corticosteroid is a glucocorticoid. In one embodiment, the corticosteroid is betamethasone, dexamethasone, prednisone, prednisolone, methylprednisolone, triamcinolone, or any combination thereof. In one embodiment, the corticosteroid is hydrocortisone, cortisone, ethamethasoneb, or any combination thereof. In one embodiment, the steroid is fludrocortisone. In one embodiment, the steroid is dexamethasone.

Combination Therapy: Side-Effect Ameliorating Agent, Antihistamine

In one embodiment, the side-effect ameliorating agent is an antihistamine. In one embodiment, the antihistamine is an $H_1$ antagonist. In one embodiment, the $H_1$ antagonist is acrivastine, azelastine, bilastine, bromodiphenhydramine, brompheniramine, buclizine, carbinoxamine, cetirizine (Zyrtec®), chlorodiphenhydramine, chlorphenamine, clemastine, cyclizine, cyproheptadine, dexbrompheniramine, dexchlorpheniramine, dimenhydrinate, dimetindene, diphenhydramine, doxylamine, ebastine, embramine, fexofenadine (Allegra hydroxyzine)(Vistaril®), loratadine (Claritin®), meclizine, mirtazapine, olopatadine, orphenadrine, phenindamine, pheniramine, phenyltoloxamine, promethazine, quetiapine (Seroquel®), rupatadine (Alergoliber®), tripelennamine, triprolidine, or any combination thereof.

In one embodiment, the antihistamine is acrivastine. In one embodiment, the antihistamine is cetirizine. In one embodiment, the antihistamine is diphenhydramine. In one embodiment, the antihistamine is Benadryl®.

In one embodiment, the antihistamine is an $H_1$ inverse agonist. In one embodiment, the $H_1$ inverse agonist is acrivastine, cetirizine, levocetirizine, desloratadine, pyrilamine, or any combination thereof.

In one embodiment, the antihistamine is an $H_2$ antihistamine. In one embodiment, the $H_2$ antihistamine is an $H_2$ antagonist. In one embodiment, the $H_2$ antihistamine is an $H_2$ inverse agonist. In one embodiment, the $H_2$ antihistamine is cimetidine, famotidine, lafutidine, nizatidine, ranitidine, roxatidine, tiotidine, or any combination thereof.

Combination Therapy: Side-Effect Ameliorating Agent, Anti-Allergy Agent

In one embodiment, the side-effect ameliorating agent is an antiallergy agent. In one embodiment, the side-effect ameliorating agent is antihistamines, glucocorticoids, epinephrine (adrenaline), mast cell stabilizers, antileukotriene agents, anti-cholinergics, decongestants, or any combination thereof. In one embodiment, the side-effect ameliorating agent is a decongestant. In one embodiment, the side-effect ameliorating agent is an adrenaline releasing agent. In one embodiment, the side-effect ameliorating agent is levomethamphetamine, phenylpropanolamine, propylhexedrine (Benzedrex®), loratadine, or any combination thereof. In one embodiment, the side-effect ameliorating agent is an α-adrenergic receptor agonist. In one embodiment, the side-effect ameliorating agent is naphazoline, oxymetazoline, phenylephrine, synephrine, tetryzoline, tramazoline, xylometazoline, or any combination thereof.

Combination Therapy: Side-Effect Ameliorating Agent, Antinausea Agents (or Anti-Emetic)

In one embodiment, the side-effect ameliorating agent is an antinausea agent. In one embodiment, the side-effect ameliorating agent is an antiemetic agent. In one embodiment, the side-effect ameliorating agent is a 5-$HT_3$ receptor antagonist. In one embodiment, the side-effect ameliorating agent is a dolasetron (Anzemet®), granisetron (Kytril®, Sancuso®), ondansetron (Zofran®), tropisetron (Setrovel®, Navoban®), palonosetron (Aloxi®), mirtazapine (Remeron®), or any combination thereof. In one embodiment, the side-effect ameliorating agent is a dopamine antagonist. In one embodiment, the side-effect ameliorating agent is a 5-$HT_3$ receptor antagonist. In one embodiment, the side-effect ameliorating agent is domperidone (Motilium®), olanzapine (Zyprexa®), droperidol, haloperidol, chlorpromazine, prochlorperazine, alizapride, prochlorperazine (Compazine®, Stemzine®, Buccastem®, Stemetil®, Phenotil®), metoclopramide (Reglan), or any combination thereof. In one embodiment, the side-effect ameliorating agent is a NK1 receptor antagonist. In one embodiment, the side-effect ameliorating agent is aprepitant or fosaprepitant (Emend), casopitant, rolapitant (Varubi), or any combination thereof. In one embodiment, the side-effect ameliorating agent is an anticholinergic. In one embodiment, the side-effect ameliorating agent is scopolamine.

Combination Therapy: Side-Effect Ameliorating Agent, Analgesic and/or Antipyretic Agent In one embodiment, the side-effect ameliorating agent is an analgesic agent. In one embodiment, the side-effect ameliorating agent is an antipyretic agent. In one embodiment, the side-effect ameliorating agent is a salicylate, any derivative thereof, or any combination thereof. In one embodiment, the salicylate is selected from the group consisting of aspirin, diflunisal, salsalate, salicylic acid, any derivative thereof, or any combination thereof. In one embodiment, the salicylate is choline salicylate, magnesium salicylate, sodium salicylate, or any combination thereof. In one embodiment, the side-effect ameliorating agent is aspirin. In one embodiment, the side-effect ameliorating agent is acetaminophen, any derivative thereof. In one embodiment, the side-effect ameliorating agent is an NSAID, any derivative thereof. In one embodiment, the NSAID is a propionic acid derivative. In one embodiment, the NSAID is ibuprofen, dexibuprofen, naproxen, fenoprofen, ketoprofen, dexketoprofen, flurbiprofen, oxaprozin, loxoprofen, any derivative thereof, or any combination thereof. In one embodiment, the NSAID is ibuprofen. In one embodiment, the NSAID is naproxen. In one embodiment, the NSAID is an acetic acid derivative. In one embodiment, the NSAID is indomethacin, tolmetin, sulindac, etodolac, ketorolac, diclofenac, aceclofenac, nabumetone, any derivative thereof, or any combination thereof. In one embodiment, the NSAID is an enolic acid derivative. In one embodiment, the NSAID is piroxicam, meloxicam, tenoxicam, droxicam, lornoxicam, phenylbutazone, any derivative thereof, or any combination thereof. In one embodiment, the NSAID is an anthranilic acid derivative. In one embodiment, the NSAID is mefenamic acid, meclofenamic acid, flufenamic acid, tolfenamic acid, any derivative thereof, or any combination thereof. In one embodiment, the side-effect ameliorating agent is phenazone, metamizole, nabumetone, any derivative thereof, or any combination thereof. In one embodiment, the side-effect ameliorating agent is an opiate. In one embodiment, the side-effect ameliorating agent is codeine, morphine, thebaine, fentanyl, or any combination thereof. In one embodiment, the side-effect ameliorating agent is dihydrocodeine, oxymorphol, oxycodone, oxymorphone, metopon, or any combination thereof.

Combination Therapy: Side-Effect Ameliorating Agent, Cytoprotective Agent

In one embodiment, the side-effect ameliorating agent is a cytoprotective agent. In one embodiment, the side-effect ameliorating agent is an aminothiol compound. In one embodiment, the side-effect ameliorating agent is amifostine. In one embodiment, the side-effect ameliorating agent is bleomycin, dexrazoxane, coenzyme M, or any combination thereof.

Combination Therapy: Side-Effect Ameliorating Agent, Vasopressor Agent

In one embodiment, the side-effect ameliorating agent is a vasopressor agent. In one embodiment, the vasopressor agent is norepinephrine, phenylephrine, epinephrine, ephedrine, dopamine, vasopressin, or any combination thereof. In one embodiment, the vasopressor agent is dobutamine, midodrine, amezinium, or any combination thereof.

Combination Therapy: Side-Effect Ameliorating Agent, Anticonvulsant Agent

In one embodiment, the side-effect ameliorating agent is an anticonvulsant agent. In one embodiment, the anticonvulsant is an aldehyde. In one embodiment, the aldehyde is paraldehyde. In one embodiment, the anticonvulsant is an aromatic allylic alcohol. In one embodiment, the aromatic allylic alcohol is stiripentol. In one embodiment, the anticonvulsant is a barbiturate. In one embodiment, the barbiturate is phenobarbital, primidone, methylphenobarbital, barbexaclone, or any combination thereof. In one embodiment, the anticonvulsant is a benzodiazepine. In one embodiment, the benzodiazepine is clobazam, clonazepam, clorazepate, diazepam, midazolam, lorazepam, nitrazepam, temazepam, nimetazepam, or any combination thereof. In one embodiment, the anticonvulsant is a carboxamide. In one embodiment, the carboxamide is carbamazepine, oxcarbazepine, eslicarbazepine acetate or any combination thereof. In one embodiment, the anticonvulsant is a fatty acid. In one embodiment, the fatty acid is a valproate. In one embodiment, the valproate is valproic acid, sodium valproate, divalproex sodium, or any combination thereof. In one embodiment, the valproate is vigabatrin, progabide, and tiagabine. In one embodiment, the anticonvulsant is a fructose derivative. In one embodiment, the fructose derivative is topiramate. In one embodiment, the anticonvulsant is a GABA analog. In one embodiment, the GABA analog is gabapentin, pregabalin, or any combination thereof. In one embodiment, the anticonvulsant is a hydantoin. In one embodiment, the hydantoin is ethotoin, phenytoin, mephenytoin, fosphenytoin, or any combination thereof. In one embodiment, the anticonvulsant is an oxazolidinedione. In one embodiment, the oxazolidinedione is paramethadione, trimethadione, ethadione, or any combination thereof. In one embodiment, the anticonvulsant is a propionate. In one embodiment, the anticonvulsant is a pyrimidinedione. In one embodiment, the anticonvulsant is a pyrrolidine. In one embodiment, the pyrrolidine is brivaracetam, etiracetam, levetiracetam, seletracetam, or any combination thereof. In one embodiment, the anticonvulsant is levetiracetam. In one embodiment, the anticonvulsant is a succinimide. In one embodiment, the succinimide is ethosuximide, phensuximide, mesuximide, or any combination thereof. In one embodiment, the anticonvulsant is a sulfonamide. In one embodiment, the succinimide is acetazolamide, sultiame, methazolamide, zonisamide, or any combination thereof. In one embodiment, the anticonvulsant is a triazine. In one embodiment, the triazine is lamotrigine. In one embodiment, the anticonvulsant is a urea. In one embodiment, the urea is pheneturide, phenacemide, or any combination thereof. In one embodiment, the anticonvulsant is a valproylamide. In one embodiment, the anticonvulsant is a valproylamide. In one embodiment, the valproylamide is valpromide, valnoctamide, or any combination thereof. In one embodiment, the anticonvulsant is perampanel, stiripentol, pyridoxine, or any combination thereof.

Combination Therapy: Side-Effect Ameliorating Agent, TNFα Inhibitor

In one embodiment, the side-effect ameliorating agent is an anti-inflammatory agent. In one embodiment, the side-effect ameliorating agent is a TNF-α inhibitor. In one embodiment, the TNF-α inhibitor is an antibody. Examples of an anti-TNFα antibody molecule such as, infliximab (Remicade®), adalimumab (Humira®), certolizumab pegol (Cimzia®), golimumab (Simponi®), or any combination thereof. Another example of a TNFα inhibitor is a fusion protein such as entanercept (Enbrel®). In one embodiment, the TNF-α inhibitor is a small molecule. Small molecule inhibitor of TNFα include, but are not limited to, xanthine derivatives (e.g., pentoxifylline), bupropion, or any combination thereof.

Combination Therapy: Side-Effect Ameliorating Agent, IL6 Inhibitor

In one embodiment, the side-effect ameliorating agent is an anti-inflammatory agent. In one embodiment, the side-effect ameliorating agent is a IL-6 inhibitor. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, FM101, or any combination thereof. In one embodiment, the anti-IL-6 antibody molecule is tocilizumab.

The methods described herein can comprise administering a bispecific antibody described herein to a human subject and further administering one or more agents to manage elevated levels of a soluble factor resulting from treatment with a bispecific antibody. In one embodiment, the soluble factor elevated in the human subject is one or more of IFN-γ, TNFα, IL-2 and IL-6. In an embodiment, the factor elevated in the human subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and inhibitor of IL-1R, and an inhibitor of IL-6. Examples include anakinra or rilonacept or canakinumab.

In one embodiment, the side-effect ameliorating agent is one that reduces an immune-mediated side effect. Exemplary immune-mediated side effects include, but are not limited to pneumonitis, colitis, hepatitis, nephritis and renal dysfunction, hypothyroidism, hyperthyroidism, and endocrinopathies (e.g., hypophysitis, Type 1 diabetes mellitus and thyroid disorders such as hypothyroidism and hyperthyroidism). In one embodiment, the side-effect ameliorating agent reduces embryofetal toxicity.

In an embodiment, the human subject can be administered an antipyretic agent. In an embodiment, the human subject can be administered an analgesic agent.

Side-Effect Combinations and Amounts

In one embodiment, a steroid is administered prior to the bispecific antibody. In one embodiment, the steroid is administered in an amount between about 5 mg and about 30 mg. In one embodiment, the steroid described herein is administered in an amount between about 5 mg and about 25 mg. In one embodiment, the steroid is administered in an amount between about 5 mg and about 15 mg. In one embodiment, the steroid is administered in an amount between about 8 mg and about 12 mg. In one embodiment, the steroid is administered in an amount between about 10 mg and about 20 mg. In one embodiment, the steroid is administered in an amount of about 10 mg. In one embodiment, the steroid is administered in an amount of 10 mg. In one embodiment, the steroid is administered in an amount between about 18 mg and about 22 mg. In one embodiment, the steroid is administered in an amount of about 20 mg. In one embodiment, the steroid is administered in an amount of 20 mg. In one embodiment, the steroid is dexamethasone. In one embodiment, the steroid is dexamethasone and is administered in an amount between about 10 mg and about 20 mg. In one embodiment, the steroid is dexamethasone and is administered in an amount of about 10 mg. In one embodiment, the steroid is dexamethasone. In one embodiment, the steroid is dexamethasone and is administered in an amount of about 20 mg. In one embodiment, the steroid is dexamethasone and is administered between about 45 minutes and 75 minutes before each administration of a bispecific anti-CD20×anti-CD3 antibody (e.g., XmAb® 13676). In one embodiment, the steroid is dexamethasone and is administered about 60 minutes before each administration of a bispecific anti-CD20×anti-CD3 antibody (e.g., XmAb® 13676). In one embodiment, the steroid is dexamethasone and is administered about 60 minutes before an administration of a bispecific anti-CD20×anti-CD3 antibody (e.g., XmAb® 13676). In one embodiment, about 20 mg of dexamethasone is administered about 60 minutes before each administration of a bispecific anti-CD20×anti-CD3 antibody (e.g., XmAb® 13676). In one embodiment, about 20 mg of dexamethasone is administered about 60 minutes before an administration of a bispecific anti-CD20×anti-CD3 antibody (e.g., XmAb® 13676).

In one embodiment, an antihistamine is administered prior to the bispecific antibody. In one embodiment, the antihistamine is an $H_1$ antagonist. In one embodiment, the $H_1$ antagonist is a first generation $H_1$ antagonist. In one embodiment, the antihistamine is an ethanolamine. In one embodiment, the ethanolamine is diphenhydramine, carbinoxamine, doxylamine, orphenadrine, bromazine, clemastine, dimenhydrinate, or any combination thereof. In one embodiment, the antihistamine is diphenhydramine. In one embodiment, the antihistamine is diphenhydramine. In one embodiment, the antihistamine is administered in an amount between about 20 mg and 60 mg. In one embodiment, the antihistamine is administered in an amount between about 20 mg and 30 mg. In one embodiment, the antihistamine is administered in an amount of about 25 mg. In one embodiment, the antihistamine is administered in an amount of 25 mg. In one embodiment, the antihistamine is administered in an amount between about 40 mg and 60 mg. In one embodiment, the antihistamine is administered in an amount between about 45 mg and 55 mg. In one embodiment, the antihistamine is administered in an amount of about 50 mg. In one embodiment, the antihistamine is administered in an amount of 50 mg. In one embodiment, the antihistamine is diphenhydramine and the amount between about 20 mg and about 30 mg. In one embodiment, the antihistamine is diphenhydramine and the amount is about 25 mg. In one embodiment, the antihistamine is diphenhydramine and is administered between about 20 minutes and 70 minutes before each administration of a bispecific anti-CD20×anti-CD3 antibody (e.g., XmAb® 13676). In one embodiment, the antihistamine is diphenhydramine and is administered between about 30 minutes and 60 minutes before each administration of a bispecific anti-CD20×anti-CD3 antibody (e.g., XmAb®13676). In one embodiment, the antihistamine is diphenhydramine and is administered between about 30 minutes and 60 minutes before an administration of a bispecific anti-CD20×anti-CD3 antibody (e.g., XmAb® 13676). In one embodiment, about 25 mg of diphenhydramine is administered between about 30 minutes and 60 minutes before each administration of a bispecific anti-CD20×anti-CD3 antibody (e.g., XmAb®13676). In one embodiment, about 25 mg of diphenhydramine is administered between about 30 minutes and 60 minutes before an administration of a bispecific anti-CD20×anti-CD3 antibody (e.g., XmAb® 13676).

In one embodiment, acetaminophen is administered prior to the bispecific antibody. In one embodiment, acetaminophen is administered in an amount between about 100 mg and 1000 mg. In one embodiment, acetaminophen is administered in an amount between about 400 mg and 600 mg. In one embodiment, acetaminophen is administered in an amount of about 500 mg. In one embodiment, acetaminophen is administered in an amount of 500 mg. In one embodiment, acetaminophen is administered in an amount between about 500 mg and 800 mg. In one embodiment, acetaminophen is administered in an amount between about 550 mg and 750 mg. In one embodiment, acetaminophen is administered in an amount between about 600 mg and 700 mg. In one embodiment, acetaminophen is administered in an amount of about 650 mg. In one embodiment, acetaminophen is administered in an amount of 650 mg. In one embodiment, the acetaminophen is administered between about 15 minutes and about 45 minutes before each administration of a bispecific anti-CD20×anti-CD3 antibody (e.g., XmAb® 13676). In one embodiment, the acetaminophen is administered about 30 minutes before each administration of a bispecific anti-CD20×anti-CD3 antibody (e.g., XmAb® 13676). In one embodiment, the acetaminophen is administered between about 60 minutes and about 30 minutes before an administration of a bispecific anti-CD20×anti- CD3 antibody (e.g., XmAb® 13676). In one embodiment, the acetaminophen is administered between about 60 minutes and about 30 minutes before each administration of a bispecific anti-CD20×anti-CD3 antibody (e.g., XmAb® 13676). In one embodiment, about 650 mg of acetaminophen is administered about 30 minutes before each administration of a bispecific anti-CD20×anti-CD3 antibody (e.g., XmAb® 13676).

In one embodiment, a steroid, an $H_1$ antagonist, and acetaminophen are administered prior to the bispecific anti-CD20×anti-CD3 antibody (e.g., XmAb® 13676). In one embodiment, dexamethasone, an $H_1$ antagonist, and acetaminophen are administered prior to the bispecific anti-CD20×anti-CD3 antibody (e.g., XmAb® 13676). In one embodiment, a steroid, diphenhydramine, and acetaminophen are administered prior to the bispecific anti-CD20× anti-CD3 antibody (e.g., XmAb® 13676). In one embodiment, dexamethasone, diphenhydramine, and acetaminophen are administered prior to the bispecific anti-CD20×anti-CD3 antibody (e.g., XmAb® 13676). In one embodiment, dexamethasone is administered in an amount of about 10 mg or about 20 mg, diphenhydramine is administered in an amount of about 25 mg, and acetaminophen is administered in an amount of about 650 mg prior to the bispecific anti-CD20×anti-CD3 antibody (e.g., XmAb® 13676). In an exemplary embodiment, if the human subject is not experiencing CRS after 1 or 2 or 3 or 4 consecutive doses of the bispecific anti-CD20×anti-CD3 antibody (e.g., XmAb® 13676), then administration of a side-effect ameliorating agent described herein does not occur.

In one embodiment, an antinausea agent is administered prior to the bispecific antibody. In one embodiment, the antinausea agent is a 5-$HT_3$ receptor antagonist. In one embodiment, the 5-$HT_3$ receptor antagonist is administered in an amount between about 5 mg and 30 mg. In one embodiment, the 5-$HT_3$ receptor antagonist is administered in an amount between about 5 mg and 15 mg. In one embodiment, the 5-$HT_3$ receptor antagonist is administered in an amount between about 5 mg and 10 mg. In one embodiment, the 5-$HT_3$ receptor antagonist is administered in an amount of about 8 mg. In one embodiment, the 5-$HT_3$ receptor antagonist is administered in an amount of 8 mg. In one embodiment, the 5-$HT_3$ receptor antagonist is ondansetron.

In one embodiment, an NK1 receptor antagonist is administered prior to the bispecific antibody. In one embodiment, the NK1 receptor antagonist is administered in an amount between about 100 mg and 300 mg. In one embodiment, the NK1 receptor antagonist is administered in an amount between about 125 mg and 200 mg. In one embodiment, the NK1 receptor antagonist is administered in an amount between about 125 mg and 175 mg. In one embodiment, the NK1 receptor antagonist is administered in an amount of about 150 mg. In one embodiment, the NK1 receptor antagonist is administered in an amount of 150 mg. In one embodiment, the NK1 receptor antagonist is aprepitant, fosaprepitant, or combination thereof. In one embodiment, the NK1 receptor antagonist is fosaprepitant dimeglumine.

V. METHODS OF TREATMENT

In an exemplary embodiment, provided are methods for treating CD20 expressing cancers. In an exemplary embodiment, the CD20 expressing cancer is a CD20+ B cell malignancy, including, but not limited to, B-cell non-Hodgkin's lymphoma, chronic lymphocytic leukemia, small lymphocytic leukemia, B-cell prolymphoctyic leukemia, transformed leukemia, Burkitt's lymphoma, Mantle cell lymphoma, hairy cell leukemia, splenic marginal zone lymphoma, Waldenstrom's Macroglobulinemia, variant hairy cell leukemia, splenic B cell lymphoma/leukemia, lymphoplasmacytic lymphoma, extranodal marginal zone lymphoma of mucosa associated lymphoid tissue, MALT lymphoma, nodal marginal zone B cell lymphoma, follicular lymphoma, in situ follicular neoplasia, duodenal-type follicular lymphoma, large B cell lymphoma with IFR4 rearrangement, primary cutaneous follicle center lymphoma, diffuse large B-cell lymphoma (DLBCL), T-cell/histocyte-rich large B cell lymphoma, primary cutaneous DLBCL, leg type, EBV-positive DLBCL, NOS, EBV-positive mucocutaneous ulcer, DLCBL associated with chronic inflammation, lyphomatoid granulomatosis, primary mediastinal (thymic) large B cell lymphoma, intravascular large B-cell lymphoma, ALK+ large B-cell lymphoma, plasmablastic lympohma, primary effusion lymphoma, HHV8+DLBCL, Burkitt-like lymphoma with 11q aberration, high grade B cell lymphoma, B-cell lypmphoma, unclassifiable, post-transplant lymphoproliferation disorder, and PTLD.

In an exemplary embodiment, provided is a method for treating lymphoma, comprising administering to a human subject with lymphoma and in need of treatment thereof an amount of a bispecific anti-CD20×anti-CD3 antibody described herein (e.g., XmAb® 13676) in a dosage regimen described herein for a time period sufficient to treat the lymphoma (such as achieving a positive therapeutic response). In an exemplary embodiment, the lymphoma is not a Hodgkin's lymphoma. In an exemplary embodiment, the lymphoma is a non-Hodgkin's lymphoma.

In an exemplary embodiment, the CD20 expressing cancer is refractory. In an exemplary embodiment, the CD20 expressing cancer is relapsed. In an exemplary embodiment, the CD20 expressing cancer is ibrutinib-refractory. In an exemplary embodiment, the CD20 expressing cancer is CXCR4-mutated. In an exemplary embodiment, the CD20 expressing cancer is extramedullary Waldenstrom's Macroglobulinemia.

Non-Hodgkin's Lymphoma

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. NHL has been divided into low-, intermediate-, and high-grade categories by virtue of their natural histories (see "The Non-Hodgkin's Lymphoma Pathologic Classification Project," Cancer 49 (1982):2112-2135). The low-grade lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare and most human subjects eventually relapse, requiring further therapy. The intermediate- and high-grade lymphomas are more aggressive tumors, but they have a greater chance for cure with chemotherapy. However, a significant proportion of these human subjects will relapse and require further treatment.

In an exemplary embodiment, the lymphoma is a Non-Hodgkin's lymphoma (NHL). In another exemplary embodiment, the lymphoma is a B-cell NHL. In another exemplary embodiment, the lymphoma is selected from the group consisting of Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma.

In an exemplary embodiment, the disease is selected from the group consisting of low-grade and/or follicular NHL, diffuse large B cell lymphoma, Burkitt's or other high-grade NHL, mantle cell lymphoma, MALT lymphoma, Waldenstrom's macroglobulinemia.

Further disclosed herein, in certain embodiments, is a method for treating relapsed or refractory non-Hodgkin's lymphoma in a human subject in need thereof, comprising: administering to the human subject a therapeutically effective amount of a bispecific anti-CD20×anti-CD3 antibody described herein (e.g., XmAb® 13676). In some embodiments, the non-Hodgkin's lymphoma is relapsed or refractory diffuse large B-cell lymphoma (DLBCL), relapsed or refractory mantle cell lymphoma, or relapsed or refractory follicular lymphoma.

CLL/SLL

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL. In an exemplary embodiment, the disease is Richter's syndrome. In an exemplary embodiment, the disease is Richter's transformation.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13−; 2) 11q22−; 3) unmutated IgVH together with ZAP-70+ and/or CD38+; or 4) trisomy 12.

CLL treatment is typically administered when the human subject's clinical symptoms or blood counts indicate that the disease has progressed to a point where it may affect the human subject's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and human subjects tend to live many years after diagnosis. However, most human subjects are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many human subjects develop fatal complications of recurrent disease. Considering the age of the individuals typically diagnosed with CLL and SLL, there is a need in the art for a simple and effective treatment of the disease with minimum side-effects that do not impede on the human subject's quality of life. The instant invention fulfills this long standing need in the art.

In an exemplary embodiment, provided is a method for treating CLL in a human subject, comprising administering to the human subject having CLL an amount of a bispecific anti-CD20×anti-CD3 antibody described herein (e.g., XmAb® 13676) in a dosage regimen described herein for a time period sufficient to treat the CLL (such as to achieve a positive therapeutic response).

In an exemplary embodiment, provided is a method for treating SLL in a human subject, comprising administering to the human subject having SLL an amount of a bispecific anti-CD20×anti-CD3 antibody described herein (e.g., XmAb® 13676) in a dosage regimen described herein for a time period sufficient to treat the SLL (such as to achieve a positive therapeutic response).

In some embodiments, the cancer is treated according to a method described herein. In one embodiment, the cancer is treated (such as by achieving a positive therapeutic response) by administering a bispecific anti-CD20×anti-CD3 antibody described herein (e.g., XmAb® 13676) to the human subject in one or more phases. Each phase comprises dose amount(s) of a bispecific anti-CD20×anti-CD3 antibody described herein (e.g., XmAb® 13676) provided according to a dosage regimen described herein. Each phase can last for one or more weeks or months, or until a positive therapeutic response is achieved, or so long as there is a positive therapeutic response. In one embodiment, administration of the bispecific anti-CD20×anti-CD3 antibody described herein (e.g., XmAb® 13676) stops after the positive therapeutic response is achieved, and the administration of the bispecific anti-CD20×anti-CD3 antibody described herein (e.g., XmAb® 13676) begins again once the positive therapeutic response diminishes or disappears. In one embodiment, the bispecific anti-CD20×anti-CD3 antibody described herein (e.g., XmAb® 13676) is administered until partial remission. In one embodiment, the bispecific anti-CD20×anti-CD3 antibody described herein (e.g., XmAb® 13676) is administered until complete remission.

In one embodiment, the method of treatment comprises a bispecific anti-CD20×anti-CD3 antibody described herein (e.g., XmAb® 13676) being administered in one to twenty phases. In one embodiment, the method of treatment comprises a bispecific anti-CD20×anti-CD3 antibody described herein (e.g., XmAb® 13676) being administered in four or five or six or seven phases. In one embodiment, a phase has the same dosage regimen that occurs between one (1) and twenty (20) times, or until a positive therapeutic response is achieved, or so long as there is a positive therapeutic response. In one embodiment, the dosage regimen has a dose amount (quantity of an antibody) and an administration time (the length of time in which the dose amount is administered).

In one embodiment, the method comprises a first phase. In one embodiment, the method comprises a first phase and a second phase. In one embodiment, the method comprises a first phase and a second phase, where each phase is different. In one embodiment, the method comprises a first phase and a second phase and a third phase. In one embodiment, the method comprises a first phase and a second phase and a third phase, where each phase is different. In one embodiment, the method comprises a first phase and a second phase and a third phase and a fourth phase. In one embodiment, the method comprises a first phase and a second phase and a third phase and a fourth phase, where each phase is different. In one embodiment, the method comprises a first phase and a second phase and a third phase and a fourth phase and a fifth phase. In one embodiment, the method comprises a first phase and a second phase and a third phase and a fourth phase and a fifth phase, where each phase is different. In one embodiment, the method comprises a first phase and a second phase and a third phase and a fourth phase and a fifth phase and a sixth phase. In one embodiment, the method comprises a first phase and a second phase and a third phase and a fourth phase and a fifth phase and a sixth phase, where each phase is different. In one embodiment, the method comprises a first phase and a second phase and a third phase and a fourth phase and a fifth phase and a sixth phase and a seventh phase. In one embodiment, the method comprises a first phase and a second phase and a third phase and a fourth phase and a fifth phase and a sixth phase and a seventh phase, where each phase is different.

It will be understood that XmAb® 13676 can be used as the bispecific anti-CD20×anti-CD3 antibody in all methods of the invention provided herein.

It will also be understood that that a biosimilar of XmAb® 13676 can be used as the bispecific anti-CD20×anti-CD3 antibody in all methods of the invention provided herein.

It will further be understood that a bioequivalent of XmAb® 13676 can be used as the bispecific anti-CD20×anti-CD3 antibody in all methods of the invention provided herein.

In some embodiments, provided is a method of treating a CD20-expressing cancer in a subject, comprising administering to the subject a polypeptide comprising a first means capable of binding to CD3 and a second means capable of binding to CD20. In a specific embodiment, the CD20-expressing cancer is a B-cell malignancy. In some embodiments, provided is a method of treating B-cell non-Hodgkin's lymphoma in a subject, comprising administering to the subject a polypeptide comprising a first means capable of binding to CD3 and a second means capable of binding to CD20. In some embodiments, provided is a method of treating chronic lymphocytic leukemia in a subject, comprising administering to the subject a polypeptide comprising a first means capable of binding to CD3 and a second means capable of binding to CD20. In some embodiments, provided is a method of treating hairy cell leukemia in a subject, comprising administering to the subject a polypeptide comprising a first means capable of binding to CD3 and a second means capable of binding to CD20. In some embodiments, provided is a method of treating Waldenström macroglobulinemia in a subject, comprising administering to the subject a polypeptide comprising a first means capable of binding to CD3 and a second means capable of binding to CD20. In some embodiments, provided is a method of treating small lymphocytic lymphoma in a subject, comprising administering to the subject a polypeptide comprising a first means capable of binding to CD3 and a second means capable of binding to CD20. In some embodiments, provided is a method of inhibiting the growth or proliferation of CD20-expressing cancer cells in a subject, comprising administering to the subject a polypeptide comprising a first means capable of binding to CD3 and a second means capable of binding to CD20. In a specific embodiment, the CD20-expressing cancer is a B-cell malignancy. In some embodiments, provided is a method of inhibiting the growth or proliferation of B-cell non-Hodgkin's lymphoma cells in a subject a polypeptide comprising a first means capable of binding to CD3 and a second means capable of binding to CD20. In some embodiments, provided is a method of inhibiting the growth or proliferation of chronic lymphocytic leukemia cells in a subject a polypeptide comprising a first means capable of binding to CD3 and a second means capable of binding to CD20. In some embodiments, provided is a method of inhibiting the growth or proliferation of hairy cell leukemia cells in a subject, comprising administering to the subject a polypeptide comprising a first means capable of binding to CD3 and a second means capable of binding to CD20. In some embodiments, provided is a method of inhibiting the growth or proliferation of Waldenström macroglobulinemia cells in a subject, comprising administering to the subject a polypeptide comprising a first means capable of binding to CD3 and a second means capable of binding to CD20. In some embodiments, provided is a method of inhibiting the growth or proliferation of small lymphocytic lymphoma cells in a subject, comprising administering to the subject a polypeptide comprising a first means capable of binding to CD3 and a second means capable of binding to CD20. In some embodiments, the polypeptide is a multispecific antibody. In some embodiments, the polypeptide is a bispecific antibody. In one embodiment, the multispecific antibody comprises a bispecific antibody. In one embodiment, the first means is a CD3 antigen binding domain. In one embodiment, the second means is a CD20 antigen binding domain. In one embodiment, the first means is a CD3 antigen binding fragment. In one embodiment, the second means is a CD20 antigen binding fragment. In a specific embodiment, the bispecific antibody is a bispecific anti-CD20×anti-CD3 antibody. In a specific embodiment, the bispecific anti-CD20×anti-CD3 antibody is XmAb® 13676.

V. a. Dose

A dose has a specific amount of antibody that is administered to a human subject over a defined time period. The amount of antibody administered to a human subject is also known as the dose amount. The time over which the dose amount is administered to a human subject is also known as the administration time.

V.a.i. Dose Amount

The dose amount may be determined or adjusted by measuring the amount of bispecific anti-CD20×anti-CD3 antibody (e.g., XmAb® 13676) in the blood upon administration, for instance taking out a biological sample and using anti-idiotypic antibodies which target the antigen binding region of the bispecific anti-CD20×anti-CD3 antibody (e.g., XmAb® 13676). The dosage may be determined based upon the weight of the human subject, such as by multiplying the weight (in kg, for example) of the human subject by a dose amount (such as those described herein). Prior to the administering of the first phase, such as the day before the first phase administration, the weight of the human subject can be assessed. For human subjects whose weight exceeds 100 kg, the intravenous dose can be calculated based on a weight of 100 kg rather than being calculated based upon the human subject's actual body weight.

Following the first dose of the first phase administration, subsequent doses may be modified if the human subject's weight changes by a certain amount (for example, more than by about 5%, more than by about 10%, from the weight assessment prior to the first phase assessment). At such a point, the weight may be recalculated for that infusion day using the current weight.

In some embodiments, a priming dose of the bispecific anti-CD20×anti-CD3 antibody of the disclosure (e.g., XmAb® 13676) is administered to a subject. In some embodiments, the priming dose is the first dose of the bispecific anti-CD20×anti-CD3 antibody of the disclosure that is administered to the subject. In some embodiments, the priming dose is the dose of the bispecific anti-CD20×anti-CD3 antibody of the disclosure that is administered to the subject in the first phase. In some embodiments, the priming dose is a lower dose amount than a subsequent dose (e.g., second dose, third dose, fourth dose, and/or any subsequent dose). In some embodiments, the priming dose is the lowest dose with occurrence of a single DLT. In some embodiments, a priming dose is a dose that does not result in the development of a cytokine release syndrome (CRS). In some embodiments, the priming dose is administered on the first phase or corresponds to the first phase of treatment of the bispecific anti-CD20×anti-CD3 antibody of the disclosure (e.g., XmAb® 13676). In some embodiments, the priming dose is administered on day 1 of cycle 1. In some embodiments, more than one priming dose is administered to the subject (e.g., the first dose and/or the second dose are priming doses). In some embodiments, the priming dose is administered only on the first day of treatment with the bispecific anti-CD20×anti-CD3 antibody of the disclosure. In some embodiments, the priming dose ranges from about 5 µg/kg to about 20 µg/kg, from about 5 µg/kg to about 90 µg/kg, from about 8 µg/kg to about 12 µg/kg, from about 20 µg/kg to about 30 µg/kg, from about 23 µg/kg to about 27 µg/kg, from about 40 µg/kg to about 50 µg/kg, from about 43 µg/kg to about 47 µg/kg, from about 70 µg/kg to about 90 µg/kg, or from about 75 µg/kg to about 85 µg/kg. In some embodiments, the priming dose is about, at least about, or at most about 90 µg/kg. In some embodiments, the priming dose is about, at least about, or at most about 80 µg/kg. In some embodiments, the priming dose is about, at least about, or at most about 45 µg/kg. In some embodiments, the priming dose is about, at least about, or at most about 25 µg/kg. In some embodiments, the priming dose is about, at least about, or at most about 10 µg/kg. In some embodiments, the priming dose is independent of the weight of the subject. In some embodiments, the priming dose is about or at most about 0.8 mg. In some embodiments, the priming dose is about or at most about: 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, or 2 mg. In some embodiments, the priming dose is between about 0.5 mg to about 1.2 mg, between about 0.7 mg to about 1 mg, between about 0.7 mg to about 0.9 mg, between about 0.2 mg to about 1.5 mg, between about 0.1 mg to about 1.8 mg, or between about 0.1 mg to about 2 mg.

The dose amount may also be provided to the human subject in a weight-independent manner. Please see Paragraphs P-U for examples.

PARAGRAPH A includes the following dose amounts: In one embodiment, the dose amount is between about 0.5 µg/kg and about 650 µg/kg. In one embodiment, the dose amount is between about 15 µg/kg and about 650 µg/kg. In one embodiment, the dose amount is between about 35 µg/kg and about 650 µg/kg. In one embodiment, the dose amount is between about 35 µg/kg and about 525 µg/kg. In one embodiment, the dose amount is between about 40 µg/kg and about 500 µg/kg.

PARAGRAPH B includes any one of the following dose amounts: In one embodiment, the dose amount is between about 0.1 µg/kg and about 1 µg/kg. In one embodiment, the dose amount is between about 0.3 µg/kg and about 1 µg/kg. In one embodiment, the dose amount is between about 0.5 µg/kg and about 0.9 µg/kg. In one embodiment, the dose amount is between about 0.6 µg/kg and about 0.8 µg/kg. In one embodiment, the dose amount is about 0.7 µg/kg. In one embodiment, the dose amount is 0.7 µg/kg.

PARAGRAPH C includes any one of the following dose amounts: In one embodiment, the dose amount is between about 0.9 µg/kg and about 5 µg/kg. In one embodiment, the dose amount is between about 1.5 µg/kg and about 4 µg/kg. In one embodiment, the dose amount is between about 1.8 µg/kg and about 3.5 µg/kg. In one embodiment, the dose amount is between about 2.0 µg/kg and about 3.0 µg/kg. In one embodiment, the dose amount is between about 2.2 µg/kg and about 2.6 µg/kg. In one embodiment, the dose amount is about 2.4 µg/kg. In one embodiment, the dose amount is 2.4 µg/kg.

PARAGRAPH D includes any one of the following dose amounts: In one embodiment, the dose amount is between about 2 µg/kg and about 20 µg/kg. In one embodiment, the dose amount is between about 3 µg/kg and about 16 µg/kg. In one embodiment, the dose amount is between about 4 µg/kg and about 14 µg/kg. In one embodiment, the dose amount is between about 5 µg/kg and about 12 µg/kg. In one embodiment, the dose amount is between about 6 µg/kg and about 10 µg/kg. In one embodiment, the dose amount is between about 7 µg/kg and about 9 µg/kg. In one embodiment, the dose amount is between about 7 µg/kg and about 8 µg/kg. In one embodiment, the dose amount is between about 7.2 µg/kg and about 7.8 µg/kg. In one embodiment, the dose amount is about 7.5 µg/kg. In one embodiment, the dose amount is 7.5 µg/kg. In one embodiment, the dose amount is between about 6 µg/kg and about 14 µg/kg. In one embodiment, the dose amount is between about 7 µg/kg and about 13 µg/kg. In one embodiment, the dose amount is between about 8 µg/kg and about 12 µg/kg. In one embodiment, the dose amount is between about 9 µg/kg and about 11 µg/kg. In one embodiment, the dose amount is between about 9.5 µg/kg and about 10.5 µg/kg. In one embodiment, the dose amount is about 10 µg/kg. In one embodiment, the dose amount is 10 µg/kg.

PARAGRAPH E includes any one of the following dose amounts: In one embodiment, the dose amount is between about 5 µg/kg and about 50 µg/kg. In one embodiment, the dose amount is between about 10 µg/kg and about 40 µg/kg. In one embodiment, the dose amount is between about 15 µg/kg and about 35 µg/kg. In one embodiment, the dose amount is between about 20 µg/kg and about 30 µg/kg. In one embodiment, the dose amount is between about 22 µg/kg and about 28 µg/kg. In one embodiment, the dose amount is between about 24 µg/kg and about 26 µg/kg. In one embodiment, the dose amount is about 25 µg/kg. In one embodiment, the dose amount is 25 µg/kg. In one embodiment, the dose amount is between about 15 µg/kg and about 30 µg/kg. In one embodiment, the dose amount is between about 15 µg/kg and about 25 µg/kg. In one embodiment, the dose amount is about 20 µg/kg. In one embodiment, the dose amount is 20 µg/kg.

PARAGRAPH F includes any one of the following dose amounts: In one embodiment, the dose amount is between about 15 µg/kg and about 65 µg/kg. In one embodiment, the dose amount is between about 20 µg/kg and about 60 µg/kg. In one embodiment, the dose amount is between about 25 µg/kg and about 55 µg/kg. In one embodiment, the dose amount is between about 30 µg/kg and about 50 µg/kg. In one embodiment, the dose amount is between about 35 µg/kg and about 50 µg/kg. In one embodiment, the dose amount is between about 40 µg/kg and about 50 µg/kg. In one embodiment, the dose amount is between about 42 µg/kg and about 48 µg/kg. In one embodiment, the dose amount is about 45 µg/kg. In one embodiment, the dose amount is 45 µg/kg.

PARAGRAPH G includes any one of the following dose amounts: In one embodiment, the dose amount is between about 25 µg/kg and about 75 µg/kg. In one embodiment, the dose amount is between about 35 µg/kg and about 65 µg/kg. In one embodiment, the dose amount is between about 40 µg/kg and about 60 µg/kg. In one embodiment, the dose amount is between about 45 µg/kg and about 55 µg/kg. In one embodiment, the dose amount is about 50 µg/kg. In one embodiment, the dose amount is 50 µg/kg.

PARAGRAPH H includes any one of the following dose amounts: In one embodiment, the dose amount is between about 20 µg/kg and about 140 µg/kg. In one embodiment, the dose amount is between about 40 µg/kg and about 120 µg/kg. In one embodiment, the dose amount is between about 45 µg/kg and about 115 µg/kg. In one embodiment, the dose amount is between about 50 µg/kg and about 110 µg/kg. In one embodiment, the dose amount is between about 55 µg/kg and about 105 µg/kg. In one embodiment, the dose amount is between about 60 µg/kg and about 100 µg/kg. In one embodiment, the dose amount is between about 65 µg/kg and about 95 µg/kg. In one embodiment, the dose amount is between about 70 µg/kg and about 90 µg/kg. In one embodiment, the dose amount is between about 75 µg/kg and about 85 µg/kg. In one embodiment, the dose amount is about 80 µg/kg. In one embodiment, the dose amount is 80 µg/kg.

PARAGRAPH I includes any one of the following dose amounts: In one embodiment, the dose amount is between about 65 µg/kg and about 175 µg/kg. In one embodiment, the dose amount is between about 75 µg/kg and about 165 µg/kg. In one embodiment, the dose amount is between about 85 µg/kg and about 155 µg/kg. In one embodiment, the dose amount is between about 95 µg/kg and about 145 µg/kg. In one embodiment, the dose amount is between about 105 µg/kg and about 135 µg/kg. In one embodiment, the dose amount is between about 115 µg/kg and about 135 µg/kg. In one embodiment, the dose amount is between about 120 µg/kg and about 130 µg/kg. In one embodiment, the dose amount is about 125 µg/kg. In one embodiment, the dose amount is 125 µg/kg.

PARAGRAPH J includes any one of the following dose amounts: In one embodiment, the dose amount is between about 140 µg/kg and about 200 µg/kg. In one embodiment, the dose amount is between about 145 µg/kg and about 195 µg/kg. In one embodiment, the dose amount is between about 150 µg/kg and about 190 µg/kg. In one embodiment, the dose amount is between about 155 µg/kg and about 185 µg/kg. In one embodiment, the dose amount is between about 160 µg/kg and about 180 µg/kg. In one embodiment, the dose amount is between about 165 µg/kg and about 175 µg/kg. In one embodiment, the dose amount is about 170 µg/kg. In one embodiment, the dose amount is 170 µg/kg.

PARAGRAPH K includes any one of the following dose amounts: In one embodiment, the dose amount is between about 180 µg/kg and about 320 µg/kg. In one embodiment, the dose amount is between about 190 µg/kg and about 310 µg/kg. In one embodiment, the dose amount is between about 200 µg/kg and about 300 µg/kg. In one embodiment, the dose amount is between about 210 µg/kg and about 290 µg/kg. In one embodiment, the dose amount is between about 220 µg/kg and about 280 µg/kg. In one embodiment, the dose amount is between about 230 µg/kg and about 270 µg/kg. In one embodiment, the dose amount is between about 240 µg/kg and about 260 µg/kg. In one embodiment, the dose amount is about 250 µg/kg. In one embodiment, the dose amount is 250 µg/kg.

PARAGRAPH L includes any one of the following dose amounts: In one embodiment, the dose amount is between about 240 µg/kg and about 460 µg/kg. In one embodiment, the dose amount is between about 250 µg/kg and about 450 µg/kg. In one embodiment, the dose amount is between about 260 µg/kg and about 440 µg/kg. In one embodiment, the dose amount is between about 270 µg/kg and about 430 µg/kg. In one embodiment, the dose amount is between about 280 µg/kg and about 420 µg/kg. In one embodiment, the dose amount is between about 290 µg/kg and about 410 µg/kg. In one embodiment, the dose amount is between about 300 µg/kg and about 400 µg/kg. In one embodiment, the dose amount is between about 310 µg/kg and about 400 µg/kg. In one embodiment, the dose amount is between about 320 µg/kg and about 400 µg/kg. In one embodiment, the dose amount is between about 330 µg/kg and about 390 µg/kg. In one embodiment, the dose amount is between about 340 µg/kg and about 380 µg/kg. In one embodiment, the dose amount is between about 350 µg/kg and about 370 µg/kg. In one embodiment, the dose amount is about 360 µg/kg. In one embodiment, the dose amount is 360 µg/kg.

PARAGRAPH M includes any one of the following dose amounts: In one embodiment, the dose amount is between about 350 µg/kg and about 650 µg/kg. In one embodiment, the dose amount is between about 400 µg/kg and about 600 µg/kg. In one embodiment, the dose amount is between about 400 µg/kg and about 500 µg/kg. In one embodiment, the dose amount is between about 425 µg/kg and about 475 µg/kg. In one embodiment, the dose amount is between about 450 µg/kg and about 470 µg/kg. In one embodiment, the dose amount is about 460 µg/kg. In one embodiment, the dose amount is 460 µg/kg. In one embodiment, the dose amount is between about 525 µg/kg and about 600 µg/kg. In one embodiment, the dose amount is between about 550 µg/kg and about 600 µg/kg. In one embodiment, the dose amount is between about 560 µg/kg and about 580 µg/kg. In one embodiment, the dose amount is about 570 µg/kg. In one embodiment, the dose amount is 570 μg/kg. In one embodiment, the dose amount is about 575 μg/kg. In one embodiment, the dose amount is 575 μg/kg. In one embodiment, the dose amount is between about 450 μg/kg and about 550 μg/kg. In one embodiment, the dose amount is between about 475 μg/kg and about 525 μg/kg. In one embodiment, the dose amount is about 500 μg/kg. In one embodiment, the dose amount is 500 μg/kg.

PARAGRAPH N includes any one of the following dose amounts: In one embodiment, the dose amount is between about 600 μg/kg and about 1,000 μg/kg. In one embodiment, the dose amount is between about 600 μg/kg and about 950 μg/kg. In one embodiment, the dose amount is between about 600 μg/kg and about 900 μg/kg. In one embodiment, the dose amount is between about 600 μg/kg and about 850 μg/kg. In one embodiment, the dose amount is between about 625 μg/kg and about 825 μg/kg. In one embodiment, the dose amount is between about 650 μg/kg and about 800 μg/kg. In one embodiment, the dose amount is between about 650 μg/kg and about 775 μg/kg. In one embodiment, the dose amount is between about 650 μg/kg and about 750 μg/kg. In one embodiment, the dose amount is between about 675 μg/kg and about 725 μg/kg. In one embodiment, the dose amount is about 700 μg/kg. In one embodiment, the dose amount is 700 μg/kg.

PARAGRAPH O includes any one of the following dose amounts: In one embodiment, the dose amount is between about 900 μg/kg and about 1,600 μg/kg. In one embodiment, the dose amount is between about 950 μg/kg and about 1,600 μg/kg. In one embodiment, the dose amount is between about 1,100 μg/kg and about 1,550 μg/kg. In one embodiment, the dose amount is between about 1,100 μg/kg and about 1,500 μg/kg. In one embodiment, the dose amount is between about 1,150 μg/kg and about 1,500 μg/kg. In one embodiment, the dose amount is between about 1,200 μg/kg and about 1,500 μg/kg. In one embodiment, the dose amount is between about 1,250 μg/kg and about 1,500 μg/kg. In one embodiment, the dose amount is between about 1,300 μg/kg and about 1,500 μg/kg. In one embodiment, the dose amount is between about 1,325 μg/kg and about 1,475 μg/kg. In one embodiment, the dose amount is between about 1,350 μg/kg and about 1,450 μg/kg. In one embodiment, the dose amount is between about 1,375 μg/kg and about 1,425 μg/kg. In one embodiment, the dose amount is about 1,400 μg/kg. In one embodiment, the dose amount is 1,400 μg/kg.

PARAGRAPH P includes any one of the following dose amounts: In one embodiment, the dose amount is between about 0.2 mg and about 1.2 mg. In one embodiment, the dose amount is between about 0.4 mg and about 1.2 mg. In one embodiment, the dose amount is between about 0.5 mg and about 1.1 mg. In one embodiment, the dose amount is between about 0.6 mg and about 1.0 mg. In one embodiment, the dose amount is between about 0.7 mg and about 0.9 mg. In one embodiment, the dose amount is about 0.8 mg. In one embodiment, the dose amount is 0.8 mg.

PARAGRAPH Q includes any one of the following dose amounts: In one embodiment, the dose amount is between about 1 mg and about 3 mg. In one embodiment, the dose amount is between about 1.2 mg and about 2.8 mg. In one embodiment, the dose amount is between about 1.4 mg and about 2.6 mg. In one embodiment, the dose amount is between about 1.6 mg and about 2.4 mg. In one embodiment, the dose amount is between about 1.8 mg and about 2.2 mg. In one embodiment, the dose amount is between about 1.9 mg and about 2.1 mg. In one embodiment, the dose amount is about 2 mg. In one embodiment, the dose amount is 2 mg.

PARAGRAPH R includes any one of the following dose amounts: In one embodiment, the dose amount is between about 3 mg and about 7 mg. In one embodiment, the dose amount is between about 3.1 mg and about 7 mg. In one embodiment, the dose amount is between about 3.5 mg and about 6.5 mg. In one embodiment, the dose amount is between about 4 mg and about 6 mg. In one embodiment, the dose amount is between about 4.5 mg and about 5.5 mg. In one embodiment, the dose amount is between about 4.8 mg and about 5.2 mg. In one embodiment, the dose amount is about 5 mg. In one embodiment, the dose amount is 5 mg.

PARAGRAPH S includes any one of the following dose amounts: In one embodiment, the dose amount is between about 7 mg and about 30 mg. In one embodiment, the dose amount is between about 7 mg and about 15 mg. In one embodiment, the dose amount is between about 15 mg and about 25 mg. In one embodiment, the dose amount is between about 16 mg and about 24 mg. In one embodiment, the dose amount is between about 17 mg and about 23 mg. In one embodiment, the dose amount is between about 18 mg and about 22 mg. In one embodiment, the dose amount is between about 19 mg and about 21 mg. In one embodiment, the dose amount is about 20 mg. In one embodiment, the dose amount is 20 mg.

PARAGRAPH T includes any one of the following dose amounts: In one embodiment, the dose amount is between about 30 mg and about 40 mg. In one embodiment, the dose amount is between about 31 mg and about 39 mg. In one embodiment, the dose amount is between about 32 mg and about 38 mg. In one embodiment, the dose amount is between about 33 mg and about 37 mg. In one embodiment, the dose amount is between about 34 mg and about 36 mg. In one embodiment, the dose amount is about 35 mg. In one embodiment, the dose amount is 35 mg.

PARAGRAPH U includes any one of the following dose amounts: In one embodiment, the dose amount is between about 40 mg and about 55 mg. In one embodiment, the dose amount is between about 42 mg and about 54 mg. In one embodiment, the dose amount is between about 44 mg and about 53 mg. In one embodiment, the dose amount is between about 46 mg and about 52 mg. In one embodiment, the dose amount is between about 48 mg and about 51 mg. In one embodiment, the dose amount is about 50 mg. In one embodiment, the dose amount is 50 mg.

In one embodiment, the dose to the human subject is administered between about 5 minutes and about 10 hours. In one embodiment, the dose to the human subject is administered between about 5 minutes and about 5 hours. In one embodiment, the dose to the human subject is administered between about 5 minutes and about 60 minutes. In one embodiment, the dose to the human subject is administered between about 5 minutes and about 30 minutes. In one embodiment, the dose to the human subject is administered between about 30 minutes and about 60 minutes. In one embodiment, the dose to the human subject is administered between about 60 minutes and about 90 minutes. In one embodiment, the dose to the human subject is administered between about 90 minutes and about 2 hours. In one embodiment, the dose to the human subject is administered between about one hour and about three hours. In one embodiment, the dose to the human subject is administered between about two hours and about four hours. In one embodiment, the dose to the human subject is administered between about three hours and about five hours. In one embodiment, the dose to the human subject is administered between about four hours and about six hours. In one embodiment, the dose to the human subject is administered between about five hours and about seven hours. In one embodiment, the dose to the human subject is administered between about six hours and about eight hours. In one embodiment, the dose to the human subject is administered between about seven hours and about nine hours. In one embodiment, the dose to the human subject is administered between about eight hours and about ten hours. In one embodiment, the dose to the human subject is administered over about one hour or about three hours or about four hours or about five hours or about six hours or about seven hours or about eight hours or about nine hours or about ten hours. In one embodiment, the dose to the human subject is administered between about 90 minutes and about 150 minutes. In one embodiment, the dose to the human subject is administered between about 105 minutes and about 135 minutes. In one embodiment, the dose to the human subject is administered between about 115 minutes and about 125 minutes. In one embodiment, the dose to the human subject is administered over about two hours. In one embodiment, the dose to the human subject is administered over two hours.

V.b. Dosage Regimen

In one embodiment, each dosage regimen comprises at least one dose of the bispecific anti-CD20×anti-CD3 antibody (e.g., XmAb® 13676) provided to the human subject (per week or per month/over a set period of day(s) or week(s)). Dosage regimens are adjusted to provide the optimum desired response (e.g., a positive therapeutic response). The efficient dosages and the dosage regimens for the bispecific anti-CD20×anti-CD3 antibodies used in the present methods depend on the disease or condition to be treated. In a specific embodiment, the bispecific anti-CD20× anti-CD3 antibody is XmAb® 13676.

Once a Week Dosage Regimen

In one embodiment, the bispecific anti-CD20×anti-CD3 antibody (e.g., XmAb® 13676) dose is administered once a week, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered once a week, in a dose amount disclosed in any one of Paragraph P or Paragraph Q or Paragraph R or Paragraph S or Paragraph T or Paragraph U, or any combination thereof. The administration time can be any described throughout the specification.

In an exemplary embodiment, the dose is administered once between about 5 and about 10 days. In an exemplary embodiment, the dose is administered once every 5-10 days. In an exemplary embodiment, the dose is administered once between about 5 and about 9 days. In an exemplary embodiment, the dose is administered once every 5-9 days. In an exemplary embodiment, the dose is administered once between about 6 and about 8 days. In an exemplary embodiment, the dose is administered once every 6-8 days. In an exemplary embodiment, the dose is administered once between about 6 and about 10 days. In an exemplary embodiment, the dose is administered once every 6-10 days. In an exemplary embodiment, the dose is administered once between about 7 and about 9 days. In an exemplary embodiment, the dose is administered once every 7-9 days. In an exemplary embodiment, the intravenous dose of XmAb® 13676 is administered once about every 7 days. In an exemplary embodiment, the dose is administered once every 7 days. In an exemplary embodiment, the dose is administered about once a week. In an exemplary embodiment, the intravenous dose of XmAb® 13676 is administered once a week.

In specific embodiments of the methods of treatment provided herein, the bispecific anti-CD20×anti-CD3 antibody that is administered about once a week is XmAb® 13676. In some embodiments, the XmAb® 13676 is administered intravenously about once a week. In specific embodiments of the methods of treatment provided herein, the bispecific anti-CD20×anti-CD3 antibody that is administered once a week is XmAb® 13676. In some embodiments, the XmAb® 13676 is administered intravenously once a week.

Every Two Weeks Dosage Regimen

In one embodiment, the bispecific anti-CD20×anti-CD3 antibody (e.g., XmAb® 13676) dose is administered once every two weeks, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered once every two weeks, in a dose amount disclosed in any one of Paragraph P or Paragraph Q or Paragraph R or Paragraph S or Paragraph T or Paragraph U, or any combination thereof. The administration time can be any described throughout the specification.

In an exemplary embodiment, the dose is administered once between about 10 and about 18 days. In an exemplary embodiment, the dose is administered once every 10-18 days. In an exemplary embodiment, the dose is administered once between about 11 and about 17 days. In an exemplary embodiment, the dose is administered once every 11-17 days. In an exemplary embodiment, the dose is administered once between about 12 and about 16 days. In an exemplary embodiment, the dose is administered once every 12-16 days. In an exemplary embodiment, the dose is administered once between about 13 and about 15 days. In an exemplary embodiment, the dose is administered once every 13-15 days. In an exemplary embodiment, the intravenous dose of XmAb® 13676 is administered about once about every 14 days. In an exemplary embodiment, the dose is administered once every 7 days. In an exemplary embodiment, the dose is administered about once a week. In an exemplary embodiment, the intravenous dose of XmAb® 13676 is administered once a week.

In specific embodiments of the methods of treatment provided herein, the bispecific anti-CD20×anti-CD3 antibody that is administered about every two weeks is XmAb® 13676. In some embodiments, the XmAb® 13676 is administered intravenously about every two weeks. In specific embodiments of the methods of treatment provided herein, the bispecific anti-CD20×anti-CD3 antibody that is administered every two weeks is XmAb® 13676. In some embodiments, the XmAb® 13676 is administered intravenously every two weeks.

Every Three Weeks Dosage Regimen

In one embodiment, the bispecific anti-CD20×anti-CD3 antibody (e.g., XmAb® 13676) dose is administered once every three weeks, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered once every three weeks, in a dose amount disclosed in any one of Paragraph P or Paragraph Q or Paragraph R or Paragraph S or Paragraph T or Paragraph U, or any combination thereof. The administration time can be any described throughout the specification.

In specific embodiments of the methods of treatment provided herein, the bispecific anti-CD20×anti-CD3 antibody administered three a week is XmAb® 13676. In some embodiments, the XmAb® 13676 is administered intravenously once a week.

In specific embodiments of the methods of treatment provided herein, the bispecific anti-CD20×anti-CD3 antibody that is administered about every three weeks is XmAb® 13676. In some embodiments, the XmAb® 13676 is administered intravenously about every three weeks. In specific embodiments of the methods of treatment provided herein, the bispecific anti-CD20×anti-CD3 antibody that is administered every three weeks is XmAb® 13676. In some embodiments, the XmAb® 13676 is administered intravenously every three weeks.

Every Four Weeks Dosage Regimen

In one embodiment, the bispecific anti-CD20×anti-CD3 antibody (e.g., XmAb® 13676) dose is administered once every four weeks, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered once every four weeks, in a dose amount disclosed in any one of Paragraph P or Paragraph Q or Paragraph R or Paragraph S or Paragraph T or Paragraph U, or any combination thereof. The administration time can be any described throughout the specification.

In specific embodiments of the methods of treatment provided herein, the bispecific anti-CD20×anti-CD3 antibody that is administered about every four weeks is XmAb® 13676. In some embodiments, the XmAb® 13676 is administered intravenously about every four weeks. In specific embodiments of the methods of treatment provided herein, the bispecific anti-CD20×anti-CD3 antibody that is administered every four weeks is XmAb® 13676. In some embodiments, the XmAb® 13676 is administered intravenously every four weeks.

Two Times a Month Dosage Regimen

In one embodiment, the bispecific anti-CD20×anti-CD3 antibody (e.g., XmAb® 13676) dose is administered two times a month, in a dose amount selected from the from the group consisting of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered two times a month, in a dose amount disclosed in any one of Paragraph P or Paragraph Q or Paragraph R or Paragraph S or Paragraph T or Paragraph U, or any combination thereof. The administration time can be any described throughout the specification.

In specific embodiments of the methods of treatment provided herein, the bispecific anti-CD20×anti-CD3 antibody that is administered about two times a month is XmAb® 13676. In some embodiments, the XmAb® 13676 is administered intravenously about two times a month. In specific embodiments of the methods of treatment provided herein, the bispecific anti-CD20×anti-CD3 antibody that is administered two times a month is XmAb® 13676. In some embodiments, the XmAb® 13676 is administered intravenously two times a month.

Three Times a Month Dosage Regimen

In one embodiment, the bispecific anti-CD20×anti-CD3 antibody (e.g., XmAb® 13676) dose is administered three times a month, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered three times a month, in a dose amount disclosed in any one of Paragraph P or Paragraph Q or Paragraph R or Paragraph S or Paragraph T or Paragraph U, or any combination thereof. The administration time can be any described throughout the specification.

In specific embodiments of the methods of treatment provided herein, the bispecific anti-CD20×anti-CD3 antibody that is administered about three times a month is XmAb® 13676. In some embodiments, the XmAb® 13676 is administered intravenously about three times a month. In specific embodiments of the methods of treatment provided herein, the bispecific anti-CD20×anti-CD3 antibody that is administered three times a month is XmAb® 13676. In some embodiments, the XmAb® 13676 is administered intravenously three times a month.

Monthly Dosage Regimen

In one embodiment, the bispecific anti-CD20×anti-CD3 antibody (e.g., XmAb® 13676) dose is administered once a month, in a dose amount disclosed in any one of Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M or Paragraph N or Paragraph 0, or any combination thereof. In one embodiment, the bispecific anti-CD20×anti-CD3 antibody (e.g., XmAb® 13676) dose is administered once a month, in a dose amount disclosed in any one of Paragraph P or Paragraph Q or Paragraph R or Paragraph S or Paragraph T or Paragraph U, or any combination thereof. The administration time can be any described throughout the specification.

In specific embodiments of the methods of treatment provided herein, the bispecific anti-CD20×anti-CD3 antibody that is administered about once per month is XmAb® 13676. In some embodiments, the XmAb® 13676 is administered intravenously about once per month. In specific embodiments of the methods of treatment provided herein, the bispecific anti-CD20×anti-CD3 antibody that is administered once per month is XmAb® 13676. In some embodiments, the XmAb® 13676 is administered intravenously once per month.

Other Dosing Regimens

In one aspect, provided herein is a method for treating a CD20-expressing cancer in a human subject in need thereof, comprising administering to the subject a bispecific antibody, wherein the bispecific antibody comprises a first antigen binding domain that binds to CD20 and a second antigen binding domain that binds to CD3 (an anti-CD20× anti-CD3 antibody), wherein the subject is first administered a first dose of the anti-CD20×anti-CD3 antibody on day 1, and subsequently administered a second dose of the anti-CD20×anti-CD3 antibody about 1 week after the first dose and at regular intervals thereafter. In a specific embodiment, the second dose is administered at regular intervals of about 1 week (weekly doses). In another aspect, provided herein is a method for treating a CD20-expressing cancer in a human subject in need thereof, comprising administering to the subject a bispecific antibody, wherein the bispecific antibody comprises a first antigen binding domain that binds to CD20 and a second antigen binding domain that binds to CD3 (an anti-CD20×anti-CD3 antibody), wherein the subject is first administered a first dose of the anti-CD20×anti-CD3 antibody on day 1, and subsequently administered a second dose of the anti-CD20×anti-CD3 antibody about 2 weeks after the first dose and at regular intervals thereafter. In a specific embodiment, the second dose is administered at regular intervals of about 2 weeks (bimonthly doses). In another aspect, provided herein is a method for treating a CD20-expressing cancer in a human subject in need thereof, comprising administering to the subject a bispecific antibody, wherein the bispecific antibody comprises a first antigen binding domain that binds to CD20 and a second antigen binding domain that binds to CD3 (an anti-CD20×anti-CD3 antibody), wherein the subject is first administered a first dose of the anti-CD20×anti-CD3 antibody on day 1, and subsequently administered a second dose of the anti-CD20×anti-CD3 antibody about one month after the first dose and at regular intervals thereafter. In a specific embodiment, the second dose is administered at regular intervals of about a month (monthly doses). In specific embodiments, the anti-CD20×anti-CD3 antibody is intravenously administered. In one embodiment, the first dose is administered to the subject in an amount of about 0.7 μg/kg. In one embodiment, the first dose is administered to the subject in an amount of about 2.4 μg/kg. In one embodiment, the first dose is administered to the subject in an amount of about 7.5 μg/kg. In one embodiment, the first dose is administered to the subject in an amount of about 20 μg/kg. In one embodiment, the first dose is administered to the subject in an amount of about 45 μg/kg. In one embodiment, the first dose is administered to the subject in an amount of about 80 μg/kg. In one embodiment, the first dose is administered to the subject in an amount of about 125 μg/kg. In one embodiment, the first dose is administered to the subject in an amount of about 170 μg/kg. In one embodiment, the first dose is administered to the subject in an amount of about 250 μg/kg. In one embodiment, the first dose is administered to the subject in an amount of about 360 μg/kg. In one embodiment, the first dose is administered to the subject in an amount of about 500 μg/kg. In one embodiment, the first dose is administered to the subject in an amount of about 0.8 mg. In one embodiment, the first dose is administered to the subject in an amount of about 0.8 mg, and the second dose is administered to the subject in an amount of about 25 μg/kg. In one embodiment, the first dose is administered to the subject in an amount of about 0.8 mg, and the second dose is administered to the subject in an amount of about 50 μg/kg. In one embodiment, the first dose is administered to the subject in an amount of about 0.8 mg, and the second dose is administered to the subject in an amount of about 80 μg/kg. In one embodiment, the first dose is administered to the subject in an amount of about 0.8 mg, and the second dose is administered to the subject in an amount of about 125 μg/kg. In one embodiment, the first dose is administered to the subject in an amount of about 0.8 mg, and the second dose is administered to the subject in an amount of about 170 μg/kg. In one embodiment, the first dose is administered to the subject in an amount of about 0.8 mg, and the second dose is administered to the subject in an amount of about 250 μg/kg. In one embodiment, the first dose is administered to the subject in an amount of about 0.8 mg, and the second dose is administered to the subject in an amount of about 360 μg/kg. In one embodiment, the first dose is administered to the subject in an amount of about 0.8 mg, and the second dose is administered to the subject in an amount of about 2 mg. In one embodiment, the first dose is administered to the subject in an amount of about 0.8 mg, and the second dose is administered to the subject in an amount of about 20 mg. In one embodiment, the first dose is administered to the subject in an amount of about 0.8 mg, and the second dose is administered to the subject in an amount of about 35 mg. In one embodiment, the first dose is administered to the subject in an amount of about 0.8 mg, and the second dose is administered to the subject in an amount of about 50 mg. In one embodiment, the first dose is administered to the subject in an amount of about 0.7 μg/kg, and the second dose is administered to the subject in an amount of about 50 μg/kg. In one embodiment, the first dose is administered to the subject in an amount of about 0.7 μg/kg, and the second dose is administered to the subject in an amount of about 80 μg/kg. In one embodiment, the first dose is administered to the subject in an amount of about 0.7 μg/kg, and the second dose is administered to the subject in an amount of about 125 μg/kg. In one embodiment, the first dose is administered to the subject in an amount of about 0.7 μg/kg, and the second dose is administered to the subject in an amount of about 170 μg/kg. In one embodiment, the first dose is administered to the subject in an amount of about 0.7 μg/kg, and the second dose is administered to the subject in an amount of about 250 μg/kg. In one embodiment, the first dose is administered to the subject in an amount of about 0.7 μg/kg, and the second dose is administered to the subject in an amount of about 360 μg/kg. In one embodiment, the first dose is administered to the subject in an amount of about 0.7 μg/kg, and the second dose is administered to the subject in an amount of about 2 mg. In one embodiment, the first dose is administered to the subject in an amount of about 0.7 μg/kg, and the second dose is administered to the subject in an amount of about 20 mg. In one embodiment, the first dose is administered to the subject in an amount of about 0.7 μg/kg, and the second dose is administered to the subject in an amount of about 35 mg. In one embodiment, the first dose is administered to the subject in an amount of about 0.7 μg/kg, and the second dose is administered to the subject in an amount of about 50 mg. In one embodiment, the first dose is administered to the subject in an amount of about 2.4 μg/kg, and the second dose is administered to the subject in an amount of about 50 μg/kg. In one embodiment, the first dose is administered to the subject in an amount of about 2.4 μg/kg, and the second dose is administered to the subject in an amount of about 80 μg/kg. In one embodiment, the first dose is administered to the subject in an amount of about 2.4 μg/kg, and the second dose is administered to the subject in an amount of about 125 μg/kg. In one embodiment, the first dose is administered to the subject in an amount of about 2.4 μg/kg, and the second dose is administered to the subject in an amount of about 170 μg/kg. In one embodiment, the first dose is administered to the subject in an amount of about 2.4 μg/kg, and the second dose is administered to the subject in an amount of about 250 μg/kg. In one embodiment, the first dose is administered to the subject in an amount of about 2.4 μg/kg, and the second dose is administered to the subject in an amount of about 360 μg/kg. In one embodiment, the first dose is administered to the subject in an amount of about 2.4 μg/kg, and the second dose is administered to the subject in an amount of about 2 mg. In one embodiment, the first dose is administered to the subject in an amount of about 2.4 μg/kg, and the second dose is administered to the subject in an amount of about 20 mg.

In one embodiment, the first dose is administered to the subject in an amount of about 2.4 μg/kg, and the second dose is administered to the subject in an amount of about 35 mg. In one embodiment, the first dose is administered to the subject in an amount of about 2.4 μg/kg, and the second dose is administered to the subject in an amount of about 50 mg. In one embodiment, the first dose is administered to the subject in an amount of about 7.5 μg/kg, and the second dose is administered to the subject in an amount of about 50 μg/kg. In one embodiment, the first dose is administered to the subject in an amount of about 7.5 μg/kg, and the second dose is administered to the subject in an amount of about 80 μg/kg. In one embodiment, the first dose is administered to the subject in an amount of about 7.5 μg/kg, and the second dose is administered to the subject in an amount of about 125 μg/kg. In one embodiment, the first dose is administered to the subject in an amount of about 7.5 μg/kg, and the second dose is administered to the subject in an amount of about 170 μg/kg. In one embodiment, the first dose is administered to the subject in an amount of about 7.5 μg/kg, and the second dose is administered to the subject in an amount of about 250 μg/kg. In one embodiment, the first dose is administered to the subject in an amount of about 7.5 μg/kg, and the second dose is administered to the subject in an amount of about 360 μg/kg. In one embodiment, the first dose is administered to the subject in an amount of about 7.5 μg/kg, and the second dose is administered to the subject in an amount of about 2 mg. In one embodiment, the first dose is administered to the subject in an amount of about 7.5 μg/kg, and the second dose is administered to the subject in an amount of about 20 mg. In one embodiment, the first dose is administered to the subject in an amount of about 7.5 μg/kg, and the second dose is administered to the subject in an amount of about 35 mg. In one embodiment, the first dose is administered to the subject in an amount of about 7.5 μg/kg, and the second dose is administered to the subject in an amount of about 50 mg. In one embodiment, the first dose is administered to the subject in an amount of about 20 μg/kg, and the second dose is administered to the subject in an amount of about 50 μg/kg. In one embodiment, the first dose is administered to the subject in an amount of about 20 μg/kg, and the second dose is administered to the subject in an amount of about 80 μg/kg. In one embodiment, the first dose is administered to the subject in an amount of about 20 μg/kg, and the second dose is administered to the subject in an amount of about 125 μg/kg. In one embodiment, the first dose is administered to the subject in an amount of about 20 μg/kg, and the second dose is administered to the subject in an amount of about 170 μg/kg. In one embodiment, the first dose is administered to the subject in an amount of about 20 μg/kg, and the second dose is administered to the subject in an amount of about 250 μg/kg. In one embodiment, the first dose is administered to the subject in an amount of about 20 μg/kg, and the second dose is administered to the subject in an amount of about 360 μg/kg. In one embodiment, the first dose is administered to the subject in an amount of about 20 μg/kg, and the second dose is administered to the subject in an amount of about 2 mg. In one embodiment, the first dose is administered to the subject in an amount of about 20 μg/kg, and the second dose is administered to the subject in an amount of about 20 mg. In one embodiment, the first dose is administered to the subject in an amount of about 20 μg/kg, and the second dose is administered to the subject in an amount of about 35 mg. In one embodiment, the first dose is administered to the subject in an amount of about 20 μg/kg, and the second dose is administered to the subject in an amount of about 50 mg. In one embodiment, the first dose is administered to the subject in an amount of about 45 μg/kg, and the second dose is administered to the subject in an amount of about 50 μg/kg. In one embodiment, the first dose is administered to the subject in an amount of about 45 μg/kg, and the second dose is administered to the subject in an amount of about 80 μg/kg. In one embodiment, the first dose is administered to the subject in an amount of about 45 μg/kg, and the second dose is administered to the subject in an amount of about 125 μg/kg. In one embodiment, the first dose is administered to the subject in an amount of about 45 μg/kg, and the second dose is administered to the subject in an amount of about 170 μg/kg. In one embodiment, the first dose is administered to the subject in an amount of about 45 μg/kg, and the second dose is administered to the subject in an amount of about 250 μg/kg. In one embodiment, the first dose is administered to the subject in an amount of about 45 μg/kg, and the second dose is administered to the subject in an amount of about 360 μg/kg. In one embodiment, the first dose is administered to the subject in an amount of about 45 μg/kg, and the second dose is administered to the subject in an amount of about 2 mg. In one embodiment, the first dose is administered to the subject in an amount of about 45 μg/kg, and the second dose is administered to the subject in an amount of about 20 mg. In one embodiment, the first dose is administered to the subject in an amount of about 45 μg/kg, and the second dose is administered to the subject in an amount of about 35 mg. In one embodiment, the first dose is administered to the subject in an amount of about 45 μg/kg, and the second dose is administered to the subject in an amount of about 50 mg. In one embodiment, the first dose is administered to the subject in an amount of about 80 μg/kg, and the second dose is administered to the subject in an amount of about 80 μg/kg. In one embodiment, the first dose is administered to the subject in an amount of about 80 μg/kg, and the second dose is administered to the subject in an amount of about 125 μg/kg. In one embodiment, the first dose is administered to the subject in an amount of about 80 μg/kg, and the second dose is administered to the subject in an amount of about 170 μg/kg. In one embodiment, the first dose is administered to the subject in an amount of about 80 μg/kg, and the second dose is administered to the subject in an amount of about 250 μg/kg. In one embodiment, the first dose is administered to the subject in an amount of about 80 μg/kg, and the second dose is administered to the subject in an amount of about 360 μg/kg. In one embodiment, the first dose is administered to the subject in an amount of about 80 μg/kg, and the second dose is administered to the subject in an amount of about 2 mg. In one embodiment, the first dose is administered to the subject in an amount of about 80 μg/kg, and the second dose is administered to the subject in an amount of about 20 mg. In one embodiment, the first dose is administered to the subject in an amount of about 80 μg/kg, and the second dose is administered to the subject in an amount of about 35 mg. In one embodiment, the first dose is administered to the subject in an amount of about 80 μg/kg, and the second dose is administered to the subject in an amount of about 50 mg. In one embodiment, the first dose is administered to the subject in an amount of about 125 μg/kg, and the second dose is administered to the subject in an amount of about 125 μg/kg. In one embodiment, the first dose is administered to the subject in an amount of about 125 μg/kg, and the second dose is administered to the subject in an amount of about 170 μg/kg. In one embodiment, the first dose is administered to the subject in an amount of about 125 μg/kg, and the second dose is administered to the subject in an amount of about 250 μg/kg. In one embodiment, the first dose is administered to the subject in an amount of about 125 μg/kg, and the second dose is administered to the subject in an amount of about 360 μg/kg. In one embodiment, the first dose is administered to the subject in an amount of about 125 μg/kg, and the second dose is administered to the subject in an amount of about 2 mg. In one embodiment, the first dose is administered to the subject in an amount of about 125 μg/kg, and the second dose is administered to the subject in an amount of about 20 mg. In one embodiment, the first dose is administered to the subject in an amount of about 125 μg/kg, and the second dose is administered to the subject in an amount of about 35 mg. In one embodiment, the first dose is administered to the subject in an amount of about 125 μg/kg, and the second dose is administered to the subject in an amount of about 50 mg. In one embodiment, the first dose is administered to the subject in an amount of about 170 μg/kg, and the second dose is administered to the subject in an amount of about 170 μg/kg. In one embodiment, the first dose is administered to the subject in an amount of about 170 μg/kg, and the second dose is administered to the subject in an amount of about 250 μg/kg. In one embodiment, the first dose is administered to the subject in an amount of about 170 μg/kg, and the second dose is administered to the subject in an amount of about 360 μg/kg. In one embodiment, the first dose is administered to the subject in an amount of about 170 μg/kg, and the second dose is administered to the subject in an amount of about 2 mg. In one embodiment, the first dose is administered to the subject in an amount of about 170 μg/kg, and the second dose is administered to the subject in an amount of about 20 mg. In one embodiment, the first dose is administered to the subject in an amount of about 170 μg/kg, and the second dose is administered to the subject in an amount of about 35 mg. In one embodiment, the first dose is administered to the subject in an amount of about 170 μg/kg, and the second dose is administered to the subject in an amount of about 50 mg. In one embodiment, the first dose is administered to the subject in an amount of about 250 μg/kg, and the second dose is administered to the subject in an amount of about 250 μg/kg. In one embodiment, the first dose is administered to the subject in an amount of about 250 μg/kg, and the second dose is administered to the subject in an amount of about 360 μg/kg. In one embodiment, the first dose is administered to the subject in an amount of about 250 μg/kg, and the second dose is administered to the subject in an amount of about 2 mg. In one embodiment, the first dose is administered to the subject in an amount of about 250 μg/kg, and the second dose is administered to the subject in an amount of about 20 mg. In one embodiment, the first dose is administered to the subject in an amount of about 250 μg/kg, and the second dose is administered to the subject in an amount of about 35 mg. In one embodiment, the first dose is administered to the subject in an amount of about 250 μg/kg, and the second dose is administered to the subject in an amount of about 50 mg. In one embodiment, the first dose is administered to the subject in an amount of about 360 μg/kg, and the second dose is administered to the subject in an amount of about 360 μg/kg. In one embodiment, the first dose is administered to the subject in an amount of about 360 μg/kg, and the second dose is administered to the subject in an amount of about 2 mg. In one embodiment, the first dose is administered to the subject in an amount of about 360 μg/kg, and the second dose is administered to the subject in an amount of about 20 mg. In one embodiment, the first dose is administered to the subject in an amount of about 360 μg/kg, and the second dose is administered to the subject in an amount of about 35 mg. In one embodiment, the first dose is administered to the subject in an amount of about 360 μg/kg, and the second dose is administered to the subject in an amount of about 50 mg. In one embodiment, the first dose is administered to the subject in an amount of about 500 μg/kg, and the second dose is administered to the subject in an amount of about 2 mg. In one embodiment, the first dose is administered to the subject in an amount of about 500 μg/kg, and the second dose is administered to the subject in an amount of about 20 mg. In one embodiment, the first dose is administered to the subject in an amount of about 500 μg/kg, and the second dose is administered to the subject in an amount of about 35 mg. In one embodiment, the first dose is administered to the subject in an amount of about 500 μg/kg, and the second dose is administered to the subject in an amount of about 50 mg. In one embodiment, the first dose is administered to the subject in an amount of about 0.8 mg, and the second dose is administered to the subject in an amount of about 2 mg. In one embodiment, the first dose is administered to the subject in an amount of about 0.8 mg, and the second dose is administered to the subject in an amount of about 20 mg. In one embodiment, the first dose is administered to the subject in an amount of about 0.8 mg, and the second dose is administered to the subject in an amount of about 35 mg. In one embodiment, the first dose is administered to the subject in an amount of about 0.8 mg, and the second dose is administered to the subject in an amount of about 50 mg. In a specific embodiment of the aforementioned methods, the bispecific anti-CD20×anti-CD3 antibody is XmAb® 13676 (plamotamab). In a specific embodiment of the aforementioned methods, the bispecific anti-CD20×anti-CD3 antibody is a biosimilar of XmAb® 13676. In a specific embodiment of the aforementioned methods, the bispecific anti-CD20×anti-CD3 antibody is a bioequivalent of XmAb® 13676.

V.c. Phase

In one embodiment, a phase comprises a certain number of occurrences of a dosage regimen. In one embodiment, a dosage regimen occurs one time in a phase. In one embodiment, a dosage regimen occurs two times in a phase. In one embodiment, a dosage regimen occurs three times in a phase. In one embodiment, a dosage regimen occurs four times in a phase. In one embodiment, a dosage regimen occurs five times in a phase. In one embodiment, a dosage regimen occurs six times in a phase. In one embodiment, a dosage regimen occurs seven times in a phase. In one embodiment, a dosage regimen occurs eight times in a phase. In one embodiment, a dosage regimen occurs nine times in a phase. In one embodiment, a dosage regimen occurs ten times in a phase. In one embodiment, a dosage regimen occurs eleven times in a phase. In one embodiment, a dosage regimen occurs twelve times in a phase. In one embodiment, a dosage regimen occurs thirteen times in a phase. In one embodiment, a dosage regimen occurs fourteen times in a phase. In one embodiment, a dosage regimen occurs fifteen times in a phase. In one embodiment, a dosage regimen occurs sixteen times in a phase. In one embodiment, a dosage regimen occurs seventeen times in a phase. In one embodiment, a dosage regimen occurs eighteen times in a phase. In one embodiment, a dosage regimen occurs nineteen times in a phase. In one embodiment, a dosage regimen occurs twenty times in a phase. In one embodiment, a dosage regimen continues until the cancer (e.g., hematological cancer) has a positive therapeutic response (e.g., complete or partial).

In one embodiment, the phase is a once a week dosage regimen described herein, with a duration of one week. In one embodiment, the phase is a once a week dosage regimen described herein, with a duration of two weeks. In one embodiment, the phase is a once a week dosage regimen described herein, with a duration of three weeks. In one embodiment, the phase is a once a week dosage regimen described herein, with a duration of four weeks.

V.d. Positive Therapeutic Response

In some embodiments, the bispecific anti-CD20×anti-CD3 antibody (e.g., XmAb®13676) treats a refractory leukemia or lymphoma. In one embodiment, for any method described herein, when there is a positive therapeutic response for the CD20-expressing cancer, such as partial remission and/or complete remission, the method further includes providing the bispecific anti-CD20×anti-CD3 antibody (e.g., XmAb® 13676) according to a dosage regimen described herein, at the same dose amount for the positive therapeutic response, such as partial remission and/or complete remission, or within about 10% of the dose amount (plus or minus), or within about 20% of the dose amount (plus or minus), of within about 30% of the dose amount (plus or minus), until non-efficacy is determined, an unacceptable level of toxicity is observed, or is terminated by the human subject. In one embodiment, for any method described herein, when there is a positive therapeutic response for the CD20-expressing cancer, such as partial remission and/or complete remission, the method further includes providing the bispecific anti-CD20×anti-CD3 antibody (e.g., XmAb® 13676) according to a once a week dosage regimen described herein or a once every three weeks dosage regimen described herein or a once every four weeks dosage regimen described herein or a two times a month dosage regimen described herein or a three times a month dosage regimen described herein or a monthly dosage regimen described herein, at the same dose amount for the positive therapeutic response, such as partial remission and/or complete remission, or within about 10% of the dose amount (plus or minus), or within about 20% of the dose amount (plus or minus), of within about 30% of the dose amount (plus or minus), until non-efficacy is determined, an unacceptable level of toxicity is observed, or is terminated by the human subject.

VI. EMBODIMENTS

One Phase

The method of treatment disclosed herein can comprise a first phase, for example, where the first phase is administered according to a specific dosage regimen, a specific dose amount, and for a specific administration time. In one embodiment, the method comprises a first phase where the bispecific antibody (e.g., XmAb® 13676) is administered once a week. In one embodiment, the method comprises a first phase where the bispecific antibody (e.g., XmAb® 13676) is administered once a week.

In one embodiment, where the method comprises a first phase where the bispecific anti-CD20×anti-CD3 antibody (e.g., XmAb® 13676) provided herein is administered once a week, the dose amount can be any one of the dose amounts as described in Paragraph A or Paragraph B or Paragraph C or Paragraph D or Paragraph E or Paragraph F or Paragraph G or Paragraph H or Paragraph I or Paragraph J or Paragraph K or Paragraph L or Paragraph M. This first phase can continue until there is a positive therapeutic response for the cancer (e.g., a CD20-expressing cancer).

In a specific embodiment of the methods of treatment comprising a first phase provided herein, the bispecific anti-CD20×anti-CD3 antibody is XmAb® 13676. In certain embodiments, the XmAb® 13676 is administered intravenously.

Cohort 8A

In one embodiment, the method of treatment comprises a first phase, where in the first phase the bispecific anti-CD20× anti-CD3 antibody (e.g., XmAb® 13676) is administered at least once in a first phase dose amount described within Paragraph J, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20× anti-CD3 antibody (e.g., XmAb® 13676) is administered at least once in a first phase dose amount between about 160 µg/kg and about 180 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20× anti-CD3 antibody (e.g., XmAb® 13676) is administered at least once in a first phase dose amount of about 170 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 9A

In one embodiment, the method of treatment comprises a first phase, where in the first phase the bispecific anti-CD20× anti-CD3 antibody (e.g., XmAb® 13676) is administered at least once in a first phase dose amount described within Paragraph K, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20× anti-CD3 antibody (e.g., XmAb® 13676) is administered at least once in a first phase dose amount between about 240 µg/kg and about 260 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb®13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20× anti-CD3 antibody (e.g., XmAb® 13676) is administered at least once in a first phase dose amount of about 250 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 10A

In one embodiment, the method of treatment comprises a first phase, where in the first phase the bispecific anti-CD20× anti-CD3 antibody (e.g., XmAb® 13676) is administered at least once in a first phase dose amount described within Paragraph L, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20×anti-CD3 antibody (e.g., XmAb® 13676) is administered at least once in a first phase dose amount between about 350 µg/kg and about 370 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20×anti-CD3 antibody (e.g., XmAb® 13676) is administered at least once in a first phase dose amount of about 360 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 11A

In one embodiment, the method of treatment comprises a first phase, where in the first phase the bispecific anti-CD20×anti-CD3 antibody (e.g., XmAb® 13676) is administered at least once in a first phase dose amount described within Paragraph M, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20×anti-CD3 antibody (e.g., XmAb® 13676) is administered at least once in a first phase dose amount between about 475 µg/kg and about 525 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, where in the first phase the bispecific anti-CD20×anti-CD3 antibody (e.g., XmAb® 13676) is administered at least once in a first phase dose amount of about 500 µg/kg, wherein the first phase continues with each first phase dose amount administered between about 6 and about 8 days after the previous first phase dose amount, until a positive therapeutic response is achieved, or so long as there is a positive therapeutic response. In an exemplary embodiment, the first phase is administered eight times. In one embodiment, after a positive therapeutic response is achieved, the first phase continues until there is no longer a positive therapeutic response, non-efficacy is determined, an unacceptable level of toxicity is observed, or treatment is terminated. In one embodiment, after a positive therapeutic response is achieved or after the first phase is administered eight times, the method further comprises a second phase wherein the bispecific anti-CD20×anti-CD3 antibody (e.g., XmAb® 13676) is administered according to an every two weeks dosage regimen described herein or a monthly dosage regimen described herein, at about the first phase dose amount, or within about 10% or about 20% or about 30% of the first phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Two Phases

The method of treatment disclosed herein can comprise a first phase and a second phase. In the first phase, the bispecific anti-CD20×anti-CD3 antibody (e.g., XmAb® 13676) provided herein can be administered according to a first dosage regimen, with a first phase dose amount. In the second phase, the bispecific anti-CD20×anti-CD3 antibody (e.g., XmAb® 13676) provided herein can be administered according to a second dosage regimen, with a second phase dose amount. In one embodiment, the second phase continues until a positive therapeutic response is achieved, or so as long as there is a positive therapeutic response. In one embodiment, after a positive therapeutic response is achieved, the method further comprises a third phase wherein the bispecific anti-CD20×anti-CD3 antibody (e.g., XmAb® 13676) is administered according to an every two weeks dosage regimen described herein or a monthly dosage regimen described herein, at about the second phase dose amount, or within about 10% or about 20% or about 30% of the second phase dose amount (plus or minus), until non-efficacy is determined, an unacceptable level of toxicity is observed, or is terminated by the human subject. The administration times can independently be any described throughout the specification.

In a specific embodiment of the methods of treatment comprising a first phase and a second phase provided herein, the bispecific anti-CD20×anti-CD3 antibody is XmAb® 13676. In certain embodiments, the XmAb® 13676 is administered intravenously.

Cohort 1B

In one embodiment, the method of treatment comprises a first phase and a second phase, where in the first phase the bispecific anti-CD20×anti-CD3 antibody (e.g., XmAb® 13676) is administered once in a first phase dose amount described within Paragraph H, then between about 6 and about 8 days later, in the second phase the bispecific anti-CD20×anti-CD3 antibody (e.g., XmAb® 13676) is administered once in a second phase dose amount described within Paragraph I, wherein the second phase continues with each second phase dose amount administered between about 6 and about 8 days after the previous second phase dose amount, until a positive therapeutic response is achieved, or so long as there is a positive therapeutic response. In an exemplary embodiment, the second phase is administered seven times. In one embodiment, after a positive therapeutic response is achieved, the second phase continues until there is no longer a positive therapeutic response, non-efficacy is determined, an unacceptable level of toxicity is observed, or treatment is terminated. In one embodiment, after a positive therapeutic response is achieved or after the second phase is administered seven times, the method further comprises a third phase wherein the bispecific anti-CD20×anti-CD3 antibody (e.g., XmAb® 13676) is administered according to an every two weeks dosage regimen described herein or a monthly dosage regimen described herein, at about the second phase dose amount, or within about 10% or about 20% or about 30% of the second phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase and a second phase, where in the first phase the bispecific anti-CD20×anti-CD3 antibody (e.g., XmAb® 13676) is administered once in a first phase dose amount between about 75 µg/kg and about 85 µg/kg, then between about 6 and about 8 days later, in the second phase the bispecific anti-CD20×anti-CD3 antibody (e.g., XmAb® 13676) is administered at least once in a second phase dose amount between about 120 µg/kg and about 130 µg/kg, wherein the second phase continues with each second phase dose amount administered between about 6 and about 8 days after the previous second phase dose amount, until a positive therapeutic response is achieved, or so long as there is a positive therapeutic response. In an exemplary embodiment, the second phase is administered seven times. In one embodiment, after a positive therapeutic response is achieved, the second phase continues until there is no longer a positive therapeutic response, non-efficacy is determined, an unacceptable level of toxicity is observed, or treatment is terminated. In one embodiment, after a positive therapeutic response is achieved or after the second phase is administered seven times, the method further comprises a third phase wherein the bispecific anti-CD20×anti-CD3 antibody (e.g., XmAb® 13676) is administered according to an every two weeks dosage regimen described herein or a monthly dosage regimen described herein, at about the second phase dose amount, or within about 10% or about 20% or about 30% of the second phase dose amount (plus or minus), until there is no longer a positive therapeutic response, non-efficacy is determined, an unacceptable level of toxicity is observed, or is terminated by the human subject. The administration times can independently be any described throughout the specification.

In some embodiments, a method of treatment of the disclosure comprises administering the bispecific anti-CD20×anti-CD3 antibody of the disclosure (e.g., XmAb® 13676) to a subject in a first phase and a second phase. In some embodiments, the method comprises more than two phases (e.g., three, four, five, six, seven, eight, nine, ten, or more than ten phases). In some embodiments, the bispecific anti-CD20×anti-CD3 antibody of the disclosure is administered to the subject in an amount of about 70 µg/kg and about 90 µg/kg in the first phase. In some embodiments, the bispecific anti-CD20×anti-CD3 antibody of the disclosure is administered to the subject in an amount of about 120 µg/kg and about 130 µg/kg in the second phase. In some embodiments, the bispecific anti-CD20×anti-CD3 antibody of the disclosure is administered to the subject in an amount of about 120 µg/kg and about 130 µg/kg in each subsequent phase after the second phase (e.g., third, fourth, five, sixth, seventh, or more than seventh phase). In some embodiments, the bispecific anti-CD20×anti-CD3 antibody of the disclosure is administered to the subject in an amount of about 80 µg/kg in the first phase. In some embodiments, the bispecific anti-CD20×anti-CD3 antibody of the disclosure is administered to the subject in an amount of about 125 µg/kg in the second phase. In some embodiments, the bispecific anti-CD20×anti-CD3 antibody of the disclosure is administered to the subject in an amount of about 125 µg/kg in each subsequent phase after the second phase (e.g., third, fourth, fifth, sixth, seventh, or more than seventh phase). In some embodiments, a following phase is administered about 6 days to about 8 days after the previous phase. In some embodiments, a following phase is administered about 13 days to about 17 days after the previous phase. In some embodiments, a following phase is administered about 13 days to about 15 days after the previous phase. In some embodiments, a following phase is administered about 5, 6, 7, 8, 9, 10, 11, 12, 13, 14, 15, 16, 17, 18, 19, 20, or more than about 20 days after the previous phase.

In a specific embodiment of the methods of treatment provided herein, the bispecific anti-CD20×anti-CD3 antibody is XmAb® 13676. In certain embodiments, the XmAb® 13676 is administered intravenously.

Specific Doses

In one embodiment, the method of treatment comprises a first phase and a second phase, where in the first phase the bispecific anti-CD20×anti-CD3 antibody (e.g., XmAb® 13676) is administered once in a first phase dose amount which is about 80 µg/kg, then between about 6 and about 8 days later, in the second phase the bispecific anti-CD20× anti-CD3 antibody (e.g., XmAb® 13676) is administered at least once in a second phase dose amount which is about 125 µg/kg, wherein the second phase continues with each second phase dose amount administered between about 6 and about 8 days after the previous second phase dose amount, until a positive therapeutic response is achieved, or so long as there is a positive therapeutic response. In an exemplary embodiment, the second phase is administered seven times. In one embodiment, after a positive therapeutic response is achieved, the second phase continues until there is no longer a positive therapeutic response, non-efficacy is determined, an unacceptable level of toxicity is observed, or treatment is terminated. In one embodiment, after a positive therapeutic response is achieved or after the second phase is administered seven times, the method further comprises a third phase wherein the bispecific anti-CD20×anti-CD3 antibody (e.g., XmAb® 13676) is administered according to an every two weeks dosage regimen described herein or a monthly dosage regimen described herein, at about the second phase dose amount, or within about 10% or about 20% or about 30% of the second phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Three Phases

In one embodiment, the method of treatment comprises a first phase, a second phase, and a third phase, where in the first phase, the bispecific anti-CD20×anti-CD3 antibody (e.g., XmAb® 13676) provided herein is administered in a first phase dose amount, where in the second phase, the bispecific anti-CD20×anti-CD3 antibody (e.g., XmAb® 13676) provided herein is administered in a second phase dose amount, and where in the third phase, the bispecific anti-CD20×anti-CD3 antibody (e.g., XmAb® 13676) provided herein is administered in a third phase dose amount. In one embodiment, the first, second, and third phase dose amounts are the same. In one embodiment, two of the first, second, and third phase dose amounts are the same (i.e., two are the same and one is different). In one embodiment, the first, second, and third phase dose amounts are different. In one embodiment, the third phase continues until a positive therapeutic response is achieved, or so as long as there is a positive therapeutic response. In one embodiment, after a positive therapeutic response is achieved, the method further comprises a fourth phase wherein the bispecific anti-CD20× anti-CD3 antibody (e.g., XmAb® 13676) is administered according to an every two weeks dosage regimen described herein or a monthly dosage regimen described herein, at about the third phase dose amount, or within about 10% or about 20% or about 30% of the third phase dose amount (plus or minus), until non-efficacy is determined, an unacceptable level of toxicity is observed, or is terminated by the human subject. The administration times can independently be any described throughout the specification.

In a specific embodiment of the methods of treatment comprising a first phase, a second phase and a third phase provided herein, the bispecific anti-CD20×anti-CD3 antibody is XmAb® 13676. In certain embodiments, the XmAb® 13676 is administered intravenously.

Four Phases

The method of treatment disclosed herein can comprise a first phase, a second phase, a third phase, and a fourth phase, where in the first phase the bispecific anti-CD20×anti-CD3 antibody (e.g., XmAb® 13676) provided herein is administered in a first phase dose amount, where in the second phase the bispecific anti-CD20×anti-CD3 antibody (e.g., XmAb® 13676) provided herein is administered in a second phase dose amount, where in the third phase the bispecific anti-CD20×anti-CD3 antibody (e.g., XmAb® 13676) provided herein is administered in a third phase dose amount, and where in the fourth phase the bispecific anti-CD20× anti-CD3 antibody (e.g., XmAb® 13676) provided herein is administered in a fourth phase dose amount. In one embodiment, the first, second, third, and fourth phase dose amounts are the same. In one embodiment, three of the first, second, third, and fourth phase dose amounts are the same (i.e., three are the same and one is different). In one embodiment, two of the first, second, third, and fourth phase dose amounts are the same (i.e., two are the same and two are different). In one embodiment, the first, second, third, and fourth phase dose amounts are different. In one embodiment, the fourth phase continues until a positive therapeutic response is achieved, or so as long as there is a positive therapeutic response. In one embodiment, after a positive therapeutic response is achieved, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until non-efficacy is determined, an unacceptable level of toxicity is observed, or is terminated by the human subject. The administration times can independently be any described throughout the specification.

In a specific embodiment of the methods of treatment comprising a first phase, a second phase, a third phase, and a fourth phase provided herein, the bispecific anti-CD20× anti-CD3 antibody is XmAb® 13676. In certain embodiments, the XmAb® 13676 is administered intravenously.

Cohort 2B

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount described within Paragraph F, then between about 6 and about 8 days later, in the second phase the bispecific anti-CD20×anti-CD3 antibody (e.g., XmAb® 13676) is administered once in a second phase dose amount described within Paragraph H, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered at least once in a fourth phase dose amount described within Paragraph J, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fourth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount between about 40 µg/kg and about 50 µg/kg, then between about 6 and about 8 days later, in the second phase the bispecific anti-CD20×anti-CD3 antibody (e.g., XmAb® 13676) is administered once in a second phase dose amount between about 75 µg/kg and about 85 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered at least once in a fourth phase dose amount between about 160 µg/kg and about 180 µg/kg, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount which is about 45 µg/kg, then between about 6 and about 8 days later, in the second phase the bispecific anti-CD20×anti-CD3 antibody (e.g., XmAb® 13676) is administered once in a second phase dose amount which is about 80 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered at least once in a fourth phase dose amount which is about 170 µg/kg, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort-1C (De-Escalation)

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount described within Paragraph P, then between about 6 and about 8 days later, in the second phase the bispecific anti-CD20×anti-CD3 antibody (e.g., XmAb® 13676) is administered once in a second phase dose amount described within Paragraph Q, then between about 6 and about 8 days later, in the third phase the bispecific anti-CD20×anti-CD3 antibody (e.g., XmAb® 13676) is administered once in a third phase dose amount described within Paragraph S, then between about 6 and about 8 days later, in the fourth phase the bispecific anti-CD20×anti-CD3 antibody (e.g., XmAb® 13676) is administered at least once in a fourth phase dose amount described within Paragraph T, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount between about 0.6 mg and about 1 mg, then between about 6 and about 8 days later, in the second phase the bispecific anti-CD20×anti-CD3 antibody (e.g., XmAb® 13676) is administered once in a second phase dose amount between about 1.2 mg and about 2.8 mg, then between about 6 and about 8 days later, in the third phase the bispecific anti-CD20×anti-CD3 antibody (e.g., XmAb® 13676) is administered once in a third phase dose amount between about 15 mg and about 25 mg, then between about 6 and about 8 days later, in the fourth phase the bispecific anti-CD20×anti-CD3 antibody (e.g., XmAb® 13676) is administered at least once in a fourth phase dose amount between about 30 mg and about 40 mg, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount which is about 0.8 mg, then between about 6 and about 8 days later, in the second phase the bispecific anti-CD20×anti-CD3 antibody (e.g., XmAb® 13676) is administered once in a second phase dose amount which is about 2 mg, then between about 6 and about 8 days later, in the third phase the bispecific anti-CD20×anti-CD3 antibody (e.g., XmAb® 13676) is administered once in a third phase dose amount which is about 20 mg, then between about 6 and about 8 days later, in the fourth phase the bispecific anti-CD20×anti-CD3 antibody (e.g., XmAb® 13676) is administered at least once in a fourth phase dose amount which is about 35 mg, then between about 6 and about 8 days later, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 2C

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount described within Paragraph P, then between about 6 and about 8 days later, in the second phase the bispecific anti-CD20×anti-CD3 antibody (e.g., XmAb® 13676) is administered once in a second phase dose amount described within Paragraph Q, then between about 6 and about 8 days later, in the third phase the bispecific anti-CD20×anti-CD3 antibody (e.g., XmAb® 13676) is administered once in a third phase dose amount described within Paragraph S, then between about 6 and about 8 days later, in the fourth phase the bispecific anti-CD20×anti-CD3 antibody (e.g., XmAb® 13676) is administered at least once in a fourth phase dose amount described within Paragraph U, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount between about 0.6 mg and about 1 mg, then between about 6 and about 8 days later, in the second phase the bispecific anti-CD20×anti-CD3 antibody (e.g., XmAb® 13676) is administered once in a second phase dose amount between about 1.2 mg and about 2.8 mg, then between about 6 and about 8 days later, in the third phase the bispecific anti-CD20×anti-CD3 antibody (e.g., XmAb® 13676) is administered once in a third phase dose amount between about 15 mg and about 25 mg, then between about 6 and about 8 days later, in the fourth phase the bispecific anti-CD20×anti-CD3 antibody (e.g., XmAb® 13676) is administered at least once in a fourth phase dose amount between about 45 mg and about 55 mg, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, and a fourth phase, where in the first phase the bispecific anti-CD20×anti-CD3 antibody (e.g., XmAb® 13676) is administered once in a first phase dose amount which is about 0.8 mg, then between about 6 and about 8 days later, in the second phase the bispecific anti-CD20×anti-CD3 antibody (e.g., XmAb® 13676) is administered once in a second phase dose amount which is about 2 mg, then between about 6 and about 8 days later, in the third phase the bispecific anti-CD20×anti-CD3 antibody (e.g., XmAb® 13676) is administered once in a third phase dose amount which is about 20 mg, then between about 6 and about 8 days later, in the fourth phase the bispecific anti-CD20×anti-CD3 antibody (e.g., XmAb® 13676) is administered at least once in a fourth phase dose amount which is about 50 mg, then between about 6 and about 8 days later, wherein the fourth phase continues with each fourth phase dose amount administered between about 6 and about 8 days after the previous fourth phase dose amount, until a positive therapeutic response is achieved, or so long as there is a positive therapeutic response. In an exemplary embodiment, the fourth phase is administered five times. In one embodiment, after a positive therapeutic response is achieved, the fourth phase continues until there is no longer a positive therapeutic response, non-efficacy is determined, an unacceptable level of toxicity is observed, or treatment is terminated. In one embodiment, after a positive therapeutic response is achieved or after the fourth phase is administered five times, the method further comprises a fifth phase wherein the bispecific anti-CD20×anti-CD3 antibody (e.g., XmAb® 13676) is administered according to an every two weeks dosage regimen described herein or a monthly dosage regimen described herein, at about the fourth phase dose amount, or within about 10% or about 20% or about 30% of the fourth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Five Phases

The method of treatment disclosed herein can comprise a first phase, a second phase, a third phase, a fourth phase, and a fifth phase, where in the first phase the bispecific anti-CD20×anti-CD3 antibody (e.g., XmAb® 13676) provided herein is administered in a first phase dose amount, where in the second phase the bispecific anti-CD20×anti-CD3 antibody (e.g., XmAb® 13676) provided herein is administered in a second phase dose amount, where in the third phase the bispecific anti-CD20×anti-CD3 antibody (e.g., XmAb® 13676) provided herein is administered in a third phase dose amount, where in the fourth phase the bispecific anti-CD20×anti-CD3 antibody (e.g., XmAb® 13676) provided herein is administered in a fourth phase dose amount, and where in the fifth phase the bispecific anti-CD20×anti-CD3 antibody (e.g., XmAb® 13676) provided herein is administered in a fifth phase dose amount. In one embodiment, the first, second, third, fourth, and fifth phase dose amounts are the same. In one embodiment, four of the first, second, third, fourth, and fifth phase dose amounts are the same (i.e., four are the same and one is different). In one embodiment, three of the first, second, third, fourth, and fifth phase dose amounts are the same (i.e., three are the same and two are different). In one embodiment, two of the first, second, third, fourth, and fifth phase dose amounts are the same (i.e., two are the same and three are different). In one embodiment, the first, second, third, fourth, and fifth phase dose amounts are different. In one embodiment, the fifth phase continues until a positive therapeutic response is achieved, or so as long as there is a positive therapeutic response. In one embodiment, after a positive therapeutic response is achieved, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 3B

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount described within Paragraph F, then between about 6 and about 8 days later, in the second phase the bispecific anti-CD20×anti-CD3 antibody (e.g., XmAb® 13676) is administered once in a second phase dose amount described within Paragraph H, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered at least once in a fifth phase dose amount described within Paragraph K, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount between about 40 µg/kg and about 50 µg/kg, then between about 6 and about 8 days later, in the second phase the bispecific anti-CD20×anti-CD3 antibody (e.g., XmAb® 13676) is administered once in a second phase dose amount between about 75 µg/kg and about 85 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered at least once in a fifth phase dose amount between about 240 µg/kg and about 260 µg/kg, then between about 6 and about 8 days later, wherein the fifth phase continues with each fifth phase dose amount administered between about 6 and about 8 days after the previous fifth dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount which is about 45 µg/kg, then between about 6 and about 8 days later, in the second phase the bispecific anti-CD20×anti-CD3 antibody (e.g., XmAb® 13676) is administered once in a second phase dose amount which is about 80 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20×anti-CD3 antibody (e.g., XmAb® 13676) is administered at least once in a fifth phase dose amount which is about 250 µg/kg, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment comprising a first phase, a second phase, a third phase, a fourth phase, and a fifth phase provided herein, the bispecific anti-CD20×anti-CD3 antibody is XmAb® 13676. In certain embodiments, the XmAb® 13676 is administered intravenously.

Cohort 3Bi

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount described within Paragraph E, then between about 6 and about 8 days later, in the second phase the bispecific anti-CD20×anti-CD3 antibody (e.g., XmAb® 13676) is administered once in a second phase dose amount described within Paragraph G, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered at least once in a fifth phase dose amount described within Paragraph K, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount between about 20 µg/kg and about 30 µg/kg, then between about 6 and about 8 days later, in the second phase the bispecific anti-CD20×anti-CD3 antibody (e.g., XmAb® 13676) is administered once in a second phase dose amount between about 45 µg/kg and about 55 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered at least once in a fifth phase dose amount between about 240 µg/kg and about 260 µg/kg, then between about 6 and about 8 days later, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount which is about 25 µg/kg, then between about 6 and about 8 days later, in the second phase the bispecific anti-CD20×anti-CD3 antibody (e.g., XmAb® 13676) is administered once in a second phase dose amount which is about 50 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20×anti-CD3 antibody (e.g., XmAb® 13676) is administered at least once in a fifth phase dose amount which is about 250 µg/kg, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times.

In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Modified Cohort 5B

In one embodiment, the method of treatment comprises a first phase, a second phase, a third phase, a fourth phase, a fifth phase, a sixth phase, and a seventh phase where in the first phase the bispecific anti-CD20×anti-CD3 antibody (e.g., XmAb® 13676) is administered once in a first phase dose amount described within Paragraph D, then between about 6 and about 8 days later, in the second phase the bispecific anti-CD20×anti-CD3 antibody (e.g., XmAb® 13676) is administered once in a second phase dose amount described within Paragraph E, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered once in a fifth phase dose amount described within Paragraph K, then between about 6 and about 8 days later, in the sixth phase the bispecific anti-CD20×anti-CD3 antibody (e.g., XmAb® 13676) is administered once in a sixth phase dose amount described within Paragraph L, then between about 6 and about 8 days later, in the seventh phase the bispecific anti-CD20×anti-CD3 antibody (e.g., XmAb® 13676) is administered at least once in a seventh phase dose amount described within Paragraph M, wherein the seventh phase continues with each seventh phase dose amount administered between about 6 and about 8 days or between about 13 and 17 days after the previous seventh phase dose amount, until a positive therapeutic response is achieved, or so long as there is a positive therapeutic response. In an exemplary embodiment, the seventh phase is administered four times. In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered four times, the method further comprises an eighth- phase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, a sixth phase, and a seventh phase where in the first phase the bispecific anti-CD20×anti-CD3 antibody (e.g., XmAb® 13676) is administered once in a first phase dose amount between about 8 µg/kg and about 12 µg/kg, then between about 6 and about 8 days later, in the second phase the bispecific anti-CD20×anti-CD3 antibody (e.g., XmAb® 13676) is administered once in a second phase dose amount between about 20 µg/kg and about 30 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered once in a fifth phase dose amount between about 210 µg/kg and about 290 µg/kg, then between about 6 and about 8 days later, in the sixth phase the bispecific anti-CD20×anti-CD3 antibody (e.g., XmAb® 13676) is administered once in a sixth phase dose amount between about 300 µg/kg and about 400 µg/kg, then between about 6 and about 8 days later, in the seventh phase the bispecific anti-CD20×anti-CD3 antibody (e.g., XmAb® 13676) is administered at least once in a seventh phase dose amount between about 450 µg/kg and about 550 µg/kg, wherein the seventh phase continues with each seventh phase dose amount administered between about 6 and about 8 days after the previous seventh phase dose amount, until a positive therapeutic response is achieved, or so long as there is a positive therapeutic response. In an exemplary embodiment, the seventh phase is administered four times. In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered four times, the method further comprises an eighth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, a sixth phase, and a seventh phase, where in the first phase the bispecific anti-CD20×anti-CD3 antibody (e.g., XmAb® 13676) is administered once in a first phase dose amount which is about 10 µg/kg, then between about 6 and about 8 days later, in the second phase the bispecific anti-CD20×anti-CD3 antibody (e.g., XmAb® 13676) is administered once in a second phase dose amount which is about 25 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20× anti-CD3 antibody (e.g., XmAb® 13676) is administered once in a fifth phase dose amount which is about 250 µg/kg, then between about 6 and about 8 days later, in the sixth phase the bispecific anti-CD20×anti-CD3 antibody (e.g., XmAb® 13676) is administered once in a sixth phase dose amount which is about 360 µg/kg, then between about 6 and about 8 days later, in the seventh phase the bispecific anti-CD20×anti-CD3 antibody (e.g., XmAb® 13676) is administered at least once in a seventh phase dose amount which is about 500 µg/kg, wherein the seventh phase continues with each seventh phase dose amount administered between about 6 and about 8 days or between about 13 and 17 days after the previous seventh phase dose amount, until a positive therapeutic response is achieved, or so long as there is a positive therapeutic response. In an exemplary embodiment, the seventh phase is administered four times.

In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered four times, the method further comprises an eighthphase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Cohort 1C

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount described within Paragraph P, then between about 6 and about 8 days later, in the second phase the bispecific anti-CD20×anti-CD3 antibody (e.g., XmAb® 13676) is administered once in a second phase dose amount described within Paragraph Q, then between about 6 and about 8 days later, in the third phase the bispecific anti-CD20×anti-CD3 antibody (e.g., XmAb® 13676) is administered once in a third phase dose amount described within Paragraph S, then between about 6 and about 8 days later, in the fourth phase the bispecific anti-CD20×anti-CD3 antibody (e.g., XmAb® 13676) is administered once in a fourth phase dose amount described within Paragraph T, then between about 6 and about 8 days later, in the fifth phase the bispecific anti-CD20×anti-CD3 antibody (e.g., XmAb® 13676) is administered at least once in a fifth phase dose amount described within Paragraph U, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount between about 0.6 mg and about 1 mg, then between about 6 and about 8 days later, in the second phase the bispecific anti-CD20×anti-CD3 antibody (e.g., XmAb® 13676) is administered once in a second phase dose amount between about 1.2 mg and about 2.8 mg, then between about 6 and about 8 days later, in the third phase the bispecific anti-CD20×anti-CD3 antibody (e.g., XmAb® 13676) is administered once in a third phase dose amount between about 15 mg and about 25 mg, then between about 6 and about 8 days later, in the fourth phase the bispecific anti-CD20×anti-CD3 antibody (e.g., XmAb® 13676) is administered once in a fourth phase dose amount between about 30 mg and about 40 mg, then between about 6 and about 8 days later, in the fifth phase the bispecific anti-CD20×anti-CD3 antibody (e.g., XmAb® 13676) is administered at least once in a fifth phase dose amount between about 42 mg and about 54 mg, then between about 6 and about 8 days later, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20×anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, and a fifth phase, where in the first phase the bispecific anti-CD20×anti-CD3 antibody (e.g., XmAb® 13676) is administered once in a first phase dose amount which is about 0.8 mg, then between about 6 and about 8 days later, in the second phase the bispecific anti-CD20×anti-CD3 antibody (e.g., XmAb® 13676) is administered once in a second phase dose amount which is about 2 mg, then between about 6 and about 8 days later, in the third phase the bispecific anti-CD20×anti-CD3 antibody (e.g., XmAb® 13676) is administered once in a third phase dose amount which is about 20 mg, then between about 6 and about 8 days later, in the fourth phase the bispecific anti-CD20×anti-CD3 antibody (e.g., XmAb® 13676) is administered once in a fourth phase dose amount which is about 35 mg, then between about 6 and about 8 days later, in the fifth phase the bispecific anti-CD20×anti-CD3 antibody (e.g., XmAb® 13676) is administered at least once in a fifth phase dose amount which is about 50 mg, wherein the fifth phase continues with each fifth phase dose amount administered between about 6 and about 8 days after the previous fifth phase dose amount, until a positive therapeutic response is achieved, or so long as there is a positive therapeutic response. In an exemplary embodiment, the fifth phase is administered four times. In one embodiment, after a positive therapeutic response is achieved, the fifth phase continues until there is no longer a positive therapeutic response, non-efficacy is determined, an unacceptable level of toxicity is observed, or treatment is terminated. In one embodiment, after a positive therapeutic response is achieved or after the fifth phase is administered four times, the method further comprises a sixth phase wherein the bispecific anti-CD20× anti-CD3 antibody (e.g., XmAb® 13676) is administered according to an every two weeks dosage regimen described herein or a monthly dosage regimen described herein, at about the fifth phase dose amount, or within about 10% or about 20% or about 30% of the fifth phase dose amount (plus or minus), until there is no longer a positive therapeutic response, non-efficacy is determined, an unacceptable level of toxicity is observed, or is terminated by the human subject. The administration times can independently be any described throughout the specification.

In some embodiments, a method of treatment of the disclosure comprises administering the bispecific anti-CD20×anti-CD3 antibody of the disclosure (e.g., XmAb® 13676) to a subject in a first phase, a second phase, a third phase, a fourth phase, and a fifth phase. In some embodiments, the method comprises more than five phases (e.g., six, seven, eight, nine, ten, or more than ten phases). In some embodiments, the bispecific anti-CD20×anti-CD3 antibody of the disclosure is administered to the subject in an amount of about 0.5 mg and about 1.5 mg in the first phase. In some embodiments, the bispecific anti-CD20×anti-CD3 antibody of the disclosure is administered to the subject in an amount of about 1.5 mg and about 2.5 mg in the second phase. In some embodiments, the bispecific anti-CD20×anti-CD3 antibody of the disclosure is administered to the subject in an amount of about 15 mg and about 25 mg in the third phase. In some embodiments, the bispecific anti-CD20×anti-CD3 antibody of the disclosure is administered to the subject in an amount of about 30 mg and about 35 mg in the fourth phase. In some embodiments, the bispecific anti-CD20×anti-CD3 antibody of the disclosure is administered to the subject in an amount of about 45 mg and about 55 mg in the fifth phase. In some embodiments, the bispecific anti-CD20×anti-CD3 antibody of the disclosure is administered to the subject in an amount of about 45 mg and about 55 mg in each subsequent phase after the fifth phase (e.g., sixth, seventh, or more than seventh phase). In some embodiments, the bispecific anti-CD20×anti-CD3 antibody of the disclosure is administered to the subject in an amount of about 0.8 mg in the first phase. In some embodiments, the bispecific anti-CD20×anti-CD3 antibody of the disclosure is administered to the subject in an amount of about 2 mg in the second phase. In some embodiments, the bispecific anti-CD20×anti-CD3 antibody of the disclosure is administered to the subject in an amount of about 20 mg in the third phase. In some embodiments, the bispecific anti-CD20×anti-CD3 antibody of the disclosure is administered to the subject in an amount of about 35 mg in the fourth phase. In some embodiments, the bispecific anti-CD20×anti-CD3 antibody of the disclosure is administered to the subject in an amount of about 50 mg in the fifth phase. In some embodiments, the bispecific anti-CD20×anti-CD3 antibody of the disclosure is administered to the subject in an amount of about 50 mg in each subsequent phase after the fifth phase (e.g., sixth, seventh, or more than seventh phase). In some embodiments, a following phase is administered about 6 days to about 8 days after the previous phase (e.g., second phase is administered about 6 days to about 8 days after the first phase). In some embodiments, a following phase is administered about 13 days to about 17 days after the previous phase. In some embodiments, a following phase is administered about 13 days to about 15 days after the previous phase. In some embodiments, a following phase is administered about 5, 6, 7, 8, 9, 10, 11, 12, 13, 14, 15, 16, 17, 18, 19, 20, or more than about 20 days after the previous phase.

In a specific embodiment of the methods of treatment provided herein, the bispecific anti-CD20×anti-CD3 antibody is XmAb® 13676. In certain embodiments, the XmAb® 13676 is administered intravenously.

Six Phases

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) provided herein is administered in a first phase dose amount, where in the second phase the bispecific anti-CD20×anti-CD3 antibody (e.g., XmAb® 13676) provided herein is administered in a second phase dose amount, where in the third phase the bispecific anti-CD20×anti-CD3 antibody (e.g., XmAb® 13676) provided herein is administered in a third phase dose amount, where in the fourth phase the bispecific anti-CD20×anti-CD3 antibody (e.g., XmAb® 13676) provided herein is administered in a fourth phase dose amount, where in the fifth phase the bispecific anti-CD20×anti-CD3 antibody (e.g., XmAb® 13676) provided herein is administered in a fifth phase dose amount, and where in the sixth phase the bispecific anti-CD20×anti-CD3 antibody (e.g., XmAb® 13676) provided herein is administered in a sixth phase dose amount. In one embodiment, the first, second, third, fourth, fifth, and sixth phase dose amounts are the same. In one embodiment, five of the first, second, third, fourth, fifth, and sixth phase dose amounts are the same (i.e., five are the same and one is different). In one embodiment, four of the first, second, third, fourth, fifth, and sixth phase dose amounts are the same (i.e., four are the same and two are different). In one embodiment, three of the first, second, third, fourth, fifth, and sixth phase dose amounts are the same (i.e., three are the same and three are different). In one embodiment, two of the first, second, third, fourth, fifth, and sixth phase dose amounts are the same (i.e., two are the same and four are different). In one embodiment, the first, second, third, fourth, fifth, and sixth phase dose amounts are different. In one embodiment, the sixth phase continues until a positive therapeutic response is achieved, or so as long as there is a positive therapeutic response. In one embodiment, after a positive therapeutic response is achieved, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until non-efficacy is determined, an unacceptable level of toxicity is observed, or is terminated by the human subject. The administration times can independently be any described throughout the specification.

In a specific embodiment of the methods of treatment comprising a first phase, a second phase, a third phase, a fourth phase, a fifth phase, and a sixth phase provided herein, the bispecific anti-CD20×anti-CD3 antibody is XmAb® 13676. In certain embodiments, the XmAb® 13676 is administered intravenously.

Cohort 4B

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) is administered once in a first phase dose amount described within Paragraph E, then between about 6 and about 8 days later, in the second phase the bispecific anti-CD20×anti-CD3 antibody (e.g., XmAb® 13676) is administered once in a second phase dose amount described within Paragraph G, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered once in a fifth phase dose amount described within Paragraph K, then between about 6 and about 8 days later, in the sixth phase the bispecific anti-CD20×anti-CD3 antibody (e.g., XmAb® 13676) is administered at least once in a sixth phase dose amount described within Paragraph L, wherein the sixth phase continues with each sixth phase dose amount administered between about 6 and about 8 days after the previous sixth phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) is administered once in a first phase dose amount between about 20 µg/kg and about 30 µg/kg, then between about 6 and about 8 days later, in the second phase the bispecific anti-CD20×anti-CD3 antibody (e.g., XmAb® 13676) is administered once in a second phase dose amount between about 45 µg/kg and about 55 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered once in a fifth phase dose amount between about 240 µg/kg and about 260 µg/kg, then between about 6 and about 8 days later, in the sixth phase the bispecific anti-CD20×anti-CD3 antibody (e.g., XmAb® 13676) is administered at least once in a sixth phase dose amount between about 340 µg/kg and about 380 µg/kg, wherein the sixth phase continues with each sixth phase dose amount administered between about 6 and about 8 days after the previous sixth phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb®

13676) is administered once in a first phase dose amount which is about 25 µg/kg, then between about 6 and about 8 days later, in the second phase the bispecific anti-CD20×anti-CD3 antibody (e.g., XmAb® 13676) is administered once in a second phase dose amount which is about 50 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20×anti-CD3 antibody (e.g., XmAb® 13676) is administered once in a fifth phase dose amount which is about 250 µg/kg, then between about 6 and about 8 days later, in the sixth phase the bispecific anti-CD20×anti-CD3 antibody (e.g., XmAb® 13676) is administered at least once in a sixth phase dose amount which is about 360 µg/kg, wherein the sixth phase continues with each phase dose amount administered between about 6 and about 8 days after the previous phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Modified Cohort 4B

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) is administered once in a first phase dose amount described within Paragraph D, then between about 6 and about 8 days later, in the second phase the bispecific anti-CD20×anti-CD3 antibody (e.g., XmAb® 13676) is administered once in a second phase dose amount described within Paragraph E, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered once in a fifth phase dose amount described within Paragraph K, then between about 6 and about 8 days later, in the sixth phase the bispecific anti-CD20×anti-CD3 antibody (e.g., XmAb® 13676) is administered at least once in a sixth phase dose amount described within Paragraph L, wherein the sixth phase continues with each sixth phase dose amount administered between about 6 and about 8 days after the previous sixth phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) is administered once in a first phase dose amount between about 8 µg/kg and about 12 µg/kg, then between about 6 and about 8 days later, in the second phase the bispecific anti-CD20×anti-CD3 antibody (e.g., XmAb® 13676) is administered once in a second phase dose amount between about 20 µg/kg and about 30 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered once in a fifth phase dose amount between about 240 µg/kg and about 260 µg/kg, then between about 6 and about 8 days later, in the sixth phase the bispecific anti-CD20×anti-CD3 antibody (e.g., XmAb® 13676) is administered at least once in a sixth phase dose amount between about 340 µg/kg and about 380 µg/kg, wherein the sixth phase continues with each sixth phase dose amount administered between about 6 and about 8 days after the previous sixth phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, and a sixth phase, where in the first phase the bispecific anti-CD20×anti-CD3 antibody (e.g., XmAb® 13676) is administered once in a first phase dose amount which is about 10 µg/kg, then between about 6 and about 8 days later, in the second phase the bispecific anti-CD20×anti-CD3 antibody (e.g., XmAb® 13676) is administered once in a second phase dose amount which is about 25 µg/kg, then between about 6 and about 8 days later, in the third phase the bispecific anti-CD20×anti-CD3 antibody (e.g., XmAb® 13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20×anti-CD3 antibody (e.g., XmAb® 13676) is administered once in a fifth phase dose amount which is about 250 µg/kg, then between about 6 and about 8 days later, in the sixth phase the bispecific anti-CD20×anti-CD3 antibody (e.g., XmAb® 13676) is administered at least once in a sixth phase dose amount which is about 360 µg/kg, wherein the sixth phase continues with each phase dose amount administered between about 6 and about 8 days after the previous phase dose amount, until a positive therapeutic response is achieved, or so long as there is a positive therapeutic response. In an exemplary embodiment, the sixth phase is administered three times. In one embodiment, after a positive therapeutic response is achieved, the sixth phase continues until there is no longer a positive therapeutic response, non-efficacy is determined, an unacceptable level of toxicity is observed, or treatment is terminated. In one embodiment, after a positive therapeutic response is achieved or after the sixth phase is administered three times, the method further comprises a seventh phase wherein the bispecific anti-CD20×anti-CD3 antibody (e.g., XmAb® 13676) is administered according to an every two weeks dosage regimen described herein or a monthly dosage regimen described herein, at about the sixth phase dose amount, or within about 10% or about 20% or about 30% of the sixth phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

Seven Phases

The method of treatment disclosed herein can comprise a first phase, a second phase, a third phase, a fourth phase, a fifth phase, a sixth phase, and a seventh phase, where in the first phase the bispecific anti-CD20×anti-CD3 antibody (e.g., XmAb® 13676) provided herein is administered in a first phase dose amount, where in the second phase the bispecific anti-CD20×anti-CD3 antibody (e.g., XmAb® 13676) provided herein is administered in a second phase dose amount, where in the third phase the bispecific anti-CD20×anti-CD3 antibody (e.g., XmAb® 13676) provided herein is administered in a third phase dose amount, where in the fourth phase the bispecific anti-CD20×anti-CD3 antibody (e.g., XmAb® 13676) provided herein is administered in a fourth phase dose amount, where in the fifth phase the bispecific anti-CD20×anti-CD3 antibody (e.g., XmAb® 13676) provided herein is administered in a fifth phase dose amount, where in the sixth phase the bispecific anti-CD20×anti-CD3 antibody (e.g., XmAb® 13676) provided herein is administered in a sixth phase dose amount and where in the seventh phase the bispecific anti-CD20×anti-CD3 antibody (e.g., XmAb® 13676) provided herein is administered in a seventh phase dose amount. In one embodiment, the first, second, third, fourth, fifth, sixth, and seventh phase dose amounts are the same. In one embodiment, six of the first, second, third, fourth, fifth, sixth, and seventh phase dose amounts are the same (i.e., six are the same and one is different). In one embodiment, five of the first, second, third, fourth, fifth, sixth, and seventh phase dose amounts are the same (i.e., five are the same and two are different). In one embodiment, four of the first, second, third, fourth, fifth, sixth, and seventh phase dose amounts are the same (i.e., four are the same and three are different). In one embodiment, three of the first, second, third, fourth, fifth, sixth, and seventh phase dose amounts are the same (i.e., three are the same and four are different). In one embodiment, two of the first, second, third, fourth, fifth, sixth, and seventh phase dose amounts are the same (i.e., two are the same and five are different). In one embodiment, the first, second, third, fourth, fifth, sixth, and seventh phase dose amounts are different. In one embodiment, the seventh phase continues until a positive therapeutic response is achieved, or so long as there is a positive therapeutic response. In one embodiment, after a positive therapeutic response is achieved, the method further comprises an eighth phase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until non-efficacy is determined, an unacceptable level of toxicity is observed, or is terminated by the human subject. The administration times can independently be any described throughout the specification.

In a specific embodiment of the methods of treatment comprising a first phase, a second phase, a third phase, a fourth phase, a fifth phase, a sixth phase, and a seventh phase provided herein, the bispecific anti-CD20×anti-CD3 antibody is XmAb® 13676. In certain embodiments, the XmAb® 13676 is administered intravenously.

Cohort 5B

In one embodiment, the method of treatment comprises a first phase, a second phase, a third phase, a fourth phase, a fifth phase, a sixth phase, and a seventh phase, where in the first phase the bispecific anti-CD20×anti-CD3 antibody (e.g., XmAb® 13676) is administered once in a first phase dose amount described within Paragraph E, then between about 6 and about 8 days later, in the second phase the bispecific anti-CD20×anti-CD3 antibody (e.g., XmAb® 13676) is administered once in a second phase dose amount described within Paragraph G, then between about 6 and about 8 days later, in the third phase the bispecific anti-CD20×anti-CD3 antibody (e.g., XmAb® 13676) is administered once in a third phase dose amount described within Paragraph I, then between about 6 and about 8 days later, in the fourth phase the bispecific anti-CD20×anti-CD3 antibody (e.g., XmAb® 13676) is administered once in a fourth phase dose amount described within Paragraph J, then between about 6 and about 8 days later, in the fifth phase the bispecific anti-CD20×anti-CD3 antibody (e.g., XmAb® 13676) is administered once in a fifth phase dose amount described within Paragraph K, then between about 6 and about 8 days later, in the sixth phase the bispecific anti-CD20×anti-CD3 antibody (e.g., XmAb® 13676) is administered once in a sixth phase dose amount described within Paragraph L, then between about 6 and about 8 days later, and in the seventh phase the bispecific anti-CD20×anti-CD3 antibody (e.g., XmAb® 13676) is administered at least once in a seventh phase dose amount described within Paragraph M, wherein the seventh phase continues with each seventh phase dose amount administered between about 6 and about 8 days after the previous seventh phase dose amount, until a positive therapeutic response is achieved, or so long as there is a positive therapeutic response. In an exemplary embodiment, the seventh phase is administered two times. In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered two times, the method further comprises an eighth phase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, a sixth phase, and a seventh phase, where in the first phase the bispecific anti-CD20×anti-CD3 antibody (e.g., XmAb® 13676) is administered once in a first phase dose amount between about 20 µg/kg and about 30 µg/kg, then between about 6 and about 8 days later, in the second phase the bispecific anti-CD20×anti-CD3 antibody (e.g., XmAb® 13676) is administered once in a second phase dose amount between about 45 µg/kg and about 55 µg/kg, then between about 6 and about 8 days later, in the third phase the bispecific anti-CD20×anti-CD3 antibody (e.g., XmAb® 13676) is administered once in a third phase dose amount between about 120 µg/kg and about 130 µg/kg, then between about 6 and about 8 days later, in the fourth phase the bispecific anti-CD20×anti-CD3 antibody (e.g., XmAb® 13676) is administered once in a fourth phase dose amount between about 160 µg/kg and about 180 µg/kg, then between about 6 and about 8 days later, in the fifth phase the bispecific anti-CD20×anti-CD3 antibody (e.g., XmAb® 13676) is administered once in a fifth phase dose amount between about 240 µg/kg and about 260 µg/kg, then between about 6 and about 8 days later, in the sixth phase the bispecific anti-CD20×anti-CD3 antibody (e.g., XmAb® 13676) is administered once in a sixth phase dose amount between about 340 µg/kg and about 380 µg/kg, then between about 6 and about 8 days later, in the seventh phase the bispecific anti-CD20×anti-CD3 antibody (e.g., XmAb® 13676) is administered at least once in a seventh phase dose amount between about 475 µg/kg and about 525 µg/kg, wherein the seventh phase continues with each seventh phase dose amount administered between about 6 and about 8 days after the previous seventh dose amount, until a positive therapeutic response is achieved, or so long as there is a positive therapeutic response. In an exemplary embodiment, the seventh phase is administered two times. In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered two times, the method further comprises an eighth phase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In one embodiment, the method of treatment comprises a first phase, a second phase, a third phase, a fourth phase, a fifth phase, a sixth phase, and a seventh phase, where in the first phase the bispecific anti-CD20×anti-CD3 antibody (e.g., XmAb® 13676) is administered once in a first phase dose amount which is about 25 µg/kg, then between about 6 and about 8 days later, in the second phase the bispecific anti-CD20×anti-CD3 antibody (e.g., XmAb® 13676) is administered once in a second phase dose amount which is about 50 µg/kg, then between about 6 and about 8 days later, in the third phase the bispecific anti-CD20×anti-CD3 antibody (e.g., XmAb®13676) is administered once in a third phase dose amount which is about 125 µg/kg, then between about 6 and about 8 days later, in the fourth phase the bispecific anti-CD20×anti-CD3 antibody (e.g., XmAb® 13676) is administered once in a fourth phase dose amount which is about 170 µg/kg, then between about 6 and about 8 days later, in the fifth phase the bispecific anti-CD20×anti-CD3 antibody (e.g., XmAb® 13676) is administered once in a fifth phase dose amount which is about 250 µg/kg, then between about 6 and about 8 days later, in the sixth phase the bispecific anti-CD20×anti-CD3 antibody (e.g., XmAb® 13676) is administered once in a sixth phase dose amount which is about 360 µg/kg, then between about 6 and about 8 days later, in the seventh phase the bispecific anti-CD20×anti-CD3 antibody (e.g., XmAb® 13676) is administered at least once in a seventh phase dose amount which is about 500 µg/kg, wherein the seventh phase continues with each seventh phase dose amount administered between about 6 and about 8 days after the previous seventh phase dose amount, until a positive therapeutic response is achieved, or so long as there is a positive therapeutic response. In an exemplary embodiment, the seventh phase is administered two times. In one embodiment, after a positive therapeutic response is achieved, the seventh phase continues until there is no longer a positive therapeutic response, non-efficacy is determined, an unacceptable level of toxicity is observed, or treatment is terminated. In one embodiment, after a positive therapeutic response is achieved or after the seventh phase is administered two times, the method further comprises an eighth phase wherein the bispecific anti-CD20×anti-CD3 antibody (e.g., XmAb® 13676) is administered according to an every two weeks dosage regimen described herein or a monthly dosage regimen described herein, at about the seventh phase dose amount, or within about 10% or about 20% or about 30% of the seventh phase dose amount (plus or minus), until there is no longer a positive therapeutic response, non-efficacy is determined, an unacceptable level of toxicity is observed, or is terminated by the human subject. The administration times can independently be any described throughout the specification.

In a specific embodiment of the methods of treatment provided herein, the bispecific anti-CD20×anti-CD3 antibody is XmAb® 13676. In certain embodiments, the XmAb® 13676 is administered intravenously.

VII. HUMAN SUBJECT SELECTION

Human subjects can be selected based on criteria described herein. In an exemplary embodiment, the human subject is 18 years or older. In an exemplary embodiment, the human subject has been diagnosed with a cancer described herein. In an exemplary embodiment, the human subject can be selected based on CD20 expression level in a sample (e.g., a tissue sample or a blood sample) obtained from the human subject. CD20 expression level can be determined by an assay known in the art, e.g., flow cytometry or immunohistochemistry. In an exemplary embodiment, the human subject has an Eastern Cooperative Oncology Group (ECOG) performance status of 0, 1, or 2. In an exemplary embodiment, the human subject has a confirmed diagnosis of DLBCL or transformed low-grade lymphoma with measurable disease. In an exemplary embodiment, the human subject has one of the following diagnoses: DLBCL, not otherwise specified (NOS); T-cell/histiocyte-rich large B-cell lymphoma; primary mediastinal (thymic) large B-cell lymphoma; intravascular large B-cell lymphoma; primary cutaneous DLBCL leg type; EBV+DLBCL, NOS; DLBCL associated with chronic inflammation; high-grade B-cell lymphoma, with MYC and BCL2 and/or BCL6 rearrangements; high-grade B-cell lymphoma, NOS; Grade 3b follicular lymphoma; or transformed follicular lymphoma. In an exemplary embodiment, the human subject is refractory or has relapsed after 2 or more standard therapeutic options, at least one of which must have included anti-CD20 antibody therapy. In an exemplary embodiment, for a human subject with transformed follicular lymphoma, the human subject has relapsed/refractory disease after a total of 2 or more prior lines of chemoimmunotherapy (at least one of which must have been directed at the transformed DLBCL). In an exemplary embodiment, the human subject is not a candidate for or refusing treatment with hematopoietic stem cell transplantation. In an exemplary embodiment, the human subject has a diagnosis of follicular lymphoma Grades 1-3a. In an exemplary embodiment, the human subject is ineligible for or has exhausted standard therapeutic options and/or has had 2 or more prior systemic regimens. In an exemplary embodiment, the human subject has a diagnosis of mantle cell lymphoma. In an exemplary embodiment, the human subject has a diagnosis of Waldenström macroglobulinemia. In an exemplary embodiment, the human subject has a diagnosis of Richter transformation. In an exemplary embodiment, the human subject has a diagnosis of other indolent B-cell, non-Hodgkin's lymphomas, specifically the following: MALT lymphoma, nodal marginal zone lymphoma, and splenic marginal zone lymphoma.

Human subjects can be selected based on CD20 expression level in a sample (e.g., a tissue sample or a blood sample) obtained from the human subject. CD20 expression level can be determined by an assay known in the art, e.g., flow cytometry, immunohistochemistry, Western blotting, immunofluorescent assay, radioimmunoassay (RIA), enzyme-linked immunosorbent assay (ELISA), homogeneous time resolved fluorescence (HTRF), positron emission tomography (PET), or any other immune detection with an antibody or antibody fragment against CD20 protein. In an exemplary embodiment, the human subject has exhausted standard therapeutic options. In an exemplary embodiment, the human subject is not a candidate for hematopoietic stem cell transplantation. In an exemplary embodiment, the human subject refuses hematopoietic stem cell transplantation. In an exemplary embodiment, the human subject last received a dose of an anti-CD20 antibody at least 4 weeks before the first administration of XmAb® 13676. In an exemplary embodiment, the human subject has an Eastern Cooperative Oncology Group (ECOG) performance status of 0 or 1 or 2.

Blood samples can be collected from a human subject using any method known in the art, e.g., by venipuncture or fingerstick. Particular types of blood cells can be isolated, expanded, frozen, and used at a later time. Tissue samples can be obtained from a human subject using any method known in the art, e.g., by biopsy or surgery. CT imaging, ultrasound, or an endoscope can be used to guide this type of procedure. The sample may be flash frozen and stored at −80° C. for later use. The sample may also be fixed with a fixative, such as formaldehyde, paraformaldehyde, or acetic acid/ethanol. RNA or protein may be extracted from a fresh, frozen or fixed sample for analysis.

Whereas particular embodiments provided herein have been described above for purposes of illustration, it will be appreciated by those skilled in the art that numerous variations of the details can be made without departing from the invention as described in the appended claims.

EXAMPLES

Examples are administered below to illustrate the methods described throughout. These examples are not meant to constrain the methods to any particular application or theory of operation. For all constant region positions discussed, numbering is according to the EU index as in Kabat (Kabat et al., 1991, Sequences of Proteins of Immunological Interest, 5th Ed., United States Public Health Service, National Institutes of Health, Bethesda, entirely incorporated by reference). A skilled artisan will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in U.S. Pat. Appl. Pubs. 2015/0307629, 2014/0288275, 2014/294823, 2016/0229924, and 2016/0355608, which are herein incorporated by reference in their entirety.

Example 1

XmAb® 13676 Treatment Plan

This is a Phase 1, multiple-dose dose-escalation study designed to define a safe initial priming dose and a maximal tolerated dose and schedule, to describe safety and tolerability, to assess PK and immunogenicity, and to preliminarily assess potential anti-tumor activity of XmAb® 13676 in human subjects with relapsed or refractory B cell malignancies. An exemplary flow chart is provide in FIG. 12.

This study will enroll two parallel Disease Groups of human subjects: dosing cohorts that establish a priming dose and maximal tolerated dose (MTD) or recommended dose (RD) and schedule in human subjects with non-CLL B cell malignancies (Group NHL; Group N); and dosing cohorts that establish a priming dose and MTD/RD and schedule for human subjects with CLL/SLL (Group CLL; Group C).

This study is designed in three parts:
Part A, escalating dose cohorts that establish an initial "priming dose" (the lowest initial dose with an occurrence of a single DLT) as part of repeated weekly infusions at a fixed dose in a 28-day cycle;
Part B, escalating dose cohorts that establish an MTD/RD for a dosing schedule consisting of a "priming dose" on Cycle 1 Day 1, established in Part A, followed by cohort escalation of fixed or escalating step-up dose weekly infusions for Cycle 1 Day 8 through Cycle 2 Day 22; and
Part C, a two-dose cohort to establish an RD for a dosing schedule consisting of a "priming dose" on Cycle 1 Day 1, followed by escalating step-up dose infusions through Cycle 2 Day 1 (in initial Cohort 1C). Dosing will convert to once every 2 weeks beginning on Cycle 3 Day 1 and continue on Day 1 and Day 15 of each subsequent cycle.

In both Disease Groups, escalation to higher dose (or dose schedule) cohorts will be made based on Dose Escalation Review Committee (DERC) review of the aggregate safety data. The DERC will be allowed to make adaptations to the dosing schema if felt to be needed, in accordance with evolving trial safety and tolerability findings, as long as changes do not significantly affect the risk profile of the study.

Once the MTD/RD and dosing schedule are established in Part B and/or Part C, the following Disease Groups may be expanded with up to 20 evaluable human subjects per expansion group: diffuse large B-cell lymphoma (DLBCL), follicular lymphoma (FL), mantle cell lymphoma (MCL), Waldenström Macroglobulinemia (WM), Richter transformation, and other indolent lymphomas. For each cohort, in all groups, the first human subject will be dosed and observed for a minimum of 48 hours before study drug is administered to the next human subject. No 2 of the first 3 human subjects in each cohort will start treatment with XmAb® 13676 on the same day.

Human subjects in Part A, Part B, and Part C will be admitted and continuously monitored for a minimum of 72 hours after the first dose of XmAb® 13676. The experience with the first 44 human subjects in this study indicated that nearly all cases of documented CRS beginning with the second (C1D8) dose, have occurred within 24 hours of XmAb® 13676 administration. The single exception occurred in a human subject who developed Grade 1 CRS 34 hours after C1D22 XmAb® 13676 infusion. Based on this, human subjects will be admitted for 48 hours on the second infusion (C1D8) and subsequent dose escalation. This applies to step-up dosing in Part B or any intra-human subject dose escalation approved by the DERC.

All human subjects will be assessed for the development of DLTs during treatment with XmAb® 13676. The assessment period is defined as:
Cycle 1, Days 1 through 28 for study Part A
Cycle 1, Day 8 through 6 days following the last step-up dose for Part B, Part C, and expansion In addition, the safety of the priming dose in Part B will be followed by DLT assessment through Cycle 1 Day 7 following the priming dose in all Part B cohorts.

Each human subject will be administered XmAb® 13676 IV over a minimum of a 2-hour period (±5 minute window) at a constant infusion rate once every 7 days (±1 day) or 14 days (±1 day) for 2 cycles. Cycles will consist of 4 weekly doses or 2 every-2-weeks (Q2W) doses, every 28 days. The initial treatment period for each human subject will be two cycles in Part A, Part B and Part C.

Adjustments may be made to infusion rates to increase the length of the infusion time based on the site's judgement for safety.

Due to pump accuracy variations, infusions ending within 5 minutes prior to the required 2-hour period will not be considered a deviation.

Dose levels are defined in Table 3.2 and Table 3.3. The dose is based on the human subject's actual baseline weight measurement in kilograms on Day −1. The XmAb® 13676 dose for human subjects whose weight exceeds 100 kg will be calculated based on a weight of 100 kg. Following the first dose, subsequent doses will only be modified if the human subject's weight changes by more than 10% from the Day −1 weight, at which point it will be recalculated for that infusion day using the current weight. If a patient has a weight change that is more than 10% that persists for a full cycle, the patient's baseline weight for dose calculation will be re-baselined tr the next cycle Day 1 visit.

Prior to administration, plamotamab (XmAb® 13676) will be diluted to the required final concentration in one or more 240 mL IV bags containing 0.9% Sodium Chloride Injection, USP and 10 mL IV Solution Stabilizer. Prior to dilution, the vial containing parenteral drug product should be inspected visually. If particulate matter and/or discoloration are noted, drug should not be administered, and the Sponsor should be notified. After dilution, the bag containing plamotamab (XmAb® 13676) should be gently inverted 2 to 3 times to mix the solution. The bag must not be shaken since excess agitation may cause aggregate formation. See the plamotamab (XmAb® 13676) Pharmacy Manual for additional details.

All human subjects will be premedicated for all XmAb® 13676 doses with the following medications:
Dexamethasone 20 mg IV approximately 1 hour prior to the start of XmAb® 13676 administration
Diphenhydramine 25 mg by mouth (PO) or IV approximately 30 to 60 minutes prior to the start of XmAb® 13676 administration (cetirizine or other antihistamine may be used in place of diphenhydramine)
Acetaminophen 650 mg PO approximately 30 to 60 minutes prior to the start of XmAb® 13676 administration Human subjects that have received 4 consecutive infusions at a stable dose and schedule without CRS or infusion reactions may have their premedication modified at the discretion of the investigator.

Number of Subjects
Up to 160 human subjects will be enrolled (the numbers required in escalation and expansion); the total number required will depend on dosing the number of evaluable patients needed for analysis, with the total study number not exceeding 160. Up to 50 clinical investigational sites will enroll human subjects to this study.

Primary/Secondary Endpoints

Primary and secondary endpoints include:
1. Safety and tolerability of plamotamab, as assessed by
   Incidence of treatment-emergent AEs
   Incidence of clinically significant changes in safety laboratory tests, PE findings, vital signs, and ECGs
   Incidence and severity of CRS and/or infusion reactions as defined in the Statistical Analysis Plan
2. Identification of the MTD and/or recommended initial infusion dose
3. PK characterization based on the parameters of Cmax, tmax, t½, $AUC_{0-\infty}$, CL, and volume of distribution (Vd).
4. PD characterization by flow cytometry of depletion of CD20-expressing cell populations in blood and marrow during therapy, and degree of recovery at 4 weeks following the end of therapy
5. Assessment of immunogenicity by incidence and titer of anti-plamotamab antibodies and qualitative assessment of safety outcomes Exploratory endpoints include:
1. Preliminary antitumor activity assessed for each diagnosis using appropriate disease-specific response criteria as well as aggregate data for all patients, including ORR
   Duration of response
   PFS
   Overall survival
2. Assessment of peripheral blood and bone marrow by flow cytometry evaluating:
   Changes in T cell activation due to plamotamab (XmAb® 13676) administration as assessed by changes in activation marker expression
   Changes in T-lymphocyte subsets in response to plamotamab (XmAb® 13676) administration
3. Additional exploratory markers of potential future interest may be explored using remaining serum, PBMC, and BMMC samples. If evidence of therapeutic activity is seen with XmAb® 13676 (plamotamab), biobanked samples may be assessed for genetic and immunologic factors that might predict response or non-response (optional part of study and may be reported separately from the clinical study report).
   Samples will not be retained for more than 10 years.

Dose-Escalation Scheme—Part A

Part A will determine the priming dose to be used in Part B. The priming dose to be used in Part B will be the lowest dose with occurrence of a single DLT. Once the lowest dose with occurrence of a single DLT has been determined in Part A, enrollment to Part A will cease and Part B may commence.

Human subjects will be enrolled in parallel to both the NHL and CLL Disease Groups, and dose escalation in each Group will be essentially independent. Dose level increases will initially proceed according to an accelerated titration design (see Table 3.2 and Table 3.3). This design allows for more efficient dose escalation while maintaining safety standards by implementing conservative triggers for cohort expansion during the accelerated escalation phase, and may limit the number of human subjects exposed to potentially sub-therapeutic doses of XmAb® 13676.

Enrolled human subjects will be assigned to an open-dose cohort. The first human subject will be dosed and observed for a minimum of 48 hours before study drug is administered to the next human subject. No 2 of the first 3 human subjects in each cohort will start treatment with XmAb® 13676 on the same day.

During the initial accelerated dose escalation phase (NHL Cohorts 1A, 2A, 3A, and CLL Cohorts 1A, 2A, and 3A), dose escalation may occur after treatment of 1 human subject per cohort provided that there has been:

No DLT, and

No non-hematologic ≥Grade 2 toxicity unless clearly and directly related to preexisting disease, and No new hematologic ≥Grade 2 toxicity or no ≥1 grade increase in any preexisting ≤Grade 2 hematologic toxicity, unless clearly and directly related to preexisting disease In all cases, the human subject must have met minimum safety assessment requirements.

If this occurs, the accelerated escalation phase will end, the standard dose escalation phase will begin, and the cohort in which the event(s) occurred will be expanded to a total of at least 3 human subjects (2 additional human subjects will be enrolled) unless there has been a DLT, at which time accrual to Part A will end and accrual to Part B will commence. Regardless, accelerated titration will end with the beginning of NHL Cohort 4A and CLL Cohort 4A.

TABLE 3.2

Dose-Escalation Cohorts--Group NHL (Part A)

| Group | Cohort NHL | Planned Weekly Dose[a] | Human subjects |
|---|---|---|---|
| Non-CLL B cell malignancies (Group NHL) | 1A | 0.7 µg/kg | 1 (+2 + 3) |
| | 2A | 2.4 µg/kg | 1 (+2 + 3) |
| | 3A | 7.5 µg/kg | 1 (+2 + 3) |
| | 4A | 20 µg/kg | 3 (+3) |
| | 5A | 45 µg/kg | 3 (+3) |
| | 6A | 80 µg/kg | 3 (+3) |
| | 7A | 125 µg/kg | 3 (+3) |
| | 8A | 170 µg/kg | 3 (+3) |

A = Part A; CLL = chronic lymphocytic leukemia; NHL = non-Hodgkin's lymphoma.
[a]Doses will be capped at 100 kg body weight.

TABLE 3.3

Dose-Escalation Cohorts--Group CLL (Part A)

| Group | Cohort CLL | Planned Weekly Dose[a] | Human subjects |
|---|---|---|---|
| CLL/SLL (Group CLL) | 1A | 0.7 µg/kg | 1 (+2 + 3) |
| | 2A | 2.4 µg/kg | 1 (+2 + 3) |
| | 3A | 7.5 µg/kg | 1 (+2 + 3) |
| | 4A | 20 µg/kg | 3 (+3) |
| | 5A | 45 µg/kg | 3 (+3) |
| | 6A | 80 µg/kg | 3 (+3) |
| | 7A | 125 µg/kg | 3 (+3) |
| | 8A | 170 µg/kg | 3 (+3) |
| | 9A | 250 µg/kg | 3 (+3) |
| | 10A | 360 µg/kg | 3 (+3) |
| | 11A | 500 µg/kg | 3 (+3) |

A = Part A; CLL = chronic lymphocytic leukemia; SLL = small lymphocytic lymphoma.
[a]Doses will be capped at 100 kg body weight.

TABLE 3.4

| | Dose-Escalation Scheme (Part A only) | |
|---|---|---|
| Accelerated Dose-Escalation Phase | | |
| Number of Human subjects with Event | Number of Human subjects Enrolled and Assessable for Safety Following Four Doses of XmAb ®13676 | Escalation Decision |
| 0 | 1 | Escalate to the next higher dose level. |
| 1 ≥ Grade 2 toxicity | 1 | Enroll 2 additional human subjects on the same dose level and revert to Standard Dose Escalation (3 + 3) design below. |
| 1 DLT | Any number | Cease enrollment to Part A and begin Part B using the current dosage as the priming dose. |
| Standard Dose-Escalation Phase | | |
| Number of Human subjects with at Least One DLT | Number of Human subjects Enrolled and Assessable for Safety Following Four Doses of XmAb ®13676 | Escalation Decision |
| 0 | 3 | Escalate to the next higher dose level. |
| 1 | Any number | Cease enrollment to Part A and begin Part B using the current dosage as the priming dose. |

DLT = dose-limiting toxicity.

From this cohort forward (or beginning with NHL Cohort 4A or CLL Cohort 4A [20 µg/kg], whichever comes first) the following rules will apply:

If zero of 3 human subjects have a DLT, then dose escalation to the next level will occur.

If at any time a DLT occurs, enrollment to Part A will stop and Part B will begin using the current dosage as the priming dose.

Before a dose-escalation decision can be reached, at least 1 human subject (in the accelerated dose escalation phase of the study) or 3 human subjects (in the standard escalation phase of the study) must meet all requirements for dose escalation safety assessment.

For the purpose of determining the incidence of DLT and escalating to a higher-dose cohort, only human subjects who experience DLT and those with sufficient safety data/follow-up will be evaluated. Human subjects who experience the following will be considered to have sufficient safety data/follow-up:

1. Receive all 4 weekly doses of XmAb® 13676 in Cycle 1, and
2. Undergo all planned safety evaluations through Cycle 1 Day 28
3. If a human subject's dose is not given within ±3 days scheduled, the dose should be considered missed, and the human subject is no longer considered to have sufficient safety data.

Human subjects who withdraw from study before completing Day 28 of treatment for reasons other than meeting DLT criteria will be considered to have inadequate data to support dose escalation. In such cases, replacement human subjects may be enrolled to receive the same dose of XmAb® 13676 as the human subjects who withdraw prematurely.

If at any time during the 28-day observation period a DLT occurs, 3 additional human subjects will be added to the cohort. In addition, if zero of 3 human subjects experience a DLT in a cohort, the Medical Monitor may also deem it appropriate to enroll additional human subjects for up to a total of 6 evaluable human subjects per dose level.

The decision to advance dosing to the next cohort level will be made by the DERC after review of all required dose escalation safety assessment data from human subjects in a cohort. PK, cytokine, and ADA data may not be routinely available during the safety assessment period as these samples may be batched for analysis so that a more uniform drug exposure analysis and ADA analysis can be performed across all study samples. However, if a patient safety issue arises and the treating physician feels that information around drug exposure and/or ADA analysis would be useful information in determining the treatment plan for the human subjects, PK and ADA analysis may be performed on the patient samples that have been collected to date.

The dose escalation scheme may be modified (eg, smaller increases or decreases in dose level may be permitted, additional human subjects in a cohort may be enrolled, infusion duration and scheduling may be modified) based on the type and severity of toxicities observed in this trial, upon agreement of the DERC as long as changes do not significantly affect the risk profile of the study. Enrolling additional human subjects beyond 216 requires a protocol amendment.

Dose-Escalation Scheme—Part B

In Part B, the Cycle 1 Day 1 dose (the priming dose) will be fixed at the level determined in Part A for each Disease Group. The C1D8 and subsequent doses will then be escalated in steps as indicated in Table 3.5 in an effort to reduce the incidence and severity of CRS.

TABLE 3.5

Study Cohorts- Part B: Group NHL

| | Cohort NHL | Cycle 1 Day 1 (Priming Dose) | Cycle 1 Day 8 | Cycle 1 Day 15 | Cycle 1 Day 22 | Cycle 2 Day 1 | Cycle 2 Day 8 | Cycle 2 Day 15 and subsequent | Human subjects |
|---|---|---|---|---|---|---|---|---|---|
| Part B (Group NHL) | 1B | 80 μg/kg | 125 μg/kg | 125 μg/kg | 125 μg/kg | 125 μg/kg | 125 μg/kg | 125 μg/kg | 3 (+3) |
| | 2B | 45 μg/kg | 80 μg/kg | 125 μg/kg | 170 μg/kg | 170 μg/kg | 170 μg/kg | 170 μg/kg | 3 (+3) |
| | 3B[a] | 45 μg/kg | 80 μg/kg | 125 μg/kg | 170 μg/kg | 250 μg/kg | 250 μg/kg | 250 μg/kg | 3 (+3) |
| | 3Bi | 25 μg/kg | 50 μg/kg | 125 μg/kg | 170 μg/kg | 250 μg/kg | 250 μg/kg | 250 μg/kg | 3 (+3) |
| | 4B | 25 μg/kg | 50 μg/kg | 125 μg/kg | 170 μg/kg | 250 μg/kg | 360 μg/kg | 360 μg/kg | 3 (+3) |
| | 5B | 25 μg/kg | 50 μg/kg | 125 μg/kg | 170 μg/kg | 250 μg/kg | 360 μg/kg | 500 μg/kg | 3 (+3) |
| | Modified 4B | 10 μg/kg | 25 μg/kg | 125 μg/kg | 170 μg/kg | 250 μg/kg | 360 μg/kg | 360 μg/kg | 3 (+3) |
| | Modified 5B | 10 μg/kg | 25 μg/kg | 125 μg/kg | 170 μg/kg | 250 μg/kg | 360 μg/kg | 500 μg/kg | 3 (+3) |
| | Expansion-B | | | At MTD or RD cohort | | | | | Up to 20 for each Disease Group |

B = Part B; MTD = maximum tolerated dose; NHL = non-Hodgkin's lymphoma; RD = recommended dose; X = priming dose determined in Part A (lowest dose with occurrence of a single DLT).
[a]3B is enrolling additional human subjects with lowered Cycle 1 Day 1 and Cycle 1 Day 8 doses of 25 μg/kg and 50 μg/kg, respectively, under Cohort 3Bi to reduce the incidence and severity of CRS.

Modified 4B and Modified 5B are enrolling with lowered Cycle 1 Day 1 and Cycle 1 Day 8 doses of 10 μg/kg and 25 μg/kg, respectively to reduce the incidence and severity of CRS.

Dose escalation will proceed as described for a standard 3+3 scheme (see Table 3.7) and with the same dosing levels as in Part A; however, the Cycle 1 Day 1 infusion will initially be the priming dose determined in Part A for that Disease Group. Dose escalation on each Part B cohort will be based on this starting point. For example, if the priming dose by Group NHL Part A is 20 μg/kg, the first infusion/priming dose in NHL Cohort 1B will be 20 μg/kg, and the second and subsequent infusions will be at 45 μg/kg (ie, X+1).

A minimum of 3 human subjects will be enrolled in each cohort for each Disease Group. As in Part A, the first human subject will be dosed and observed for a minimum of 48 hours before study drug is administered to the next human subject; no 2 of the first 3 human subjects in each cohort will start treatment with XmAb® 13676 on the same day.

For the purpose of determining the incidence of DLT and defining the MTD and/or recommended dosing of XmAb® 13676 for future study, only human subjects who experience DLT and those with sufficient safety data/follow-up will be evaluated. Human subjects who experience the following will be considered to have sufficient safety data/follow-up:

1. Receive all weekly doses of XmAb® 13676 through the final step-up dose, and
2. Undergo all planned safety evaluations through 6 days following the last step-up dose
3. If a human subject's dose is not given within ±3 days scheduled, the dose should be considered missed, and the human subject is no longer considered to have sufficient safety data.

Human subjects who withdraw from study before completing the last step-up dose for reasons other than meeting DLT criteria will be considered to have inadequate data to support dose escalation. In such cases, replacement human subjects may be enrolled to receive the same dose of XmAb® 13676 as the human subjects who withdraw prematurely.

The DLT observation period for the subsequent dosing escalation cohorts is Cycle 1 Day 8 through 6 days following the last step-up dose. If all 3 patients tolerate a cohort without experiencing a DLT (and the DERC agrees), enrollment will begin on the next higher cohort. If at any time during the observation period a DLT occurs, additional patients will be added to the cohort. If there is an additional DLT among the 6 patients on the cohort, the previous dosing cohort will be expanded to 6 to establish an MTD and/or RD. If this occurs on Cohort 1B, the next 3 patients will be enrolled on Cohort-1B (de-escalation cohort). See Table 3.7.

TABLE 3.7

Dose-Escalation Scheme--Part B
Part B DLT Period

| Number of Human subjects with ≥ DLT | Number of Human subjects Enrolled/ Assessable for Safety After Last Step-Up Dose | Escalation Decision |
|---|---|---|
| 0 | 3 | Escalate to the next higher dose level. |
| 1 | 3 | Enroll 3 additional human subjects on the same dose level. |

TABLE 3.7-continued

Dose-Escalation Scheme--Part B
Part B DLT Period

| Number of Human subjects with ≥ DLT | Number of Human subjects Enrolled/ Assessable for Safety After Last Step-Up Dose | Escalation Decision |
|---|---|---|
| 1 | 6 | Escalate to the next higher dose level. |
| 2 | 3 or 6 | No dose escalation may occur; MTD has been surpassed. The next lower dose level should be expanded, or if at Level NHL 1B or Level CLL 1B, use de-escalation NHL Cohort −1B or CLL Cohort −1B. |

B = Part B; CLL = chronic lymphocytic leukemia; DLT = dose-limiting toxicity; MTD = maximum tolerated dose; NHL = non-Hodgkin's lymphoma.

The DERC will decide to advance dosing to the next cohort level after it reviews all required dose-escalation safety assessment data from patients in a cohort. Pharmacokinetic, cytokine, and ADA data may not be routinely available during the safety assessment period, as these samples may be batched for analysis so that more uniform drug exposure and ADA analyses can be performed across all study samples. However, if a patient safety issue arises and the treating physician feels that drug exposure information and/or ADA analysis would be useful in determining the treatment plan for the patient, PK and ADA analysis may be performed on the patient samples that have been collected to date.

The dose-escalation scheme may be modified (e.g., smaller increases or decreases in dose level may be permitted, additional human subjects in a cohort may be enrolled, infusion duration and scheduling may be modified) based on the type and severity of toxicities observed in this trial, upon agreement of the DERC, as long as changes do not significantly affect the risk profile of the study. Enrolling additional human subjects beyond 216 requires a protocol amendment.

DLT rates for the priming dose will continue to be monitored in Parts B, C, and Expansion Cohorts for all patients. The priming dose will be decreased by one dose level if excess toxicity is seen using a Pocock boundary function, $b_n$, where n=all safety evaluable patients in the Part B MTD/RD cohorts and expansion cohort, and the toxicity events of interest are defined as DLTs during Cycle 1 Days 1-7 (see Table 3.8). The dose decrease is based on the probability of crossing the boundary when the rate of DLT is equal to the acceptable rate (event probability θ; Ivanova, 2005). This boundary is equivalent to testing after each patient the null hypothesis that the event rate θ is equal to 0.25, using a one-sided level 0.0910 test. The probability of early stopping φ* will be set at 0.2, inferring only moderate stringency for decreasing the priming dose when in fact the true DLT rate will not exceed 0.25.

All human subjects in Part B will be assessed for DLT of the priming dose through Cycle 1 Day 7, the results of which will be discussed at the time of each DERC meeting. If the DLT rate is found to be equal to or to exceed the boundary function, the priming dose will be decreased by 1 dose level (Table 3.2 and Table 3.3).

Results: At data cut-off, 44 subjects have been treated, 36 with NHL and 8 with CLL.

NHL: Subjects with relapsed/refractory ("R/R") NHL had a median age of 61.5 years (range 32-89), a median of 3.5 prior therapies (range 1-9) and had been diagnosed a median of 24.6 months (range 6.3-181.2) prior to treatment in the study. Treatment responses were assessed by the Lugano criteria or International Working Group criteria for Waldenström Macroglobulinemia (WM). There have been 7 objective responses: 2 complete responses (CR; DLBCL), 1 Very Good PR (VGPR; WM), and 4 partial responses (PR; 1FL, 3 DLBCL) at doses of 20-125 µg/kg. In the efficacy-evaluable population, at doses of 80-125 µg/kg, objective responses were observed in 6/18 human subjects. A priming dose of 45 µg/kg has been selected for Part B.

CLL: Subjects with R/R CLL had a median age of 76 years (range 62-81), a median of 4.5 prior therapies (range 2-6) and had been diagnosed a median of 76.1 months (range 17.5-328.9) prior to treatment in the study. There has been 1 CR reported (Richter transformation) in 5 subjects at 20 µg/kg, the highest dose administered thus far. The treatment response was assessed by the Lugano criteria.

Conclusions: XmAb® 13676 demonstrated evidence of clinical activity in heavily pretreated subjects with R/R NHL and R/R CLL treated at doses between 20 and 125 µg/kg. CRS was generally manageable with premedication.

Following further treatment according to Example 3, 53 subjects have been treated with XmAb® 13676 monotherapy: 45 with NHL and 8 with CLL.

TABLE 3.8

Pocock Boundary Function for Priming Dose DLT Period (Cycle 1 Days 1 through 7)

| | Human subjects, n | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| Boundary, $b_n$ | — | 2 | 3 | 3 | 4 | 4 | 4 | 5 | 5 | 5 | 6 | 6 | 6 | 7 | 7 | 7 | 8 | 8 | 8 | 9 |

Patient Disposition Data:

|  | NHL (N = 45) | CLL (N = 8) | Overall (N = 53) |
|---|---|---|---|
| Remained on treatment | 10 (22.2) | 0 (0.0) | 10 (18.9) |
| Discontinued treatment | 35 (77.8) | 8 (100.0) | 43 (81.1) |
| Adverse event | 4 (8.9) | 3 (37.5) | 7 (13.2) |
| Physician decision | 2 (4.4) | 0 | 2 (3.8) |
| Progressive disease | 15 (33.3) | 2 (25.0) | 17 (32.1) |
| Withdrawal by patient | 4 (8.9) | 0 | 4 (7.5) |
| Insufficient clinical response | 8 (17.8) | 2 (25.0) | 10 (18.9) |
| Other | 2 (4.4) | 1 (12.5) | 3 (5.7) |

Treatment Exposure—DLBCL Safety Population

|  | 0.7-45 µg/kg (N = 12) | 80-170 µg/kg (N = 18) | Overall (N = 30) |
|---|---|---|---|
| Median number of doses (range) | 7.5 (1, 16) | 8.0 (3, 37) | 8.0 (1, 37) |
| Median duration of exposure, weeks (range) | 6.6 (0.1, 15.1) | 8.1 (2.0, 37.3) | 7.1 (0.1, 37.3) |
| Median number of treatment cycles completed (range) | 1.5 (0, 4) | 2.0 (0, 9) | 2.0 (0, 9) |

Baseline Characteristics and Prior Therapies—DLBCL Safety Population (80-170 µg/kg)

|  | Overall (N = 18) |
|---|---|
| Median age, years (range) | 63.5 (48, 82) |
| Male, n (%) | 9 (50.0) |
| ECOG performance status, n (%) | |
| 0 | 6 (33.33) |
| 1 | 9 (50.00) |
| 2 | 3 (16.67) |
| Median time since initial diagnosis, months (range) | 21.5 (6, 353) |
| Ann Arbor Stage at enrollment n (%) | |
| Limited Stage II | 2 (11.1) |
| Advanced/Stage II Bulky | 1 (5.6) |
| Advanced/Stage III | 2 (11.1) |
| Advanced/Stage IV | 11 (61.1) |
| Unknown | 2 (11.1) |
| Median number of prior systemic therapy, n (range) | 3 (1, 6) |
| Best response to last systemic therapy n(%) | |
| Complete remission | 2 (11.1) |
| Partial remission | 6 (33.3) |
| Stable disease | 2 (11.1) |
| Progressive disease | 6 (33.3) |
| Not assessed | 2 (11.1) |
| Relapsed/progression after last systemic therapy n (%)* | |
| Yes | 14 (77.8) |
| No | 3 (16.7) |
| Median duration of response to last systemic therapy, weeks(range) | 21.1 (8, 60) |

*Relapse/progression status of 1 patient is missing. Three human subjects (16.7%) had prior transplantation.
ECOG: Eastern Cooperative Oncology Group.

Safety

Most events were mild or moderate in severity.

Thirty-seven (69.8%) human subjects experienced at least 1 adverse event (AE) of ≥Grade 3 in severity.

Seven (13.2%) human subjects (4 [8.9%] NHL and 3 [37.5%] CLL) discontinued treatment due to AEs.

Nervous system disorders occurred in 26 (49.1%) human subjects.

The most common nervous system events were dizziness (17%), headache (17%), paresthesia (9.4%), and lethargy (5.7%).

One (2.2%) patient experienced short-term encephalopathy (Grade 2) during a cytokine release syndrome (CRS) event that resolved concomitantly with treatment of the CRS.

One (2.2%) patient lost consciousness (Grade 1) during a bowel movement (likely vasovagal)

The treatment-emergent AE (TEAE) profile for the DLBCL safety population is similar to the NHL safety population.

Cytokine Release Syndrome (CRS)

At least 1 CRS event occurred in 28 (52.8%) human subjects:

Of these 28 CRS events, 25 (89%) were Grade 1 or 2 in severity (data not shown).

Three (5.7%) human subjects experienced CRS of Grade 3 or 4 in severity.

An additional 12 (22.6%) human subjects experienced other events that may have been consistent with symptoms of CRS with mild to moderate severity (Grade 1 or 2) (data not shown).

The most common CRS-like symptoms were pyrexia (45.3%), hypotension (20.8%), chills (18.9%), tachycardia (13.2%), and hypertension (9.4%) (data not shown).

Summary of Treatment-Emergent Adverse Events (TEAEs)

| Event, n(%) | NHL (N = 45) | CLL (N = 8) | Overall (N = 53) |
|---|---|---|---|
| Any TEAE | 45 (100.0) | 8 (100.0) | 53 (100.0) |
| Any serious TEAE | 24 (53.3) | 5 (62.5) | 29 (54.7) |
| Leading to drug withdrawn | 4 (8.9) | 3 (37.5) | 7 (13.2) |
| Most common TEAEs (≥15%) | | | |
| Pyrexia | 26 (57.8) | 3 (37.5) | 29 (54.7) |
| Cytokine release syndrome | 25 (55.6) | 3 (37.5) | 28 (52.8) |
| Anemia | 19 (42.2) | 3 (37.5) | 22 (41.5) |
| Diarrhea | 12 (26.7) | 2 (25.0) | 14 (26.4) |
| Asthenia | 10 (22.2) | 3 (37.5) | 13 (24.5) |
| Hypotension | 12 (26.7) | 1 (12.5) | 13 (24.5) |
| Thrombocytopenia | 11 (24.4) | 2 (25.0) | 13 (24.5) |
| Chills | 11 (24.4) | 1 (12.5) | 12 (22.6) |
| Cough | 10 (22.2) | 2 (25.0) | 12 (22.6) |
| Fatigue | 8 (17.8) | 4 (50.0) | 12 (22.6) |
| Neutropenia | 10 (22.2) | 2 (25.0) | 12 (22.6) |
| Constipation | 10 (22.2) | 1 (12.5) | 11 (20.8) |
| Hypokalemia | 10 (22.2) | 0 | 10 (18.9) |
| Edema peripheral | 6 (13.3) | 4 (50.0) | 10 (18.9) |
| Tachycardia | 8 (17.8) | 2 (25.0) | 10 (18.9) |
| Dizziness | 9 (20.0) | 0 | 9 (17.0) |
| Dyspnea | 7 (15.6) | 2 (25.0) | 9 (17.0) |
| Headache | 8 (17.8) | 1 (12.5) | 9 (17.0) |
| Nausea | 7 (15.6) | 1 (12.5) | 8 (15.1) |
| Upper respiratory tract infection | 7 (15.6) | 1 (12.5) | 8 (15.1) |
| Grade ≥3 events, n (%) | | | |
| Any TEAE Grade ≥3 | 31 (68.9) | 6 (75.0) | 37 (69.8) |
| Most common TEAEs (≥5%) | | | |
| Anemia | 11 (24.4) | 1 (12.5) | 12 (22.6) |
| Neutropenia | 7 (15.6) | 1 (12.5) | 8 (15.1) |
| Thrombocytopenia | 5 (11.1) | 1 (12.5) | 6 (11.3) |
| Lymphopenia | 4 (8.9) | 1 (12.5) | 5 (9.4) |
| Cytokine release syndrome | 2 (4.4) | 1 (12.5) | 3 (5.7) |
| Hypokalemia | 3 (6.7) | 0 | 3 (5.7) |

Note:
AEs were graded based on CTCAE version v4.03, except for CRS, which was graded according to the Lee criteria Summary of CRS Events

| Event, n (%) | NHL (N = 45) | CLL (N = 8) | Overall (N = 53) |
|---|---|---|---|
| Cytokine release syndrome | 25 (55.6) | 3 (37.5) | 28 (52.8) |
| Grade 1 | 7 (15.6) | 0 | 7 (13.2) |
| Grade 2 | 16 (35.6) | 2 (25.0) | 18 (34.0) |
| Grade 3 | 1 (2.2) | 1 (12.5) | 2 (3.8) |
| Grade 4 | 1 (2.2) | 0 | 1 (1.9) |

Efficacy

The data cut-off date for the efficacy analyses was 8 Nov. 2019 and includes human subjects whose highest dose with XmAb® 13676 was 80 ug/kg and above.

Tumor responses were assessed based on the Lugano criteria

XmAb® 13676 demonstrated efficacy in DLBCL at doses of 80 µg/kg and higher (top dose tested was 170 µg/kg) in a dose-dependent manner.

Best Overall Response Rates with DLBCL Human Subjects

| | Safety Population |
|---|---|
| Overall | |
| ORR | 7/18 (38.9) |
| CR | 5/18 (27.8) |
| 80 µg/kg | |
| ORR | 1/4 (25.0) |
| CR | 0 |
| 125 µg/kg* | |
| ORR | 4/10 (40.0) |
| CR | 4/10 (40.0) |
| 170 µg/kg† | |
| ORR | 2/4 (50.0) |
| CR | 1/4 (25.0) |

CR: complete response; ORR: objective response rate.
*Includes human subjects with 125 µg/kg flat dosing and 80/125 µg/kg step-up dosing;
†step-up dosing 45/80/125/170 µg/kg In the ongoing dose-escalation Phase 1 study in B-cell malignancies, the CD20×CD3 bispecific antibody XmAb® 13676 was well tolerated.

CRS was observed in 52.8% of human subjects. Other events that may have been consistent with symptoms of CRS were observed in an additional 22.6% of human subjects.

Most CRS events occurred with the first dose of XmAb® 13676 and were Grade 1 and 2 by the Lee criteria There were no Grade 3 or 4 CRS events once step-up dosing was implemented.

Nervous system disorders were generally mild and did not lead to discontinuation of treatment.

XmAb® 13676 demonstrated efficacy in DLBCL at doses of 80 µg/kg and higher (top dose tested was 170 µg/kg) in a dose-dependent manner.

In DLBCL, the objective response rate was 7/18 (38.9%), and the complete response (CR) was 5/18 (27.8%).

Additional responses have been observed in Waldenström macroglobulinemia and Richter transformation of CLL, both CRs and both at 20 µg/kg; and in follicular lymphoma at step-up dosing to 170 µg/kg, also a CR.

Dose escalation and schedule optimization are ongoing.

Dose-Escalation Scheme—Part C

In Part C, the Cycle 1 Day 1 dose (the priming dose) will be fixed at the dose level of 0.8 mg to reduce the incidence and severity of CRS. The Cycle 1 Day 8 and subsequent doses will then be escalated in steps to allow for the following: 1) a shorter step-up dosing interval to reach a potentially efficacious dose more quickly, and 2) the ability to dose at Q2W intervals.

This step-up approach takes into account data from 46 human subjects who received an initial dose (Cycle 1 Day 1) of 20 µg/kg or higher. In these human subjects, the majority of CRS events occurred on Cycle 1 Day 1, and the severity was also higher on Cycle 1 Day 1 than on subsequent dosing days. Specifically, 57% of human subjects experienced CRS with the first dose (Cycle 1 Day 1) of XmAb® 13676 (15% Grade 1; 35% Grade 2; 4% Grade 3; and 2% Grade 4). On the second dose of XmAb®13676 (Cycle 1 Day 8), 22% of human subjects experienced CRS (15% Grade 1 and 7% Grade 2). After Cycle 1 Day 8, there were only 2 Grade 2 CRS events recorded (one each on Cycle 1 Day 15 and Cycle 1 Day 22) and no Grade 3 or 4 events

TABLE 3.9

Study Cohorts- Part C: Group NHL

| | Cohort NHL | Cycle 1 Day 1 (Priming Dose) | Cycle 1 Day 8 | Cycle 1 Day 15 | Cycle 1 Day 22 | Cycle 2 Day 1 | Cycle 2 Day 8, Day 15, and Day 22 | Cycle 3 and Subsequent Q2W Dosing | Human subjects |
|---|---|---|---|---|---|---|---|---|---|
| Part C (Group NHL) | −1C (de-escalation) | X | X + 1 | X + 2 | X + 3 | X + 3 | X + 3 | X + 3 | 3 (+3) |
| | 1C | 0.8 mg | 2 mg | 20 mg | 35 mg | 50 mg | 50 mg | 50 mg | 3 (+3) |
| | 2C | 0.8 mg | 2 mg | 20 mg | 50 mg | 50 mg | 50 mg | 50 mg | 6 |

C = Part C; X = priming dose; NHL = non-Hodgkin's lymphoma; Q2W = every 2 weeks.

In Part C, dosing is weekly through Cycle 2 Day 22, and dosing will convert to once every 2 weeks beginning on Cycle 3 Day 1 and continue on Day 1 and Day 15 of each subsequent cycle.

Part C step-up dosing will initially enroll human subjects with a 3+3 design. As in Part A and B, the first patient will be dosed and observed for a minimum of 48 hours before study drug is administered to the next patient; no 2 of the first 3 human subjects in this cohort will start treatment with XmAb® 13676 on the same day.

If the step-up dosing regimen in Cohort 1C is determined not to be tolerable, dose de-escalation may be permitted by the DERC. If dose de-escalation occurs, Cohort-1C will proceed with 3+3 design.

If Cohort 1C is tolerated, 6 human subjects may be enrolled in Cohort 2C.

In addition to an initial DLT period, which is Cycle 1 Day 8 through 6 days following the last step-up dose, a second DLT observation window will begin on Cycle 3 Day 1 (the day of transition to Q2W dosing) and extend until Cycle 4 Day 7, which is 6 days after the third dose administered on a Q2W schedule.

In addition to an initial DLT period, which is Cycle 1 Day 8 through 6 days following the last step-up dose, a second DLT observation window will begin on Cycle 3 Day 1 (the day of transition to Q2W dosing) and extend until Cycle 4 Day 7, which is 6 days after the third dose administered on a Q2W schedule.

For the purpose of determining the incidence of DLTs and defining the MTD and/or RD of XmAb® 13676 for future study, only patients who experience a DLT and those with sufficient safety data/follow-up will be evaluated. Patients who experience the following will be considered to have sufficient safety data/follow-up:

1. Receive all weekly doses of XmAb® 13676 through the final step-up dose and also receives the first 3 Q2W doses (Cycle 3 Day 1 through Cycle 4 Day 1), and
2. Undergo all planned safety evaluations through 6 days following the last step-up dose and also through the first 3 Q2W doses (Cycle 3 Day 1 through Cycle 4 Day 1)
3. During the weekly dosing, if a patient's dose is not given within ±3 days scheduled, the dose should be considered missed, and the patient is no longer considered to have sufficient safety data.
4. During the Q2W dosing, if a patient's dose is not given within ±14 days scheduled, the dose should be considered missed, and the patient is no longer considered to have sufficient safety data.

Patients who withdraw from study before completing both DLT observation periods for reasons other than meeting DLT criteria will be considered to have inadequate data to support dose escalation. In such cases, replacement patients may be enrolled to receive the same doses of XmAb® 13676 as the patients who withdraw prematurely.

If at any time during either of the two observation periods, 2 DLTs occur, the DERC will review and make recommendations on how to proceed.

In addition, if 0 of 6 patients experience a DLT in Cohort 2C, the Medical Monitor may deem it appropriate to enroll additional patients for up to a total of 9 evaluable patients.

Criteria for Dose-Limiting Toxicities and Dose Adjustment

The National Cancer Institute's (NCI's) Common Terminology Criteria for Adverse Events (CTCAE), v4.03, will be used for grading toxicities, except for patients with CLL, who will be graded for hematologic toxicity using the CLL Working Group "Grading Scale for Hematologic Toxicity in CLL Studies" (Hallek, Blood. 2008; 111(12):5446-56), CRS, which will be graded using the American Society for Transplantation and Cellular Therapy (ASTCT) CRS Consensus Grading (Lee, Clin Cancer Res. 2014[B]; 20(15): 3902-7)

A DLT is defined as an AE or abnormal laboratory value not clearly attributable to the underlying malignancy or other concomitant illness, occurring during Cycle 1 through Day 28 for Part A and from Cycle 1, Day 1 through 6 days following the last step-up dose for Part B and Part C; a second DLT observation window for Part C from the first Q2W dose through 6 days following the third Q2W dose, and meeting one of the following criteria:

Non-Hematologic Toxicity

Any Grade 5 toxicity

Any grade seizures

Any ≥Grade 3 non-hematological toxicity, except:
  Grade 3 fatigue, asthenia, fever, anorexia or constipation
  Grade 3 nausea, vomiting, or diarrhea controlled by medical management
  Grade 3 or 4 tumor lysis syndrome, if it is successfully managed clinically and resolves within 7 days without end-organ damage
  ≥Grade 3 hypertension without associated symptoms of CRS that is self-limited (lasting ≤4 hours) or can be medically managed
  Any Grade 3 non-hematologic laboratory value that persists for <1 week and that does not require medical intervention or hospitalization
  Isolated Grade 3 lipase values that are not accompanied by ≥Grade 3 amylase values or clinical symptoms or radiographic evidence of pancreatitis
  Grade 3 or 4 electrolyte abnormalities (ie, those occurring without clinical consequence) that resolve, with or without intervention, to ≤Grade 2 levels in <72 hours
  Grade 3 gamma-glutamyl transferase (GGT) in absence of ≥Grade 3 hepatic transaminases or total bilirubin
  Grade 3 or 4 AST and/or ALT associated with CRS, if levels decline to Grade 1 or baseline within 7 days
  Any AE related to concomitant premedications or treatment given for CRS (eg, steroid-induced hyperglycemia)
  ≥Grade 3 SARS-CoV-2 infection not related to study drug Hematologic Toxicity (for CLL, use the CLL Working Group "Grading Scale for Hematologic Toxicity in CLL Studies" in Hallek, Blood. 2008; 111(12):5446-56).

Grade 4 neutropenia (ANC <0.5×109/L) lasting for ≥7 days

Grade ≥3 thrombocytopenia lasting ≥7 days, or Grade ≥3 thrombocytopenia of any duration if associated with Grade ≥3 bleeding If a patient does not complete the DLT period or is not assessable for toxicity throughout the period, they may be replaced. Patients who experience any toxicity should be followed until the toxicity has stabilized, returned to their baseline level or until the commencement of a new treatment.

Example 2 In Vitro Antitumor Efficacy

The ability of XmAb® 13676 to recruit and redirect T cells to kill CD20-expressing target cells (RTCC) was examined. T cell-dependent cytotoxicity of XmAb® 13676 against CD20-positive Ramos cells was examined using purified PBMC or T cell-depleted PBMC as effector cells. In addition, T cell activation was examined by quantifying CD69 induction on both CD4+ and CD8+ T cells. XENP13245, an anti-RSV×anti-CD3 bispecific antibody, and XENP14045, an anti-CD123×anti-CD3 bispecific antibody, were included as negative controls.

XmAb® 13676 displayed robust and potent killing of Ramos cells when supplied with human PBMC as an effector population (data not shown). The negative control antibodies failed to induce any tumor cell killing, suggesting that the cytotoxicity mediated by XmAb® 13676 depends on its engagement of CD20 on the target cell population. However, when T cells were depleted from PBMC, XmAb® 13676 failed to induce killing. In a second experiment, XmAb® 13676-mediated killing of Ramos cells was demonstrated with purified T cells, demonstrating that T cells alone are sufficient to mediate XmAb® 13676's cytotoxic activity.

Figure 5:
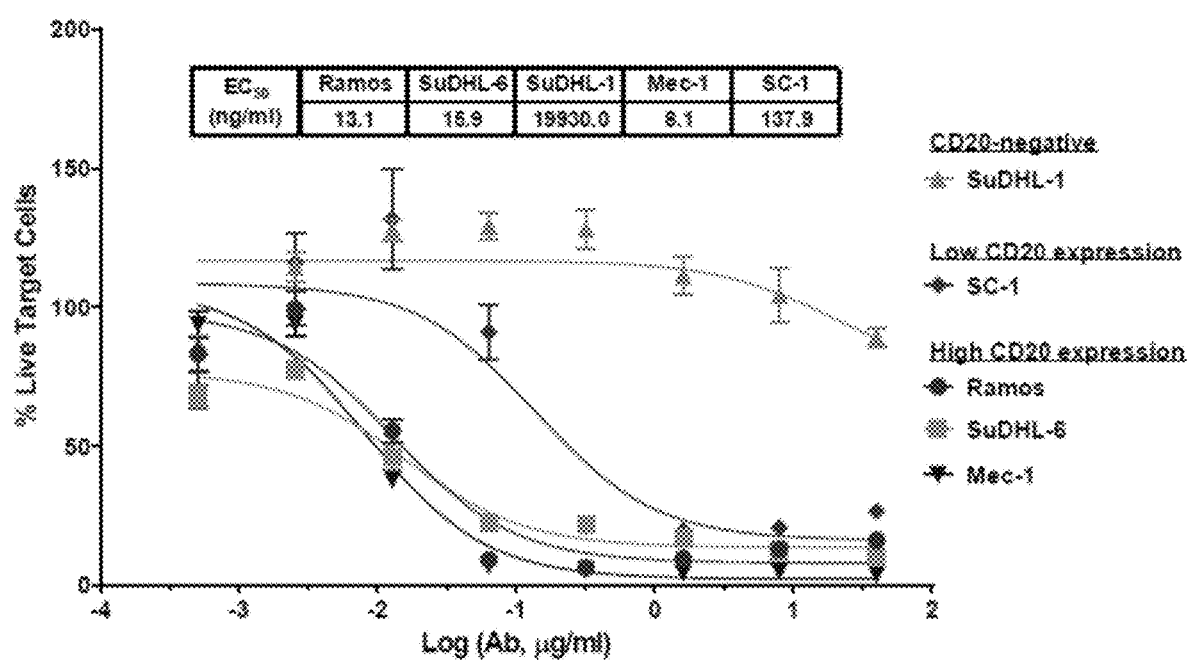
FIG. 5 is a line graph showing XmAb® 13676 potently kills multiple CD20-positive B cell lines.

Using rituximab as the detection antibody, the CD20 expression profile on various human lymphoma-derived cell lines was examined by flow cytometry. Su-DHL-6 showed the highest CD20 antigen density, with Ramos and MEC-1 showing intermediate levels, and SC-1 showing lower levels. Su-DHL-1 was used as a CD20-negative control cell line. FIG. 5 shows RTCC activity against these five cell lines using purified T cells. XmAb® 13676 showed robust depletion of all CD20-positive target cell lines in the presence of purified T cells. Potency of killing was higher for cell lines with high or intermediate CD20 levels (Su-DHL-6, Ramos and MEC-1), and reduced approximately 10-fold for the lower expressing SC-1, with $EC_{50}$ values ranging from 8 to 138 ng/ml. No significant depletion was observed for the CD20-negative cell line (Su-DHL-1).

XmAb® 13676 also induced similar robust $CD8^+$ (FIG. 6) and $CD4^+$ (not shown) T-cell activation in the presence of CD20-expressing target cells, again correlating with CD20 expression levels. In contrast, XmAb® 13676 failed to induce activation of $CD4^+$ and $CD8^+$ T-cells or target cell killing in the presence of CD20-negative SuDHL-1 cells.

To assess whether XmAb® 13676-induced cytotoxicity is affected by donor-to-donor T cell variability, purified T cells from six healthy human donors were tested in RTCC assays using Ramos as target cells. XmAb® 13676 robustly depleted Ramos target cells in the presence of effector T cells from six different healthy donors (data not shown). The depletion potency was similar across all six donors, with $EC_{50}$ values between 5.3 and 14.3 ng/ml.

Figure 7:
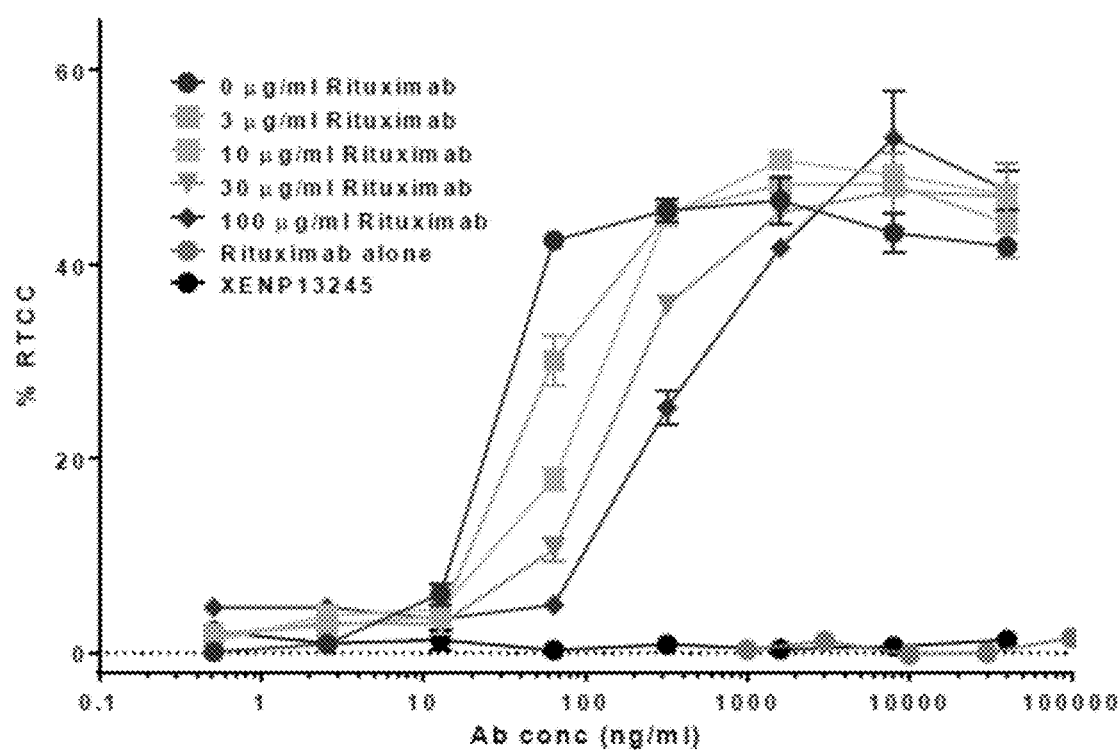
FIG. 7 is a line graph showing XmAb® 13676 retains RTCC activity in the presence of rituximab.

The anti-CD20 Fv domain of XmAb® 13676 is derived from murine antibody C2B8, the same antibody used in the chimeric antibody rituximab. Therefore, it might be possible that rituximab could interfere with the activity of XmAb® 13676 by competing for CD20 binding. To assess the effect of rituximab interference on XmAb® 13676-induced T cell-mediated cytotoxicity, its potency was evaluated in the presence of increasing amounts of rituximab. As shown in FIG. 7, XmAb® 13676 stimulated Jeko-1 target cell killing with an $EC_{50}$ of 24 ng/ml in the absence of rituximab. As rituximab was added at increasing concentrations of 3, 10, 30 and 100 µg/ml, the potency of XmAb® 13676 was correspondingly reduced (with $EC_{50}$ values increasing to 51, 93, 162 and 387 ng/ml). However, XmAb® 13676 retains RTCC activity even in the presence of a large excess concentration of rituximab. Moreover, although XmAb® 13676 became less potent in the presence of rituximab, it stimulated a similar extent of total T cell-mediated target killing efficacy. As expected, rituximab itself did not display any RTCC activity in this T cell-dependent assay.

A series of experiments was performed to assess whether XmAb® 13676 could induce T cell activity in cancer human subject samples. T cell activation and killing were examined using human subject-derived PBMC from CLL or follicular NHL (FL) human subjects. T cell activation and depletion of autologous CD20-expressing target B cells derived from normal PBMC samples were also examined as a benchmark. As a non-specific antigen control, XENP13245 (anti-RSV× anti-CD3 bsAb) was used.

Three each of CLL and normal donor PBMC samples were assessed for target cell (CD19+CD5+ lymphocytes for CLL cancer cells and CD19+ for normal B cells) and effector T cell (CD4+ and CD8+ cells) number. The number of T cells in CLL samples was significantly lower than in normal PBMC, resulting in very low effector to target (E:T) ratios.

CLL and normal PBMC samples were incubated for 24 or 48 hours with 10, 1, 0.1 µg/ml of XmAb® 13676 or 10 µg/ml of the control antibody XENP13245. After incubation, target cell counts were determined for CLL and normal PBMC samples. XmAb® 13676 induced robust B cell depletion in the normal PBMC at either 24 or 48 hours, resulting in a drop of several orders of magnitude in detectable B cells (not shown). This depletion activity appears to saturate at concentrations of 1 µg/ml or higher. However, there was no depletion of $CD19^+CD5^+$ cells in the CLL samples, presumably due to the low number of effector T cells in these samples. The nonspecific control antibody XENP13245 (10 µg/ml) did not decrease target cell counts in either sample set.

Figure 8:
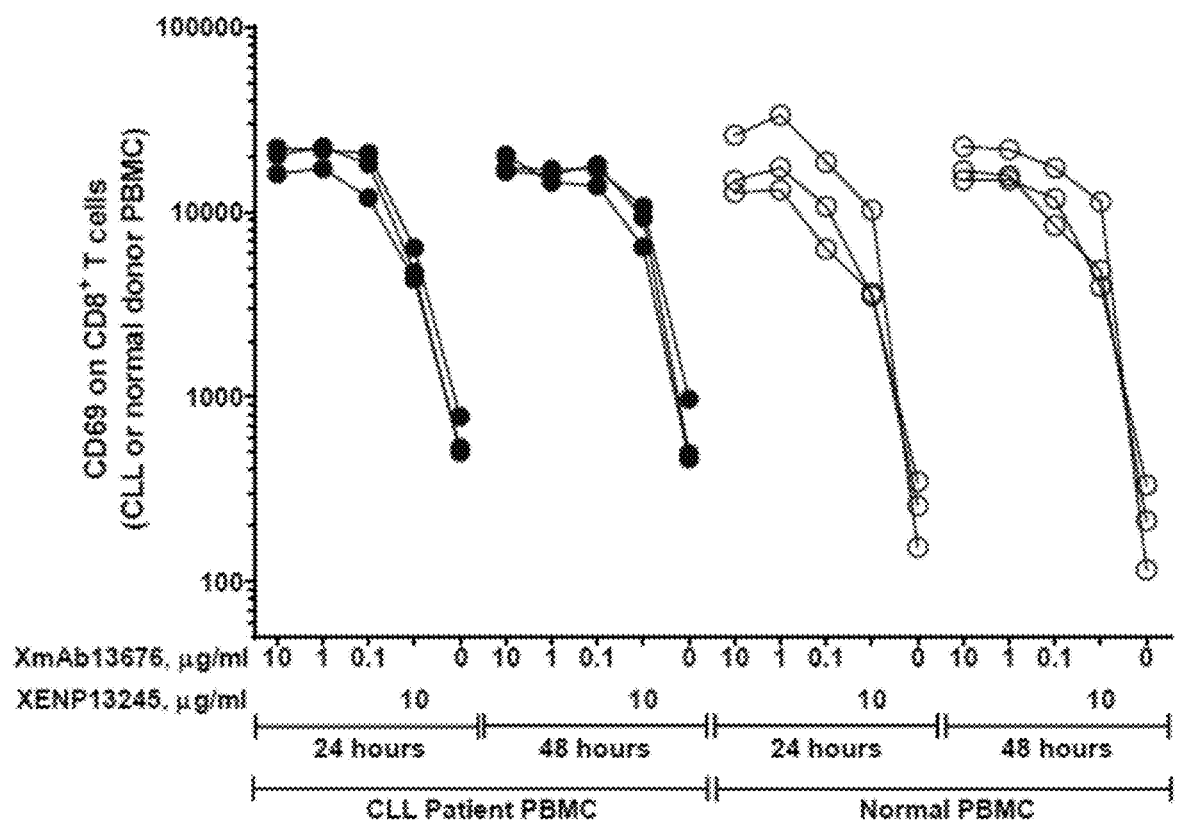
FIG. 8 is a line graph showing XmAb® 13676-mediated CD69 induction on CD8 T cells in CLL and normal PBMC.

XmAb® 13676 engagement of CD3 on the effector T cells and CD20 on the target cells is expected to activate T cells, which can be measured by detecting surface activation markers such as CD25 and CD69. As shown in FIG. 8, $CD8^+$ T cells were strongly activated by XmAb® 13676, as evidenced by the upregulation of CD69. Similar results were observed for CD25, and both CD69 and CD25 were also upregulated on $CD4^+$ T cells (data not shown). Hence, despite the lack of CLL depletion, XmAb® 13676 mediates strong activation of autologous T cells in the CLL samples. Such activation may lead to proliferation in vivo, potentially overcoming the problem with low T cell counts.

Figure 9:
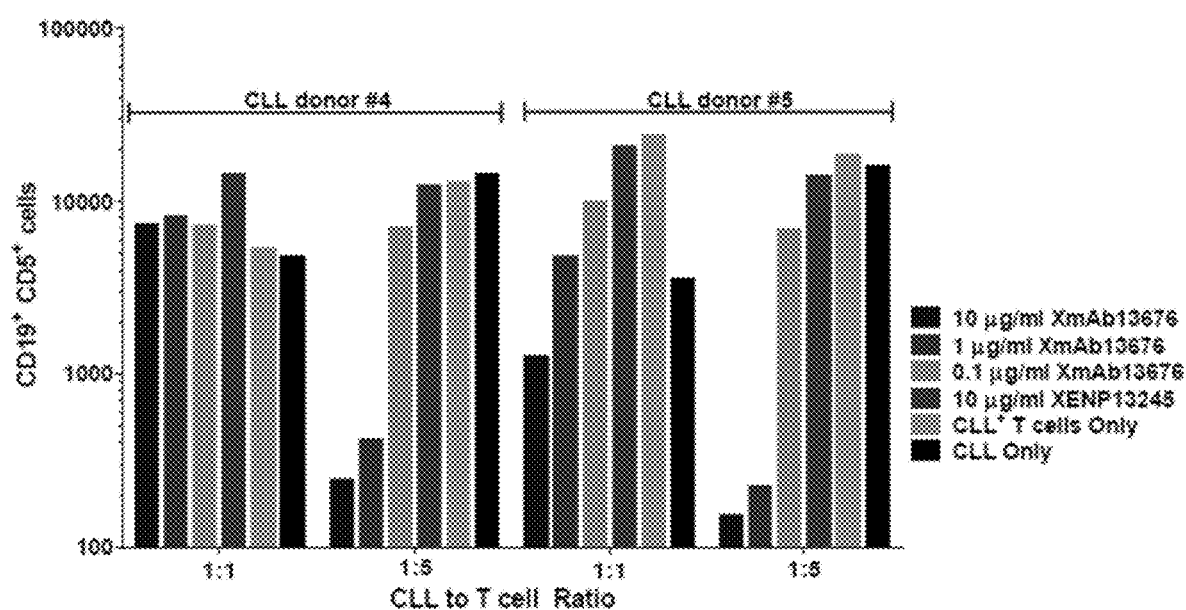
FIG. 9 is a bar graph showing CLL depletion in PBMC enriched with normal T cells.

As the number of effector T cells in the CLL samples was low, two CLL samples were supplemented with T cells purified from normal PBMC to assess the sensitivity of the CLL cancer cells to the XmAb® 13676 bispecific antibody. The number of live PBMCs assayed from each CLL donor was 250,000 and 320,000 and purified T cells from a normal PBMC were added at equal number (1:1 ratio) or 5-fold access over the CLL cells (5:1 ratio of T cells to CLL cells) and incubated for 24 hours. FIG. 9 shows the number of CLL cancer cell counts in two CLL human subject PBMC incubated with either XmAb® 13676 (at 0, 0.1, 1 or 10 µg/ml) or the negative control antibody XENP13245 (at 10 µg/ml). XmAb® 13676 induced very effective depletion of CD19+CD5+ CLL cancer cells in both CLL human subject PBMC samples at the 5:1 effector:target ratio, particularly at the highest concentration of 10 µg/ml. More modest depletion was observed at lower concentrations and at the lower 1:1 E:T ratio. In contrast, the negative control antibody XENP13245 (at 10 µg/ml) did not show any CLL cancer cell depletion at either 5:1 or 1:1 ratios. Therefore, CLL cells are sensitive to XmAb® 13676-induced T cell-mediated killing effects, in particular when sufficient T cells are present.

Figure 10:
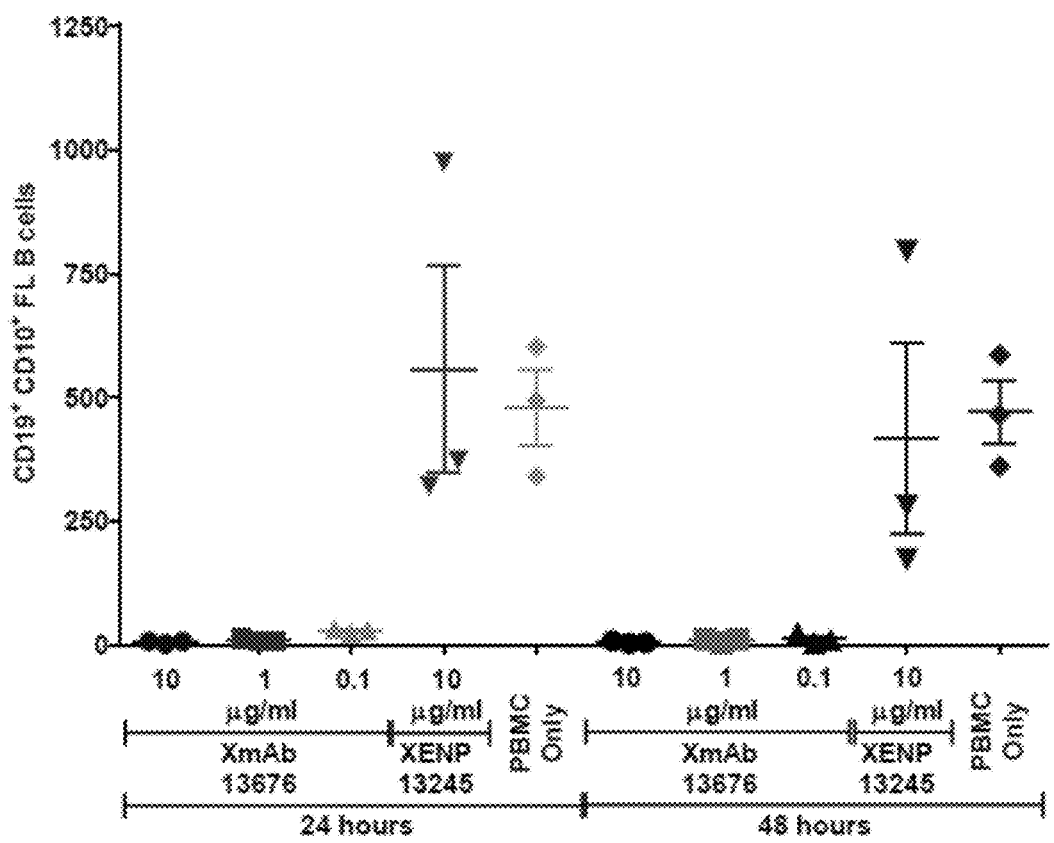
FIG. 10 is a dot graph showing XmAb® 13676 depletes follicular lymphoma (CD19+CD10+) cells in human subject PBMC samples.

PBMC samples from three FL human subjects were also characterized for XmAb® 13676-mediated cytotoxicity. Although CD19+CD10+FL cells were not high in number in these FL human subject-derived PBMC samples, counts were sufficiently high to reveal XmAb® 13676-mediated cytotoxicity of this target population. CD19+CD10+FL counts in control samples not exposed to XmAb® 13676 ranged from below 200 to almost 1000. In the presence of 0.1, 1.0, or 10 µg/ml concentrations of XmAb® 13676, these cells were nearly completely eliminated, particularly at the two higher concentrations. The nonspecific control antibody did not have any apparent impact on the FL cells. Notably, XmAb® 13676 also induced robust killing of the autologous healthy CD19+ B cells present in the PBMC samples, with a similar extent of depletion and concentration dependence, as shown in FIG. 10. Finally, in a pattern consistent with the observed depletion of B cells, XmAb® 13676 strongly activated T cells in the FL samples, as evidenced by CD69 and CD25 upregulation on both CD4 and CD8 T cells.

Example 3 Antitumor Activity in a Mouse Lymphoma Mode

Figure 11:
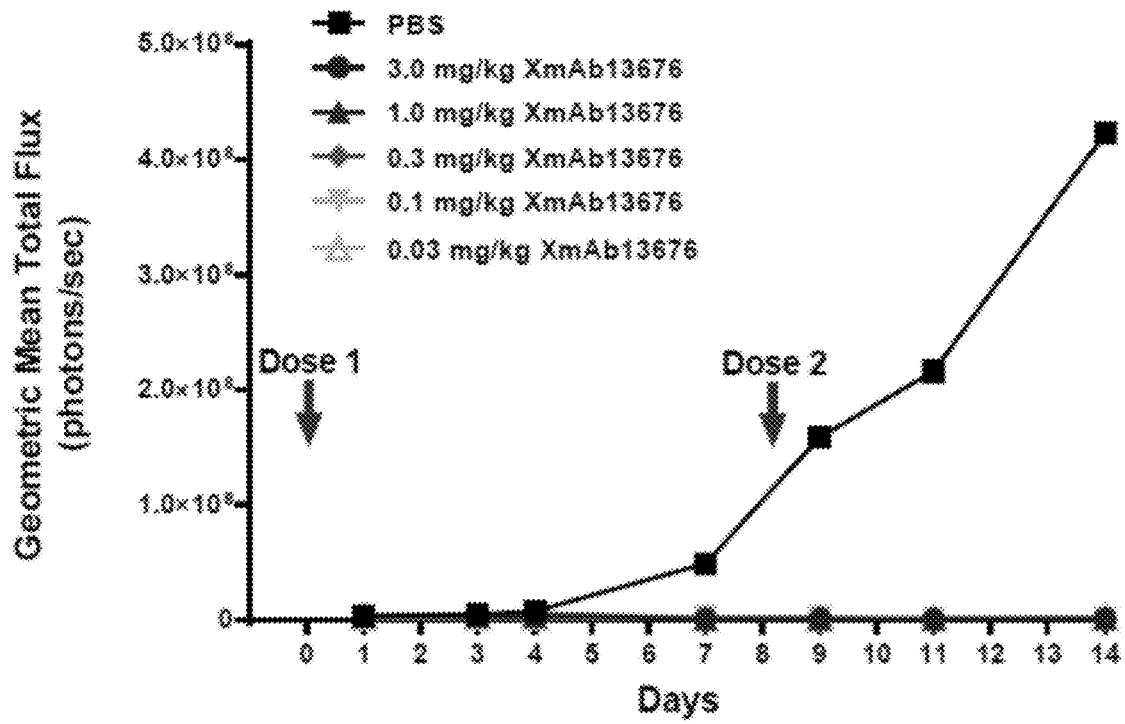
FIG. 11 is a line graph showing XmAb® 13676 prevents Raji tumor growth in huPBMC-NSG mice.

XmAb® 13676 does not cross-react with either mouse CD3 or CD20. Therefore, XmAb® 13676 was evaluated for its anti-tumor efficacy in NSG mice engrafted systemically with luciferase-transgenic human Raji cells (RajiTrS) as well as human PBMC. As shown in FIG. 11, In Vivo Imaging System (IVIS) analysis revealed that XmAb® 13676 prevented tumor growth at all doses tested, including 0.03 mg/kg, 0.1 mg/kg, 0.3 mg/kg, 1.0 mg/kg, 3.0 mg/kg. The data suggest that even lower doses would also be likely to have significant tumor prevention activity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a human subject with a CD20-expressing cancer, comprising:
    administering to the human subject a bispecific anti-CD20×anti-CD3 antibody in a first phase, a second phase, a third phase, a fourth phase, and a fifth phase,
    wherein in the first phase the bispecific anti-CD20×anti-CD3 antibody is administered once to the human subject in a first phase dose amount between about 0.5 mg and about 1.1 mg,
    in the second phase the bispecific anti-CD20×anti-CD3 antibody is administered once to the human subject in a second phase dose amount between about 1.5 mg and about 2.5 mg,
    in the third phase the bispecific anti-CD20×anti-CD3 antibody is administered once to the human subject in a third phase dose amount between about 18 mg and about 22 mg,
    in the fourth phase the bispecific anti-CD20×anti-CD3 antibody is administered once to the human subject in a fourth phase dose amount between about 30 mg and about 55 mg,
    in the fifth phase the bispecific anti-CD20×anti-CD3 antibody is administered at least once to the human subject in a fifth phase dose amount between about 45 mg and about 55 mg,
    wherein the time period between each administration is about 6 to about 8 days, wherein each of the first phase dose amount to the fifth phase dose amount is independent of the weight of the human subject, and
    wherein the bispecific anti-CD20×anti-CD3 antibody comprises a first polypeptide comprising the amino acid sequence of SEQ ID NO:1, a second polypeptide comprising the amino acid sequence of SEQ ID NO: 2, and a third polypeptide comprising the amino acid sequence of SEQ ID NO: 3.

2. The method of claim 1,
    wherein the first phase dose amount is about 0.8 mg,
    wherein the second phase dose amount is about 2.0 mg,
    wherein the third phase dose amount is about 20 mg,
    wherein the fourth phase dose amount is about 35 mg,
    wherein the fifth phase dose amount is about 50 mg.

3. The method of claim 1, wherein the fourth phase dose amount is between about 45 mg and about 55 mg.

4. The method of claim 1, wherein the fourth phase dose amount is between about 30 mg and about 40 mg.

5. The method of claim 1, further comprising a sixth phase, wherein the bispecific anti-CD20×anti-CD3 antibody is administered at least once to the human subject in a sixth phase dose amount between about 45 mg and about 55 mg, wherein if the sixth phase is administered more than once, then each sixth phase administration is between about 13 and about 15 days after the previous sixth phase administration.

6. The method of claim 1, wherein the CD20-expressing cancer is a hematologic cancer.

7. The method of claim 1, wherein the CD20-expressing cancer is a lymphoma.

8. The method of claim 7, wherein the lymphoma is a Non-Hodgkin lymphoma.

9. The method of claim 8, wherein the Non-Hodgkin lymphoma is B-cell NHL.

10. The method of claim 8, wherein the Non-Hodgkin lymphoma is selected from the group consisting of Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma.

11. The method of claim 1, further comprising administering to the human subject a combination of a corticosteroid, an antihistamine, and acetaminophen prior to each administering of the bispecific anti-CD20×anti-CD3 antibody.

12. The method of claim 1,
wherein the first phase dose amount is 0.8 mg,
wherein the second phase dose amount is 2.0 mg,
wherein the third phase dose amount is 20 mg,
wherein the fourth phase dose amount is 35 mg,
wherein the fifth phase dose amount is 50 mg.

13. The method of claim 1,
wherein the first phase dose amount is 0.8 mg,
wherein the second phase dose amount is 2.0 mg,
wherein the third phase dose amount is 20 mg,
wherein the fourth phase dose amount is 50 mg,
wherein the fifth phase dose amount is 50 mg.

14. A method for treating a human subject with a CD20-expressing cancer, comprising:
administering to the human subject a bispecific anti-CD20×anti-CD3 antibody in a first phase, a second phase, a third phase, a fourth phase, and a fifth phase,
wherein in the first phase the bispecific anti-CD20×anti-CD3 antibody is administered once to the human subject in a first phase dose amount between about 0.5 mg and about 1.1 mg,
in the second phase the bispecific anti-CD20×anti-CD3 antibody is administered once to the human subject in a second phase dose amount between about 1.5 mg and about 2.5 mg,
in the third phase the bispecific anti-CD20×anti-CD3 antibody is administered once to the human subject in a third phase dose amount between about 18 mg and about 22 mg,
in the fourth phase the bispecific anti-CD20×anti-CD3 antibody is administered once to the human subject in a fourth phase dose amount between about 30 mg and about 55 mg,
in the fifth phase the bispecific anti-CD20×anti-CD3 antibody is administered at least once to the human subject in a fifth phase dose amount between about 45 mg and about 55 mg,
wherein the time period between each administration is about 6 to about 8 days; wherein each of the first phase dose amount to the fifth phase dose amount is independent of the weight of the human subject and wherein the bispecific anti-CD20×anti-CD3 antibody comprises a first binding domain that binds to CD3 and a second binding domain that binds to CD20; wherein the first binding domain of the bispecific anti-CD20×anti-CD3 antibody that binds to CD3 comprises:
(i) a VH domain comprising a VH CDR1, a VH CDR2, and a VH CDR3 having an amino acid sequence of SEQ ID NO:22, SEQ ID NO:23, and SEQ ID NO:24, respectively; and
(ii) a VL domain comprising a VL CDR1, a VL CDR2, and VL CDR3 having an amino acid sequence of SEQ ID NO:25, SEQ ID NO:26, and SEQ ID NO:27, respectively; and/or
the second binding domain of the bispecific anti-CD20×anti-CD3 antibody that binds to CD20 comprises:
(i) a VH domain comprising a VH CDR1, VH CDR2, and a VH CDR3 having an amino acid sequence of SEQ ID NO:28, SEQ ID NO:29, and SEQ ID NO:30, respectively; and
(ii) a VL domain comprising a VL CDR1, VL CDR2, and VL CDR3 having an amino acid sequence of SEQ ID NO:31, SEQ ID NO:32, and SEQ ID NO:33, respectively.

15. The method of claim 14, further comprising a sixth phase, wherein the bispecific anti-CD20×anti-CD3 antibody is administered at least once to the human subject in a sixth phase dose amount between about 45 mg and about 55 mg, wherein if the sixth phase is administered more than once, then each sixth phase administration is between about 13 and about 15 days after the previous sixth phase administration.

16. The method of claim 14,
wherein the first phase dose amount is 0.8 mg,
wherein the second phase dose amount is 2.0 mg,
wherein the third phase dose amount is 20 mg,
wherein the fourth phase dose amount is 35 mg,
wherein the fifth phase dose amount is 50 mg.

17. The method of claim 14,
wherein the first phase dose amount is 0.8 mg,
wherein the second phase dose amount is 2.0 mg,
wherein the third phase dose amount is 20 mg,
wherein the fourth phase dose amount is 50 mg,
wherein the fifth phase dose amount is 50 mg.

18. The method of claim 14, wherein the CD20-expressing cancer is a hematologic cancer.

19. The method of claim 14, wherein the CD20-expressing cancer is a lymphoma.

20. The method of claim 19, wherein the lymphoma is a Non-Hodgkin lymphoma.

* * * * *

SEQUENCE LISTING

```
<160> NUMBER OF SEQ ID NOS: 52

<210> SEQ ID NO 1
<211> LENGTH: 450
<212> TYPE: PRT
<213> ORGANISM: Artificial Sequence
<220> FEATURE:
<223> OTHER INFORMATION: XmAb13676 Anti-CD20 VH-CH1-hinge-CH2-CH3;
      XENP13676 Anti-CD20 x Anti-CD3 Fab-scFv-Fc Heavy Chain 1
      (Anti-CD20 Fab-Fc (C2B8_H1))

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asp Thr Lys Val Asp Lys Lys Val Glu Pro Lys Ser Cys
    210                 215                 220
Asp Lys Thr His Thr Cys Pro Pro Cys Pro Ala Pro Pro Val Ala Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Lys His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Glu Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Asp Val Ser Gly Phe Tyr Pro Ser Asp Ile Ala Val Glu Trp
    370                 375                 380
Glu Ser Asp Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Glu Gln Gly Asp Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 2
<211> LENGTH: 485
<212> TYPE: PRT
<213> ORGANISM: Artificial Sequence
<220> FEATURE:
<223> OTHER INFORMATION: XmAb13676 Anti-CD3 scFv-linker-CH2-CH3;
      XENP13676 Anti-CD20 x Anti-CD3 Fab-scFv-Fc Heavy Chain 2
      (Anti-CD3 scFv-Fc (alphaCD3_H1.30_L1.47))

<400> SEQUENCE: 2

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Ala Met Asn Trp Val Arg Gln Ala Pro Gly Lys Gly Leu Glu Trp Val
        35                  40                  45
Gly Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asp Ser Tyr Val Ser Trp Phe
```

100                 105                 110
Ala Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
        130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                165                 170                 175
Ser Asn Tyr Ala Asn Trp Val Gln Gln Lys Pro Gly Lys Ser Pro Arg
            180                 185                 190
Gly Leu Ile Gly Gly Thr Asn Lys Arg Ala Pro Gly Val Pro Ala Arg
        195                 200                 205
Phe Ser Gly Ser Leu Leu Gly Gly Lys Ala Ala Leu Thr Ile Ser Gly
    210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Gly Thr Lys Leu Thr Val Leu Glu Pro
                245                 250                 255
Lys Ser Ser Asp Lys Thr His Thr Cys Pro Pro Cys Pro Ala Pro Pro
            260                 265                 270
Val Ala Gly Pro Ser Val Phe Leu Phe Pro Pro Lys Pro Lys Asp Thr
        275                 280                 285
Leu Met Ile Ser Arg Thr Pro Glu Val Thr Cys Val Val Val Asp Val
    290                 295                 300
Lys His Glu Asp Pro Glu Val Lys Phe Asn Trp Tyr Val Asp Gly Val
305                 310                 315                 320
Glu Val His Asn Ala Lys Thr Lys Pro Arg Glu Glu Gln Tyr Asn Ser
                325                 330                 335
Thr Tyr Arg Val Val Ser Val Leu Thr Val Leu His Gln Asp Trp Leu
            340                 345                 350
Asn Gly Lys Glu Tyr Lys Cys Lys Val Ser Asn Lys Ala Leu Pro Ala
        355                 360                 365
Pro Ile Glu Lys Thr Ile Ser Lys Ala Lys Gly Gln Pro Arg Glu Pro
    370                 375                 380
Gln Val Tyr Thr Leu Pro Pro Ser Arg Glu Gln Met Thr Lys Asn Gln
385                 390                 395                 400
Val Lys Leu Thr Cys Leu Val Lys Gly Phe Tyr Pro Ser Asp Ile Ala
                405                 410                 415
Val Glu Trp Glu Ser Asn Gly Gln Pro Glu Asn Asn Tyr Lys Thr Thr
            420                 425                 430
Pro Pro Val Leu Asp Ser Asp Gly Ser Phe Phe Leu Tyr Ser Lys Leu
        435                 440                 445
Thr Val Asp Lys Ser Arg Trp Gln Gln Gly Asn Val Phe Ser Cys Ser
    450                 455                 460
Val Met His Glu Ala Leu His Asn His Tyr Thr Gln Lys Ser Leu Ser
465                 470                 475                 480
Leu Ser Pro Gly Lys
            485

<210> SEQ ID NO 3
<211> LENGTH: 213
<212> TYPE: PRT
<213> ORGANISM: Artificial Sequence
<220> FEATURE:
<223> OTHER INFORMATION: XmAb13676 Anti-CD20 VL-CL; XENP13676 Anti-CD20
      x Anti-CD3 Fab-scFv-Fc Light Chain (Anti-CD20 LC (C2B8_L1))

<400> SEQUENCE: 3

```
Gln Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 4
<211> LENGTH: 450
<212> TYPE: PRT
<213> ORGANISM: Artificial Sequence
<220> FEATURE:
<223> OTHER INFORMATION: XENP13677 Anti-CD20 x Anti-CD3 Fab-scFv-Fc
      Heavy Chain 1 (Anti-CD20 Fab-Fc (C2B8_H1.202))

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Arg Leu Glu Trp Met
        35                  40                  45

Gly Ala Ile Tyr Pro Gly Asn Gly Ala Thr Ser Tyr Ser Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Met Gly Gly Asp Trp Tyr Phe Asp Val Trp Gly
            100                 105                 110
```

Ala Gly Thr Leu Val Thr Val Ser Ser Ala Ser Thr Lys Gly Pro Ser
          115                 120                 125

Val Phe Pro Leu Ala Pro Ser Ser Lys Ser Thr Ser Gly Gly Thr Ala
      130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
              165                 170                 175

Val Leu Gln Ser Ser Gly Leu Tyr Ser Leu Ser Ser Val Val Thr Val
          180                 185                 190

Pro Ser Ser Ser Leu Gly Thr Gln Thr Tyr Ile Cys Asn Val Asn His
      195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
              245                 250                 255

Ser Arg Thr Pro Glu Val Thr Cys Val Val Val Asp Val Lys His Glu
          260                 265                 270

Asp Pro Glu Val Lys Phe Asn Trp Tyr Val Asp Gly Val Glu Val His
      275                 280                 285

Asn Ala Lys Thr Lys Pro Arg Glu Glu Glu Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
              325                 330                 335

Lys Thr Ile Ser Lys Ala Lys Gly Gln Pro Arg Glu Pro Gln Val Tyr
          340                 345                 350

Thr Leu Pro Pro Ser Arg Glu Glu Met Thr Lys Asn Gln Val Ser Leu
      355                 360                 365

Thr Cys Asp Val Ser Gly Phe Tyr Pro Ser Asp Ile Ala Val Glu Trp
370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
              405                 410                 415

Lys Ser Arg Trp Glu Gln Gly Asp Val Phe Ser Cys Ser Val Met His
          420                 425                 430

Glu Ala Leu His Asn His Tyr Thr Gln Lys Ser Leu Ser Leu Ser Pro
      435                 440                 445

Gly Lys
    450

<210> SEQ ID NO 5
<211> LENGTH: 485
<212> TYPE: PRT
<213> ORGANISM: Artificial Sequence
<220> FEATURE:
<223> OTHER INFORMATION: XENP13677 Anti-CD20 x Anti-CD3 Fab-scFv-Fc
      Heavy Chain 2 (Anti-CD3 scFv-Fc (alphaCD3_H1.30_L1.47))

<400> SEQUENCE: 5

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
145                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
            210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
            275                 280                 285

Leu Met Ile Ser Arg Thr Pro Glu Val Thr Cys Val Val Val Asp Val
            290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
            355                 360                 365

Pro Ile Glu Lys Thr Ile Ser Lys Ala Lys Gly Gln Pro Arg Glu Pro
            370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430
```

Pro Pro Val Leu Asp Ser Asp Gly Ser Phe Phe Leu Tyr Ser Lys Leu
            435                 440                 445

Thr Val Asp Lys Ser Arg Trp Gln Gln Gly Asn Val Phe Ser Cys Ser
        450                 455                 460

Val Met His Glu Ala Leu His Asn His Tyr Thr Gln Lys Ser Leu Ser
465                 470                 475                 480

Leu Ser Pro Gly Lys
                485

<210> SEQ ID NO 6
<211> LENGTH: 213
<212> TYPE: PRT
<213> ORGANISM: Artificial Sequence
<220> FEATURE:
<223> OTHER INFORMATION: XENP13677 Anti-CD20 x Anti-CD3 Fab-scFv-Fc
      Light Chain (Anti-CD20 LC (C2B8_L1.113))

<400> SEQUENCE: 6

Gln Ile Val Leu Thr Gln Ser Pro Ser Ser Leu Ser Ala Ser Val Gly
1               5                   10                  15

Asp Arg Val Thr Ile Thr Cys Arg Ala Ser Trp Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr His Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 450
<212> TYPE: PRT
<213> ORGANISM: Artificial Sequence
<220> FEATURE:
<223> OTHER INFORMATION: XENP14388 Anti-CD20 x Anti-CD3 Fab-scFv-Fc
      Heavy Chain 1 (Anti-CD20 Fab-Fc (C2B8_H1.202))

<400> SEQUENCE: 7

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Asn Met His Trp Val Arg Gln Ala Pro Gly Gln Arg Leu Glu Trp Met
        35                  40                  45

Gly Ala Ile Tyr Pro Gly Asn Gly Ala Thr Ser Tyr Ser Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Met Gly Gly Asp Trp Tyr Phe Asp Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Lys His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Glu Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Asp Val Ser Gly Phe Tyr Pro Ser Asp Ile Ala Val Glu Trp
    370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Glu Gln Gly Asp Val Phe Ser Cys Ser Val Met His
            420                 425                 430
```

-continued

```
Glu Ala Leu His Asn His Tyr Thr Gln Lys Ser Leu Ser Leu Ser Pro
            435                 440                 445
Gly Lys
    450

<210> SEQ ID NO 8
<211> LENGTH: 485
<212> TYPE: PRT
<213> ORGANISM: Artificial Sequence
<220> FEATURE:
<223> OTHER INFORMATION: XENP14388 Anti-CD20 x Anti-CD3 Fab-scFv-Fc
      Heavy Chain 2 (Anti-CD3 scFv-Fc (alphaCD3_H1.31_L1.47))

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335
```

```
Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
            355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
            405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
            435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 9
<211> LENGTH: 213
<212> TYPE: PRT
<213> ORGANISM: Artificial Sequence
<220> FEATURE:
<223> OTHER INFORMATION: XENP14388 Anti-CD20 x Anti-CD3 Fab-scFv-Fc
      Light Chain (Anti-CD20 (C2B8_L1.113))

<400> SEQUENCE: 9

Gln Ile Val Leu Thr Gln Ser Pro Ser Ser Leu Ser Ala Ser Val Gly
1               5                   10                  15

Asp Arg Val Thr Ile Thr Cys Arg Ala Ser Trp Ser Val Ser Tyr Ile
            20                  25                  30

His Trp Phe Gln Gln Lys Pro Gly Lys Ser Pro Lys Pro Leu Ile Tyr
            35                  40                  45

Ala Thr Ser Asn Leu Ala Ser Gly Val Pro Val Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr His Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 10
<211> LENGTH: 450
<212> TYPE: PRT
<213> ORGANISM: Artificial Sequence
<220> FEATURE:
<223> OTHER INFORMATION: XENP14389 Anti-CD20 x Anti-CD3 Fab-scFv-Fc
      Heavy Chain 1 (Anti-CD20 Fab-Fc (C2B8_H1.202))

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Arg Leu Glu Trp Met
        35                  40                  45

Gly Ala Ile Tyr Pro Gly Asn Gly Ala Thr Ser Tyr Ser Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Met Gly Gly Asp Trp Tyr Phe Asp Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Lys His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Glu Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

-continued

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Asp Val Ser Gly Phe Tyr Pro Ser Asp Ile Ala Val Glu Trp
        370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asp Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 11
<211> LENGTH: 485
<212> TYPE: PRT
<213> ORGANISM: Artificial Sequence
<220> FEATURE:
<223> OTHER INFORMATION: XENP14389 Anti-CD20 x Anti-CD3 Fab-scFv-Fc
      Heavy Chain 2 (Anti-CD3 scFv-Fc (alphaCD3_H1.32_L1.47))

<400> SEQUENCE: 11

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240
```

Asn His Trp Val Phe Gly Gly Gly Thr Lys Leu Thr Val Leu Glu Pro
            245                 250                 255

Lys Ser Ser Asp Lys Thr His Thr Cys Pro Pro Cys Pro Ala Pro Pro
        260                 265                 270

Val Ala Gly Pro Ser Val Phe Leu Phe Pro Pro Lys Pro Lys Asp Thr
    275                 280                 285

Leu Met Ile Ser Arg Thr Pro Glu Val Thr Cys Val Val Val Asp Val
290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485

<210> SEQ ID NO 12
<211> LENGTH: 213
<212> TYPE: PRT
<213> ORGANISM: Artificial Sequence
<220> FEATURE:
<223> OTHER INFORMATION: XENP14389 Anti-CD20 x Anti-CD3 Fab-scFv-Fc
      Light Chain (Anti-CD20 (C2B8_L1.113))

<400> SEQUENCE: 12

Gln Ile Val Leu Thr Gln Ser Pro Ser Leu Ser Ala Ser Val Gly
1               5                   10                  15

Asp Arg Val Thr Ile Thr Cys Arg Ala Ser Trp Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr His Asn Pro Pro Thr
                85                  90                  95

Phe Gly Gly Gly Thr Lys Val Glu Ile Lys Arg Thr Val Ala Ala Pro

```
                100             105              110
Ser Val Phe Ile Phe Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 13
<211> LENGTH: 450
<212> TYPE: PRT
<213> ORGANISM: Artificial Sequence
<220> FEATURE:
<223> OTHER INFORMATION: XENP14390 Anti-CD20 x Anti-CD3 Fab-scFv-Fc
      Heavy Chain 1 (Anti-CD20 Fab-Fc (C2B8_H1.202))

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Arg Leu Glu Trp Met
            35                  40                  45

Gly Ala Ile Tyr Pro Gly Asn Gly Ala Thr Ser Tyr Ser Gln Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Met Gly Gly Asp Trp Tyr Phe Asp Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Lys His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Glu Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Asp Val Ser Gly Phe Tyr Pro Ser Asp Ile Ala Val Glu Trp
370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asp Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 14
<211> LENGTH: 485
<212> TYPE: PRT
<213> ORGANISM: Artificial Sequence
<220> FEATURE:
<223> OTHER INFORMATION: XENP14390 Anti-CD20 x Anti-CD3 Fab-scFv-Fc
      Heavy Chain 2 (Anti-CD3 scFv-Fc (alphaCD3_H1.33_L1.47))

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140
```

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
            165                 170                 175

Ser Asn Tyr Ala Asn Trp Val Gln Gln Lys Pro Gly Lys Ser Pro Arg
        180                 185                 190

Gly Leu Ile Gly Gly Thr Asn Lys Arg Ala Pro Gly Val Pro Ala Arg
    195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
            245                 250                 255

Lys Ser Ser Asp Lys Thr His Thr Cys Pro Pro Cys Pro Ala Pro Pro
        260                 265                 270

Val Ala Gly Pro Ser Val Phe Leu Phe Pro Pro Lys Pro Lys Asp Thr
    275                 280                 285

Leu Met Ile Ser Arg Thr Pro Glu Val Thr Cys Val Val Val Asp Val
290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
            325                 330                 335

Thr Tyr Arg Val Val Ser Val Leu Thr Val Leu His Gln Asp Trp Leu
        340                 345                 350

Asn Gly Lys Glu Tyr Lys Cys Lys Val Ser Asn Lys Ala Leu Pro Ala
    355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
            405                 410                 415

Val Glu Trp Glu Ser Asn Gly Gln Pro Glu Asn Asn Tyr Lys Thr Thr
        420                 425                 430

Pro Pro Val Leu Asp Ser Asp Gly Ser Phe Phe Leu Tyr Ser Lys Leu
    435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 15
<211> LENGTH: 213
<212> TYPE: PRT
<213> ORGANISM: Artificial Sequence
<220> FEATURE:
<223> OTHER INFORMATION: XENP14390 Anti-CD20 x Anti-CD3 Fab-scFv-Fc
      Light Chain (Anti-CD20 (C2B8_L1.113))

<400> SEQUENCE: 15

Gln Ile Val Leu Thr Gln Ser Pro Ser Ser Leu Ser Ala Ser Val Gly

```
  1               5                   10                  15
Asp Arg Val Thr Ile Thr Cys Arg Ala Ser Trp Ser Val Ser Tyr Ile
              20                  25                  30

His Trp Phe Gln Gln Lys Pro Gly Lys Ser Pro Lys Pro Leu Ile Tyr
              35                  40                  45

Ala Thr Ser Asn Leu Ala Ser Gly Val Pro Val Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Thr His Asn Pro Pro Thr
              85                  90                  95

Phe Gly Gly Gly Thr Lys Val Glu Ile Lys Arg Thr Val Ala Ala Pro
             100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
             165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
             195                 200                 205

Asn Arg Gly Glu Cys
210
```

<210> SEQ ID NO 16
<211> LENGTH: 450
<212> TYPE: PRT
<213> ORGANISM: Artificial Sequence
<220> FEATURE:
<223> OTHER INFORMATION: XENP14392 Anti-CD20 x Anti-CD3 Fab-scFv-Fc
      Heavy Chain 1 (Anti-CD20 Fab-Fc (C2B8_H1.202))

<400> SEQUENCE: 16

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
              20                  25                  30

Asn Met His Trp Val Arg Gln Ala Pro Gly Gln Arg Leu Glu Trp Met
              35                  40                  45

Gly Ala Ile Tyr Pro Gly Asn Gly Ala Thr Ser Tyr Ser Gln Lys Phe
 50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
              85                  90                  95

Ala Arg Ser Tyr Tyr Met Gly Gly Asp Trp Tyr Phe Asp Val Trp Gly
             100                 105                 110

Ala Gly Thr Leu Val Thr Val Ser Ser Ala Ser Thr Lys Gly Pro Ser
             115                 120                 125

Val Phe Pro Leu Ala Pro Ser Ser Lys Ser Thr Ser Gly Gly Thr Ala
130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Lys His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Glu Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Asp Val Ser Gly Phe Tyr Pro Ser Asp Ile Ala Val Glu Trp
        370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Glu Gln Gly Asp Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 485
<212> TYPE: PRT
<213> ORGANISM: Artificial Sequence
<220> FEATURE:
<223> OTHER INFORMATION: XENP14392 Anti-CD20 x Anti-CD3 Fab-scFv-Fc
      Heavy Chain 2 (Anti-CD3 scFv-Fc (alphaCD3_H1.89_L1.47))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

```
Gly Arg Ile Arg Ser Lys Tyr Asn Asn Tyr Ala Thr Tyr Tyr Ala Asp
    50              55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Glu Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460
```

Val Met His Glu Ala Leu His Asn His Tyr Thr Gln Lys Ser Leu Ser
465                 470                 475                 480

Leu Ser Pro Gly Lys
            485

<210> SEQ ID NO 18
<211> LENGTH: 213
<212> TYPE: PRT
<213> ORGANISM: Artificial Sequence
<220> FEATURE:
<223> OTHER INFORMATION: XENP14392 Anti-CD20 x Anti-CD3 Fab-scFv-Fc
      Light Chain (Anti-CD20 (C2B8_L1.113))

<400> SEQUENCE: 18

Gln Ile Val Leu Thr Gln Ser Pro Ser Ser Leu Ser Ala Ser Val Gly
1               5                   10                  15

Asp Arg Val Thr Ile Thr Cys Arg Ala Ser Trp Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr His Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 450
<212> TYPE: PRT
<213> ORGANISM: Artificial Sequence
<220> FEATURE:
<223> OTHER INFORMATION: XENP14393 Anti-CD20 x Anti-CD3 Fab-scFv-Fc
      Heavy Chain 1 (Anti-CD20 Fab-Fc (C2B8_H1.202))

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Arg Leu Glu Trp Met
        35                  40                  45

```
Gly Ala Ile Tyr Pro Gly Asn Gly Ala Thr Ser Tyr Ser Gln Lys Phe
 50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Tyr Tyr Met Gly Gly Asp Trp Tyr Phe Asp Val Trp Gly
                100                 105                 110

Ala Gly Thr Leu Val Thr Val Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asp Thr Lys Val Asp Lys Lys Val Glu Pro Lys Ser Cys
210                 215                 220

Asp Lys Thr His Thr Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Lys His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Glu Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Asp Val Ser Gly Phe Tyr Pro Ser Asp Ile Ala Val Glu Trp
370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Glu Gln Gly Asp Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 20
<211> LENGTH: 485
<212> TYPE: PRT
<213> ORGANISM: Artificial Sequence
<220> FEATURE:
<223> OTHER INFORMATION: XENP14393 Anti-CD20 x Anti-CD3 Fab-scFv-Fc Heavy Chain 2 (Anti-CD3 scFv-Fc (alphaCD3_H1.90_L1.47))

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365
```

-continued

```
Pro Ile Glu Lys Thr Ile Ser Lys Ala Lys Gly Gln Pro Arg Glu Pro
    370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 21
<211> LENGTH: 213
<212> TYPE: PRT
<213> ORGANISM: Artificial Sequence
<220> FEATURE:
<223> OTHER INFORMATION: XENP14393 Anti-CD20 x Anti-CD3 Fab-scFv-Fc
      Light Chain (Anti-CD20 (C2B8_L1.113))

<400> SEQUENCE: 21

Gln Ile Val Leu Thr Gln Ser Pro Ser Ser Leu Ser Ala Ser Val Gly
1               5                   10                  15

Asp Arg Val Thr Ile Thr Cys Arg Ala Ser Trp Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr His Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 22
```

```
<211> LENGTH: 5
<212> TYPE: PRT
<213> ORGANISM: Artificial Sequence
<220> FEATURE:
<223> OTHER INFORMATION: XmAb13676 Anti-CD3 VH CDR1

<400> SEQUENCE: 22

Thr Tyr Ala Met Asn
1               5

<210> SEQ ID NO 23
<211> LENGTH: 19
<212> TYPE: PRT
<213> ORGANISM: Artificial Sequence
<220> FEATURE:
<223> OTHER INFORMATION: XmAb13676 Anti-CD3 VH CDR2

<400> SEQUENCE: 23

Arg Ile Arg Ser Lys Tyr Asn Asn Tyr Ala Thr Tyr Tyr Ala Asp Ser
1               5                   10                  15

Val Lys Gly

<210> SEQ ID NO 24
<211> LENGTH: 14
<212> TYPE: PRT
<213> ORGANISM: Artificial Sequence
<220> FEATURE:
<223> OTHER INFORMATION: XmAb13676 Anti-CD3 VH CDR3

<400> SEQUENCE: 24

His Gly Asn Phe Gly Asp Ser Tyr Val Ser Trp Phe Ala Tyr
1               5                   10

<210> SEQ ID NO 25
<211> LENGTH: 14
<212> TYPE: PRT
<213> ORGANISM: Artificial Sequence
<220> FEATURE:
<223> OTHER INFORMATION: XmAb13676 Anti-CD3 VL CDR1

<400> SEQUENCE: 25

Gly Ser Ser Thr Gly Ala Val Thr Thr Ser Asn Tyr Ala Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: XmAb13676 Anti-CD3 VL CDR2

<400> SEQUENCE: 26

Gly Thr Asn Lys Arg Ala Pro
1               5

<210> SEQ ID NO 27
<211> LENGTH: 9
<212> TYPE: PRT
<213> ORGANISM: Artificial Sequence
<220> FEATURE:
<223> OTHER INFORMATION: XmAb13676 Anti-CD3 VL CDR3

<400> SEQUENCE: 27

Ala Leu Trp Tyr Ser Asn His Trp Val
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: XmAb13676 Anti-CD20 VH CDR1

<400> SEQUENCE: 28

Ser Tyr Asn Met His
1               5

<210> SEQ ID NO 29
<211> LENGTH: 17
<212> TYPE: PRT
<213> ORGANISM: Artificial Sequence
<220> FEATURE:
<223> OTHER INFORMATION: XmAb13676 Anti-CD20 VH CDR2

<400> SEQUENCE: 29

Ala Ile Tyr Pro Gly Asn Gly Asp Thr Ser Tyr Asn Gln Lys Phe Gln
1               5                   10                  15

Gly

<210> SEQ ID NO 30
<211> LENGTH: 12
<212> TYPE: PRT
<213> ORGANISM: Artificial Sequence
<220> FEATURE:
<223> OTHER INFORMATION: XmAb13676 Anti-CD20 VH CDR3

<400> SEQUENCE: 30

Ser Thr Tyr Tyr Gly Gly Asp Trp Tyr Phe Asn Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: XmAb13676 Anti-CD20 VL CDR1

<400> SEQUENCE: 31

Arg Ala Ser Ser Ser Val Ser Tyr Ile His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: XmAb13676 Anti-CD20 VL CDR2

<400> SEQUENCE: 32

Ala Thr Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: XmAb13676 Anti-CD20 VL CDR3

<400> SEQUENCE: 33

Gln Gln Trp Thr Ser Asn Pro Pro Thr
1               5
```

-continued

```
<210> SEQ ID NO 34
<211> LENGTH: 125
<212> TYPE: PRT
<213> ORGANISM: Artificial Sequence
<220> FEATURE:
<223> OTHER INFORMATION: XmAb13676 Anti-CD3 VH

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 35
<211> LENGTH: 109
<212> TYPE: PRT
<213> ORGANISM: Artificial Sequence
<220> FEATURE:
<223> OTHER INFORMATION: XmAb13676 Anti-CD3 VL

<400> SEQUENCE: 35

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 36
<211> LENGTH: 121
<212> TYPE: PRT
<213> ORGANISM: Artificial Sequence
<220> FEATURE:
<223> OTHER INFORMATION: XmAb13676 Anti-CD20 VH

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30

Asn Met His Trp Val Arg Gln Ala Pro Gly Gln Gly Leu Glu Trp Met
            35                  40                  45

Gly Ala Ile Tyr Pro Gly Asn Gly Asp Thr Ser Tyr Asn Gln Lys Phe
        50                  55                  60

Gln Gly Arg Val Thr Ile Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Leu Val Thr Val Ser Ser
            115                 120

<210> SEQ ID NO 37
<211> LENGTH: 106
<212> TYPE: PRT
<213> ORGANISM: Artificial Sequence
<220> FEATURE:
<223> OTHER INFORMATION: XmAb13676 Anti-CD20 VL

<400> SEQUENCE: 37

Gln Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gly Gly Thr Lys Val Glu Ile Lys
            100                 105

<210> SEQ ID NO 38
<211> LENGTH: 449
<212> TYPE: PRT
<213> ORGANISM: Artificial Sequence
<220> FEATURE:
<223> OTHER INFORMATION: mosunetuzumab anti-CD3e heavy chain

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Glu
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Asp Ser Tyr Ser Asn Tyr Tyr Phe Asp Tyr Trp Gly Gln Gly
            100                 105                 110

Thr Leu Val Thr Val Ser Ser Ala Ser Thr Lys Gly Pro Ser Val Glu
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Glu Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Glu Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Glu Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 39
<211> LENGTH: 219
<212> TYPE: PRT
<213> ORGANISM: Artificial Sequence
<220> FEATURE:
<223> OTHER INFORMATION: mosunetuzumab anti-CD3e light chain

<400> SEQUENCE: 39

Asp Ile Val Met Thr Gln Ser Pro Asp Ser Leu Ala Val Ser Leu Gly
```

```
1               5                   10                  15
Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Glu Ser Gly Ser Gly Ser Gly Thr Asp Glu Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Glu Asn Arg Gly Glu Cys
    210                 215

<210> SEQ ID NO 40
<211> LENGTH: 452
<212> TYPE: PRT
<213> ORGANISM: Artificial Sequence
<220> FEATURE:
<223> OTHER INFORMATION: mosunetuzumab anti-CD20 heavy chain

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Asn Met His Trp Val Arg Gln Ala Pro Gly Lys Gly Leu Glu Trp Val
                35                  40                  45

Gly Ala Ile Tyr Pro Gly Asn Gly Asp Thr Ser Tyr Asn Gln Lys Glu
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
```

```
            145                 150                 155                 160
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Trp Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Glu Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 41
<211> LENGTH: 213
<212> TYPE: PRT
<213> ORGANISM: Artificial Sequence
<220> FEATURE:
<223> OTHER INFORMATION: mosunetuzumab anti-CD20 light chain

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
                20                  25                  30

His Trp Tyr Gln Gln Lys Pro Gly Lys Ala Pro Lys Pro Leu Ile Tyr
                35                  40                  45

Ala Pro Ser Asn Leu Ala Ser Gly Val Pro Ser Arg Phe Ser Gly Ser
```

```
            50                  55                  60
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Glu Asn Pro Pro Thr
                     85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 42
<211> LENGTH: 454
<212> TYPE: PRT
<213> ORGANISM: Artificial Sequence
<220> FEATURE:
<223> OTHER INFORMATION: epcoritamab anti-CD3e heavy chain

<400> SEQUENCE: 42

Glu Val Lys Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
```

```
                195                 200                 205
Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450

<210> SEQ ID NO 43
<211> LENGTH: 215
<212> TYPE: PRT
<213> ORGANISM: Artificial Sequence
<220> FEATURE:
<223> OTHER INFORMATION: epcoritamab anti-CD3e light chain

<400> SEQUENCE: 43

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu Gly Gln Pro
```

```
                100             105             110
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 44
<211> LENGTH: 451
<212> TYPE: PRT
<213> ORGANISM: Artificial Sequence
<220> FEATURE:
<223> OTHER INFORMATION: epcoritamab  anti-CD20 heavy chain

<400> SEQUENCE: 44

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Ile Gln Tyr Gly Asn Tyr Tyr Tyr Gly Met Asp Val Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
```

-continued

```
                   245                 250                 255
    Met Ile Ser Arg Thr Pro Glu Val Thr Cys Val Val Ala Val Ser
                    260                 265                 270

His Glu Asp Pro Glu Val Lys Phe Asn Trp Tyr Val Asp Gly Val Glu
                    275                 280                 285

Val His Asn Ala Lys Thr Lys Pro Arg Glu Glu Gln Tyr Asn Ser Thr
                    290                 295                 300

Tyr Arg Val Val Ser Val Leu Thr Val Leu His Gln Asp Trp Leu Asn
    305                 310                 315                 320

Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
                    340                 345                 350

Val Tyr Thr Leu Pro Pro Ser Arg Glu Glu Met Thr Lys Asn Gln Val
                    355                 360                 365

Ser Leu Thr Cys Leu Val Lys Gly Phe Tyr Pro Ser Asp Ile Ala Val
                    370                 375                 380

Glu Trp Glu Ser Asn Gly Gln Pro Glu Asn Asn Tyr Lys Thr Thr Pro
    385                 390                 395                 400

Pro Val Leu Asp Ser Asp Gly Ser Phe Phe Leu Tyr Ser Arg Leu Thr
                    405                 410                 415

Val Asp Lys Ser Arg Trp Gln Gln Gly Asn Val Phe Ser Cys Ser Val
                    420                 425                 430

Met His Glu Ala Leu His Asn His Tyr Thr Gln Lys Ser Leu Ser Leu
                    435                 440                 445

Ser Pro Gly
                    450
```

<210> SEQ ID NO 45
<211> LENGTH: 214
<212> TYPE: PRT
<213> ORGANISM: Artificial Sequence
<220> FEATURE:
<223> OTHER INFORMATION: epcoritamab anti-CD20 light chain

<400> SEQUENCE: 45

```
    Glu Ile Val Leu Thr Gln Ser Pro Ala Thr Leu Ser Leu Ser Pro Gly
    1               5                   10                  15

Glu Arg Ala Thr Leu Ser Cys Arg Ala Ser Gln Ser Val Ser Ser Tyr
                    20                  25                  30

Leu Ala Trp Tyr Gln Gln Lys Pro Gly Gln Ala Pro Arg Leu Leu Ile
                    35                  40                  45

Tyr Asp Ala Ser Asn Arg Ala Thr Gly Ile Pro Ala Arg Phe Ser Gly
                    50                  55                  60

Ser Gly Ser Gly Thr Asp Phe Thr Leu Thr Ile Ser Ser Leu Glu Pro
    65                  70                  75                  80

Glu Asp Phe Ala Val Tyr Tyr Cys Gln Gln Arg Ser Asn Trp Pro Ile
                    85                  90                  95

Thr Phe Gly Gln Gly Thr Arg Leu Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 46
<211> LENGTH: 449
<212> TYPE: PRT
<213> ORGANISM: Artificial Sequence
<220> FEATURE:
<223> OTHER INFORMATION: odronextamab anti-CD3 heavy chain

<400> SEQUENCE: 46

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn Arg Phe Thr Gln Lys Ser Leu Ser Leu Ser Leu Gly
                435                 440                 445

Lys

<210> SEQ ID NO 47
<211> LENGTH: 214
<212> TYPE: PRT
<213> ORGANISM: Artificial Sequence
<220> FEATURE:
<223> OTHER INFORMATION: odronextamab light chain

<400> SEQUENCE: 47

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205
```

Phe Asn Arg Gly Glu Cys
     210

<210> SEQ ID NO 48
<211> LENGTH: 453
<212> TYPE: PRT
<213> ORGANISM: Artificial Sequence
<220> FEATURE:
<223> OTHER INFORMATION: odronextamab anti-CD20 heavy chain

<400> SEQUENCE: 48

Glu Val Gln Leu Val Glu Ser Gly Gly Leu Val Gln Pro Gly Arg
1               5                   10                  15

Ser Leu Arg Leu Ser Cys Val Ala Ser Gly Phe Thr Phe Asn Asp Tyr
                20                  25                  30

Ala Met His Trp Val Arg Gln Ala Pro Gly Lys Gly Leu Glu Trp Val
                35                  40                  45

Ser Val Ile Ser Trp Asn Ser Asp Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Gln Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Lys Thr Tyr
                195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
                275                 280                 285

Glu Val His Asn Ala Lys Thr Lys Pro Arg Glu Glu Gln Phe Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Gln Glu Glu Met Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
                435                 440                 445

Leu Ser Leu Gly Lys
    450

<210> SEQ ID NO 49
<211> LENGTH: 674
<212> TYPE: PRT
<213> ORGANISM: Artificial Sequence
<220> FEATURE:
<223> OTHER INFORMATION: glofitamab anti-CD20/CD3 heavy chain

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Glu Lys Val Glu Pro Lys Ser Cys Asp Gly
210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

```
Ser Ser Thr Gly Ala Val Thr Ser Asn Tyr Ala Asn Trp Val Gln
            260                 265                 270

Glu Lys Pro Gly Gln Ala Phe Arg Gly Leu Ile Gly Thr Asn Lys
            275                 280                 285

Arg Ala Pro Gly Thr Pro Ala Arg Phe Ser Gly Ser Leu Leu Gly Gly
290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
            355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
            435                 440                 445

Lys Thr His Thr Cys Pro Pro Cys Pro Ala Pro Glu Ala Ala Gly Gly
            450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
            515                 520                 525

Val Val Ser Val Leu Thr Val Leu His Gln Asp Trp Leu Asn Gly Lys
530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670
```

Gly Lys

```
<210> SEQ ID NO 50
<211> LENGTH: 232
<212> TYPE: PRT
<213> ORGANISM: Artificial Sequence
<220> FEATURE:
<223> OTHER INFORMATION: glofitamab anti-CD3e light chain

<400> SEQUENCE: 50
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

```
<210> SEQ ID NO 51
<211> LENGTH: 448
<212> TYPE: PRT
<213> ORGANISM: Artificial Sequence
<220> FEATURE:
<223> OTHER INFORMATION: glofitamab anti-CD20 heavy chain

<400> SEQUENCE: 51
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly Lys
        435                 440                 445

<210> SEQ ID NO 52
<211> LENGTH: 219
<212> TYPE: PRT
<213> ORGANISM: Artificial Sequence
<220> FEATURE:
<223> OTHER INFORMATION: glofitamab anti-CD20 light chain
```

-continued

```
<400> SEQUENCE: 52

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```